United States Patent
Nair et al.

(10) Patent No.: US 8,609,635 B2
(45) Date of Patent: Dec. 17, 2013

(54) FUSED TRICYCLIC SILYL COMPOUNDS AND METHODS OF USE THEREOF FOR THE TREATMENT OF VIRAL DISEASES

(75) Inventors: Anilkumar Gopinadhan Nair, Edison, NJ (US); Kartik M. Keertikar, East Windsor, NJ (US); Seong Heon Kim, Livingston, NJ (US); Joseph A. Kozlowski, Princeton, NJ (US); Stuart Rosenblum, West Orange, NJ (US); Oleg B. Selyutin, West Windsor, NJ (US); Michael Wong, Somerset, NJ (US); Wensheng Yu, Edison, NJ (US); Qingbei Zeng, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 34 days.

(21) Appl. No.: 13/041,082

(22) Filed: Mar. 4, 2011

(65) Prior Publication Data

US 2011/0223134 A1 Sep. 15, 2011

Related U.S. Application Data

(60) Provisional application No. 61/312,016, filed on Mar. 9, 2010, provisional application No. 61/371,935, filed on Aug. 9, 2010.

(51) Int. Cl.
 *A61K 31/695* (2006.01)
 *C07F 7/10* (2006.01)

(52) U.S. Cl.
 USPC .................. 514/63; 544/60; 544/69; 546/14; 548/110

(58) Field of Classification Search
 USPC ............ 514/63; 544/60, 69; 546/14; 548/110
 See application file for complete search history.

(56) References Cited

U.S. PATENT DOCUMENTS

| | | | |
|---|---|---|---|
| 5,935,982 A | 8/1999 | Dykstra et al. | |
| 7,438,920 B1 | 10/2008 | Kim et al. | |
| 7,659,270 B2 | 2/2010 | Bachand et al. | |
| 7,906,655 B2 | 3/2011 | Belema et al. | |
| 8,147,818 B2 | 4/2012 | Bachand et al. | |
| 8,303,944 B2 | 11/2012 | Bachand et al. | |
| 8,420,686 B2 | 4/2013 | Or et al. | |
| 8,426,458 B2 | 4/2013 | Or et al. | |
| 2006/0019974 A1 | 1/2006 | Mederski et al. | |
| 2006/0258682 A1 | 11/2006 | Liao et al. | |
| 2007/0032497 A1 | 2/2007 | Hashimoto et al. | |
| 2007/0049593 A1 | 3/2007 | Oka et al. | |
| 2007/0185175 A1 | 8/2007 | Liu et al. | |
| 2008/0044379 A1 | 2/2008 | Bachand et al. | |
| 2008/0200423 A1 | 8/2008 | Cook et al. | |
| 2009/0202478 A1* | 8/2009 | Bachand et al. | 424/85.2 |
| 2009/0202483 A1 | 8/2009 | Bachand et al. | |
| 2010/0055071 A1 | 3/2010 | Leivers et al. | |
| 2010/0087382 A1 | 4/2010 | Bailey et al. | |
| 2010/0233122 A1 | 9/2010 | Qiu et al. | |
| 2010/0316607 A1 | 12/2010 | Or et al. | |
| 2011/0223134 A1 | 9/2011 | Nair et al. | |
| 2012/0083483 A1 | 4/2012 | Coburn et al. | |
| 2012/0251491 A1 | 10/2012 | Rosenblum et al. | |
| 2012/0258078 A1 | 10/2012 | Rosenblum et al. | |
| 2012/0276047 A1 | 11/2012 | Kleber et al. | |
| 2013/0156731 A1 | 6/2013 | Chen et al. | |

FOREIGN PATENT DOCUMENTS

| | | |
|---|---|---|
| WO | 0020400 | 4/2000 |
| WO | 2010065681 | 6/2010 |
| WO | 2010096777 | 8/2010 |
| WO | 2010138790 | 12/2010 |
| WO | 2011075439 | 6/2011 |

OTHER PUBLICATIONS

U.S. Appl. No. 60/103,085, filed Oct. 5, 1998, Hataye, et al.
Wachowius et al. Synthesis and DNA duplex recognition of a triplex-forming oligonucleotide with an ureide-substituted 4-phenylimidazole nucleoside. Tetrahedron Letters 2008, 49:7264-7267.
Pujals et al. "Replacement of a proline with a silaproline causes a 20-fold increase in the cellular uptake of a Pro-Rich Peptide." J. Am. Chem. Soc. 2006, 128:8479-8483.
Uwe Koch and Frank Narjes: "Recent Progress in the Development of Inhibitors of the Hepatitis C Virus RNA-Dependent RNA Polymerase" Current Topics in Medicinal Chemistry, Bentham Science Publishers Ltd, Netherlands, vol. 7, Jan. 1, 2007, pp. 1302-1329.

* cited by examiner

*Primary Examiner* — Joseph Kosack
*Assistant Examiner* — Matthew Coughlin
(74) *Attorney, Agent, or Firm* — Sheldon O. Heber; Jeffrey P. Bergman

(57) ABSTRACT

The present invention relates to novel Fused Tricyclic Silyl Compounds of Formula (I):

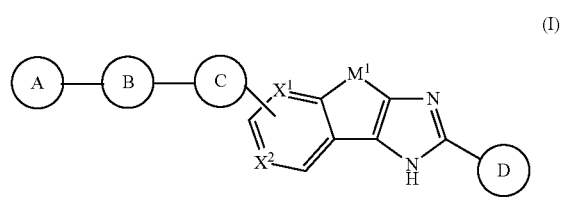

and pharmaceutically acceptable salts thereof, wherein A, B, C, D, $M^1$, $X^1$ and $X^2$ are as defined herein. The present invention also relates to compositions comprising at least one Fused Tricyclic Silyl Compound, and methods of using the Fused Tricyclic Silyl Compounds for treating or preventing HCV infection in a patient.

39 Claims, No Drawings

FUSED TRICYCLIC SILYL COMPOUNDS AND METHODS OF USE THEREOF FOR THE TREATMENT OF VIRAL DISEASES

FIELD OF THE INVENTION

The present invention relates to novel Fused Tricyclic Silyl Compounds, compositions comprising at least one Fused Tricyclic Silyl Compound, and methods of using the Fused Tricyclic Silyl Compounds for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal. HCV is a (+)-sense single-stranded enveloped RNA virus that has been implicated as the major causative agent in non-A, non-B hepatitis (NANBH), particularly in blood-associated NANBH (BB-NANBH) (see, International Publication No. WO 89/04669 and European Patent Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

It is well-established that persistent infection of HCV is related to chronic hepatitis, and as such, inhibition of HCV replication is a viable strategy for the prevention of hepatocellular carcinoma. Current therapies for HCV infection include α-interferon monotherapy and combination therapy comprising α-interferon and ribavirin. These therapies have been shown to be effective in some patients with chronic HCV infection, but suffer from poor efficacy and unfavorable side-effects and there are currently efforts directed to the discovery of HCV replication inhibitors that are useful for the treatment and prevention of HCV related disorders.

Current research efforts directed toward the treatment of HCV includes the use of antisense oligonucleotides, free bile acids (such as ursodeoxycholic acid and chenodeoxycholic acid) and conjugated bile acids (such as tauroursodeoxycholic acid). Phosphonoformic acid esters have also been proposed as potentially useful for the treatment of various viral infections, including HCV. Vaccine development, however, has been hampered by the high degree of viral strain heterogeneity and immune evasion and the lack of protection against reinfection, even with the same inoculum.

In light of these treatment hurdles, the development of small-molecule inhibitors directed against specific viral targets has become a major focus of anti-HCV research. The determination of crystal structures for NS3 protease, NS3 RNA helicase, NS5A, and NS5B polymerase, with and without bound ligands, has provided important structural insights useful for the rational design of specific inhibitors.

Recent attention has been focused toward the identification of inhibitors of HCV NS5A. HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065,681, WO 10/065,668, and WO 10/065,674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula (I)

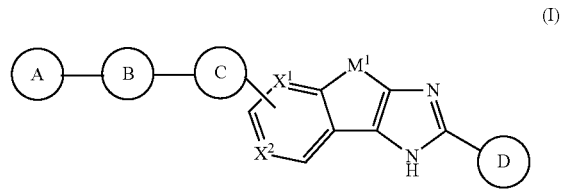

(I)

and pharmaceutically acceptable salts thereof,
wherein:

A is -alkylene-N($R^7$)($R^{11}$), -alkylene-N($R^{16}$)($R^{11}$), 4 to 7-membered monocyclic heterocycloalkyl, 4 to 7-membered monocyclic heterocycloalkenyl, 7 to 11-membered bicyclic heterocycloalkyl or $R^{15}$, wherein said 4 to 7-membered monocyclic heterocycloalkyl group, said 4 to 7-membered monocyclic heterocycloalkenyl group, said 7 to 11-membered bicyclic heterocycloalkyl group or said $R^{15}$ group can be optionally fused to a 3 to 7-membered cycloalkyl group, a 4 to 7-membered heterocycloalkyl group or an aryl group; and wherein said 4 to 7-membered monocyclic heterocycloalkyl group, said 4 to 7-membered monocyclic heterocycloalkenyl group, said 7 to 11-membered bicyclic heterocycloalkyl group or $R^{15}$ group can be optionally and independently substituted on one or more ring nitrogen atoms with $R^4$, and on one or more ring carbon atoms with $R^{12}$, such that two $R^{12}$ groups on the same ring carbon atom, together with the carbon atom to which they are attached, can join to form a spirocyclic 3 to 7-membered cycloalkyl group or a spirocyclic 4 to 7-membered heterocycloalkyl group;

B is 5-membered monocyclic heteroarylene group or a 9-membered bicyclic heteroarylene group containing at least one nitrogen atom, wherein said 5-membered monocyclic heteroarylene group and said 9-membered bicyclic heteroarylene group can be optionally fused to a benzene, pyridine or pyrimidine ring, and wherein said 5-membered monocyclic heteroarylene group or its fused counterpart and said 9-membered bicyclic heteroarylene group or it's fused counterpart, can be optionally and independently substituted on one or more ring nitrogen atoms with $R^6$ and on one or more ring carbon atoms with $R^{12}$;

C is a bond, —C($R^5$)=C($R^5$)—, —C≡C—, phenylene, monocyclic heteroarylene or bicyclic heteroarylene, wherein said phenylene group, said monocyclic heteroarylene group or said bicyclic heteroarylene group can be optionally and independently substituted on one or more ring nitrogen atoms with $R^6$ and on one or more ring carbon atoms with $R^{12}$;

D is -alkylene-N($R^7$)($R^{11}$), -alkylene-N($R^{16}$)($R^{11}$), 4 to 7-membered monocyclic heterocycloalkyl, 4 to 7-membered monocyclic heterocycloalkenyl, 7 to 11-membered bicyclic heterocycloalkyl or $R^{15}$, wherein said 4 to 7-membered monocyclic heterocycloalkyl group, said 4 to 7-membered monocyclic heterocycloalkenyl group, said 7 to 11-membered bicyclic heterocycloalkyl group or said $R^{15}$ group can be optionally fused to a 3 to 7-membered cycloalkyl group, a 4 to 7-membered heterocycloalkyl group or an aryl group; and wherein said 4 to 7-membered monocyclic heterocycloalkyl group, said 4 to 7-membered monocyclic heterocycloalkenyl group, said 7 to 11-membered bicyclic heterocycloalkyl group or $R^{15}$ group can be optionally and independently substituted on one or more ring nitrogen atoms with $R^4$, and on one or more ring carbon atoms with $R^{12}$, such that two $R^{12}$ groups on the same ring carbon atom, together with the carbon atom to which they are attached, can join to form a spirocyclic 3 to 7-membered cycloalkyl group or a spirocyclic 4 to 7-membered heterocycloalkyl group;

$M^1$ is a bond, —C($R^7$)$_2$—, —O—, —N($R^6$)—, —S(O)$_2$— —C($R^2$)=C($R^2$)—, —C($R^2$)=N—, —N=C($R^2$)—, —C($R^7$)$_2$—O—, —O—C($R^7$)$_2$—, —C($R^7$)$_2$—N($R^6$)— or —N($R^6$)—C($R^7$)$_2$—, such that two vicinal $R^7$ groups of $M^1$, together with the carbon atoms to which they are attached, can optionally join to form a 3- to 7-membered cycloalkyl group, a 3- to 7-membered heterocycloalkyl group or a 5- to 6-membered heteroaryl group;

$X^1$ is —C($R^5$)— or —N—;

$X^2$ is —C($R^5$)— or —N—;

each occurrence of $R^1$ is independently $C_1$-$C_6$ alkyl, -alkylene-O—($C_1$-$C_6$ alkyl), $C_1$-$C_6$ haloalkyl, 3- to 7-membered cycloalkyl, 4- to 7-membered heterocycloalkyl, aryl or heteroaryl, wherein said 3- to 7-membered cycloalkyl group, said 4- to 7-membered heterocycloalkyl group, said aryl group or said heteroaryl group can be optionally substituted with up to three groups, which can be the same or different, and are selected from $C_1$-$C_6$ alkyl, 3- to 7-membered cycloalkyl, 4- to 7-membered heterocycloalkyl, aryl, heteroaryl, halo, $C_1$-$C_6$ haloalkyl, —Si($R^{13}$)$_3$, —CN, —OR$^3$, —N($R^3$)$_2$, —C(O)$R^{10}$, —C(O)OR$^3$, —C(O)N($R^3$)$_2$, —NHC(O)$R^{10}$, —NHC(O)NHR$^3$, —NHC(O)OR$^3$, —OC(O)$R^{10}$, —SR$^3$ and —S(O)$_2$$R^{10}$;

each occurrence of $R^2$ is independently H, $C_1$-$C_6$ alkyl, —$C_1$-$C_6$ haloalkyl, 3 to 7-membered cycloalkyl, 4 to 7-membered heterocycloalkyl, $C_1$-$C_6$ hydroxyalkyl, —OH, —O—($C_1$-$C_6$ alkyl), halo, —CN, —NH$_2$, —NH($C_1$-$C_6$ alkyl), —N($C_1$-$C_6$ alkyl)$_2$, —NHC(O)—($C_1$-$C_6$ alkyl), —C(O)NH—($C_1$-$C_6$ alkyl), —C(O)N($C_1$-$C_6$ alkyl)$_2$, or —Si($R^{13}$)$_3$;

each occurrence of $R^3$ is independently H, $C_1$-$C_6$ alkyl, $C_1$-$C_6$ haloalkyl, —$C_1$-$C_6$ alkylene-OC(O)($C_1$-$C_6$ alkyl), $C_1$-$C_6$ hydroxyalkyl, 3 to 7-membered cycloalkyl, 4 to 7-membered heterocycloalkyl, aryl or heteroaryl wherein said 3- to 7-membered cycloalkyl group, said 4- to 7-membered heterocycloalkyl group, said aryl group or said heteroaryl group can be optionally and independently substituted with up to three groups independently selected from —OH, halo, $C_1$-$C_6$ alkyl, $C_1$-$C_6$ haloalkyl, —NH($C_1$-$C_6$ alkyl) and —N($C_1$-$C_6$ alkyl)$_2$;

each occurrence of $R^4$ is independently H, —$C_1$-$C_6$ alkyl, $C_1$-$C_6$ haloalkyl, —[C($R^7$)$_2$]$_q$N($R^6$)$_2$, —C(O)$R^1$, —C(O)—[C($R^7$)$_2$]$_q$N($R^6$)$_2$, —C(O)—[C($R^7$)$_2$]$_q$—$R^1$, —C(O)—[C($R^7$)$_2$]$_q$N($R^6$)C(O)—$R^1$, —C(O)[C($R^7$)$_2$]$_q$N($R^6$)SO$_2$—$R^1$, —C(O)—[C($R^7$)$_2$]$_q$N($R^6$)C(O)O—$R^1$, —C(O)—[C($R^7$)$_2$]$_q$C(O)O—$R^1$ or -alkylene-N($R^6$)—[C($R^7$)$_2$]$_q$—N($R^6$)—C(O)O—$R^1$;

each occurrence of $R^5$ is independently H, $C_1$-$C_6$ alkyl, —Si($R^{13}$)$_3$, 3- to 7-membered cycloalkyl, 4- to 7-membered heterocycloalkyl, aryl or heteroaryl;

each occurrence of $R^6$ is independently H, $C_1$-$C_6$ alkyl, 3- to 7-membered cycloalkyl, 4 to 7-membered heterocycloalkyl, aryl or heteroaryl, wherein said 3- to 7-membered cycloalkyl group, said 4- to 7-membered heterocycloalkyl group, said aryl group or said heteroaryl group can be optionally and independently substituted with up to two $R^8$ groups, and wherein two $R^6$ groups that are attached to a common nitrogen atom, together with the nitrogen atom to which they are attached, can optionally join to form a 4- to 7-membered heterocycloalkyl group;

each occurrence of $R^7$ is independently H, $C_1$-$C_6$ alkyl, $C_1$-$C_6$ haloalkyl, -alkylene-O—($C_1$-$C_6$ alkyl), silylalkyl, 3- to 7-membered cycloalkyl, 4 to 7-membered heterocycloalkyl, aryl or heteroaryl, wherein said 3- to 7-membered cycloalkyl group, said 4- to 7-membered heterocycloalkyl group, said aryl group or said heteroaryl group can be optionally and independently substituted with up to three $R^8$ groups, and wherein two geminal $R^7$ groups, together with the common carbon atom to which they are attached, can optionally join to form —C(=O)—, —C(=S)—, —C(=NH)—, —C(=N—OH)—, —C(=N—$C_1$-$C_6$ alkyl)-, —C(=N—O—$C_1$-$C_6$ alkyl)-, —C(=N-(3 to 7-membered cycloalkyl))-, —C(=N—O-(3- to 7-membered cycloalkyl))-, —C(=N-(4 to 7-membered heterocycloalkyl))-, —C(=N—O-(4- to 7-membered heterocycloalkyl))-, a 3 to 7-membered cycloalkyl group or a 4- to 7-membered heterocycloalkyl group, such that no two adjacent —C($R^7$)$_2$— groups can join to form a —C(=O)—C(=O)—, —C(=S)—C(=S)—, —C(=O)—C(=S)— or —C(=S)—C(=O)— group;

each occurrence of $R^8$ is independently H, $C_1$-$C_6$ alkyl, halo, —$C_1$-$C_6$ haloalkyl, $C_1$-$C_6$ hydroxyalkyl, —OH, —C(O)NH—($C_1$-$C_6$ alkyl), —C(O)N($C_1$-$C_6$ alkyl)$_2$, —O—($C_1$-$C_6$ alkyl), —NH$_2$, —NH($C_1$-$C_6$ alkyl), —N($C_1$-$C_6$ alkyl)$_2$ and —NHC(O)—($C_1$-$C_6$ alkyl) or —Si($R^{13}$)$_3$;

each occurrence of $R^{10}$ is independently $C_1$-$C_6$ alkyl, $C_1$-$C_6$ haloalkyl, 3 to 7-membered cycloalkyl, 4 to 7-membered heterocycloalkyl, aryl, or heteroaryl;

each occurrence of $R^{11}$ is independently H, $C_1$-$C_6$ alkyl, $C_1$-$C_6$ haloalkyl, —[C($R^7$)$_2$]$_q$N($R^6$)$_2$, —C(O)$R^1$, —C(O)—[C($R^7$)$_2$]$_q$N($R^6$)$_2$, —C(O)—[C($R^7$)$_2$]$_q$N($R^6$)C(O)—$R^1$, —C(O)—[C($R^7$)$_2$]$_q$N($R^6$)C(O)O—$R^1$, —C(O)—[C($R^7$)$_2$]$_q$C(O)O—$R^1$, —C(O)[C($R^7$)$_2$]$_q$N($R^6$)SO$_2$—$R^1$ or -alkylene-N($R^6$)—[C($R^7$)$_2$]$_q$—N($R^6$)—C(O)O—$R^1$;

each occurrence of $R^{12}$ is H, $C_1$-$C_6$ alkyl, $C_1$-$C_6$ haloalkyl, 3 to 7-membered cycloalkyl, 4 to 7-membered heterocycloalkyl, aryl, heteroaryl, halo, —CN, —OR$^3$, —N($R^3$)$_2$, —C(O)$R^{10}$, —C(O)OR$^3$, —C(O)N($R^3$)$_2$, —NHC(O)$R^{10}$, —NHC(O)NHR$^3$, —NHC(O)OR$^3$, —OC(O)$R^{10}$, —SR$^3$, —S(O)$_2$$R^{10}$ or Si($R^{13}$)$_3$ and wherein two $R^{12}$ groups together with the carbon atom(s) to which they are attached, can optionally join to form a 5 to 7-membered cycloalkyl or 4- to 7-membered heterocycloalkyl ring;

each occurrence of $R^{13}$ is independently selected from $C_1$-$C_6$ alkyl, 3- to 7-membered cycloalkyl, 4- to 7-membered heterocycloalkyl, aryl, heteroaryl, $C_1$-$C_6$ haloalkyl, —CN and —OR$^3$, wherein two $R^{13}$ groups, together with the silicon atom to which they are attached, can optionally join to form a 4- to 7-membered silicon-containing heterocycloalkyl ring;

each occurrence of $R^{15}$ is independently a monocyclic 5- to 7-membered silylheterocycloalkyl ring or a bicyclic 7- to 11-membered bicyclic silylheterocycloalkyl ring wherein said silylheterocycloalkyl rings contains as heteroatom ring members:

(i) one —Si($R^{13}$)$_2$—;

(ii) one —N($R^4$)—; and (iii) one optional and additional heteroatom ring member elected from the group consisting of nitrogen, oxygen and sulfur, and wherein an $R^{15}$ group can be optionally and independently substituted on one or two ring carbon atoms with $R^{12}$;

each occurrence of $R^{16}$ is independently:
(i) $C_1$-$C_6$ alkyl substituted with —Si($R^{13}$)$_3$;
(ii) 3 to 7-membered cycloalkyl substituted with —Si($R^{13}$)$_3$;
(iii) 4 to 7-membered heterocycloalkyl substituted with —Si($R^{13}$)$_3$;
(iv) phenyl substituted with —Si($R^{13}$)$_3$;
(v) 6-membered heteroaryl substituted with —Si($R^{13}$)$_3$, wherein said heteroaryl has one or two ring nitrogen atoms and no other ring heteroatoms; or
(vi) —(CH$_2$)$_r$—$R^{17}$,
and wherein when $R^{16}$ is said 3 to 7-membered cycloalkyl group, said 4- to 7-membered heterocycloalkyl group, said phenyl group or said heteroaryl group, then $R^{16}$ can be optionally substituted with up to three groups, which can be the same or different, and are selected from $C_1$-$C_6$ alkyl, halo, —$C_1$-$C_6$ haloalkyl, $C_1$-$C_6$ hydroxyalkyl, —OH, —C(O)NH—($C_1$-$C_6$ alkyl), —C(O)N($C_1$-$C_6$ alkyl)$_2$, —O—($C_1$-$C_6$ alkyl), —NH$_2$, —NH($C_1$-$C_6$ alkyl), —N($C_1$-$C_6$ alkyl)$_2$ and —NHC(O)—($C_1$-$C_6$ alkyl);

each occurrence of $R^{17}$ is independently:
(i) a 5- to 7-membered silylcycloalkyl ring having one —Si($R^{13}$)$_2$— ring member; or
(ii) a 5- to 7-membered silylheterocycloalkyl ring having one —Si($R^{13}$)$_2$— ring member, and one to two heteroatom ring members, which can be the same or different, and are selected from the group consisting of nitrogen, oxygen, and sulfur, such that the —Si($R^{13}$)$_2$— group must be bonded only to ring carbon atoms; or
(iii) a 7- to 11-membered bicyclic silylheterocycloalkyl ring having one —Si($R^{13}$)$_2$— ring member, and one to three heteroatom ring members, which can be the same or different, and are selected from the group consisting of nitrogen, oxygen, and sulfur.

and wherein an $R^{17}$ group can be optionally and independently substituted on one or two ring carbon atoms with up to two $R^{12}$ groups;

each occurrence of q is independently an integer ranging from 1 to 4; and each occurrence of r is independently an integer ranging from 0 to 6, wherein at least one of A and D is $R^{15}$ or -alkylene-N($R^{16}$)($R^{11}$).

The Compounds of Formula (I) (also referred to herein as the "Fused Tricyclic Silyl Compounds") and pharmaceutically acceptable salts thereof can be useful, for example, for inhibiting HCV viral replication or replicon activity, and for treating or preventing HCV infection in a patient. Without being bound by any specific theory, it is believed that the Fused Tricyclic Silyl Compounds inhibit HCV viral replication by inhibiting HCV NS5A.

Accordingly, the present invention provides methods for treating or preventing HCV infection in a patient, comprising administering to the patient an effective amount of at least one Fused Tricyclic Silyl Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Fused Tricyclic Silyl Compounds, compositions comprising at least one Fused Tricyclic Silyl Compound, and methods of using the Fused Tricyclic Silyl Compounds for treating or preventing HCV infection in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Fused Tricyclic Silyl Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, text-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

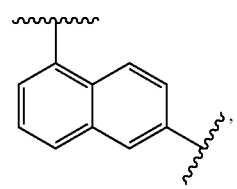 [SMILES: *c1ccc2c(*)cccc2c1]

is understood to represent both:

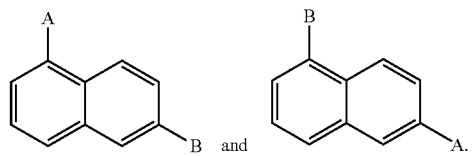

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

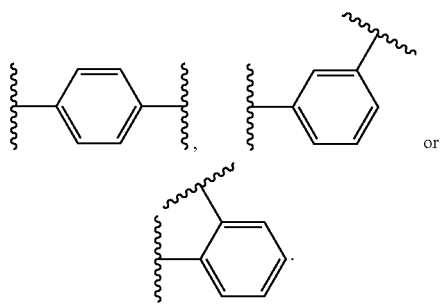

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

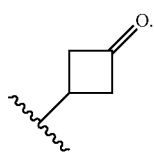 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms. Unless otherwise indicated, a cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

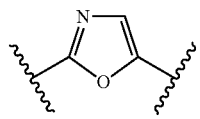 [SMILES: *c1cnc(*)o1]

is understood to represent both:

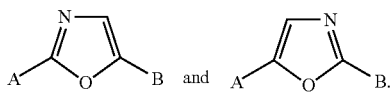

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocycle and has 5 or 6 ring atoms. In one embodiment, a heterocycloalkyl group is monocycle. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

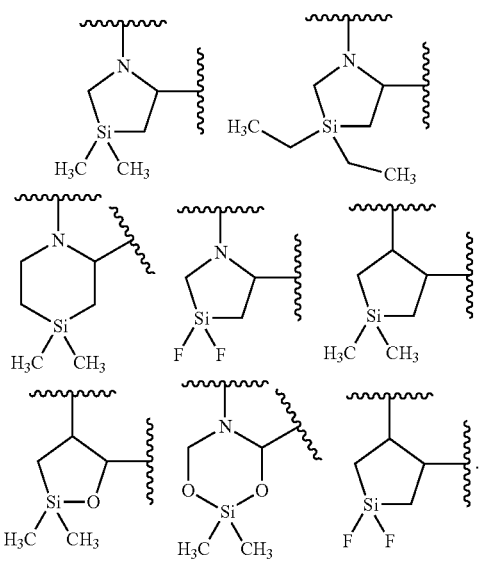

A ring carbon atom of a heterocycloalkyl group may be functionalized as a carbonyl group. An illustrative example of such a heterocycloalkyl group is:

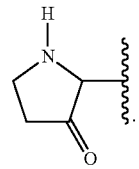 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

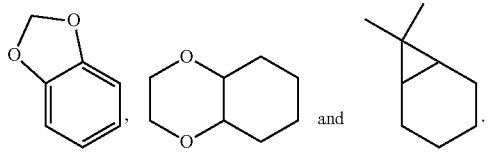

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently C$_1$-C$_6$ alkyl, phenyl or a 3- to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include
—CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^6$, R$^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tricyclic Silyl Compound or a pharmaceutically acceptable salt or solvate of the compound. The transformation may occur by various mechanisms (e.g., by metabolic or chemical processes), such as, for example, through hydrolysis in blood.

For example, if a Fused Tricyclic Silyl Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a Fused Tricyclic Silyl Compound contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a Fused Tricyclic Silyl Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)allyl, ($C_3$-$C_7$)cycloalkyl, benzyl, a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl; carboxy ($C_1$-$C_6$)alkyl; amino($C_1$-$C_4$)alkyl or mono-N— or di-N,N—($C_1$-$C_6$)alkylaminoalkyl; —C(Y$^4$)Y$^5$ wherein Y$^4$ is H or methyl and Y$^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tricyclic Silyl Compounds can form salts which are also within the scope of this invention. Reference to a Fused Tricyclic Silyl Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Fused Tricyclic Silyl Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Fused Tricyclic Silyl Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. In one embodiment, a compound of formula (I) is present as its dihydrochloride salt. In another embodiment, a compound of formula (I) is present as its dimesylate salt. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Fused Tricyclic Silyl Compounds may be atropisomers (e.g., substituted biaryls) and are considered as part of this invention. Enantiomers can also be directly separated using chiral chromatographic techniques.

It is also possible that the Fused Tricyclic Silyl Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Fused Tricyclic Silyl Compound incorporates a double bond or a fused Ting, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Fused Tricyclic Silyl Compounds, and of the salts, solvates, hydrates, esters and prodrugs of the Fused Tricyclic Silyl Compounds, are intended to be included in the present invention.

The following abbreviations are used below and have the following meanings: Ac is acyl; AcOH is acetic acid; $BF_3.OEt_2$ is boron trifluoride etherate; BOC or Boc is tert-butyloxycarbonyl; $Boc_2O$ is Boc anhydride; Boc-Pro-OH is Boc protected proline; L-Boc-Val-OH is Doc protected L-valine; n-BuLi is n-butyllithium; dba is dibenzylideneacetone; DCM is dichloromethane; DIPEA is diisopropylethylamine; DME is dimethoxyethane; DMF is N,N-dimethylformamide; dppf is diphenylphosphinoferrocene; DMSO is dimethylsulfoxide; EtOAc is ethyl acetate; $Et_2O$ is diethyl ether; $Et_3N$ is triethylamine; HATU is O-(7-azabenzotriazol-1-yl)-N,N,N',N'-tetramethyluronium hexafluorophosphate; $Hg(OAc)_2$ is mercuric acetate; HPLC is high performance liquid chromatography; HRMS is high resolution mass spectrometry; KOAc is potassium acetate; Lawesson's Reagent is 2,4-Bis(4-methoxyphenyl)-1,3-dithiadiphosphetane-2,4-disulfide; LCMS is liquid chromatography/mass spectrometry; LRMS is low resolution mass spectrometry; mCPBA is m-chloroperbenzoic acid; MeOH is methanol; MTBE is tert-butylmethyl ether; NBS is N-bromosuccinimide; $NH_4OAc$ is ammonium acetate; $Pd(PPh_3)_4$ is tetrakis(triphenylphosphine) palladium(0); $PdCl_2(dppf)_2$ is [1,1'-Bis(diphenylphosphino) ferrocene]dichloro palladium(II); $PdCl_2(dppf)_2.CH_2Cl_2$ is [1,1'-Bis(diphenylphosphino)ferrocene]dichloro palladium (II) complex with dichloromethane; $pinacol_2B_2$ is bis(pinacolato)diboron; PPTS is pyridinium p-toluene sulfonate; RPLC is reverse-phase liquid chromatography; SEM-Cl is 2-(trimethylsilyl)ethoxymethyl chloride; TBAF is tetrabutylammonium fluoride; TBAI is tetrabutylammonium iodide; TBDMSCl is tert-butyldimethylsilyl chloride; TFA is trifluoroacetic acid; THF is tetrahydrofuran; TLC is thin-layer chromatography; XPhos is 2-dicyclohexylphosphino-2',4',6'-triisopropylbiphenyl; and Z-Pro-OH is N-Benzyloxycarbonyl-L-proline.

The Compounds of Formula (I)

The present invention provides Fused Tricyclic Silyl Compounds of Formula (I):

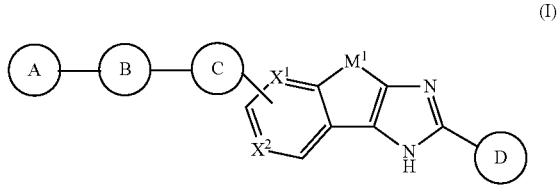

(I)

and pharmaceutically acceptable salts thereof, wherein A, B, C, D, $M^1$, $X^1$ and $X^2$ are defined above for the Compounds of Formula (I).

In one embodiment, for the Compounds of Formula (I), A is selected from:

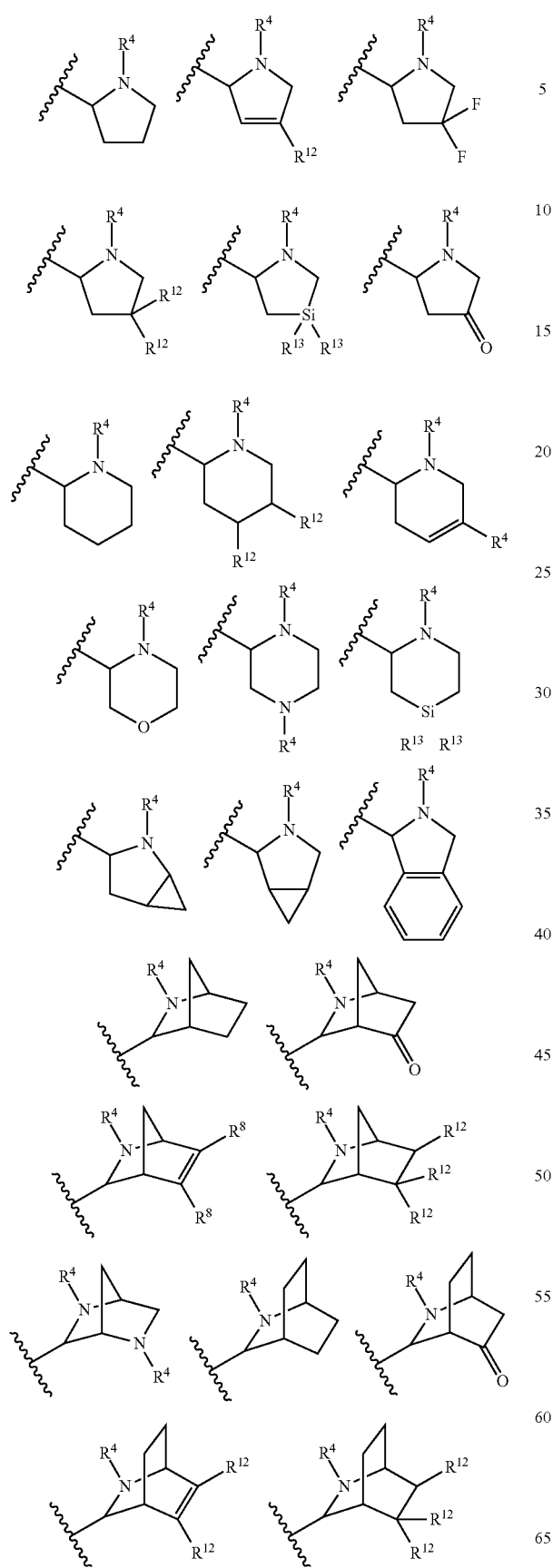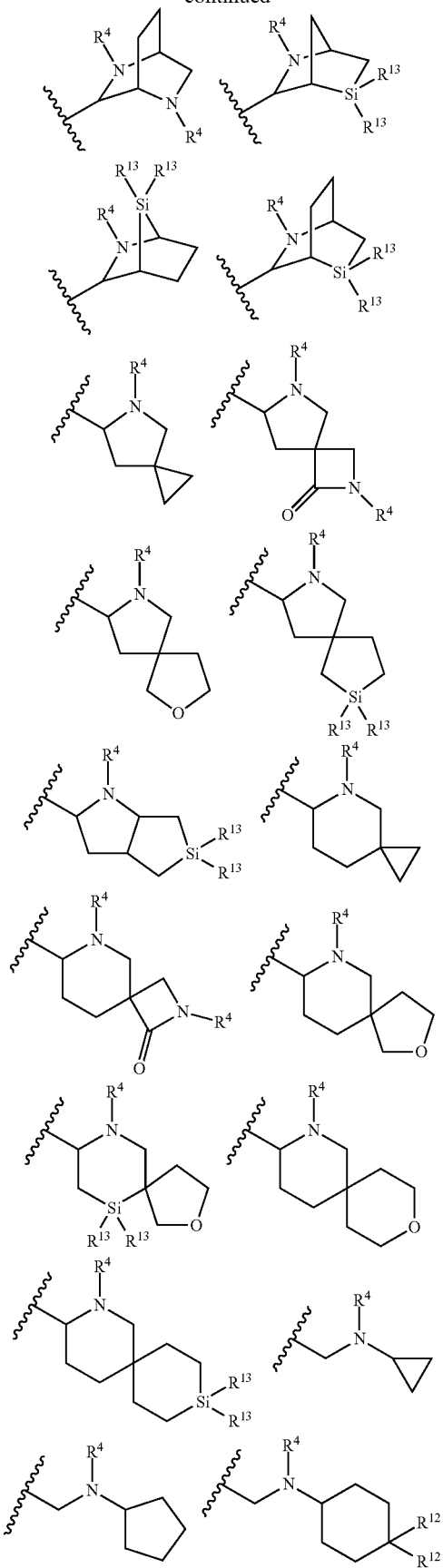

-continued

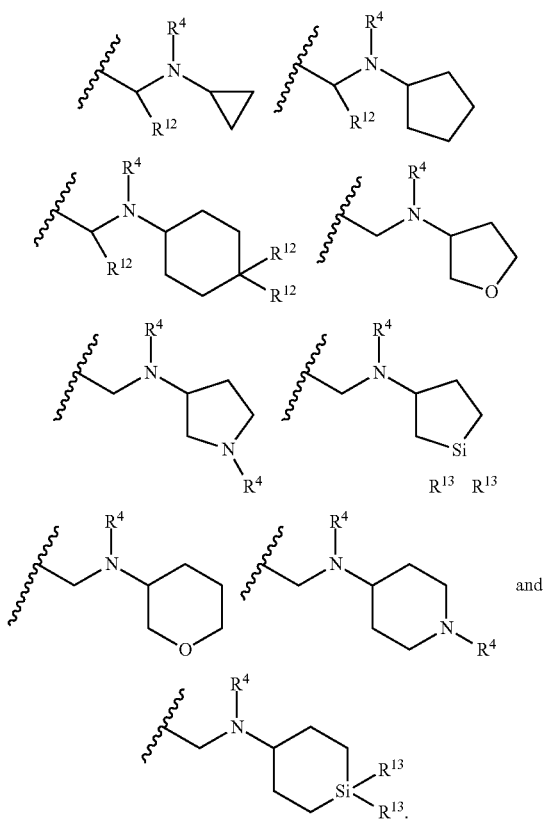

In another embodiment, for the Compounds of Formula (I), A is selected from:

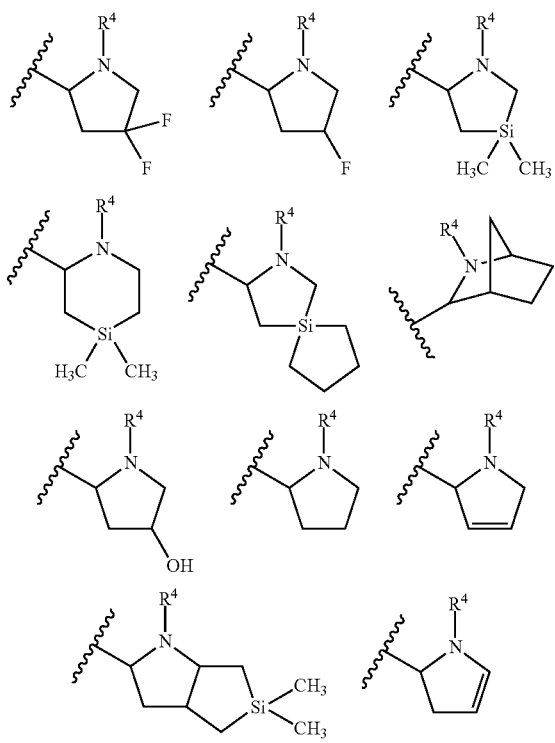

-continued

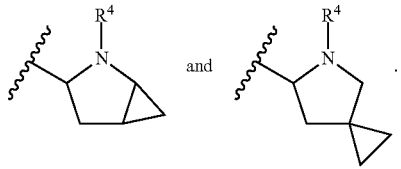

In one embodiment, for the Compounds of Formula (I), B is a 5-membered monocyclic heteroarylene.

In another embodiment, for the Compounds of Formula (I), B is:

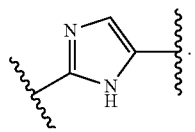

In another embodiment, for the Compounds of Formula (I), C is a monocyclic heteroarylene.

In still another embodiment, for the Compounds of Formula (I), C is a 6-membered monocyclic heteroarylene.

In another embodiment, for the Compounds of Formula (I), C is a 5-membered monocyclic heteroarylene.

In another embodiment, for the Compounds of Formula (I), C is a bicyclic heteroarylene.

In yet another embodiment, for the Compounds of Formula (I), C is

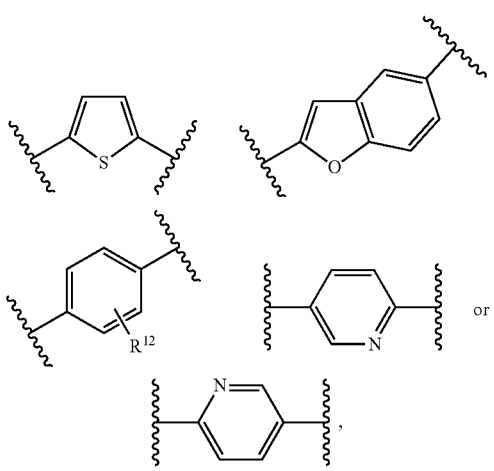

wherein $R^{12}$ is a single ring substituent selected from halo, 3- to 7-membered cycloalkyl, 5- or 6-membered heteroaryl, —O—($C_1$-$C_6$ alkyl), —O—($C_1$-$C_6$ hydroxyalkyl) and —O—($C_1$-$C_6$ alkylene)-OC(O)—($C_1$-$C_6$ alkyl).

In a further embodiment, for the Compounds of Formula (I), C is:

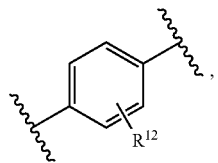
wherein R[12] is an optional ring substituent selected from F, —OCH$_3$, pyridyl, —OCH$_2$CH$_2$OH, —OCH$_2$CH$_2$OC(O)CH$_3$, cyclopropyl and thiophenyl.
In another embodiment, for the Compounds of Formula (I), C is:
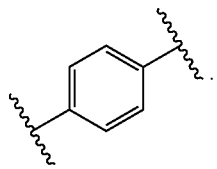 [SMILES: *c1ccc(*)cc1]
In one embodiment, for the Compounds of Formula (I), D is selected from:
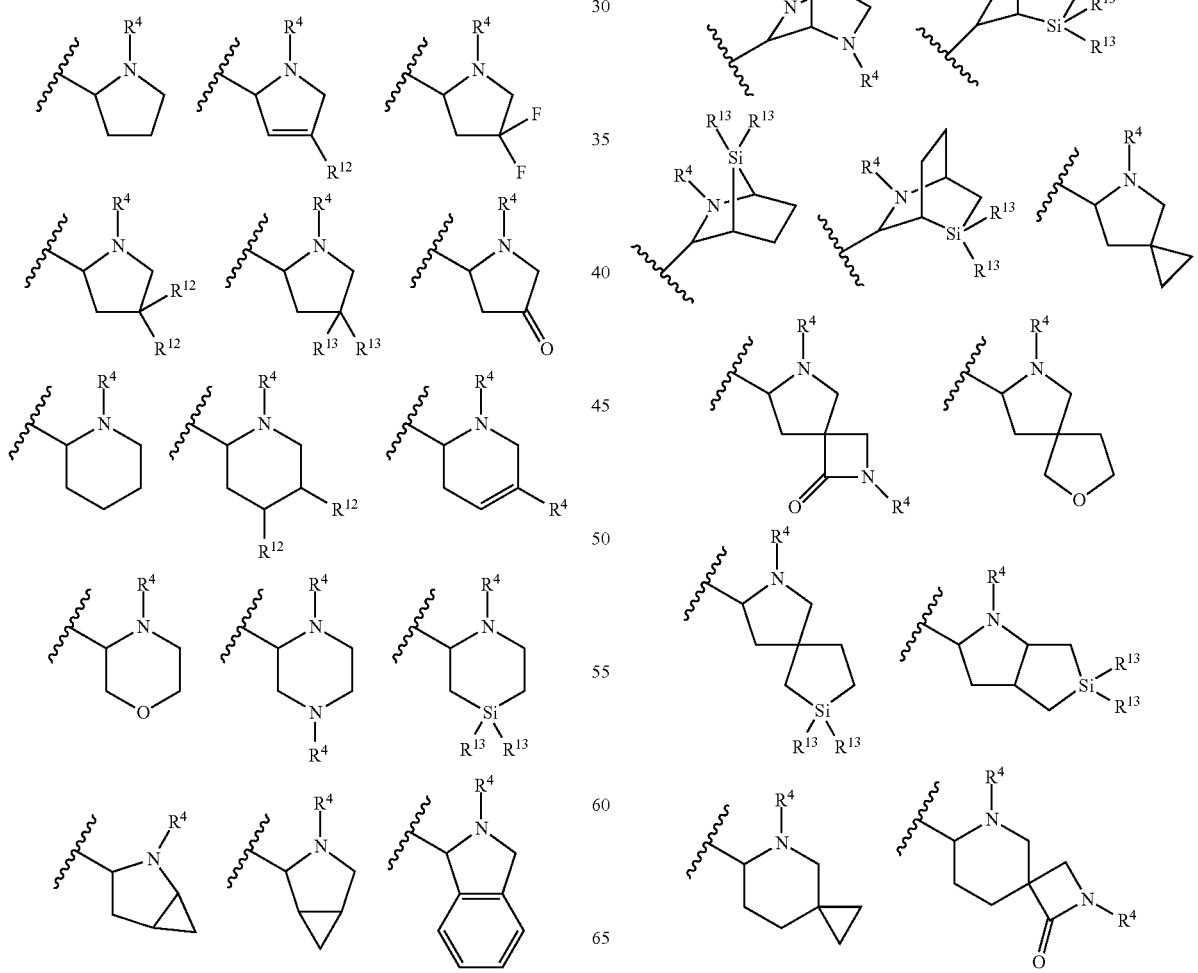

-continued
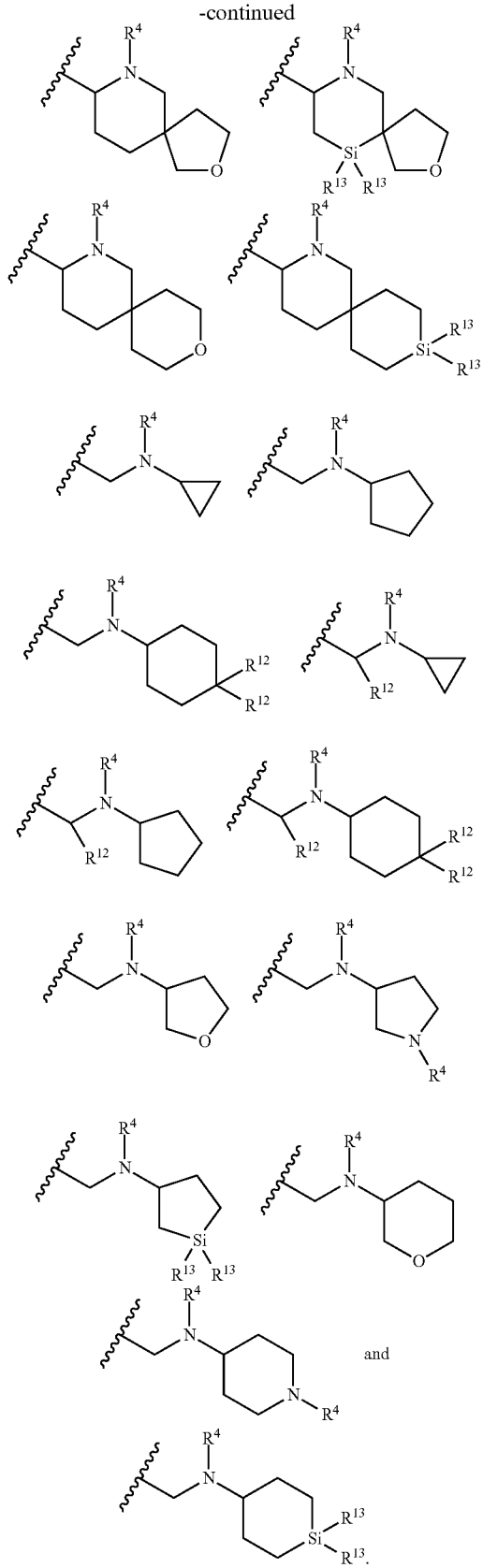
In another embodiment, for the Compounds of Formula (I), D is selected from:
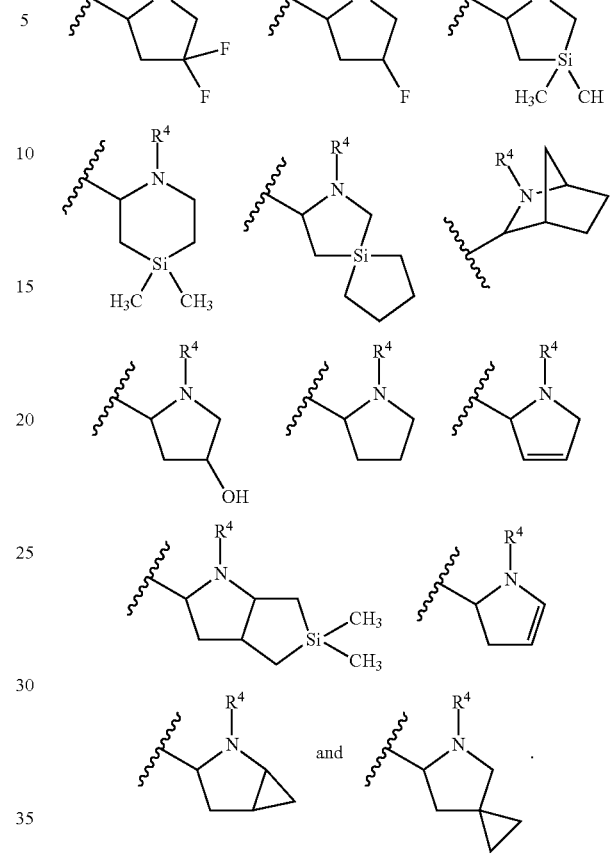
In one embodiment, for the Compounds of Formula (I), the group:
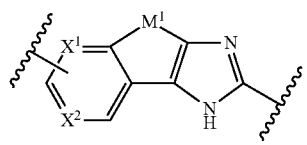
has the structure:
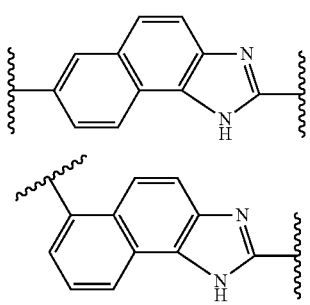

-continued
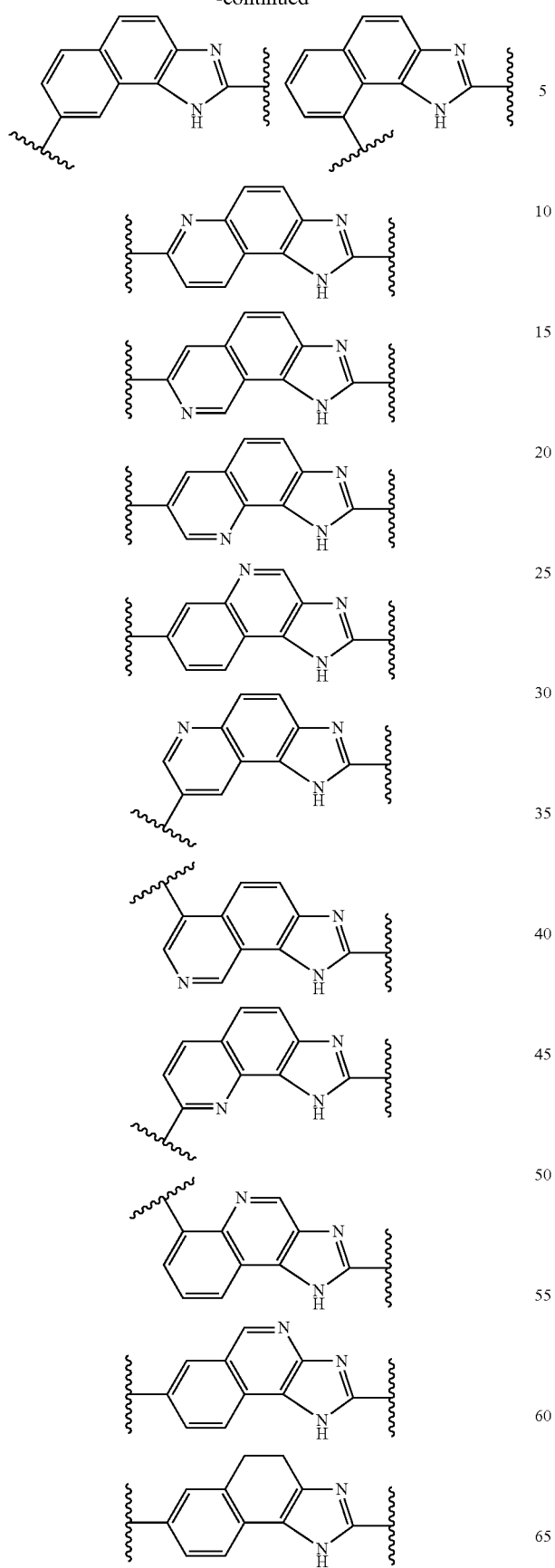
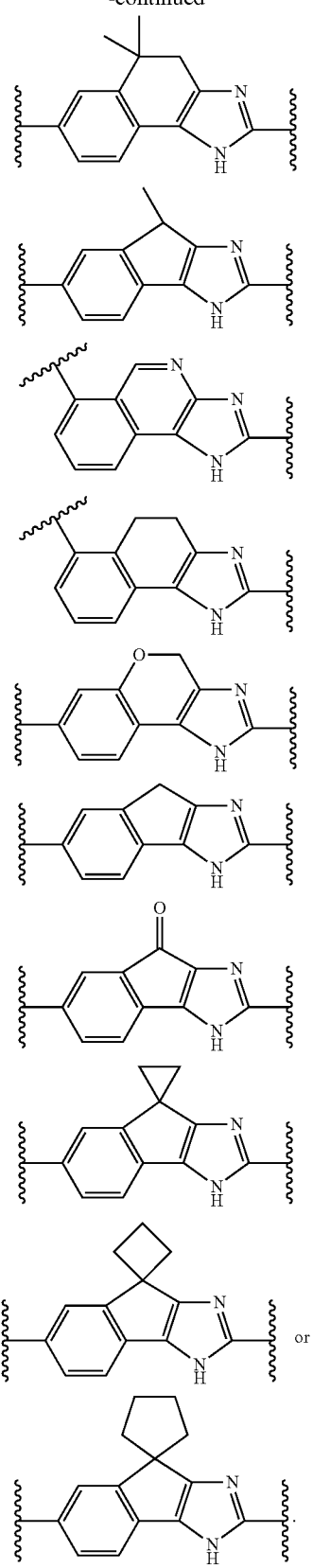
In another embodiment, for the Compounds of Formula (I), the group:

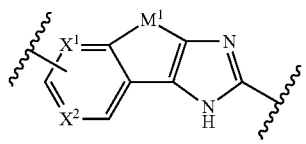
has the structure:
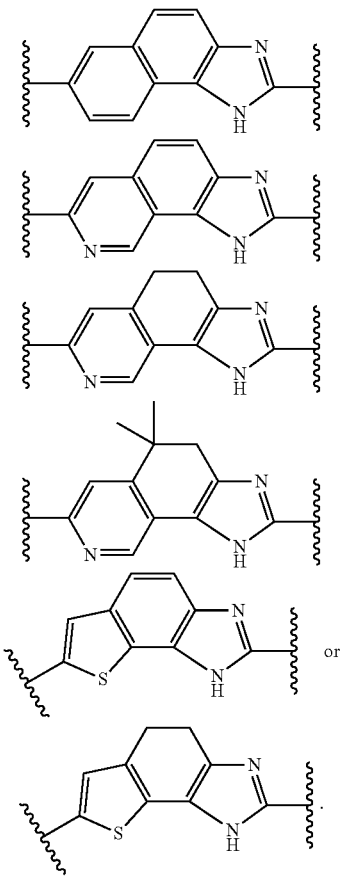
or
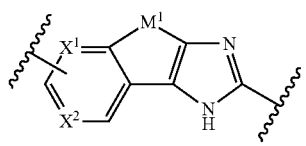
In another embodiment, for the Compounds of Formula (I), the group:
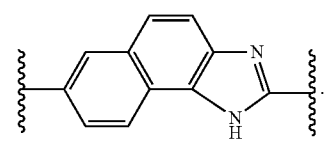 [SMILES: *c1ccc2c(ccc3nc(*)[nH]c32)c1]
has the structure:
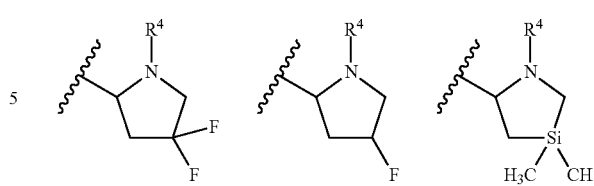
In one embodiment, for the Compounds of Formula (I), A and D are each independently selected from:
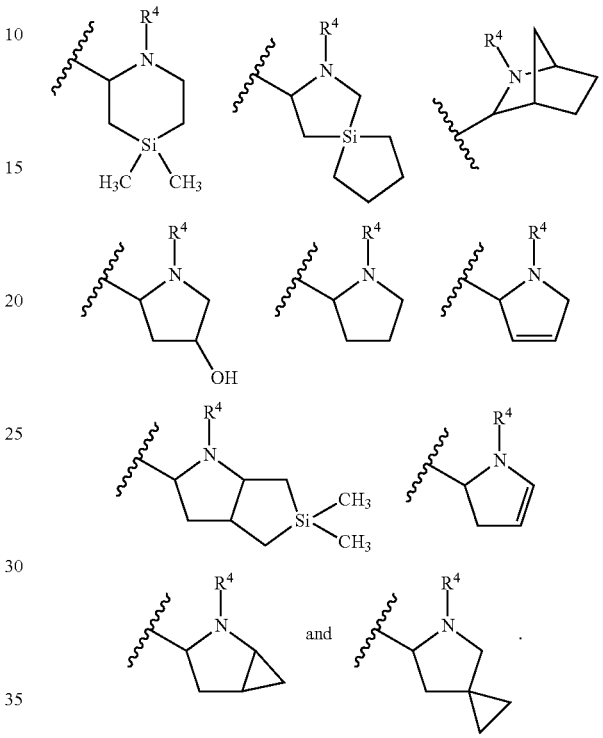
In a further embodiment, for the Compounds of Formula (I), A and D are each selected from:
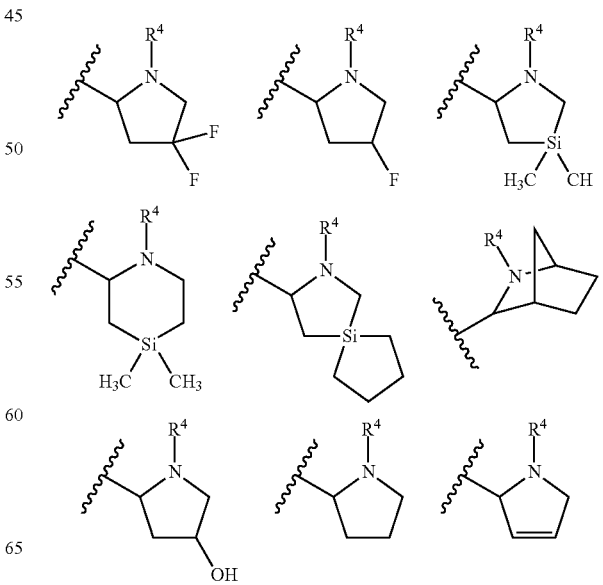

-continued

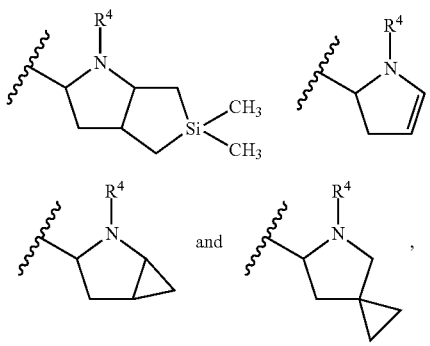

and each occurrence of R⁴ is

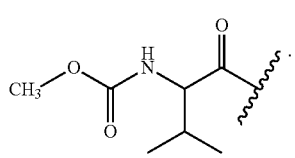

In one embodiment, for the Compounds of Formula (I), A and D are each independently selected from:

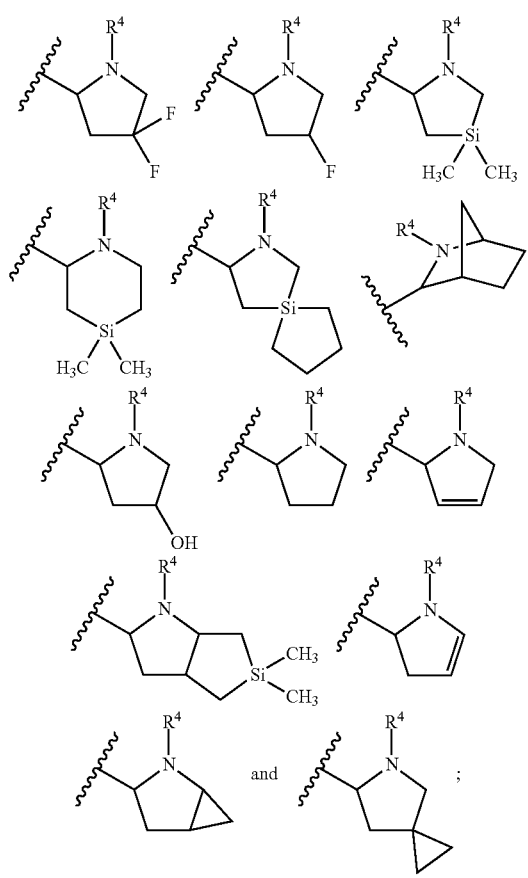

B is a 5-membered monocyclic heteroarylene;

C is:

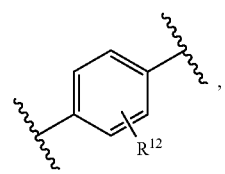

wherein R¹² is an optional ring substituent selected from F, —OCH₃, pyridyl, —OCH₂CH₂OH, —OCH₂CH₂OC(O)CH₃, cyclopropyl and thiophenyl; and
each occurrence of R⁴ is

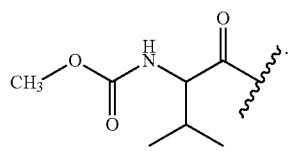 [SMILES: *C(=O)C(NC(=O)OC)C(C)C]

In one embodiment, the Compounds of Formula (I) have the formula (Ia):

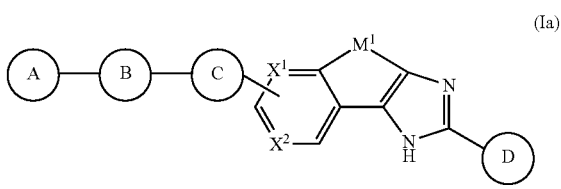

(Ia)

and pharmaceutically acceptable salts thereof, wherein

A is -alkylene-N(R⁷)(R¹¹), -alkylene-N(R¹⁶)(R¹¹), 4 to 7-membered monocyclic heterocycloalkyl, 7 to 11-membered bicyclic heterocycloalkyl or R¹⁵, wherein said 4 to 7-membered monocyclic heterocycloalkyl group, said 7 to 11-membered bicyclic heterocycloalkyl group or said R¹⁵ group can be optionally fused to a 3 to 7-membered cycloalkyl group, a 4 to 7-membered heterocycloalkyl group or an aryl group; and wherein said 4 to 7-membered monocyclic heterocycloalkyl group, said 7 to 11-membered bicyclic heterocycloalkyl group or R¹⁵ group can be optionally and independently substituted on one or more ring nitrogen atoms with R⁴, and on one or more ring carbon atoms with R¹², such that two R¹² groups on the same ring carbon atom, together with the carbon atom to which they are attached, can join to form a spirocyclic 3 to 7-membered cycloalkyl group or a spirocyclic 4 to 7-membered heterocycloalkyl group;

D is -alkylene-N(R⁷)(R¹¹), -alkylene-N(R¹⁶)(R¹¹), 4 to 7-membered monocyclic heterocycloalkyl, 7 to 11-membered bicyclic heterocycloalkyl or R¹⁵, wherein said 4 to 7-membered monocyclic heterocycloalkyl group, said 7 to 11-membered bicyclic heterocycloalkyl group or said R¹⁵ group can be optionally fused to a 3 to 7-membered cycloalkyl group, a 4 to 7-membered heterocycloalkyl group or an aryl group; and wherein said 4 to 7-membered monocyclic heterocycloalkyl group, said 7 to 11-membered bicyclic heterocycloalkyl group or R¹⁵ group can be optionally and independently substituted on one or more ring nitrogen atoms with R⁴, and on one or more ring carbon atoms with R¹², such that two R¹² groups on the same ring carbon atom, together with the carbon atom to which they are attached, can join to form a spirocyclic 3 to 7-membered cycloalkyl group or a spirocyclic 4 to 7-membered heterocycloalkyl group; and C, $M^1$, $X^1$ and $X^2$ are defined above for the Compounds of Formula (I).
In one embodiment, for the Compounds of Formula (Ia), A is selected from:
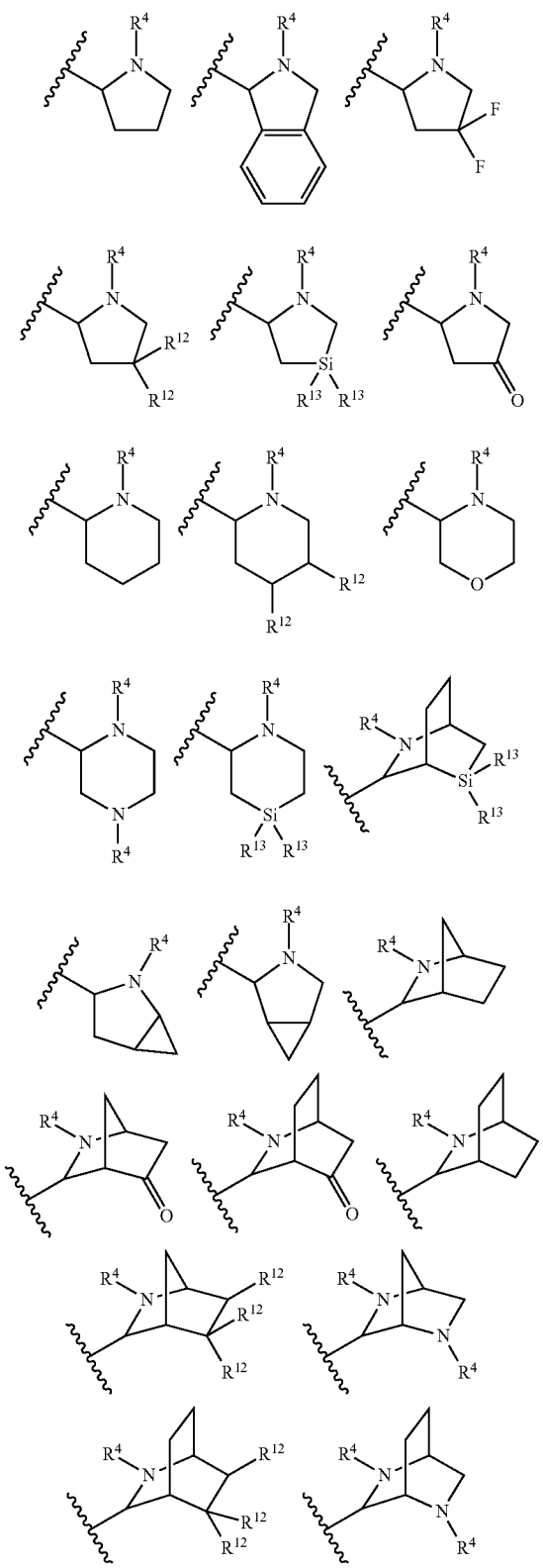
-continued
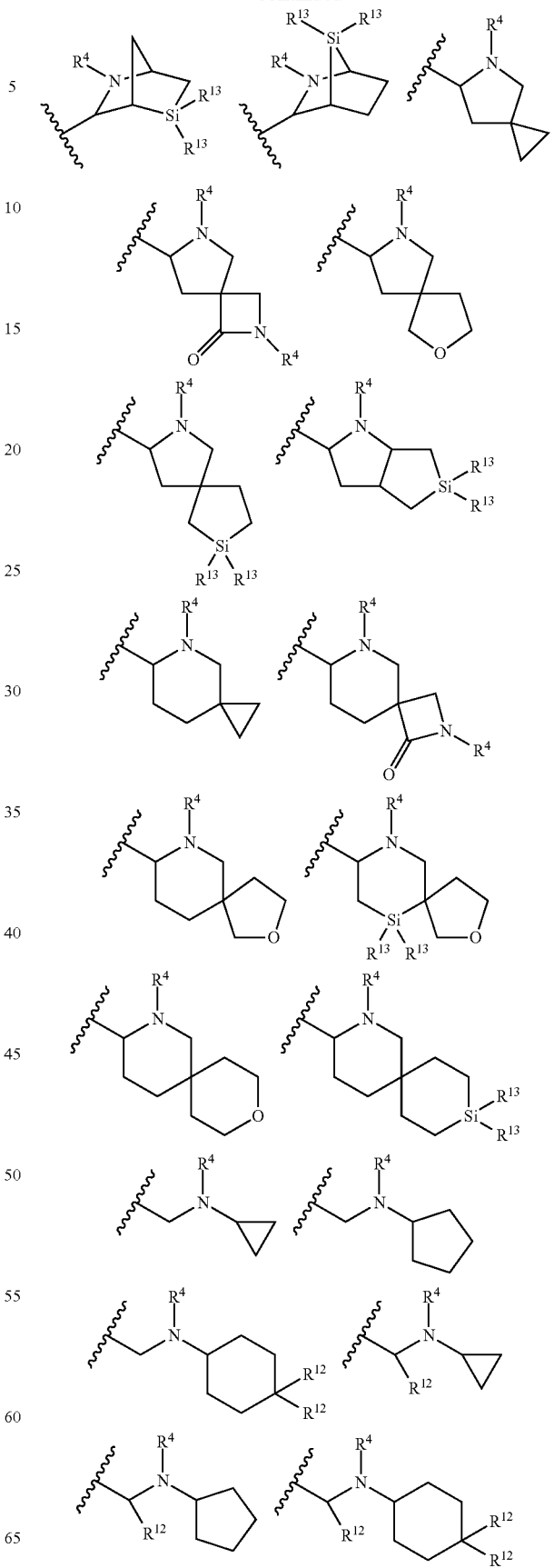

-continued

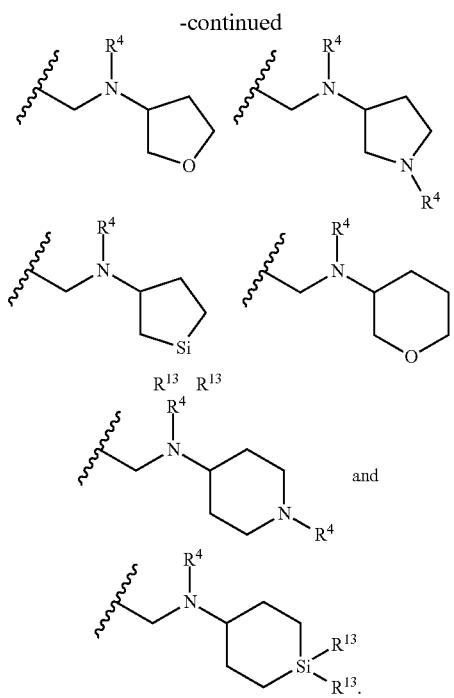

In another embodiment, for the Compounds of Formula (Ia), A is selected from:

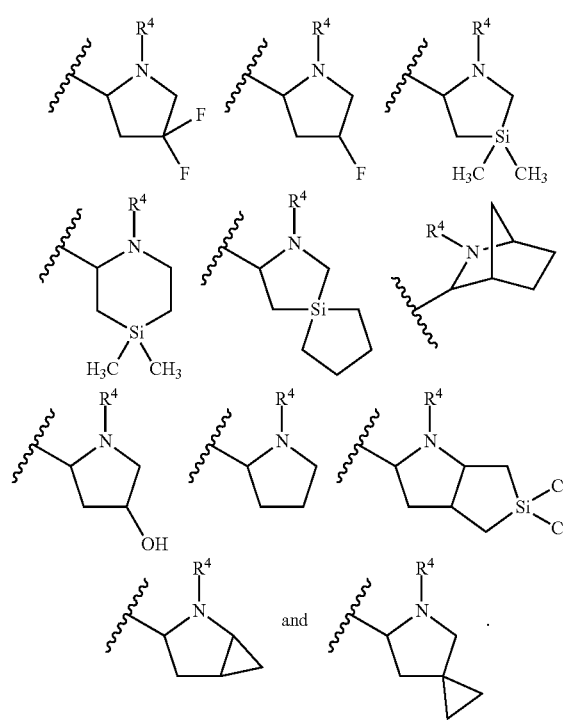

In one embodiment, for the Compounds of Formula (Ia), B is a 5-membered monocyclic heteroarylene group containing at least one nitrogen atom, wherein said 5-membered monocyclic heteroarylene group can be optionally fused to a benzene, pyridine or pyrimidine ring, and wherein said 5-membered monocyclic heteroarylene group or its fused counterpart, can be optionally and independently substituted on one or more ring nitrogen atoms with $R^6$ and on one or more ring carbon atoms with $R^{12}$.

In one embodiment, for the Compounds of Formula (Ia), B is a 5-membered monocyclic heteroarylene.

In another embodiment, for the Compounds of Formula (Ia), B is:

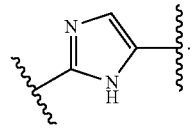

In another embodiment, for the Compounds of Formula (Ia), C is a monocyclic heteroarylene.

In still another embodiment, for the Compounds of Formula (Ia), C is a 6-membered monocyclic heteroarylene.

In another embodiment, for the Compounds of Formula (Ia), C is a 5-membered monocyclic heteroarylene.

In another embodiment, for the Compounds of Formula (Ia), C is a bicyclic heteroarylene.

In yet another embodiment, for the Compounds of Formula (Ia), C is

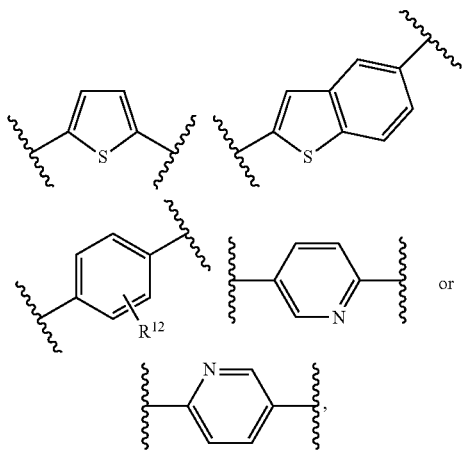

wherein $R^{12}$ is an optional ring substituent selected from halo, 3- to 7-membered cycloalkyl, 5- or 6-membered heteroaryl, —O—($C_1$-$C_6$ alkyl), —O—($C_1$-$C_6$ hydroxyalkyl) and —O—($C_1$-$C_6$ alkylene)-OC(O)—($C_1$-$C_6$ alkyl).

In a further embodiment, for the Compounds of Formula (Ia), C is:

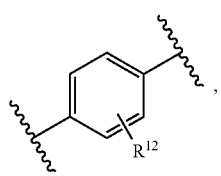

wherein $R^{12}$ is an optional ring substituent selected from F, —$OCH_3$, pyridyl, —$OCH_2CH_2OH$, —$OCH_2CH_2OC(O)CH_3$, cyclopropyl and thiophenyl.

In another embodiment, for the Compounds of Formula (Ia), C is:

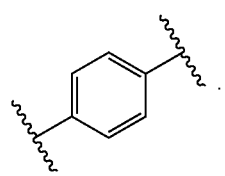 [SMILES: *c1ccc(*)cc1]
In one embodiment, for the Compounds of Formula (Ia), D is selected from:
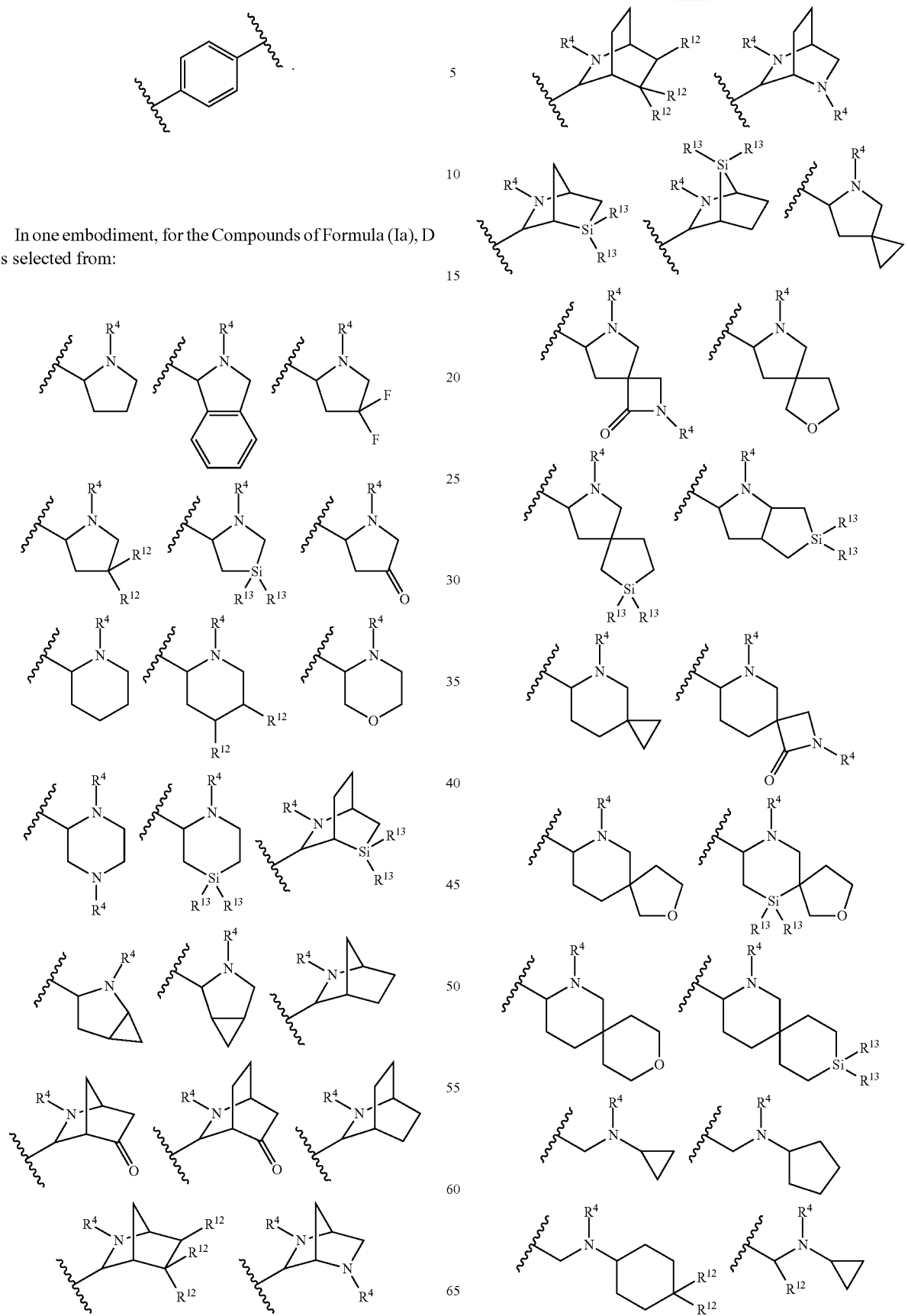

-continued
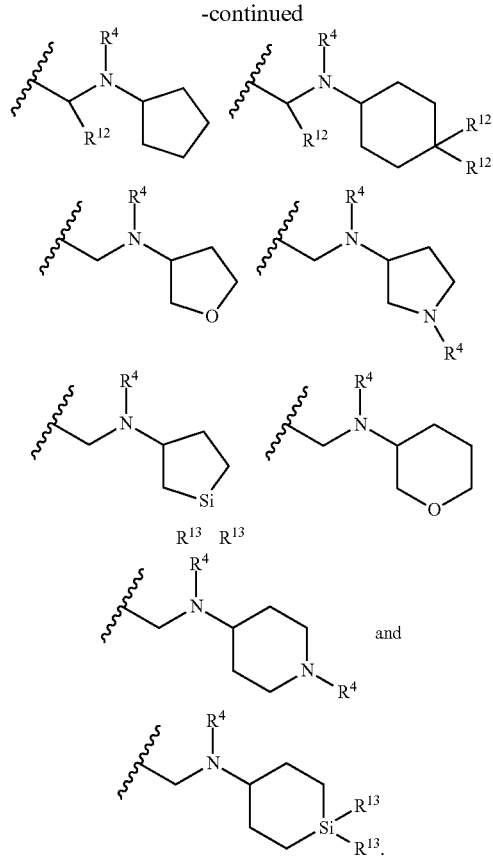
In another embodiment, for the Compounds of Formula (Ia), D is selected from:
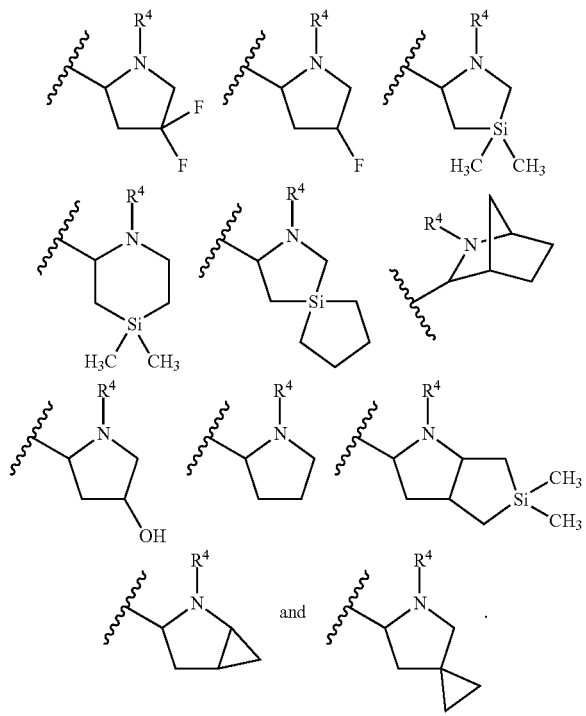
In one embodiment, for the Compounds of Formula (Ia), the group:
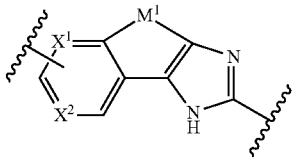
has the structure:
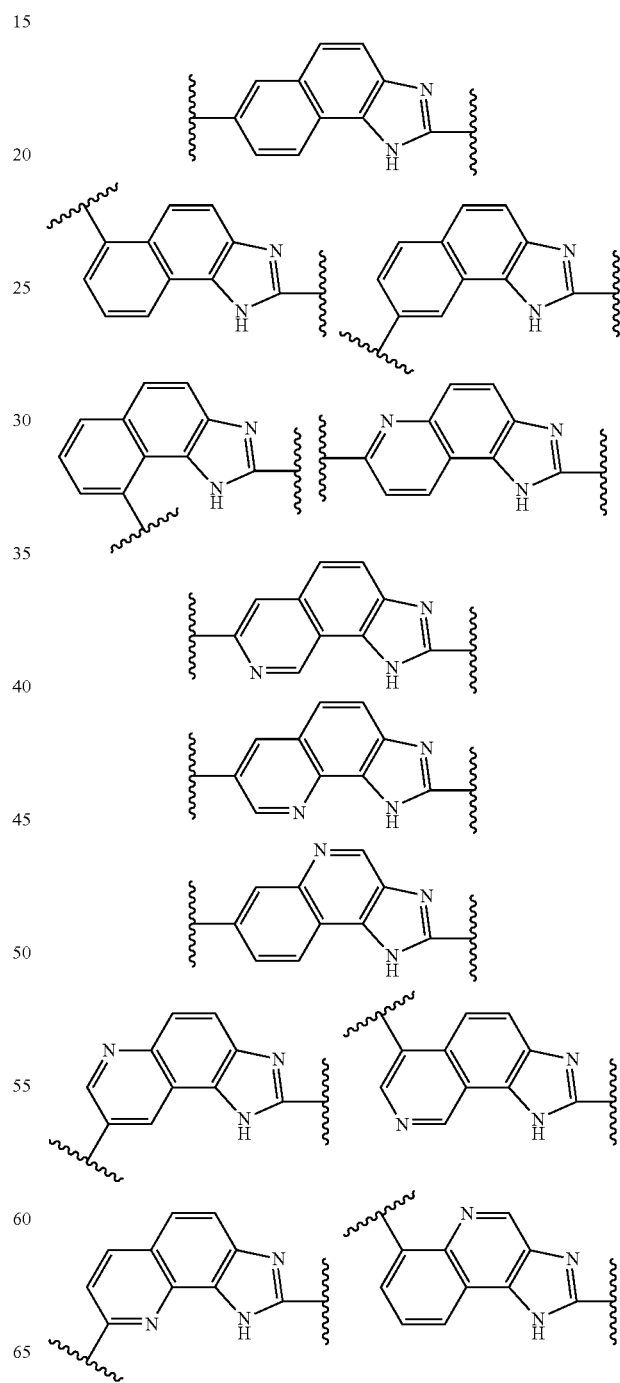

-continued
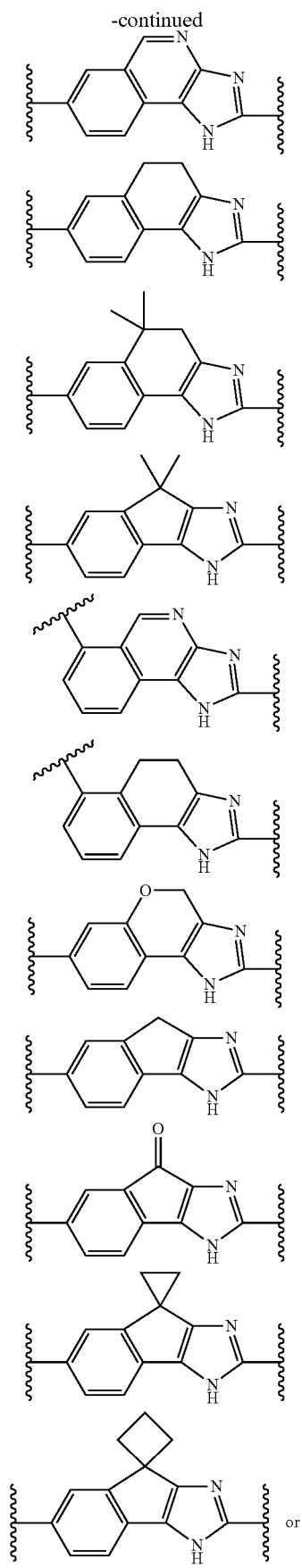
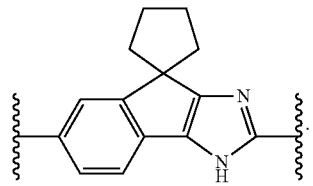
In another embodiment, for the Compounds of Formula (Ia), the group:
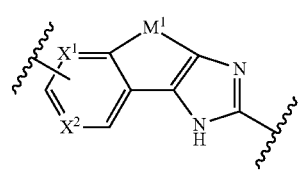
has the structure:
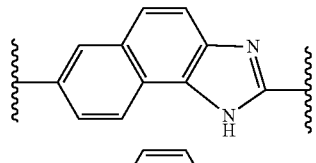
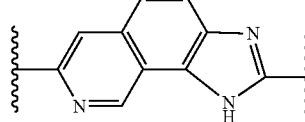
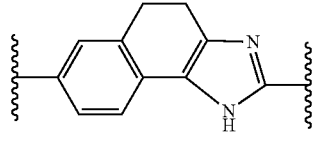
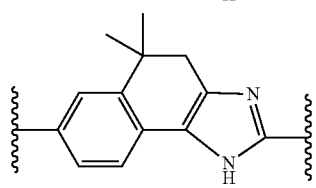
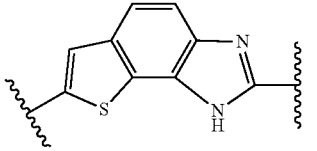
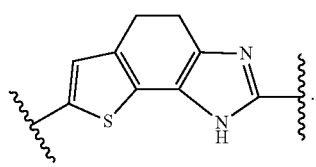
In another embodiment, for the Compounds of Formula (Ia), the group:

has the structure:

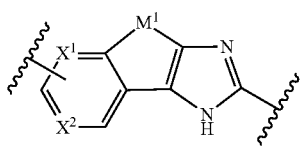

In one embodiment, for the Compounds of Formula (Ia), A and D are each independently selected from:

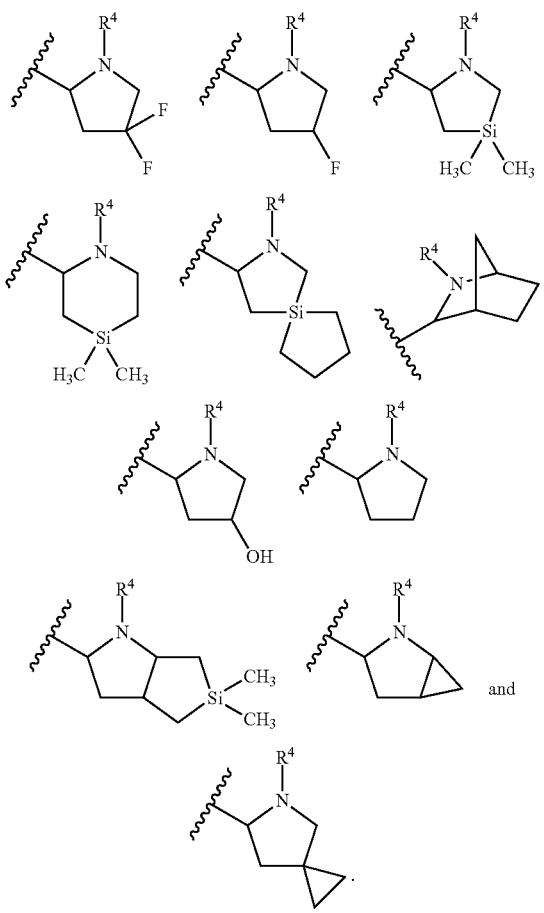

In a further embodiment, for the Compounds of Formula (Ia), A and D are each independently selected from:

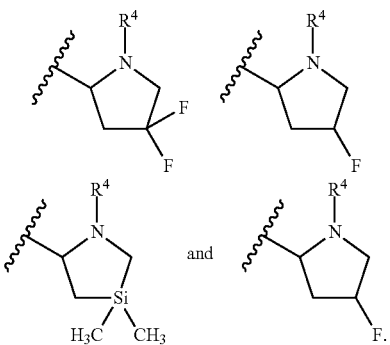

In another embodiment, for the Compounds of Formula (Ia), A and D are each selected from:

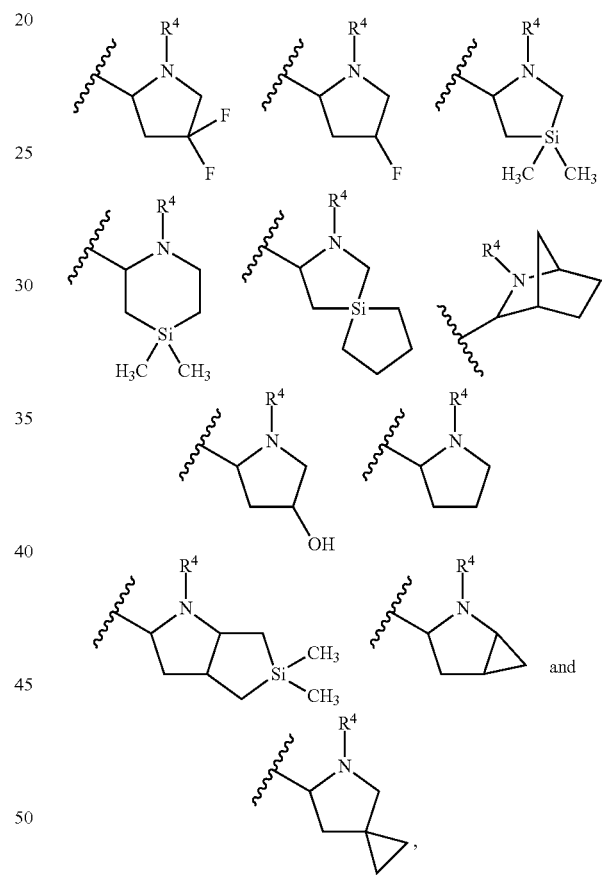

and each occurrence of $R^4$ is

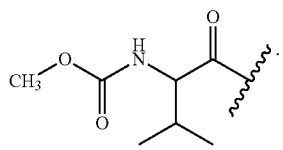 [SMILES: *C(=O)C(NC(=O)OC)C(C)C]

In one embodiment, for the Compound of Formula (Ia), A and D are each independently a 4 to 7-membered monocyclic heterocycloalkyl, 7 to 11-membered bicyclic heterocycloalkyl or $R^{15}$, wherein said 4 to 7-membered monocyclic heterocycloalkyl group or said $R^{15}$ group can be optionally fused to a 3 to 7-membered cycloalkyl group, a 4 to 7-membered heterocycloalkyl group or an aryl group; and wherein said 4 to 7-membered monocyclic heterocycloalkyl group can be optionally and independently substituted on one or more ring nitrogen atoms with $R^4$, and on one or more ring carbon atoms with $R^{12}$, such that two $R^{12}$ groups on the same ring carbon atom, together with the carbon atom to which they are attached, can join to form a spirocyclic 3 to 7-membered cycloalkyl group, or a spirocyclic 4 to 7-membered heterocycloalkyl group; wherein at least one of A and D is $R^{15}$.

In another embodiment, for the Compounds of Formula (Ia), A and D are each independently selected from:

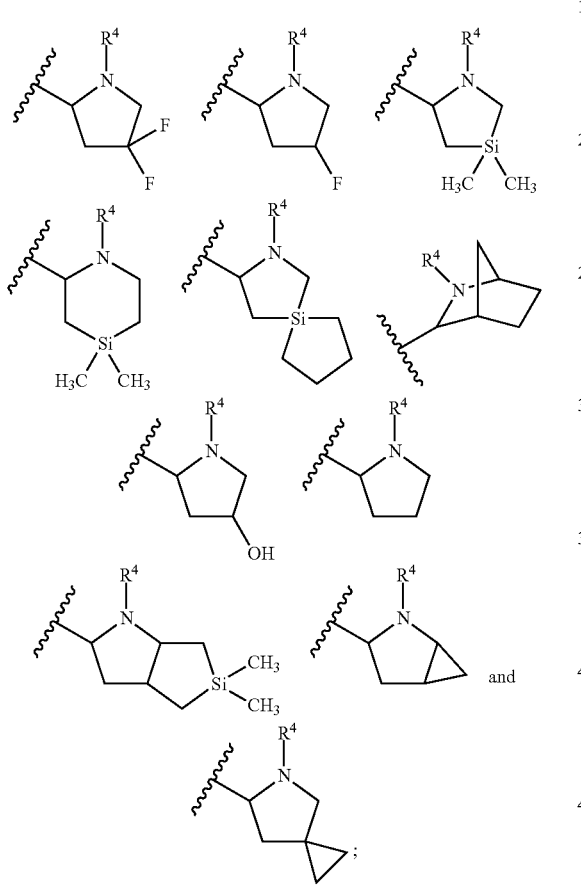

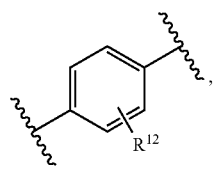

B is a 5-membered monocyclic heteroarylene;
C is:

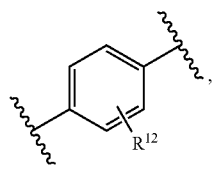

wherein $R^{12}$ is an optional ring substituent selected from F, —$OCH_3$, pyridyl, —$OCH_2CH_2OH$, —$OCH_2CH_2OC(O)$ $CH_3$, cyclopropyl and thiophenyl.

In one embodiment, for the Compounds of Formula (Ia), A and D are each independently selected from:

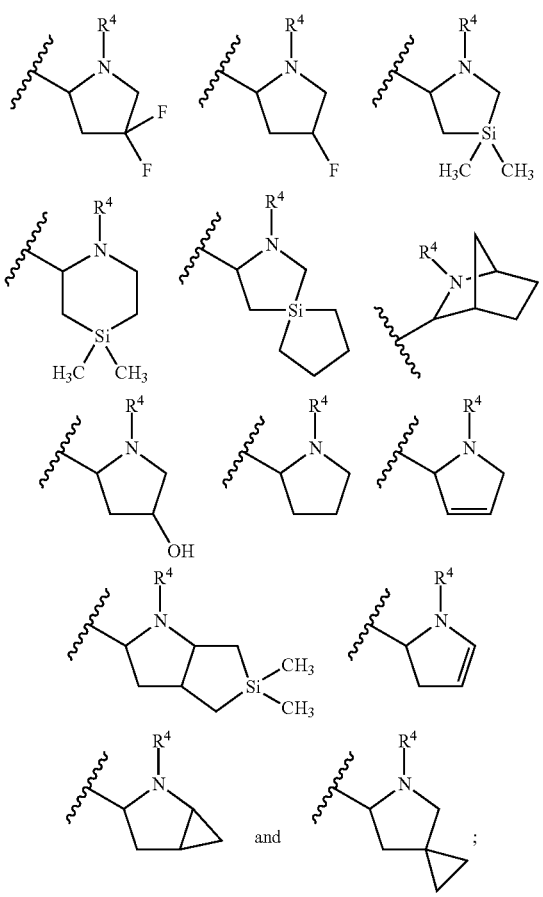

B is a 5-membered monocyclic heteroarylene;
C is:

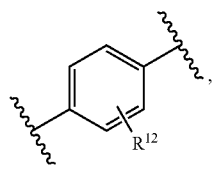

wherein $R^{12}$ is an optional ring substituent selected from F, —$OCH_3$, pyridyl, —$OCH_2CH_2OH$, —$OCH_2CH_2OC(O)$ $CH_3$, cyclopropyl and thiophenyl; and
each occurrence of $R^4$ is

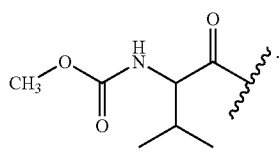 [SMILES: *C(=O)C(NC(=O)OC)C(C)C]

In another embodiment, the Compounds of Formula (I) have the formula (Ib):

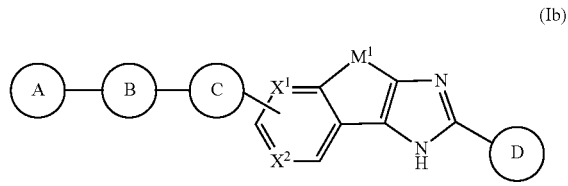
(Ib)

and pharmaceutically acceptable salts thereof, wherein A, C, D, $M^1$, $X^1$ and $X^2$ are defined above for the Compounds of Formula (Ia) and B is 5-membered monocyclic heteroarylene group containing at least one nitrogen atom, wherein said 5-membered monocyclic heteroarylene group can be optionally fused to a benzene, pyridine or pyrimidine ring, and wherein said 5-membered monocyclic heteroarylene group or its fused counterpart, can be optionally and independently substituted on one or more ring nitrogen atoms with $R^6$ and on one or more ring carbon atoms with $R^{12}$.

In one embodiment, for the Compounds of Formula (Ib), A is -alkylene-N($R^7$)($R^{11}$).

In another embodiment, for the Compounds of Formula (Ib), A is -alkylene-N($R^{16}$)($R^{11}$).

In another embodiment, for the Compounds of Formula (Ib), A is a 4 to 7-membered heterocycloalkyl.

In still another embodiment, for the Compounds of Formula (Ib), A is $R^{15}$.

In another embodiment, for the Compounds of Formula (Ib), A is selected from:

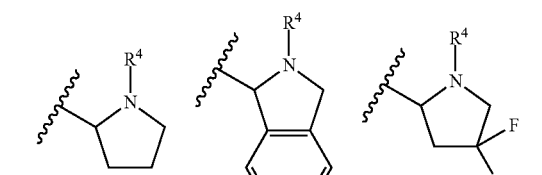

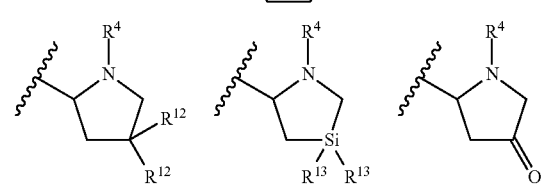

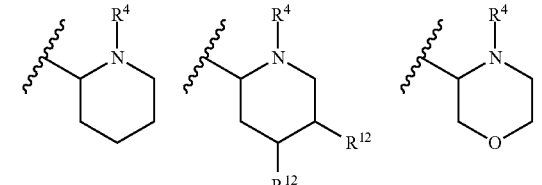

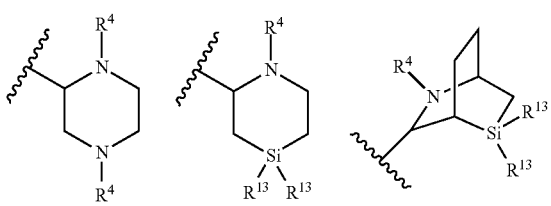

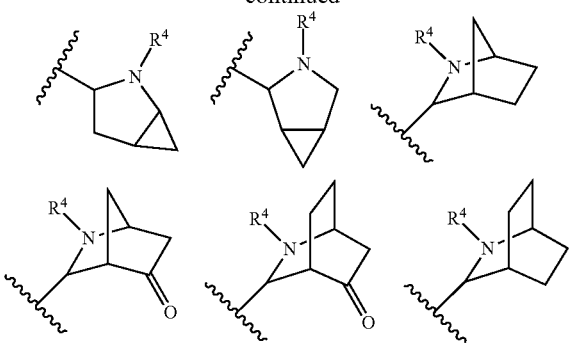

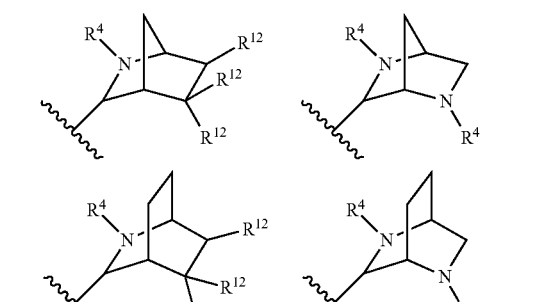

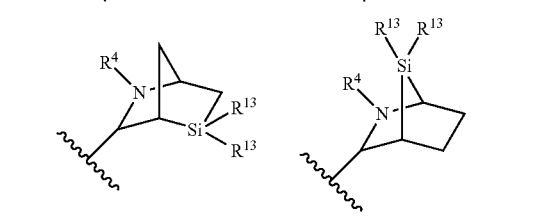

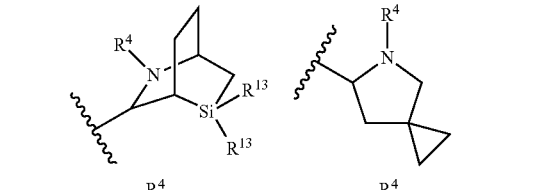

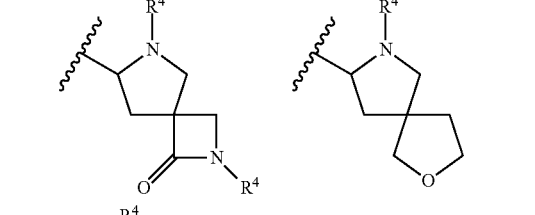

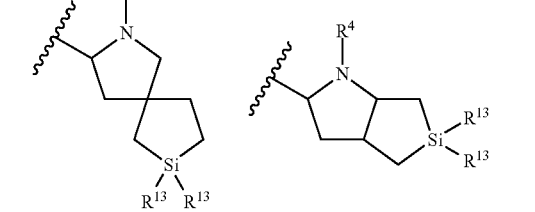

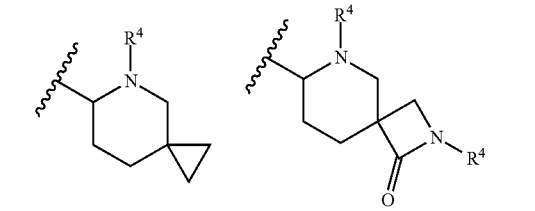

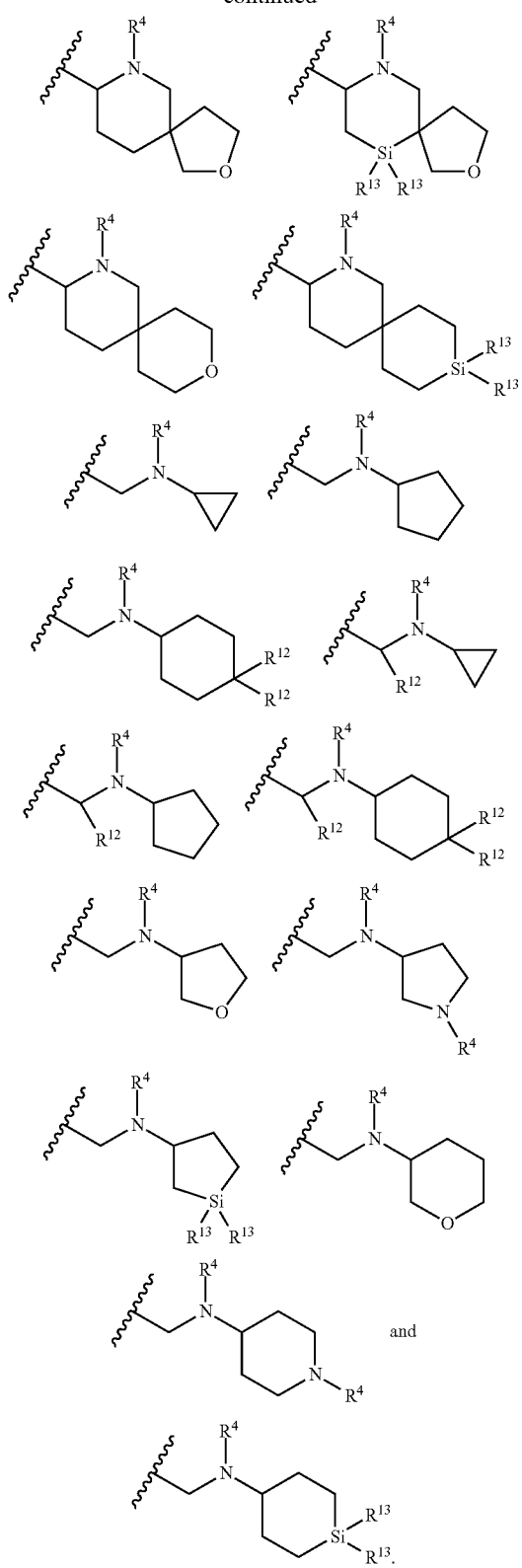
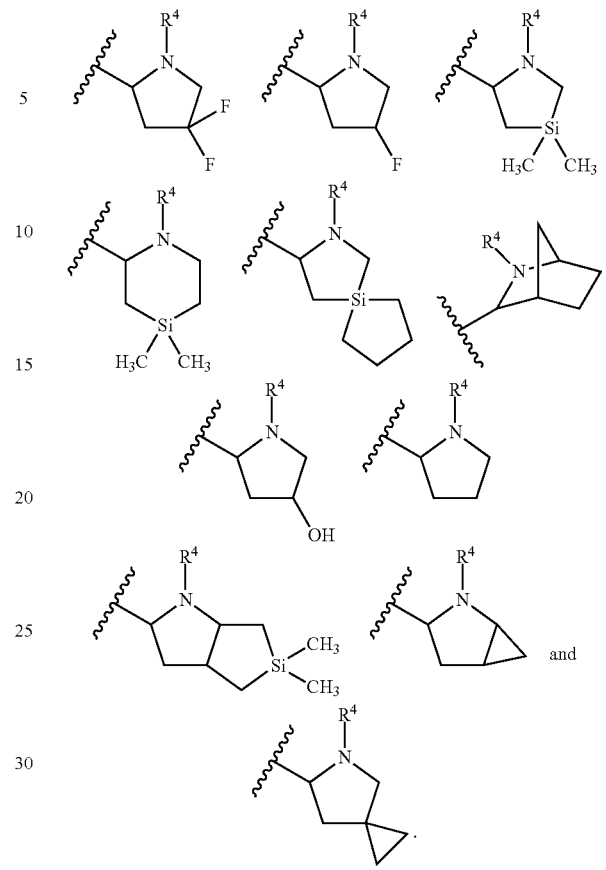
In another embodiment, for the Compounds of Formula (Ib), A is selected from:
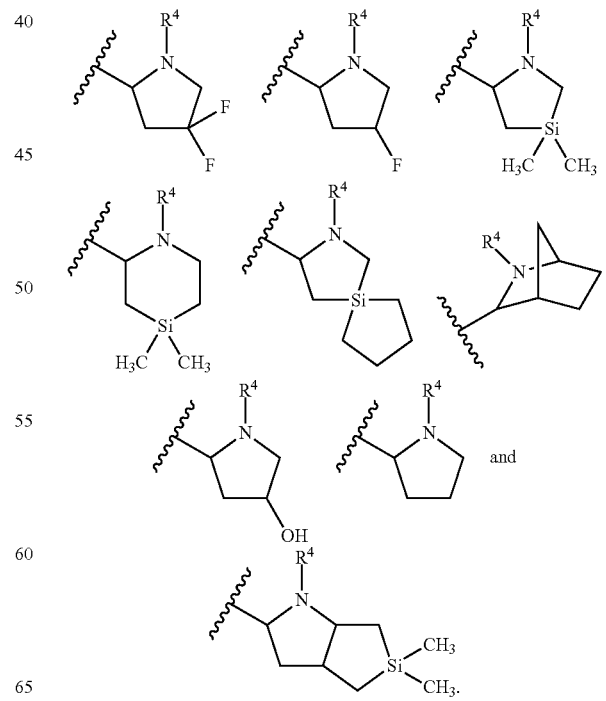
In another embodiment, for the Compounds of Formula (Ib), A is selected from:

In still another embodiment, for the Compounds of Formula (Ib), A is selected from:

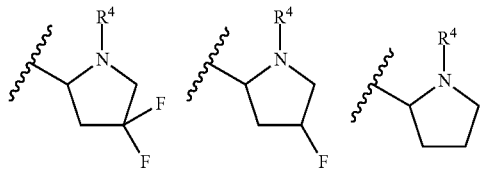

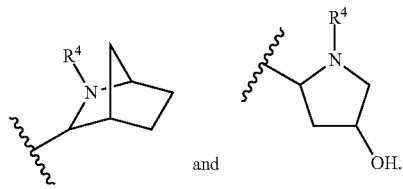

In another embodiment, for the Compounds of Formula (Ib), A is selected from:

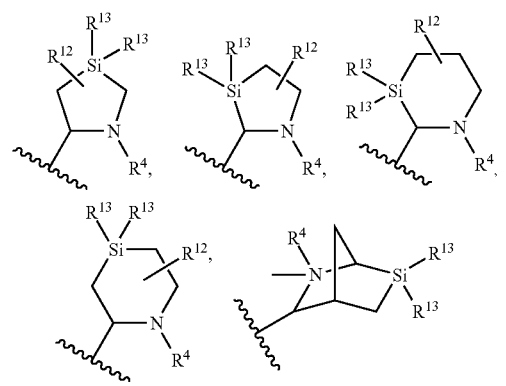

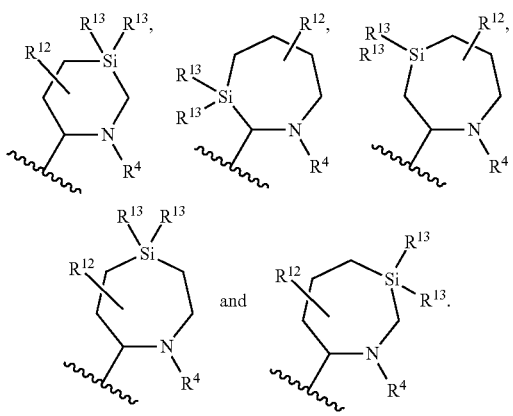

In yet another embodiment A is selected from:

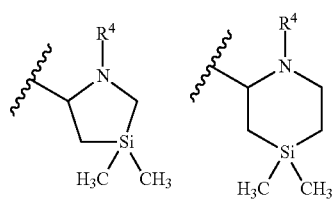

-continued

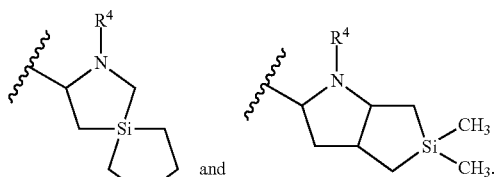

In another embodiment, for the Compounds of Formula (Ib), A is

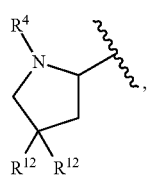

wherein each occurrence of $R^{12}$ is independently H or F.

In another embodiment, for the Compounds of Formula (Ib), A is

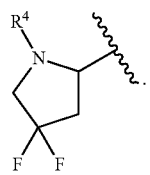

In another embodiment, for the Compounds of Formula (Ib), A is

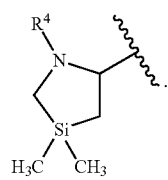

In a further embodiment, for the Compounds of Formula (Ib), A is selected from:

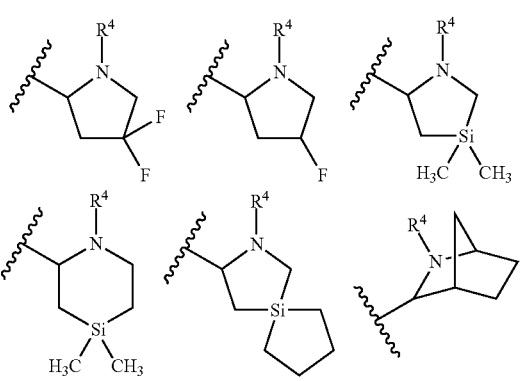

-continued

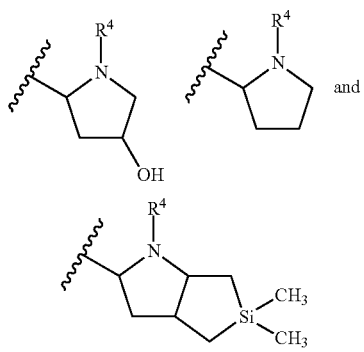

and and R⁴ is:

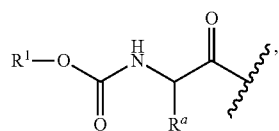

wherein R¹ is H, alkyl, haloalkyl, 3 to 7-membered cycloalkyl, 4 to 7-membered heterocycloalkyl, aryl or heteroaryl and Rᵃ is alkyl, haloalkyl, silylalkyl, 3 to 7-membered cycloalkyl or 4 to 7-membered heterocycloalkyl, aryl or heteroaryl.

In another embodiment, for the Compounds of Formula (Ib), A is selected from:

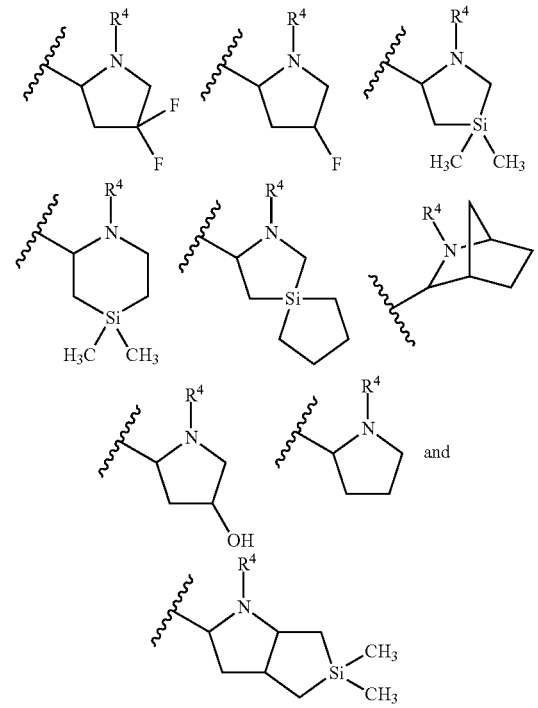

and R⁴ is:

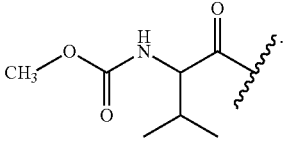

wherein $R^a$ is H, methyl, ethyl, propyl, isopropyl, t-butyl, cyclopropyl, —CH₂CH₂Si(CH₃)₃, —CH₂CH₂CF₃, pyranyl, benzyl or phenyl, and R¹ is methyl, ethyl or isopropyl.

In another embodiment, for the Compounds of Formula (Ib), A is selected from:

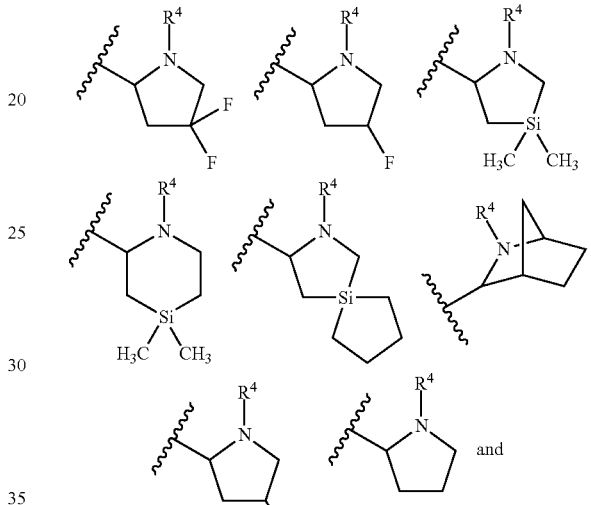

and R⁴ is:

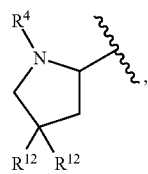

In yet another embodiment, for the Compounds of Formula (Ib), A is:

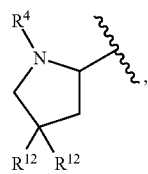

wherein each occurrence of R¹² is independently H or F; and R⁴ is

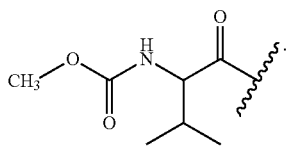 [SMILES: *C(=O)C(NC(=O)OC)C(C)C]

In yet another embodiment, for the Compounds of Formula (Ib), A is:

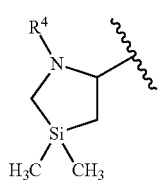

and R⁴ is

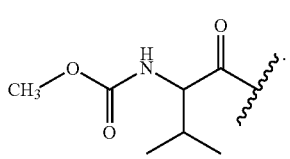 [SMILES: *C(=O)C(NC(=O)OC)C(C)C]

In another embodiment, for the Compounds of Formula (Ib), A is -alkylene-N(alkyl)-C(O)—CH(alkyl)-NHC(O)O-alkyl, -alkylene-N(cycloalkyl)-C(O)—CH(alkyl)-NHC(O)O-alkyl, -alkylene-N(cycloalkyl)-C(O)—CH(cycloalkyl)-NHC(O)O-alkyl, -alkylene-N(cycloalkyl)-C(O)—CH(aryl)-NHC(O)O-alkyl or -alkylene-N(cycloalkyl)-C(O)—CH(heteroaryl)-NHC(O)O-alkyl.

In one embodiment, for the Compounds of Formula (Ib), B is a 5-membered monocycle heteroarylene.

In another embodiment, for the Compounds of Formula (Ib), B is:

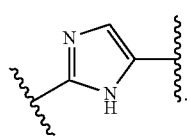

In another embodiment, for the Compounds of Formula (Ib), C is a monocyclic heteroarylene.

In still another embodiment, for the Compounds of Formula (Ib), C is a 6-membered monocyclic heteroarylene.

In another embodiment, for the Compounds of Formula (Ib), C is a 5-membered monocycle heteroarylene.

In another embodiment, for the Compounds of Formula (Ib), C is a bicyclic heteroarylene.

In yet another embodiment, for the Compounds of Formula (Ib), C is

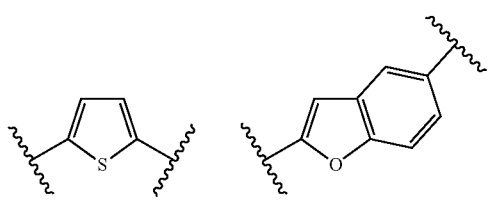
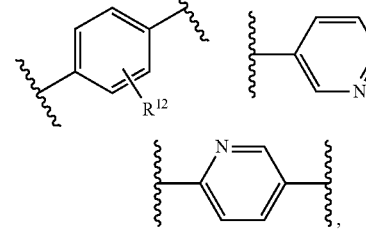

wherein $R^{12}$ is an optional ring substituent selected from halo, 3- to 7-membered cycloalkyl, 5- or 6-membered heteroaryl, —O—($C_1$-$C_6$ alkyl), —O—($C_1$-$C_6$ hydroxyalkyl) and —O—($C_1$-$C_6$ alkylene)-OC(O)—($C_1$-$C_6$ alkyl).

In a further embodiment, for the Compounds of Formula (Ib), C is:

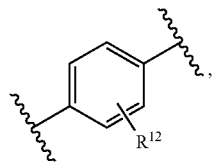

wherein $R^{12}$ is an optional ring substituent selected from F, —$OCH_3$, pyridyl, —$OCH_2CH_2OH$, —$OCH_2CH_2OC(O)CH_3$, cyclopropyl and thiophenyl.

In another embodiment, for the Compounds of Formula (Ib), C is:

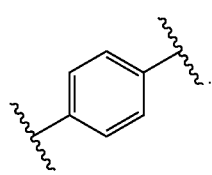 [SMILES: *c1ccc(*)cc1]

In one embodiment, for the Compounds of Formula (Ib), D is -alkylene-N($R^7$)($R^{11}$).

In another embodiment, for the Compounds of Formula (Ib), D is -alkylene-N($R^{16}$)($R^{11}$).

In another embodiment, for the Compounds of Formula (Ib), D is a 4 to 7-membered heterocycloalkyl.

In still another embodiment, for the Compounds of Formula (Ib), D is $R^{15}$.

In another embodiment, for the Compounds of Formula (Ib), D is selected from:

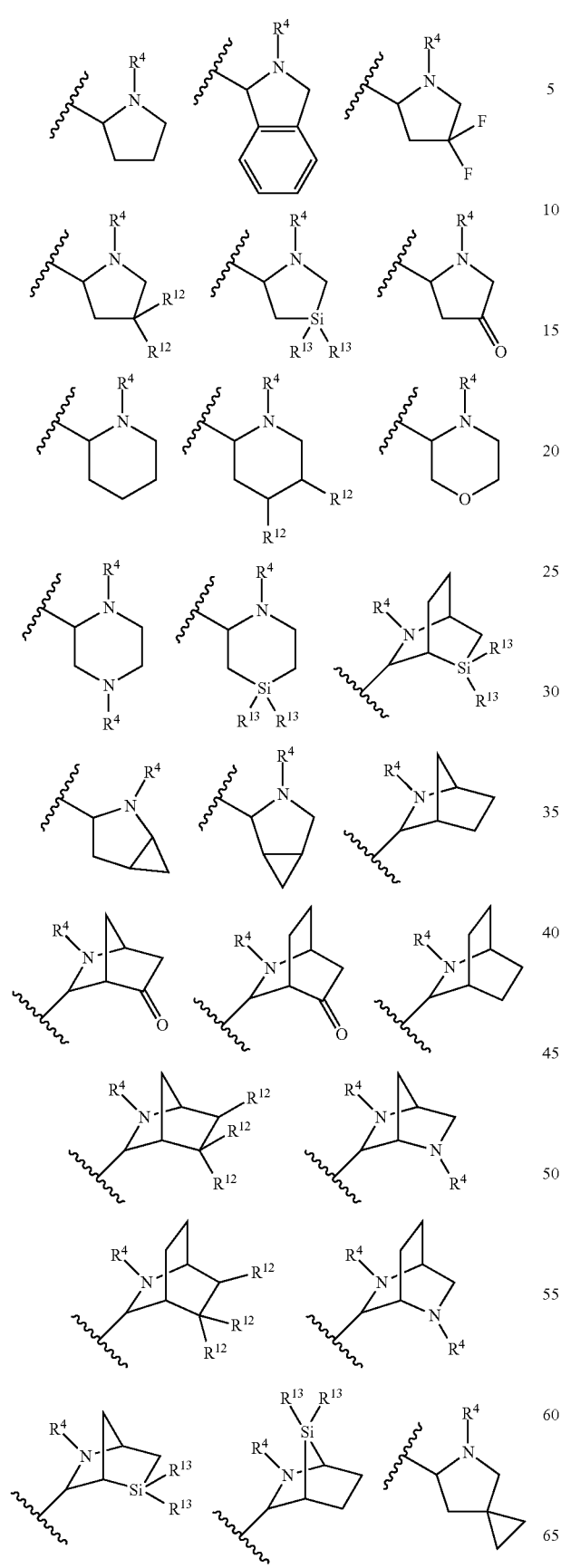
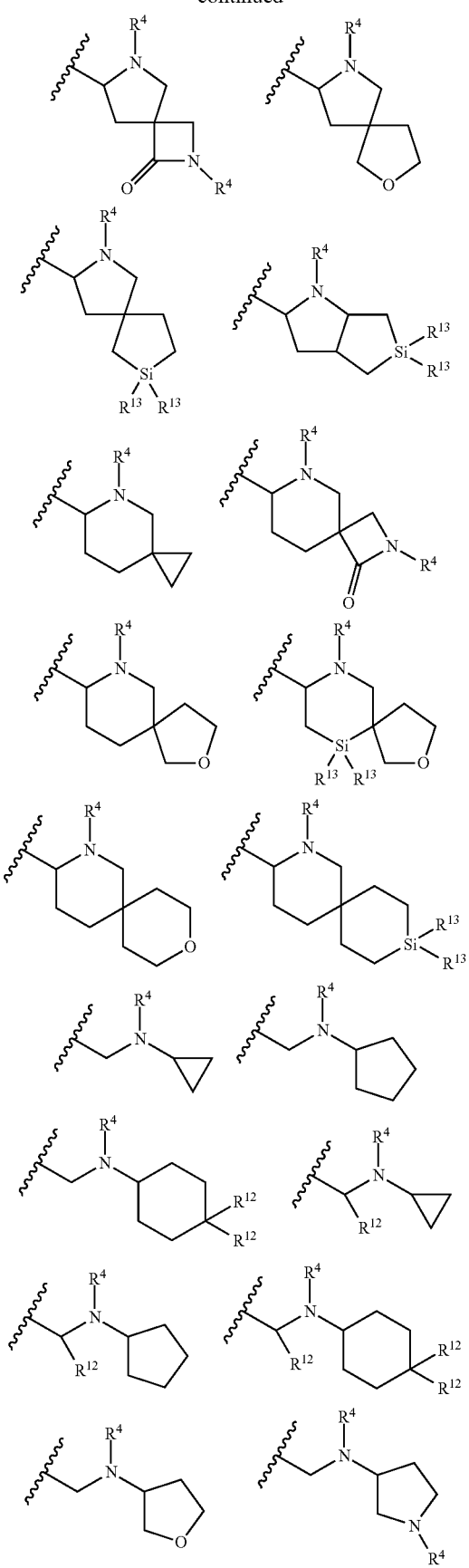

-continued
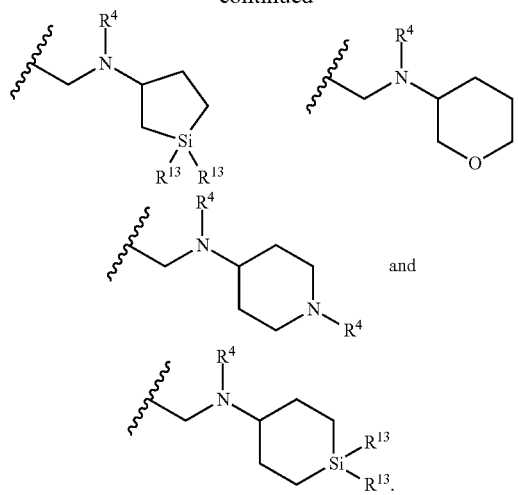
In another embodiment, for the Compounds of Formula (Ib), D is selected from:
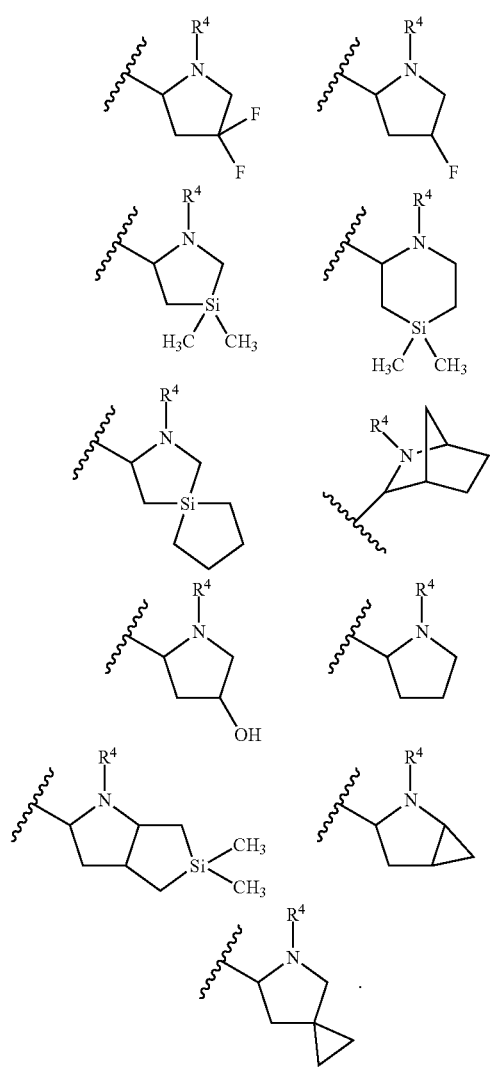
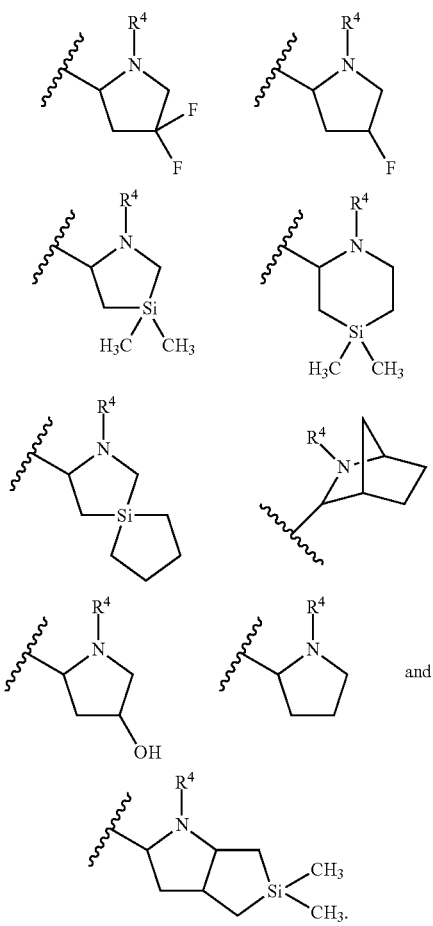
In still another embodiment, for the Compounds of Formula (Ib), D is selected from:
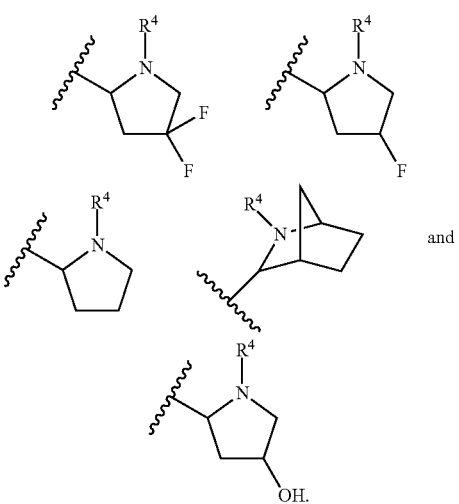
In another embodiment, for the Compounds of Formula (Ib), D is selected from:

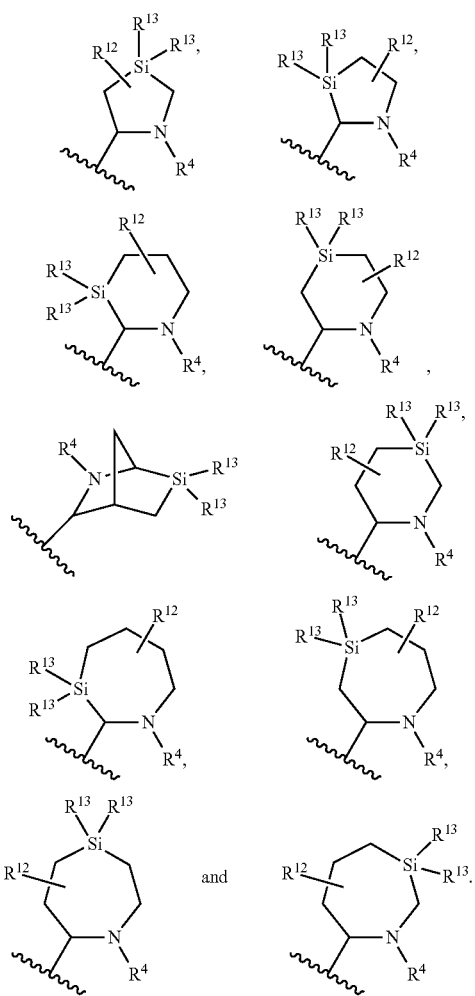
In yet another embodiment D is selected from:
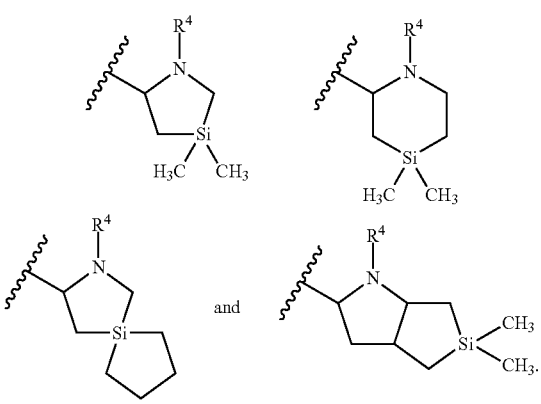
In another embodiment, for the Compounds of Formula (Ib), D is
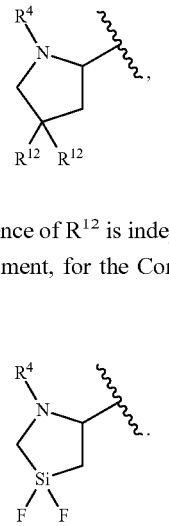
wherein each occurrence of $R^{12}$ is independently H or F.
In another embodiment, for the Compounds of Formula (Ib), D is
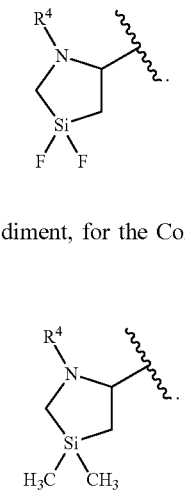
In another embodiment, for the Compounds of Formula (Ib), D is
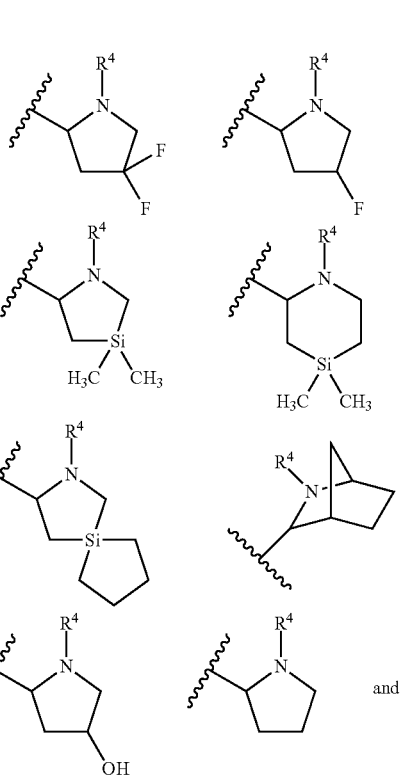
In a further embodiment, for the Compounds of Formula (Ib), D is selected from:

-continued

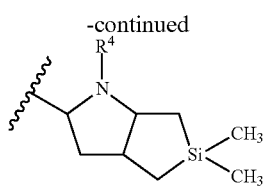

and R⁴ is:

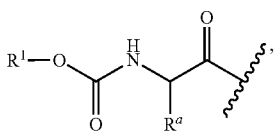

wherein R¹ is H, alkyl, haloalkyl, 3 to 7-membered cycloalkyl, 4 to 7-membered heterocycloalkyl, aryl or heteroaryl and Rᵃ is alkyl, haloalkyl, silylalkyl, 3 to 7-membered cycloalkyl or 4 to 7-membered heterocycloalkyl, aryl or heteroaryl.

In another embodiment, for the Compounds of Formula (Ib), D is selected from:

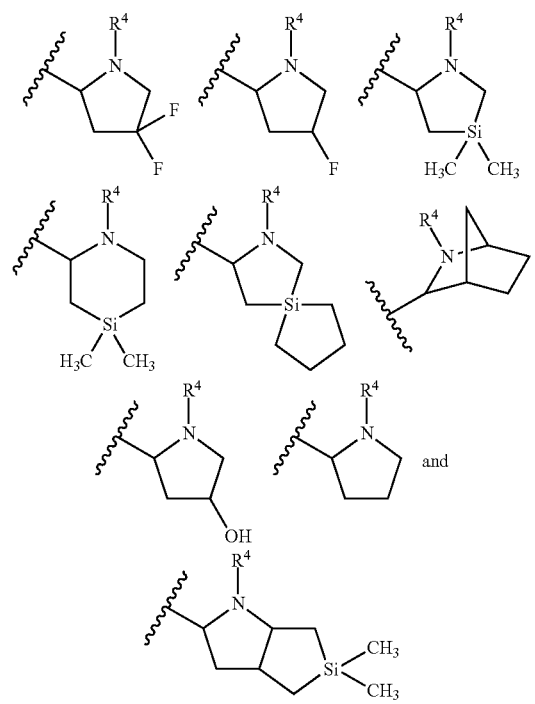

and R⁴ is:

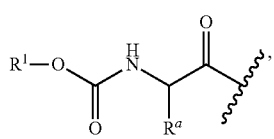

wherein Rᵃ is H, methyl, ethyl, propyl, isopropyl, t-butyl, cyclopropyl, —CH₂CH₂Si(CH₃)₃, —CH₂CH₂CF₃, pyranyl, benzyl or phenyl, and R¹ is methyl, ethyl or isopropyl.

In another embodiment, for the Compounds of Formula (Ib), D is selected from:

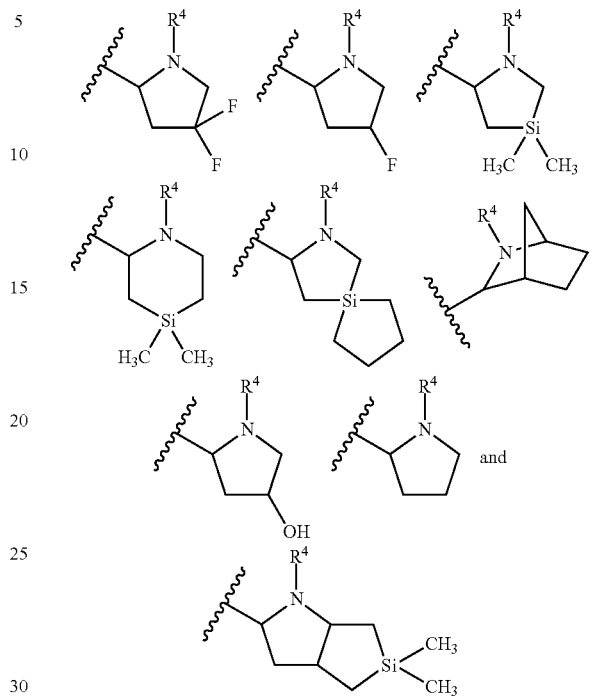

and R⁴ is:

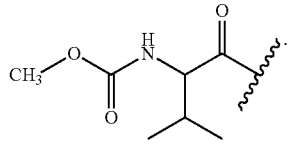 [SMILES: *C(=O)C(NC(=O)OC)C(C)C]

In yet another embodiment, for the Compounds of Formula (Ib), D is:

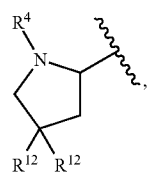

wherein each occurrence of R¹² is independently H or F; and R⁴ is

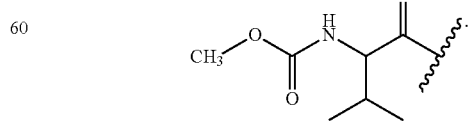

In yet another embodiment, for the Compounds of Formula (Ib), D is:

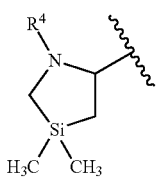

and R⁴ is

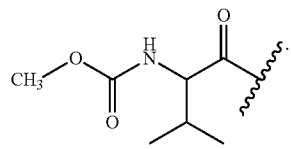 [SMILES: *C(=O)C(NC(=O)OC)C(C)C]

In another embodiment, for the Compounds of Formula (Ib), D is -alkylene-N(alkyl)-C(O)—CH(alkyl)-NHC(O)O-alkyl, -alkylene-N(cycloalkyl)-C(O)—CH(alkyl)-NHC(O)O-alkyl, -alkylene-N(cycloalkyl)-C(O)—CH(cycloalkyl)-NHC(O)O-alkyl, -alkylene-N(cycloalkyl)-C(O)—CH(aryl)-NHC(O)O-alkyl or -alkylene-N(cycloalkyl)-C(O)—CH(heteroaryl)-NHC(O)O-alkyl.

In one embodiment, for the Compounds of Formula (Ib), M¹ is a bond.

In another embodiment, for the Compounds of Formula (Ib), M¹ is —S(O)₂—

In another embodiment, for the Compounds of Formula (Ib), M¹ is —O—.

In still another embodiment, for the Compounds of Formula (Ib), M¹ is —C(R⁷)₂—.

In another embodiment, for the Compounds of Formula (Ib), M¹ is —CH₂—.

In another embodiment, for the Compounds of Formula (Ib), M¹ is —N(R⁶)—.

In yet another embodiment, for the Compounds of Formula (Ib), M¹ is a bond.

In a further embodiment, for the Compounds of Formula (Ib), M¹ is —C(R²)=C(R²)—.

In another embodiment, for the Compounds of Formula (Ib), M¹ is —CH=CH—.

In another embodiment, for the Compounds of Formula (Ib), M¹ is —CH=N—.

In still another embodiment, for the Compounds of Formula (Ib), M¹ is —N=CH—.

In another embodiment, for the Compounds of Formula (Ib), M¹ is —C(R⁷)₂—O—.

In another embodiment, for the Compounds of Formula (Ib), M¹ is —O—C(R⁷)₂—.

In yet another embodiment, for the Compounds of Formula (Ib), M¹ is —C(R⁷)₂—N(R⁶)—.

In another embodiment, for the Compounds of Formula (Ib), M¹ is —N(R⁶)—C(R⁷)₂—.

In one embodiment, for the Compounds of Formula (Ib), X¹ is =C(R⁵)—.

In another embodiment, for the Compounds of Formula (Ib), X¹ is =N—.

In another embodiment, for the Compounds of Formula (Ib), X¹ is —CH—.

In one embodiment, for the Compounds of Formula (Ib), X² is =C(R⁵)—.

In another embodiment, for the Compounds of Formula (Ib), X² is =N—.

In another embodiment, for the Compounds of Formula (Ib), X² is —CH—.

In one embodiment, for the Compounds of Formula (Ib), X¹ and X² are each —CH—.

In one embodiment, for the Compounds of Formula (Ib), the group:

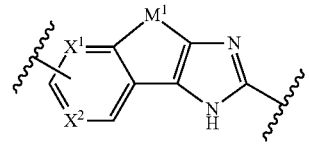

has the structure:

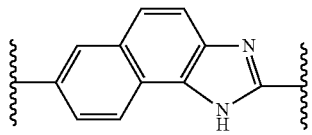

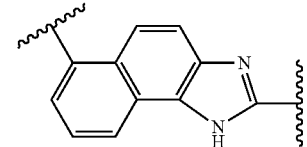

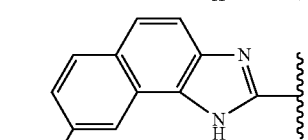

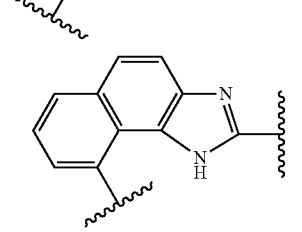

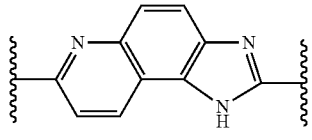

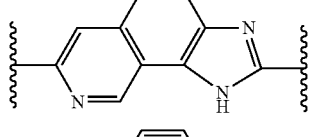

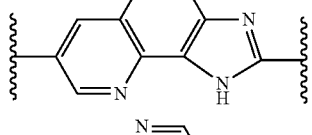

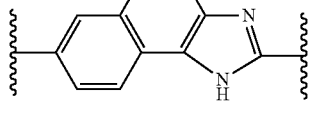

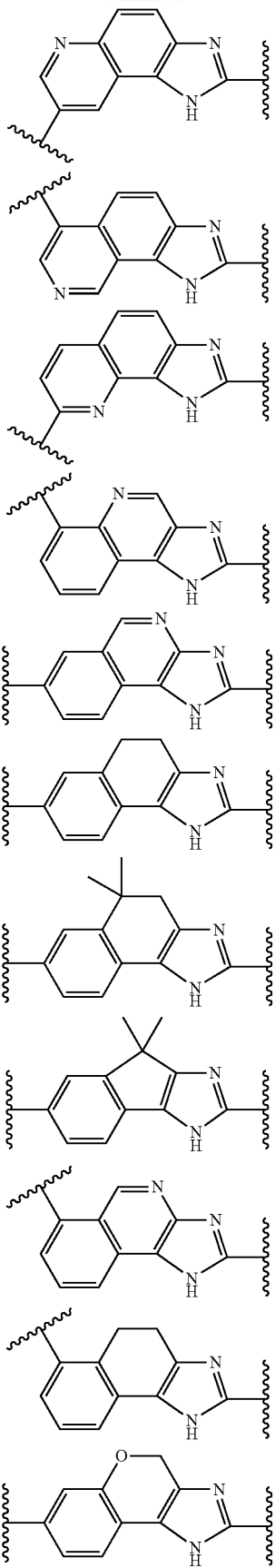
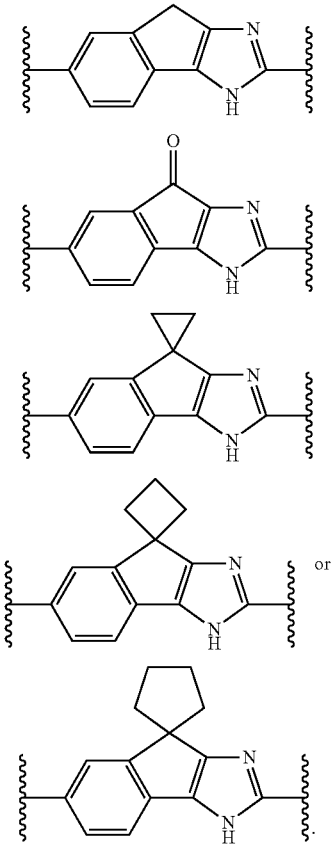
In another embodiment, for the Compounds of Formula (Ib), the group:
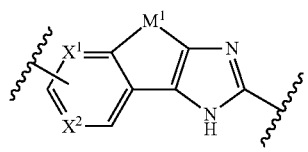
has the structure:
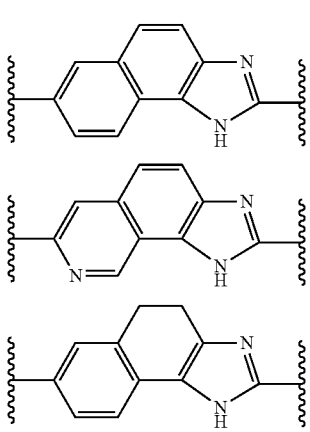

-continued

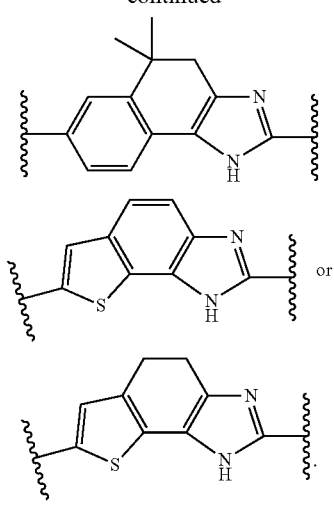

In another embodiment, for the Compounds of Formula (Ib), the group:

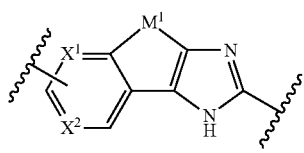

has the structure:

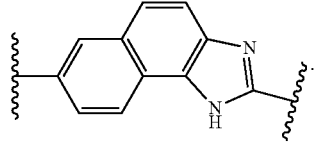 [SMILES: *c1ccc2c(ccc3nc(*)[nH]c32)c1]

In one embodiment, for the Compounds of Formula (Ib), one, but not both, of A and D is $R^{15}$.

In another embodiment, for the Compounds of Formula (Ib), each of A and D is $R^{15}$.

In another embodiment, for the Compounds of Formula (Ib), A and D are each independently selected from:

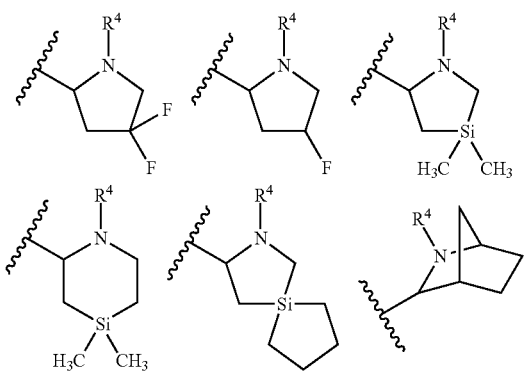

-continued

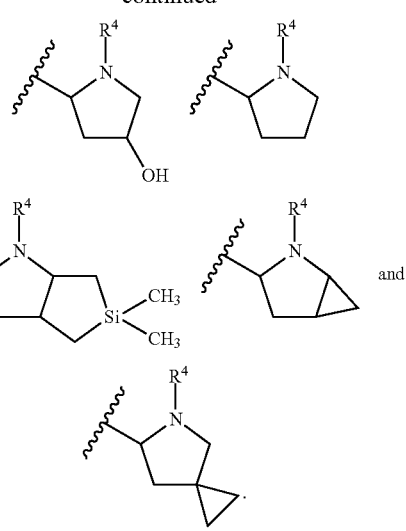

In another embodiment, for the Compounds of Formula (Ib), A and D are each independently selected from:

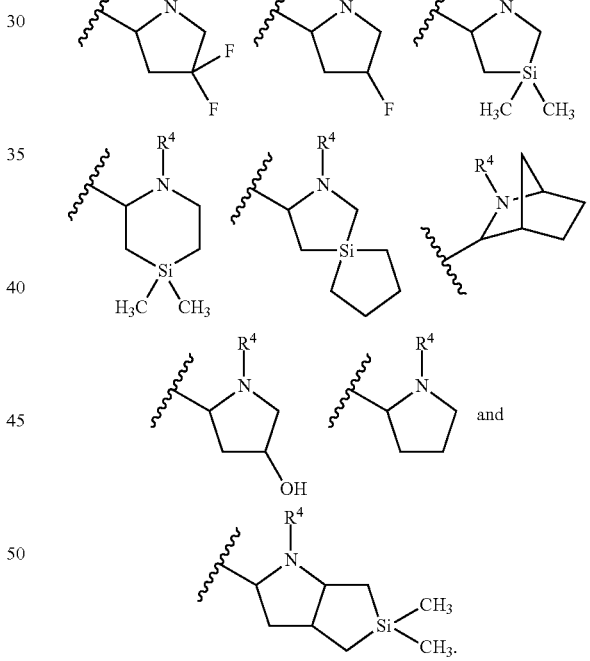

In still another embodiment, for the Compounds of Formula (Ib), one of A and D is $R^{15}$ and the other is selected from:

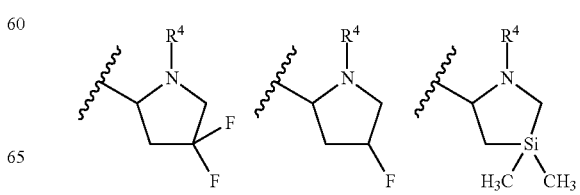

-continued

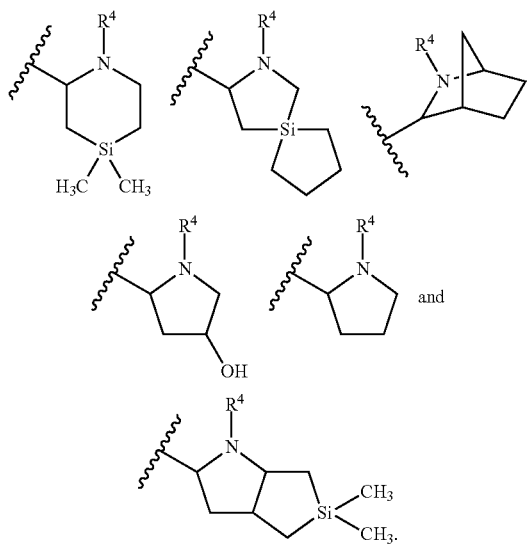

In another embodiment, for the Compounds of Formula (Ib), one of A and D is R$^{15}$ and the other is selected from:

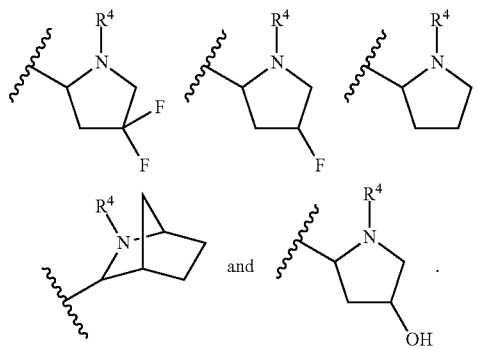

In yet another embodiment, for the Compounds of Formula (Ib), one of A and D is selected from:

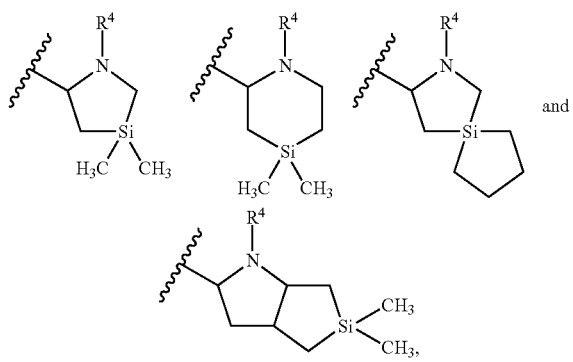

and the other of A and D is selected from:

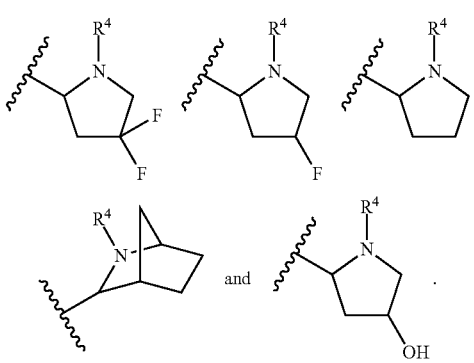

In another embodiment, for the Compounds of Formula (Ib), at least one of A and D is:

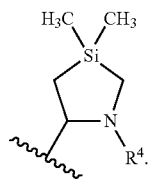

In a further embodiment, for the Compounds of Formula (Ib), A and D are each selected from:

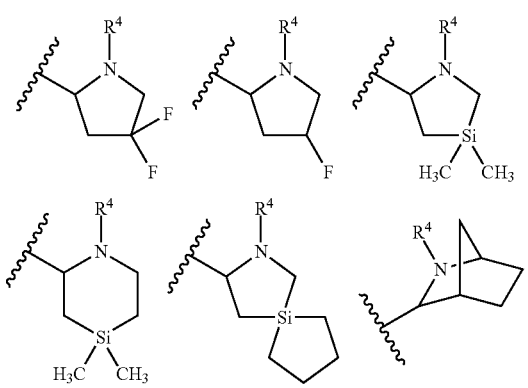

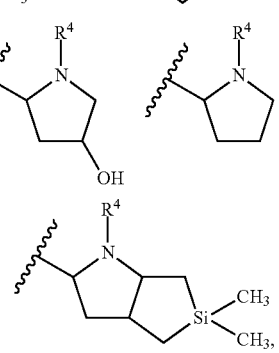

and each occurrence of R⁴ is

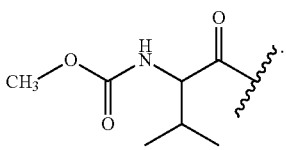 [SMILES: *C(=O)C(NC(=O)OC)C(C)C]

In another embodiment, for the Compounds of Formula (Ib), one of A and D is selected from:

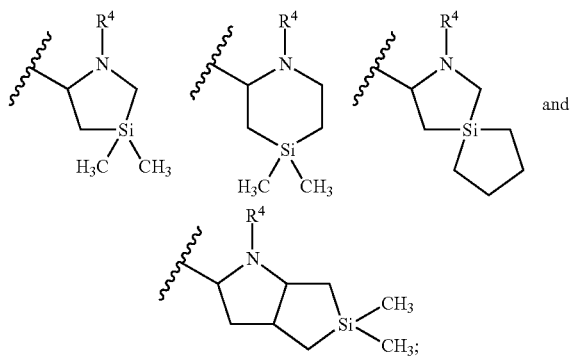

and the other of A and D is selected from:

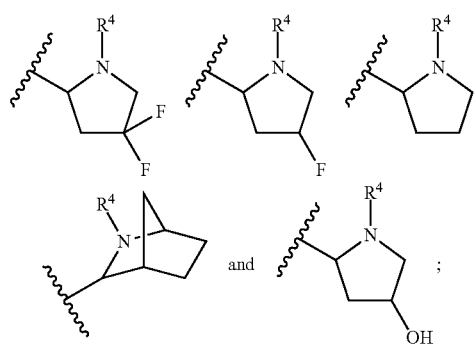

and each occurrence of R⁴ is

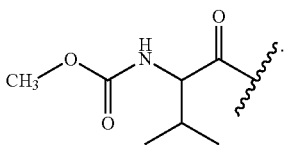 [SMILES: *C(=O)C(NC(=O)OC)C(C)C]

In another embodiment, for the Compounds of Formula (Ib), one of A and D is R¹⁵ and the other is selected from:

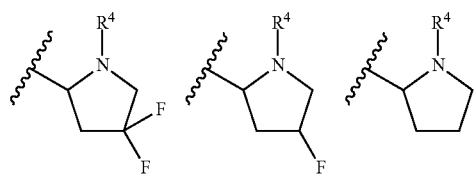

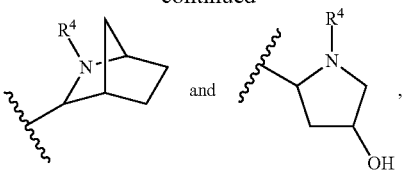

and and each occurrence of R⁴ is

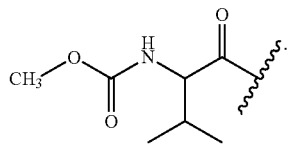 [SMILES: *C(=O)C(NC(=O)OC)C(C)C]

In still another embodiment, for the Compounds of Formula (II), one of A and D is:

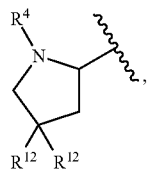

wherein each occurrence of R¹² is independently H or F; the other of A and D is selected from:

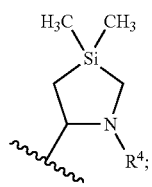

and each occurrence of R⁴ is

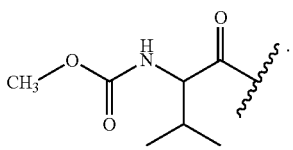 [SMILES: *C(=O)C(NC(=O)OC)C(C)C]

In one embodiment, for the Compounds of Formula (Ib), M¹ is a bond.

In another embodiment, for the Compounds of Formula (Ib), M¹ is —S(O)₂—

In another embodiment, for the Compounds of Formula (II), M¹ is —O—.

In still another embodiment, for the Compounds of Formula (Ib), M¹ is —C(R⁷)₂—.

In another embodiment, for the Compounds of Formula (Ib), M¹ is —CH₂—.

In another embodiment, for the Compounds of Formula (Ib), M¹ is —N(R⁶)—.

In yet another embodiment, for the Compounds of Formula (Ib), M¹ is a bond.

In a further embodiment, for the Compounds of Formula (Ib), $M^1$ is —C(R²)=C(R²)—.

In another embodiment, for the Compounds of Formula (Ib), $M^1$ is —CH=CH—.

In another embodiment, for the Compounds of Formula (Ib), $M^1$ is —CH=N—.

In still another embodiment, for the Compounds of Formula (Ib), $M^1$ is —N=CH—.

In another embodiment, for the Compounds of Formula (Ib), $M^1$ is —C(R⁷)₂—O—.

In another embodiment, for the Compounds of Formula (Ib), $M^1$ is —O—C(R⁷)₂—.

In yet another embodiment, for the Compounds of Formula (Ib), $M^1$ is —C(R⁷)₂—N(R⁶)—.

In another embodiment, for the Compounds of Formula (Ib), $M^1$ is —N(R⁶)—C(R⁷)₂—.

In one embodiment, for the Compounds of Formula (Ib), $X^1$ is —C(R⁵)—.

In another embodiment, for the Compounds of Formula (Ib), $X^1$ is =N—.

In another embodiment, for the Compounds of Formula (Ib), $X^1$ is —CH—.

In one embodiment, for the Compounds of Formula (Ib), $X^2$ is =C(R⁵)—.

In another embodiment, for the Compounds of Formula (Ib), $X^2$ is =N—.

In another embodiment, for the Compounds of Formula (Ib), $X^2$ is —CH—.

In one embodiment, for the Compounds of Formula (Ib), $X^1$ and $X^2$ are each —CH—.

In one embodiment, the Compounds of Formula (I) have the formula (Ic):

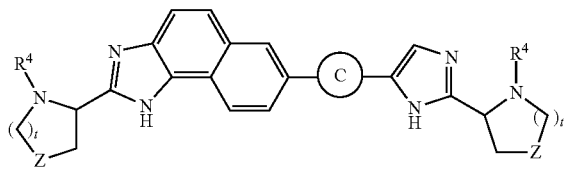

(Ic)

and pharmaceutically acceptable salts thereof,
wherein:

C is phenylene, 5- or 6-membered monocyclic heteroarylene or 9-membered bicyclic heteroarylene, wherein said phenylene group, said 5- or 6-membered monocyclic heteroarylene group or said 9-membered bicyclic heteroarylene group can be optionally and independently substituted with up to two groups, which can be the same or different, and are selected from halo, 3- to 7-membered cycloalkyl, 5- or 6-membered heteroaryl, —O—(C₁-C₆ alkyl), —O—(C₁-C₆ hydroxyalkyl), or —O—(C₁-C₆ alkylene)-OC(O)—(C₁-C₆ alkyl);

each occurrence of Z is independently —Si(Rˣ)₂—, —C(Rʸ)₂— or —S(O)₂—, such that at least one occurrence of Z is —Si(Rˣ)₂—;

each occurrence of Rˣ is independently C₁-C₆ alkyl or two Rˣ groups that are attached to the same Si atom, combine to form a —(CH₂)₄— or —(CH₂)₅— group; and each occurrence of Rʸ is independently H or F;

each occurrence of R¹ is independently C₁-C₆ alkyl;

each occurrence of R⁴ is independently —C(O)CH(R⁷)NHC(O)OR¹;

each occurrence of R⁷ is independently C₁-C₆ alkyl, C₁-C₆ silylalkyl or 4 to 7-membered heterocycloalkyl; and In one embodiment, for the Compounds of Formula (Ic), C is:

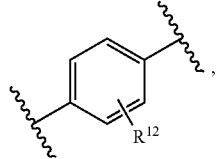

and wherein R¹² is a single ring substituent selected from halo, 3- to 7-membered cycloalkyl, 5- or 6-membered heteroaryl, —O—(C₁-C₆ alkyl), —O—(C₁-C₆ hydroxyalkyl) and —O—(C₁-C₆ alkylene)-OC(O)—(C₁-C₆ alkyl).

In another embodiment, for the Compounds of Formula (Ic), C is:

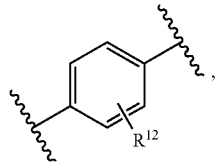

and wherein R¹² is an optional ring substituent selected from F, —OCH₃, pyridyl, —OCH₂CH₂OH, —OCH₂CH₂OC(O)CH₃, cyclopropyl and thiophenyl.

In another embodiment, for the Compounds of Formula (Ic), C is:

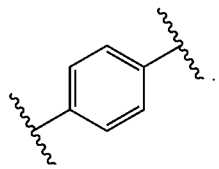 [SMILES: *c1ccc(*)cc1]

In another embodiment, for the Compounds of Formula (Ic), each occurrence of t is independently 1 or 2.

In still another embodiment, for the Compounds of Formula (Ic), each occurrence of t is 1.

In another embodiment, for the Compounds of Formula (Ic), one occurrence of Z is —Si(Rˣ)₂— and the other is —C(Rʸ)₂—.

In yet another embodiment, for the Compounds of Formula (Ic), each occurrence of Z is —Si(Rˣ)₂—.

In a further embodiment, for the Compounds of Formula (Ic), each occurrence of Z is —C(Rʸ)₂—.

In another embodiment, for the Compounds of Formula (Ic), one occurrence of Z is —Si(CH₃)₂— and the other is —C(Rʸ)₂—.

In one embodiment, the Compounds of Formula (I) have the formula (Id):

(Id)

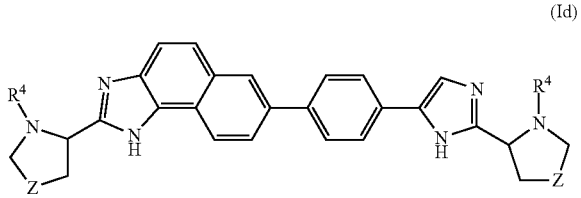

wherein
each occurrence of R⁴ is:

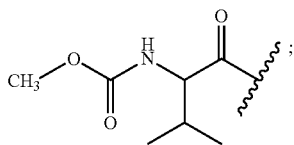 [SMILES: *C(=O)C(NC(=O)OC)C(C)C]

each occurrence of Z is independently —Si(R$^x$)$_2$— or —C(R$^y$)$_2$—;
each occurrence of R$^x$ is independently $C_1$-$C_6$ alkyl or two R$^x$ groups that are attached to the same Si atom, combine to form a —(CH$_2$)$_4$— or —(CH$_2$)$_5$— group; and
each occurrence of R$^y$ is independently H or F,
such that at least one occurrence of Z is —Si(R$^x$)$_2$—.

In another embodiment, for the Compounds of Formula (Id), one occurrence of Z is —Si(R$^x$)$_2$— and the other is —C(R$^y$)$_2$—.

In another embodiment, for the Compounds of Formula (Id), each occurrence of Z is —Si(R$^x$)$_2$—.

In still another embodiment, for the Compounds of Formula (Id), one occurrence of Z is —CF$_2$—.

In yet another embodiment, for the Compounds of Formula (Id), one occurrence of Z is —Si(CH$_3$)$_2$— and the other is —CF$_2$—.

In one embodiment, the Compounds of Formula (I) have the formula (Ie):

(Ie)

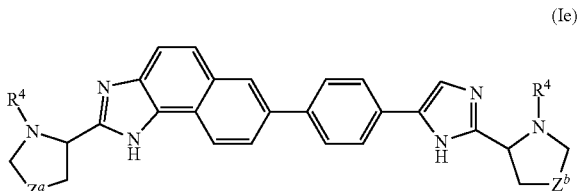

wherein
each occurrence of R⁴ is:

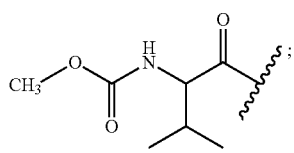 [SMILES: *C(=O)C(NC(=O)OC)C(C)C]

$Z^a$ is —Si(R$^x$)$_2$—;
$Z^b$ is —C(R$^y$)$_2$—;
each occurrence of R$^x$ is independently $C_1$-$C_6$ alkyl or two R$^x$ groups that are attached to the same Si atom, combine to form a —(CH$_2$)$_4$— or —(CH$_2$)$_5$— group; and
each occurrence of R$^y$ is independently H or F.

In another embodiment, for the Compounds of Formula (Id), each occurrence of R$^x$ is methyl. of Z is —CF$_2$—.

In another embodiment, for the Compounds of Formula (Id), each occurrence of R$^y$ is F.

In one embodiment, variables A, B, C, D, M¹, X¹ and X² in the Compounds of Formula (I) are selected independently from each other.

In another embodiment, a Compound of Formula (I) is in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) inhibiting HCV replication or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 1-406, as set forth below. Compounds 1, 2, 15, 16, 20, 42, 44-51, 53-58, 60, 61, 65-67, 70-74, 76-81, 83-97 and 99-106 were made using the methods described in the Schemes and Examples herein. Compounds 3-14, 17-19, 21-41, 43, 52, 59, 62-64, 68, 75, 82 and 98 can be made using the methods described in the Schemes and Examples herein.

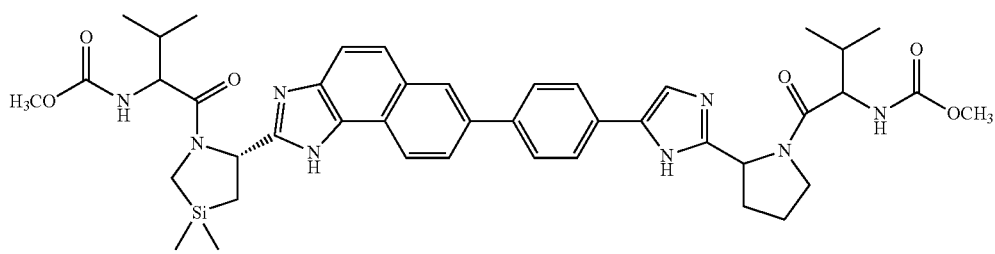

1

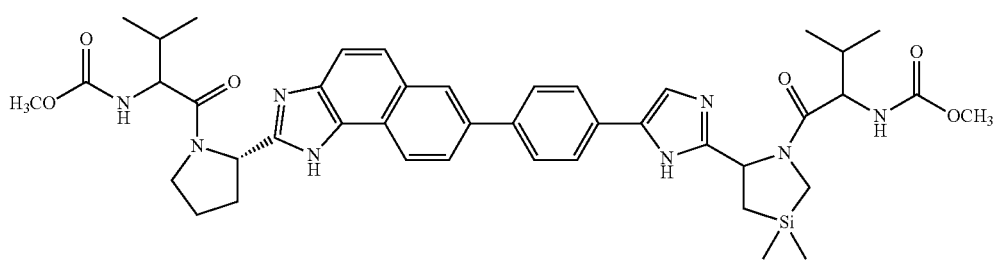

2

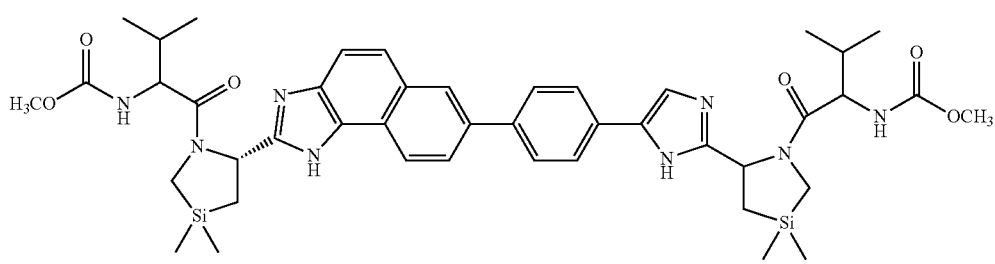

3

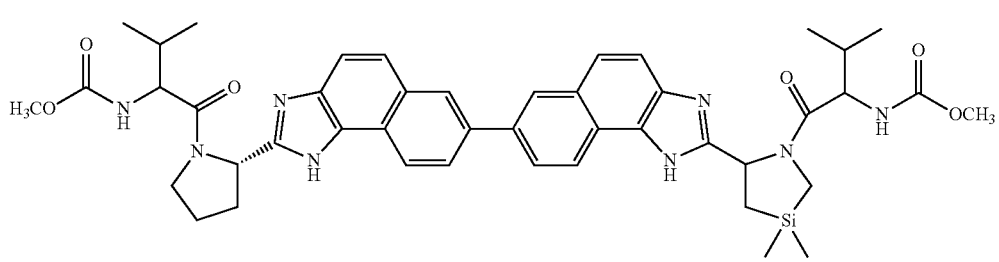

4

5
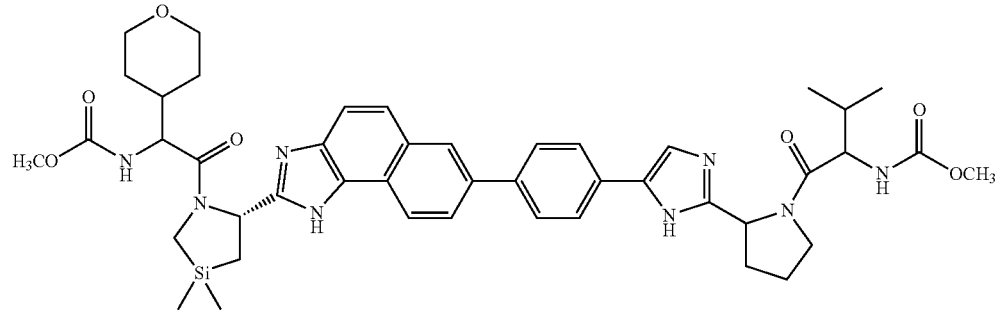
6
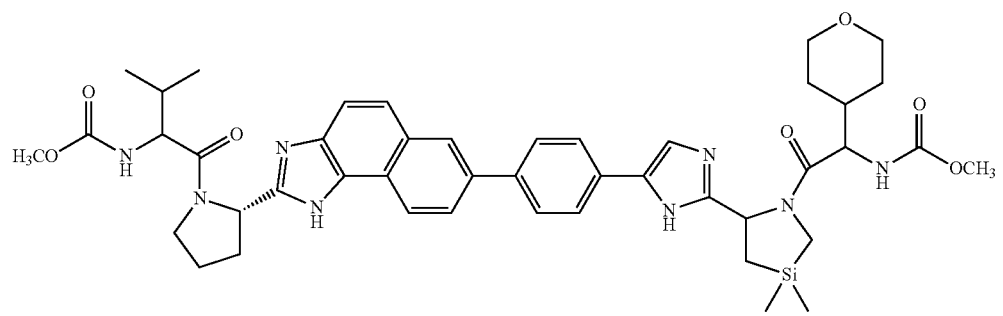
7
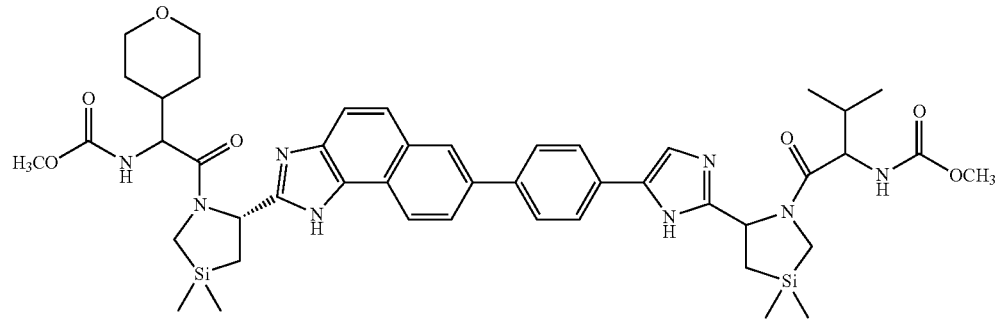
8
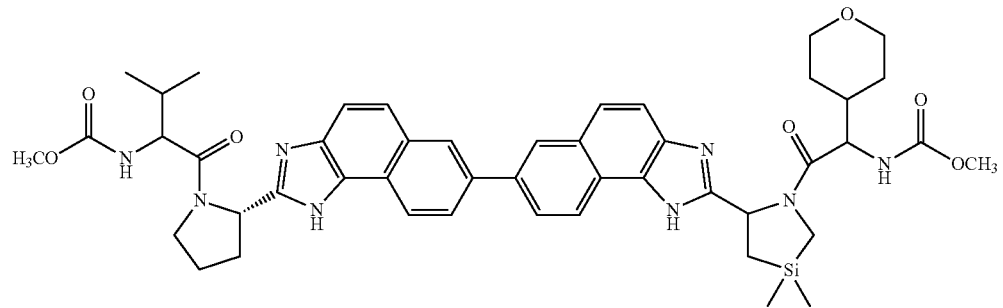
9
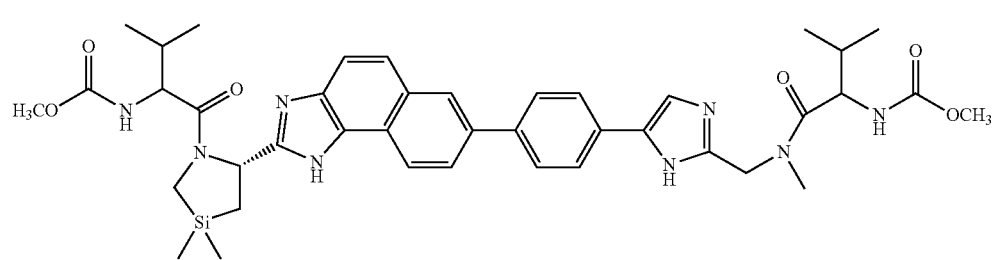

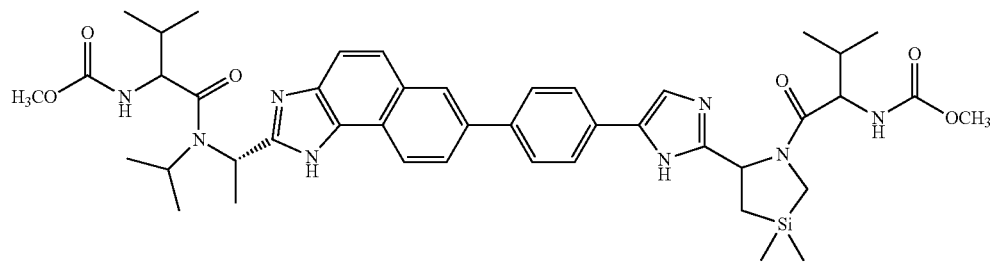
10
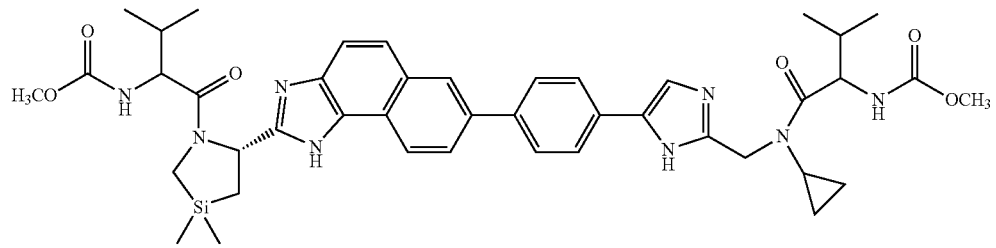
11
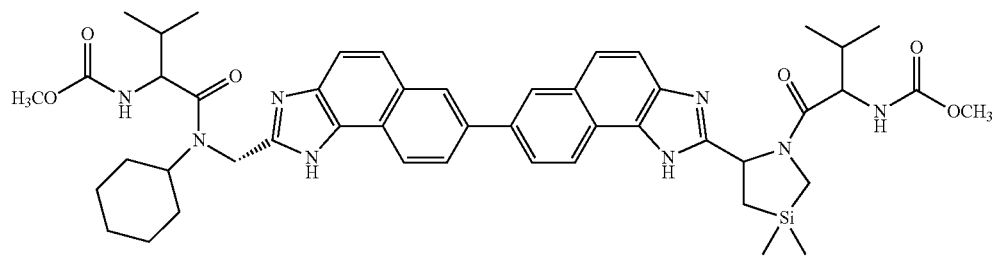
12
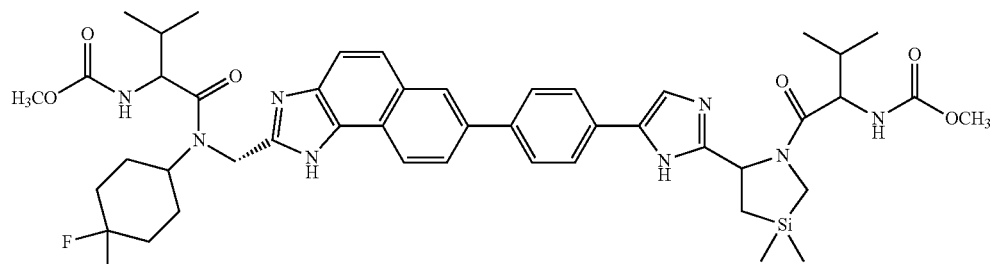
13
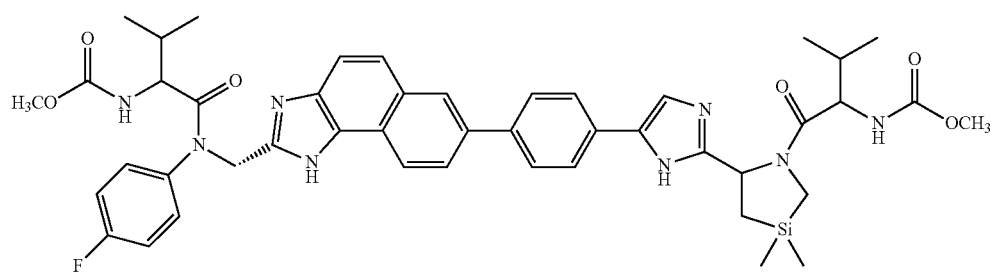
14
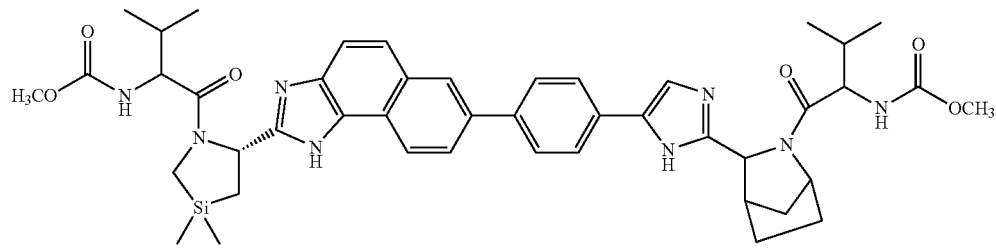
15

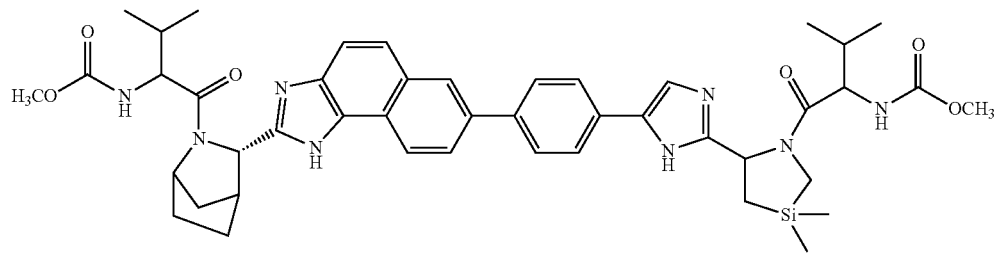
16
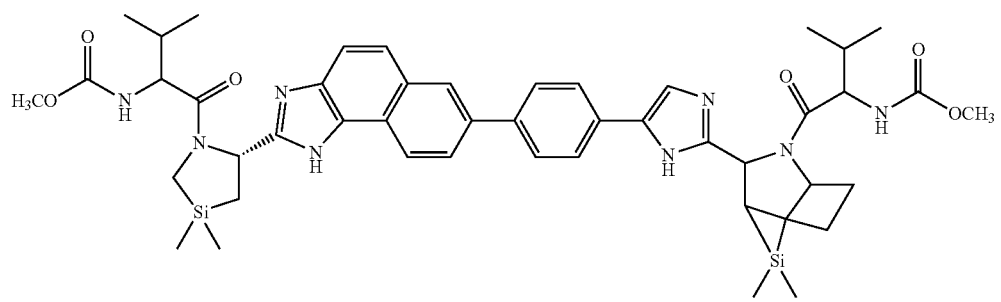
17
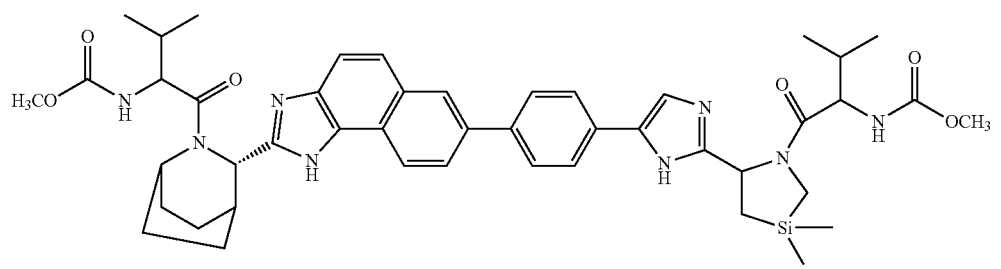
18
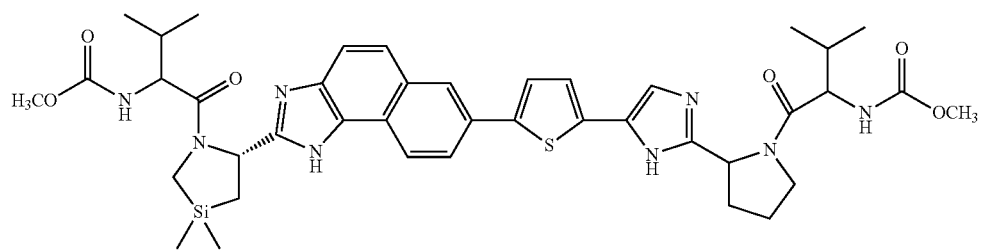
19
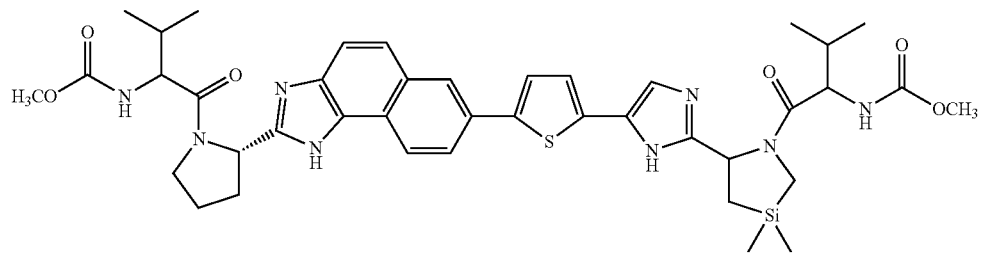
20
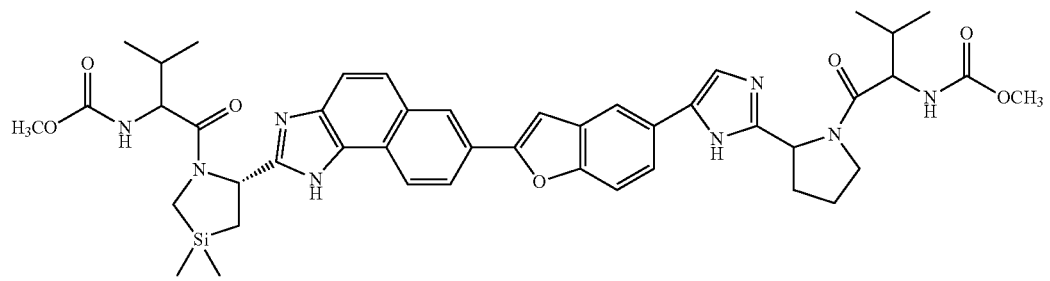
21

22
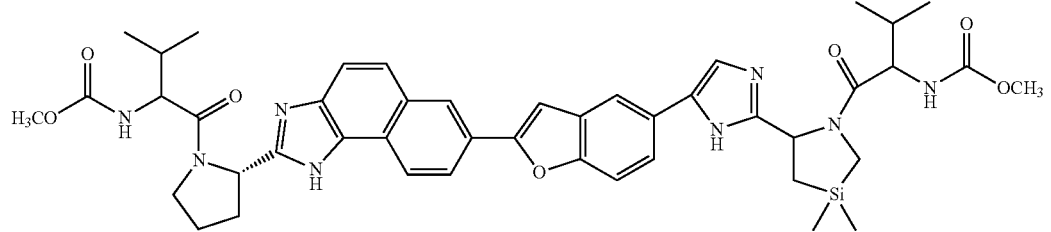
23
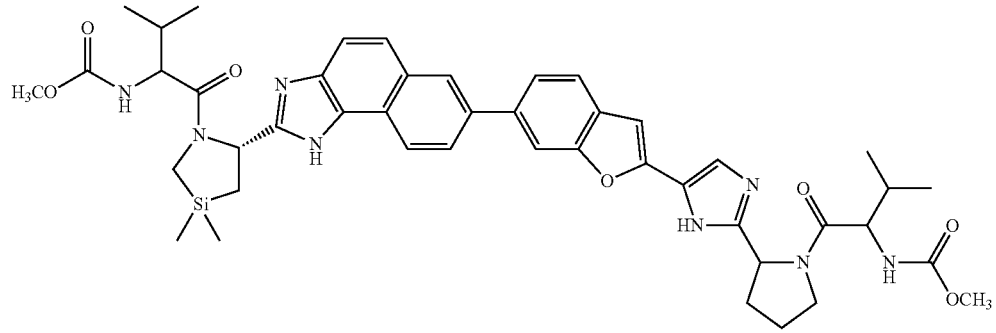
24
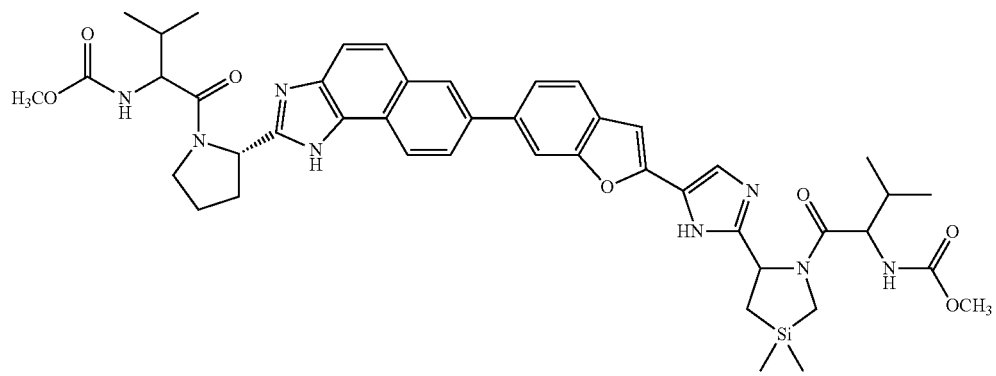
25
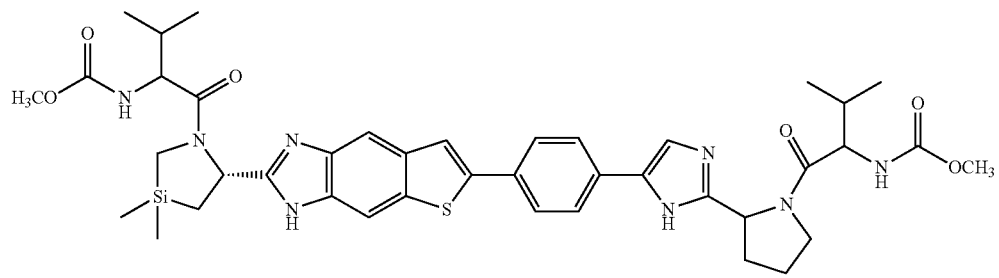
26
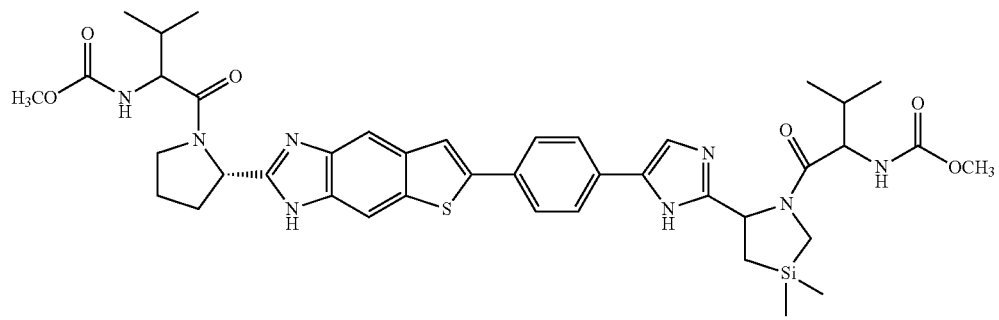

27
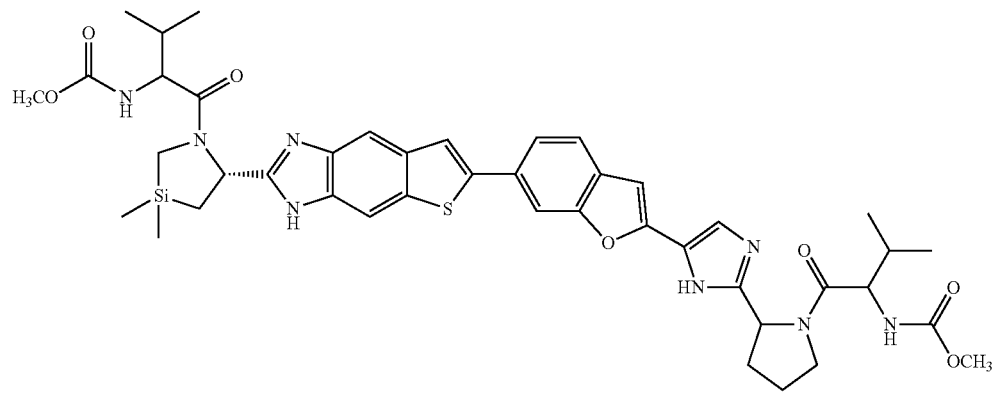
28
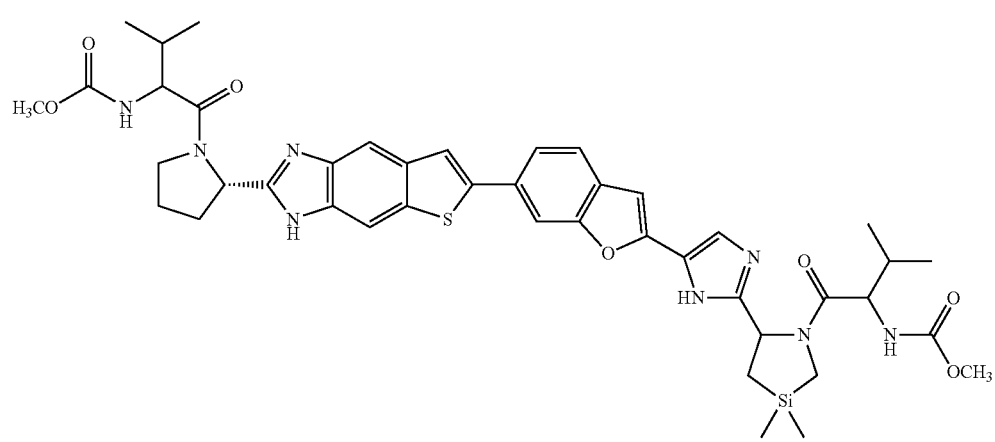
29
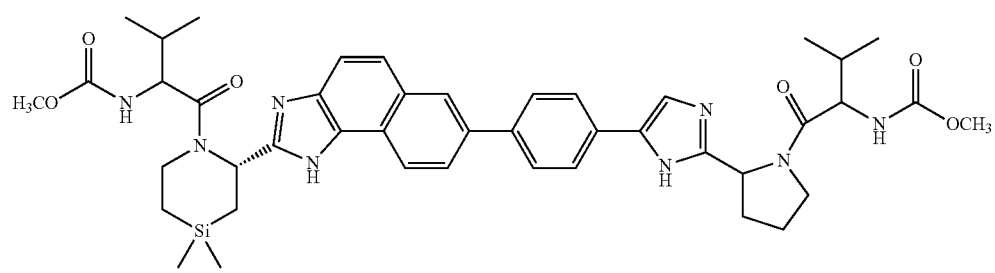
30
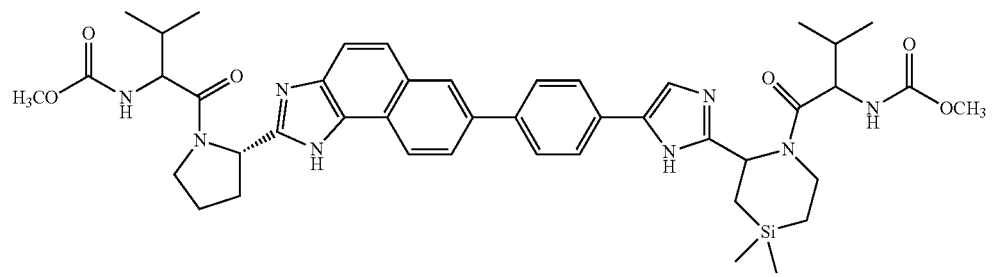
31
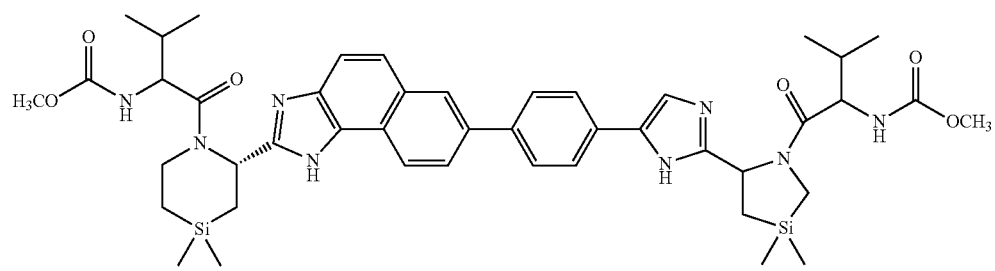

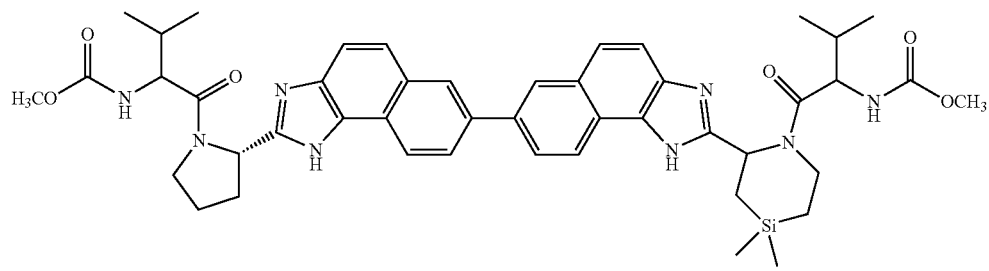
32
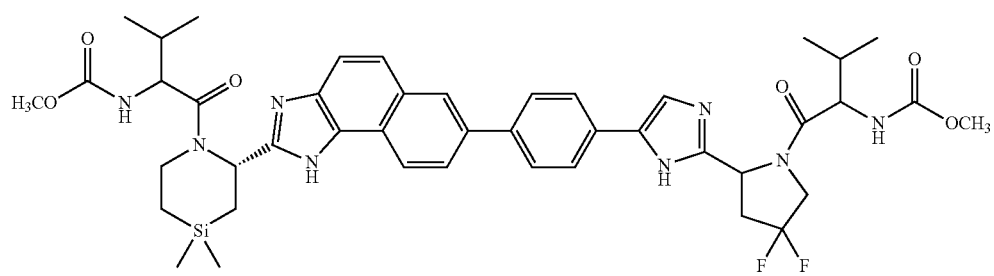
33
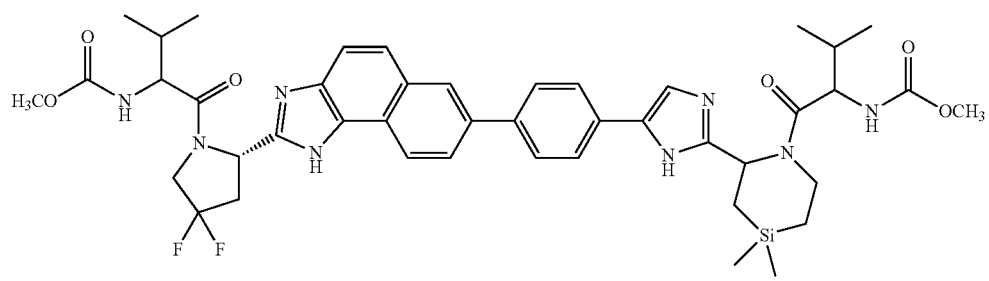
34
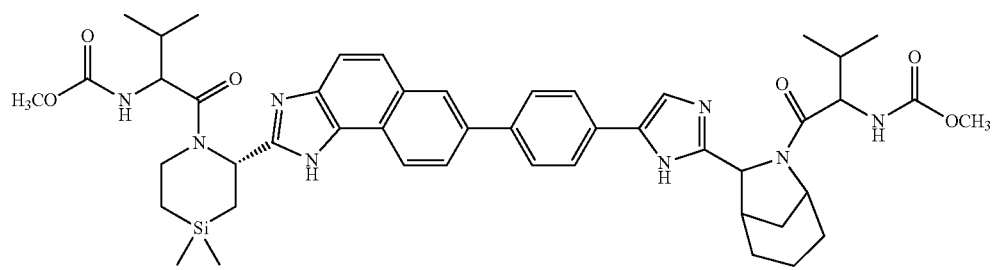
35
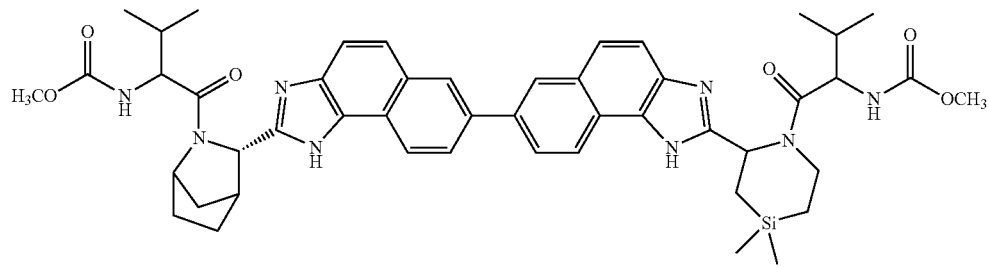
36
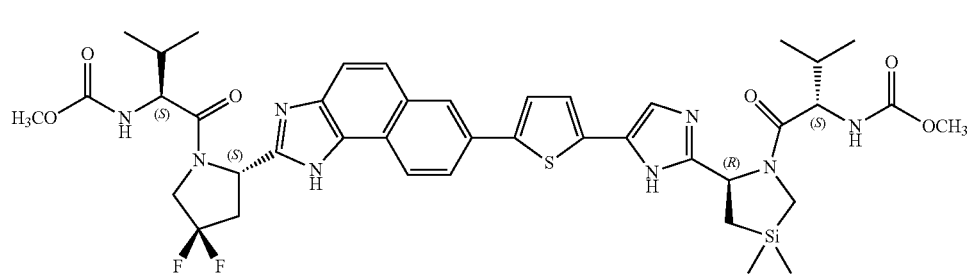
37

38 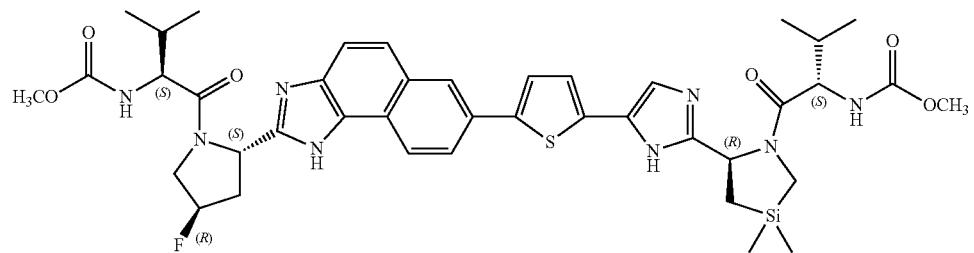
39 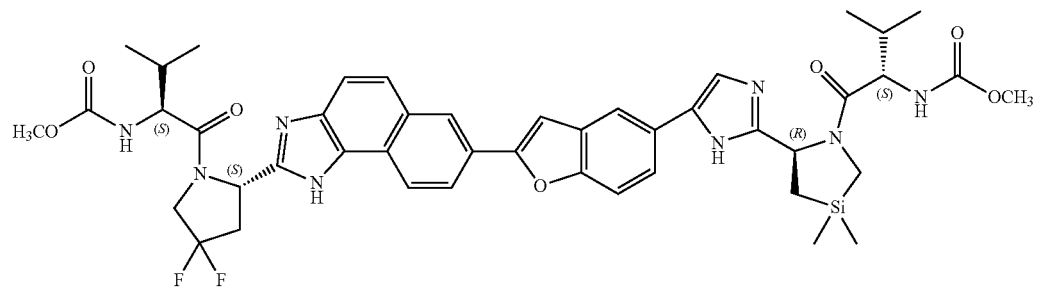
40 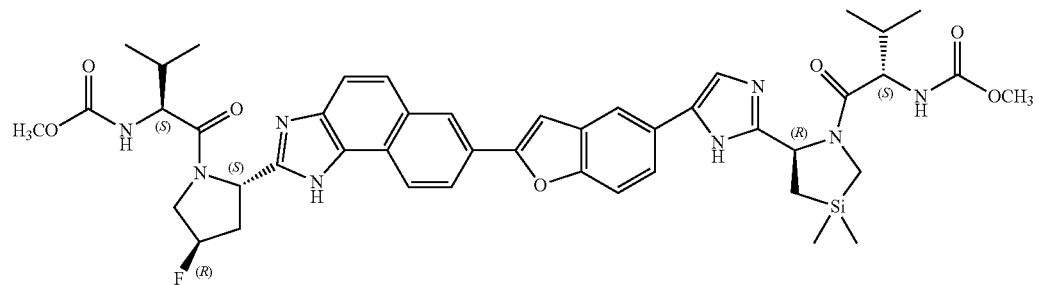
41 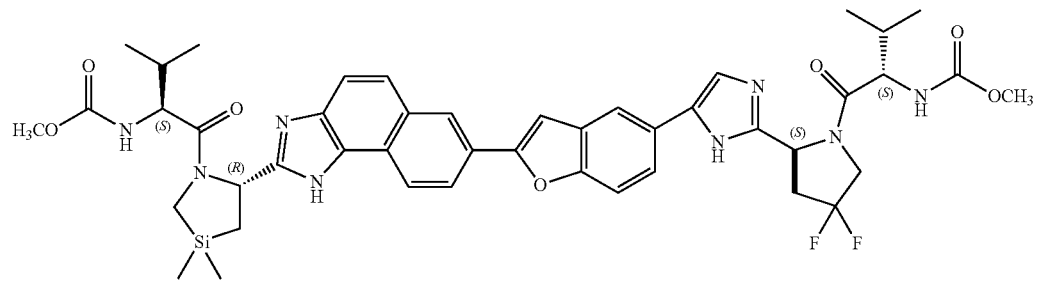
42 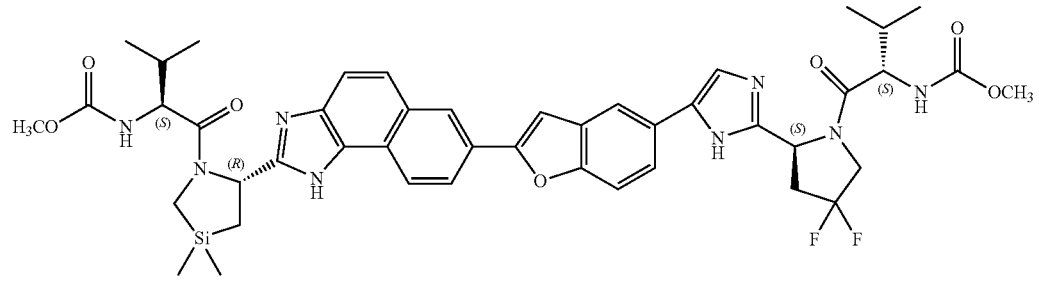

43
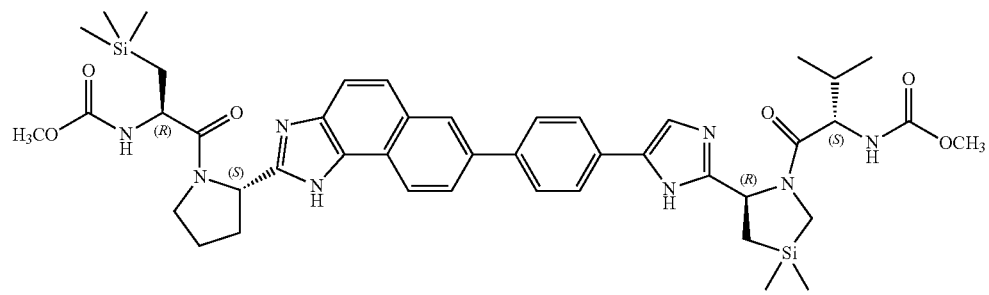
44
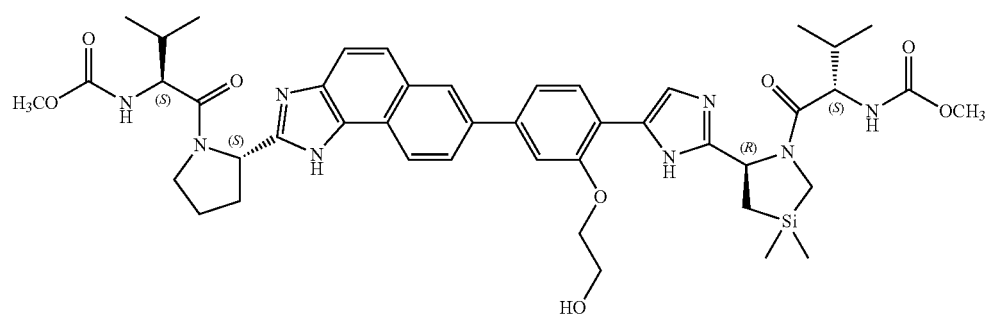
45
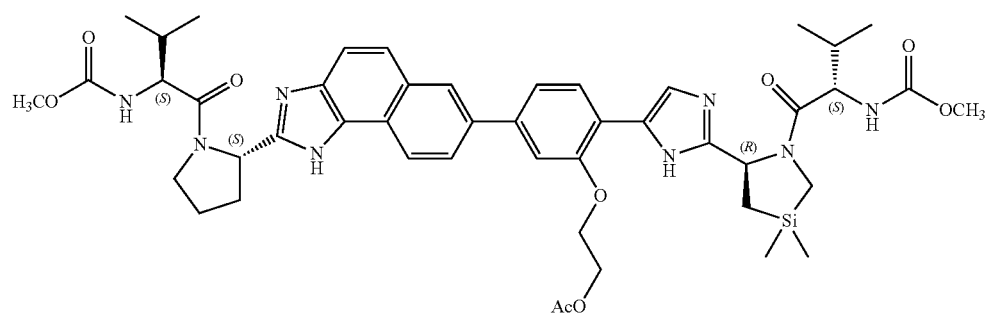
46
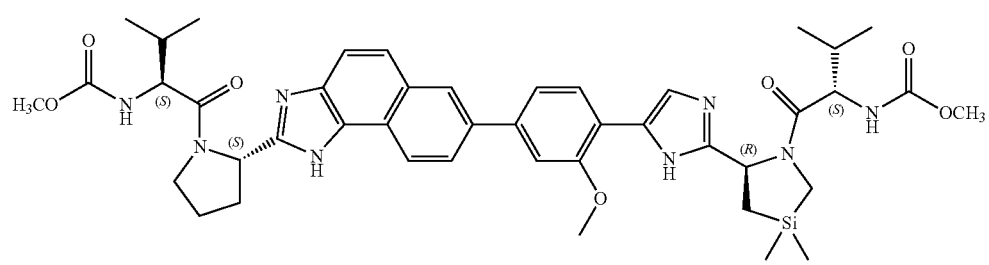
47
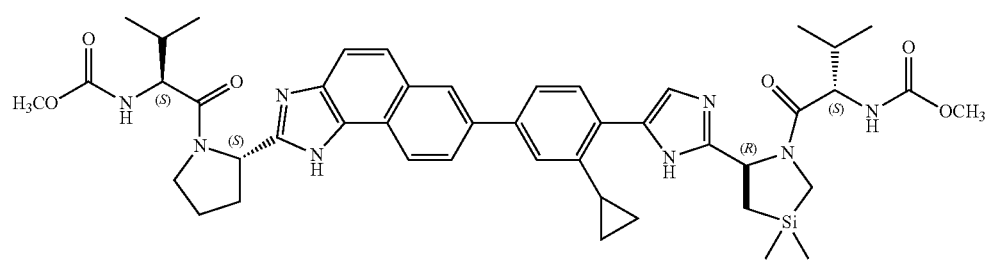

48
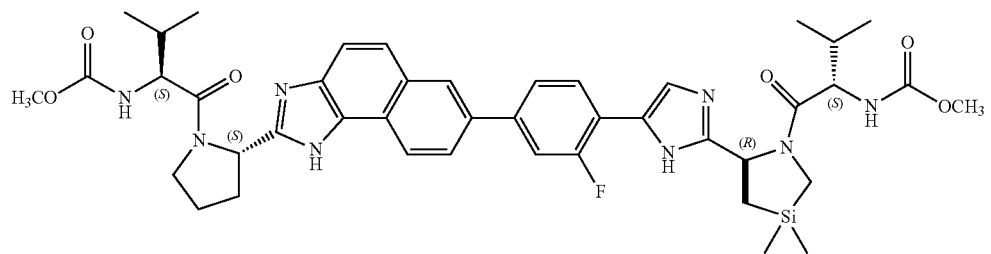
49
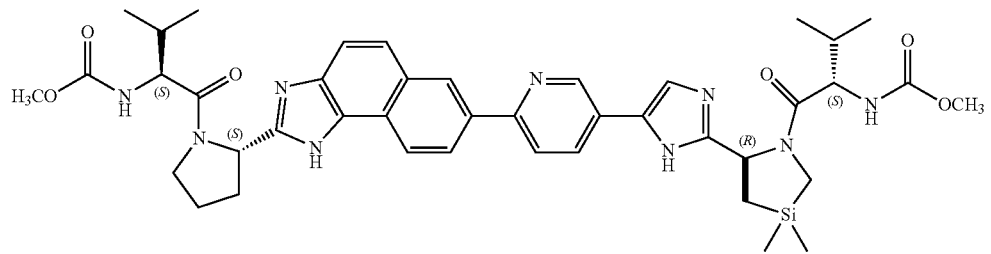
50
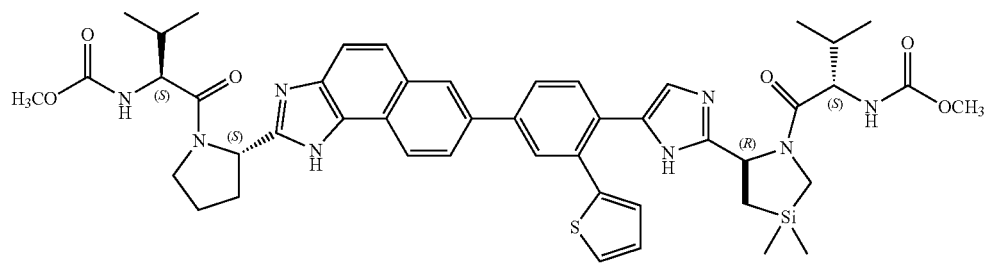
51
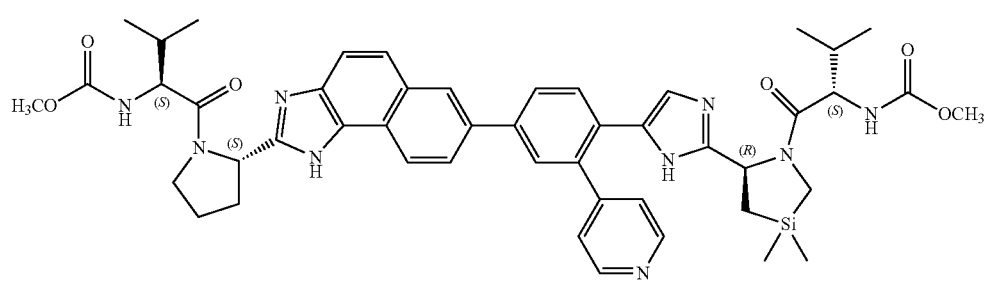
52
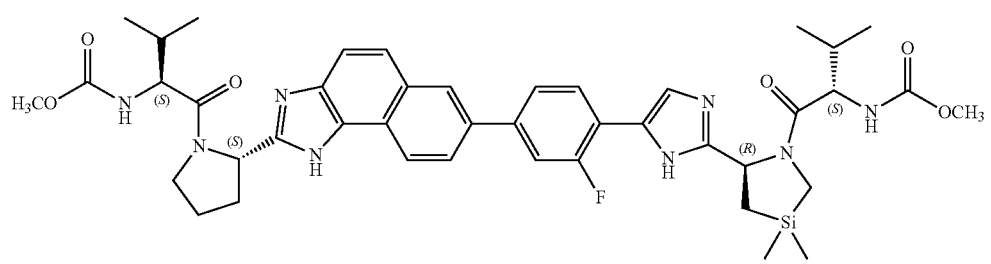
53
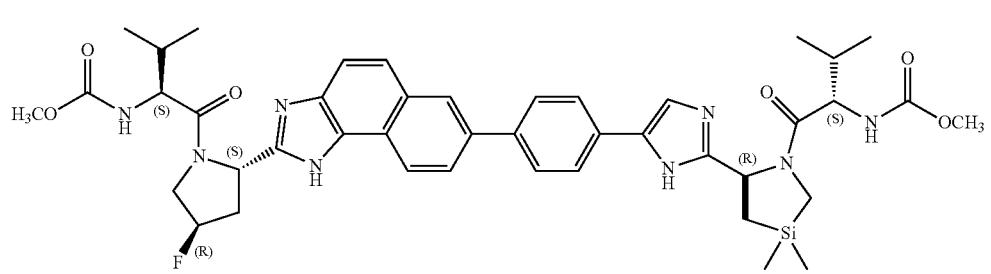

54
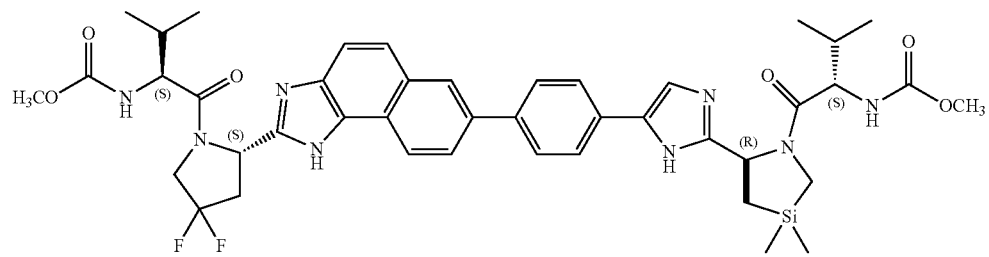
55
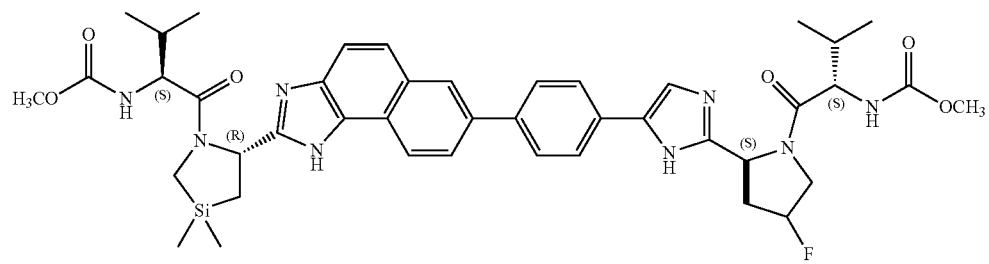
56
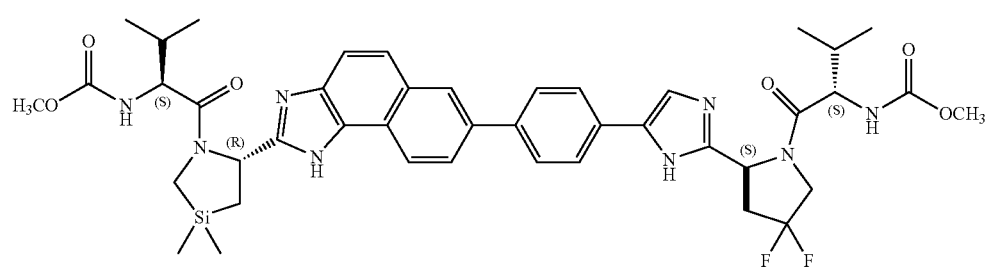
57
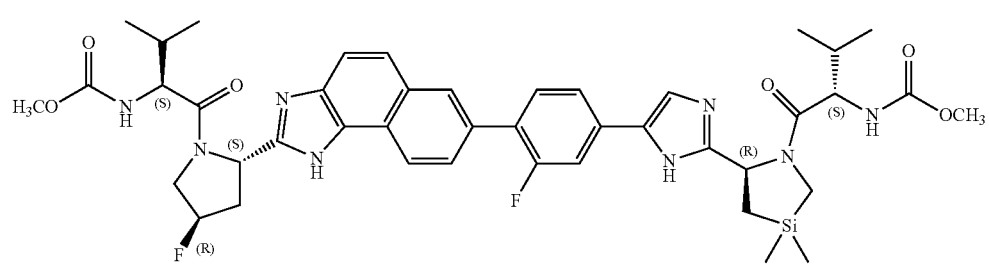
58
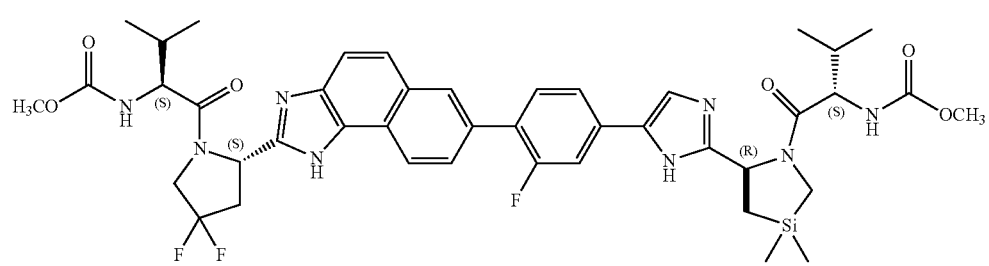
59
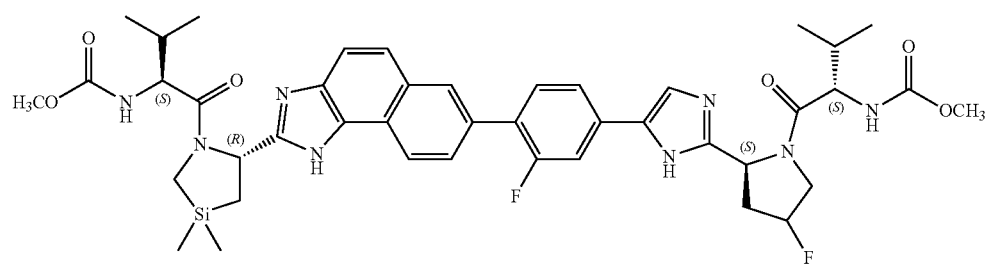

-continued
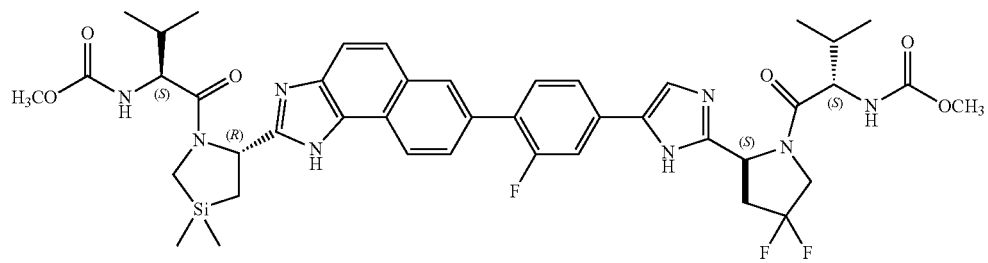
60
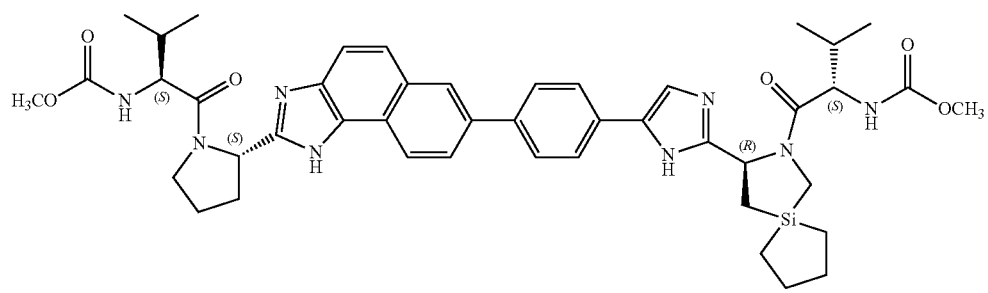
61
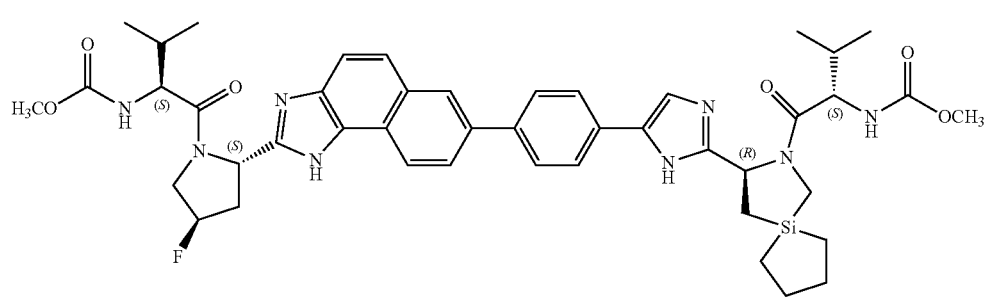
62
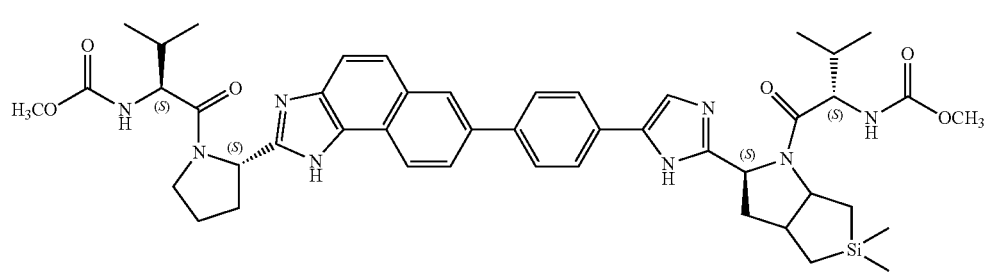
63
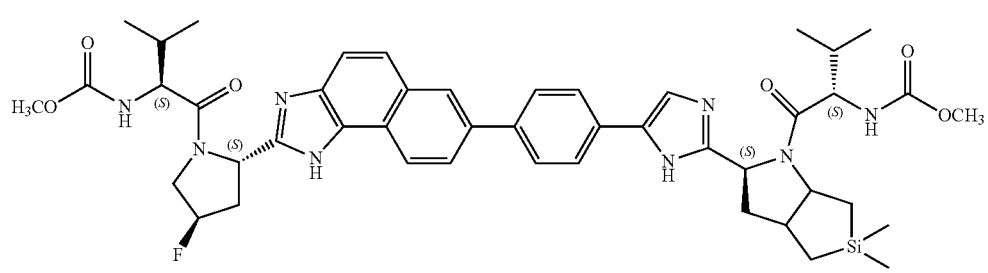
64
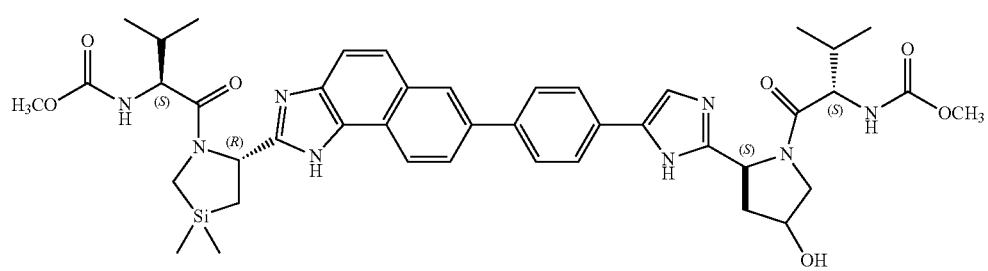
65

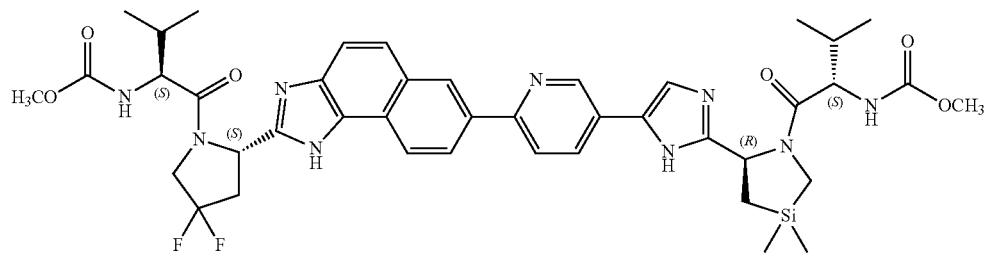
66
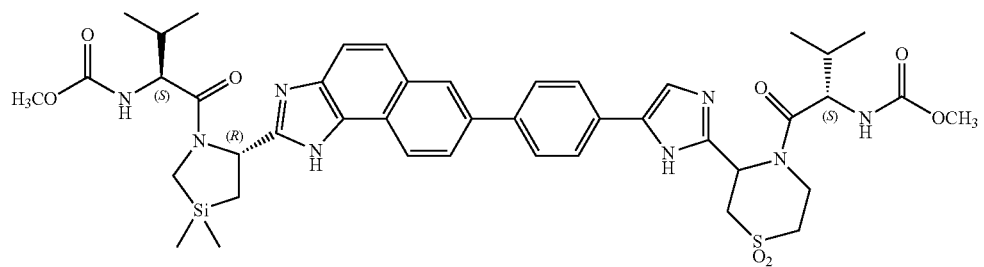
67
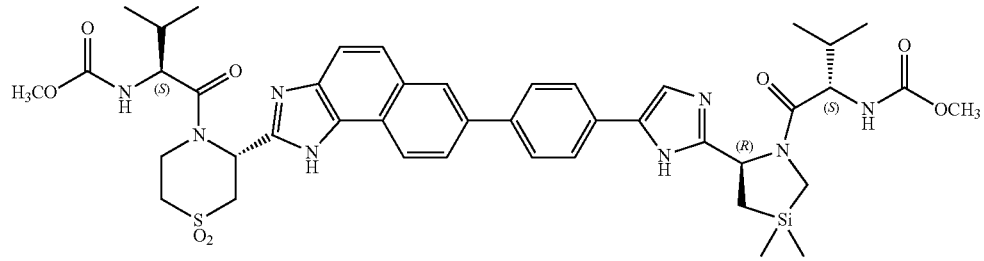
68
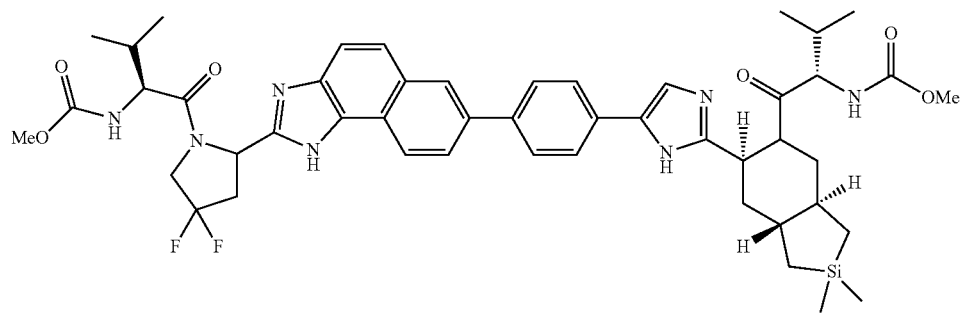
69
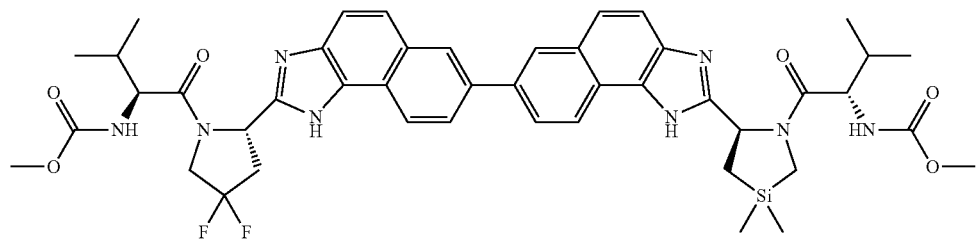
70
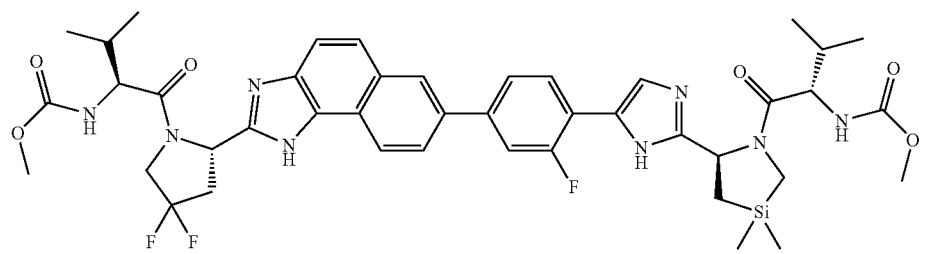
71

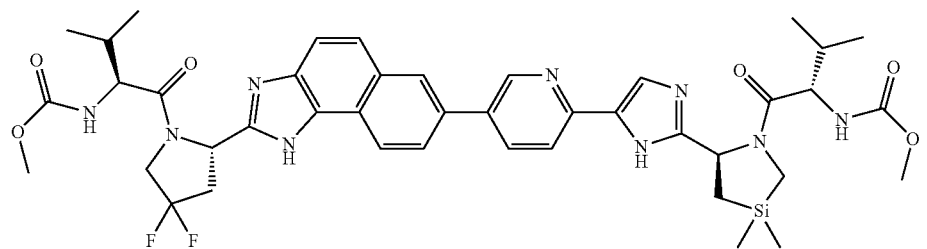
72
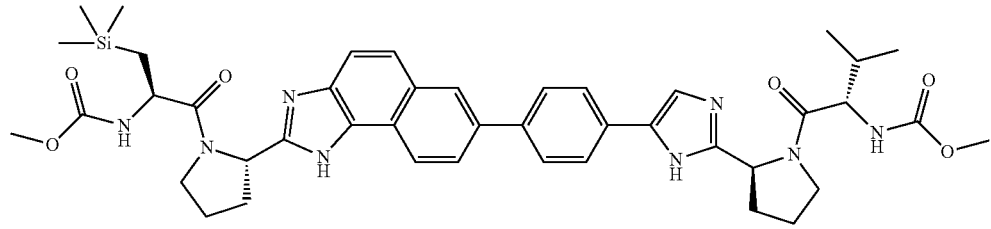
73
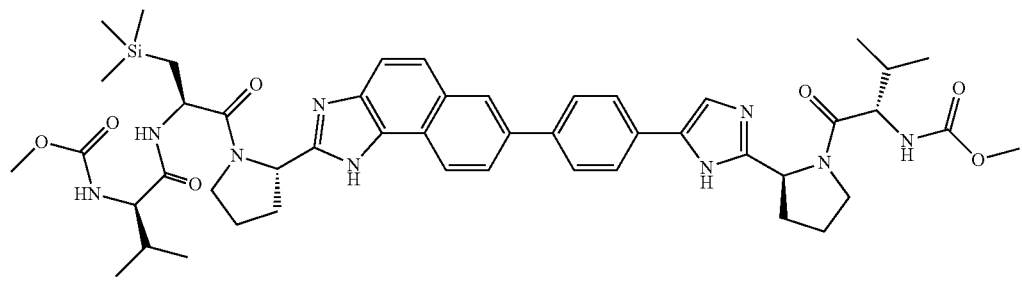
74
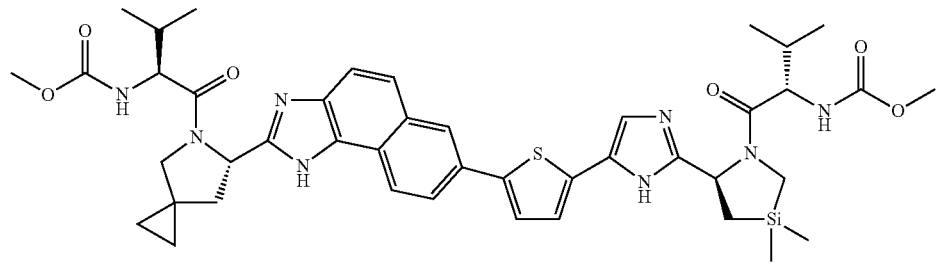
75
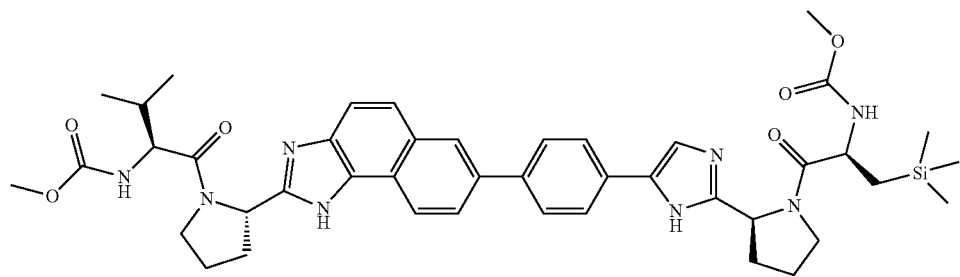
76
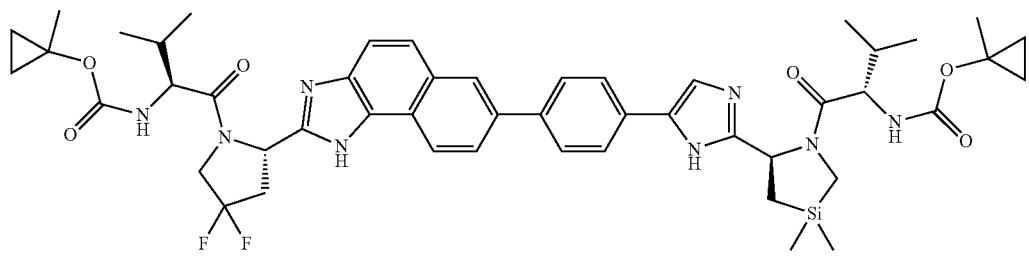
77

78
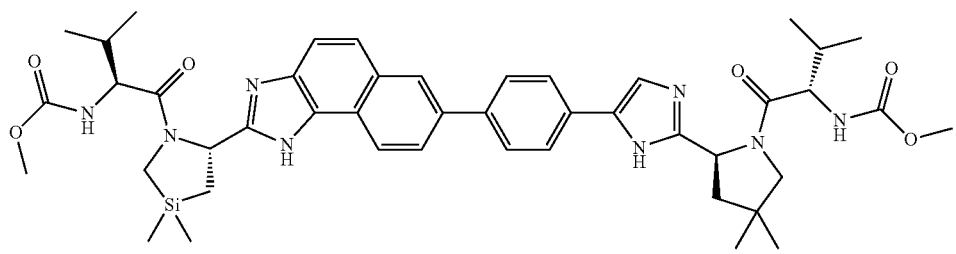
79
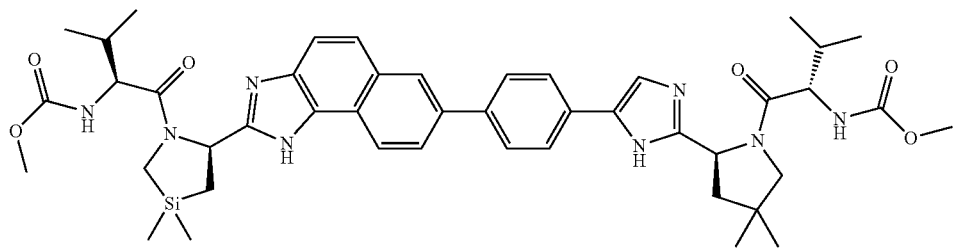
80
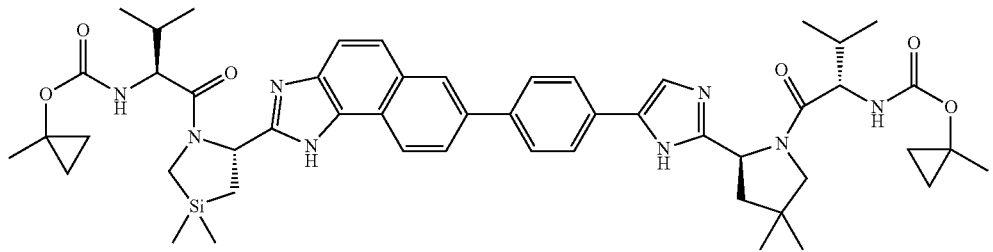
81
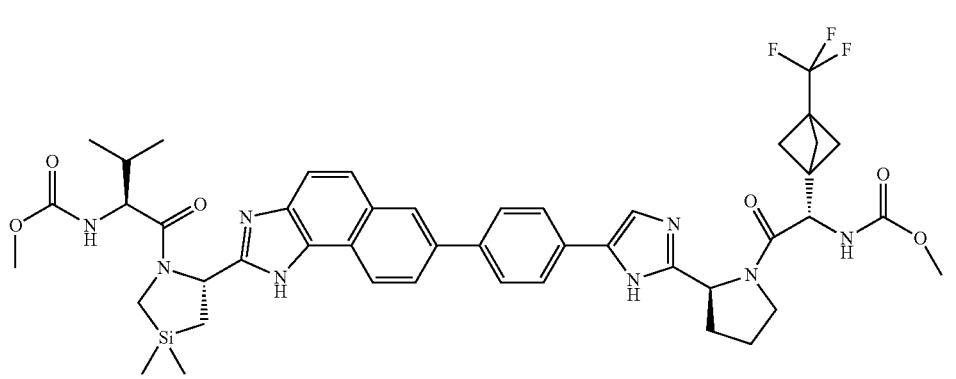
82
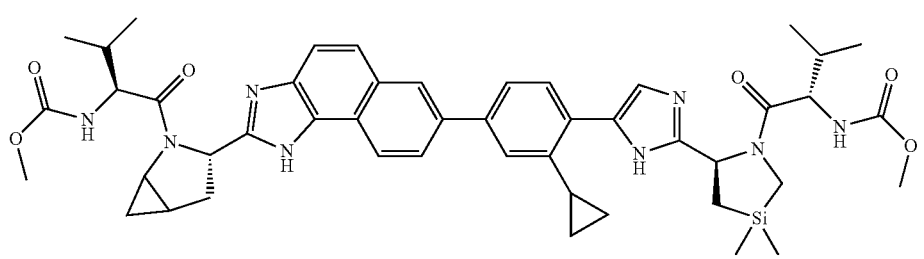
83
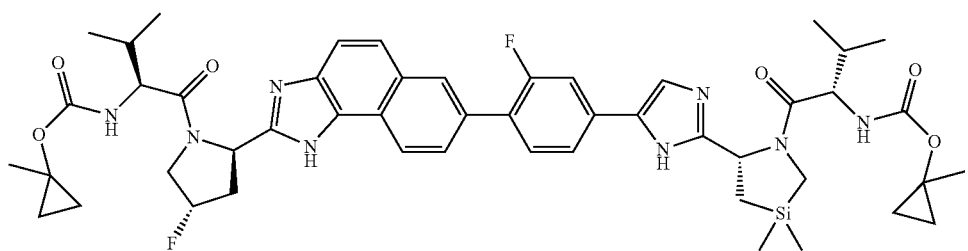

84
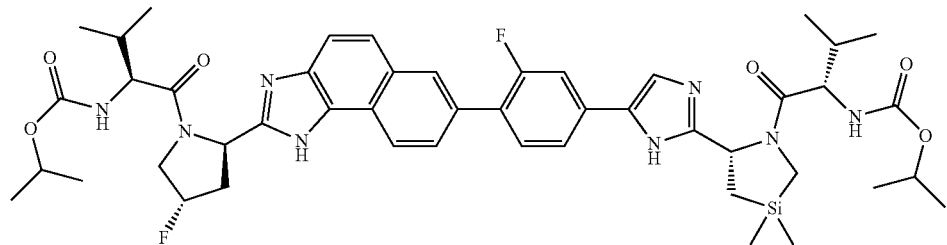
91
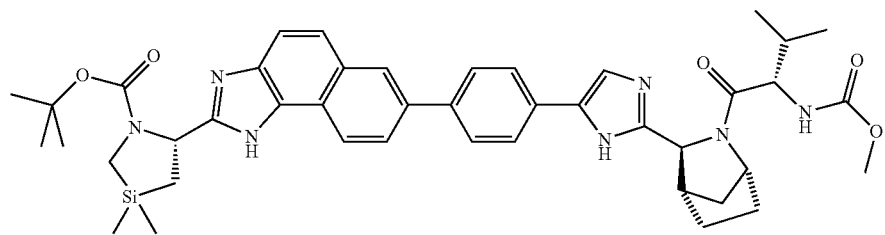
92
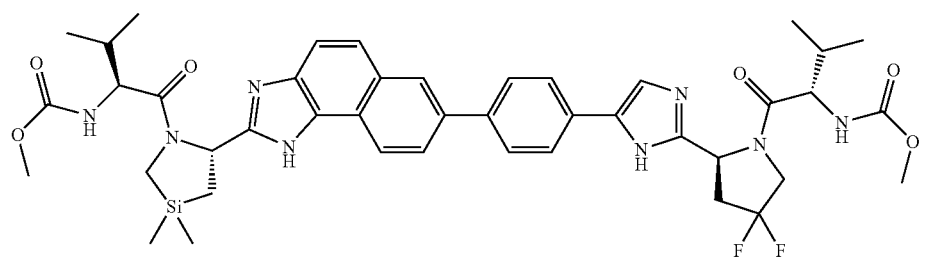
93
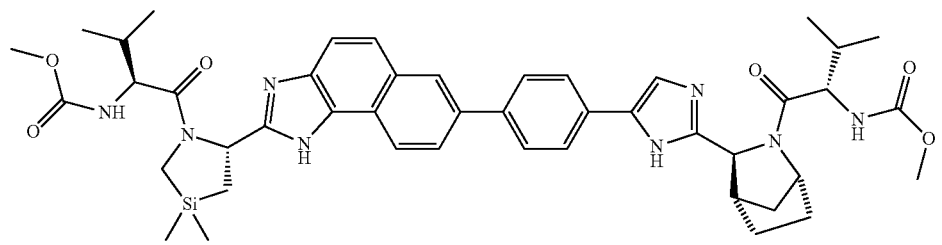
94
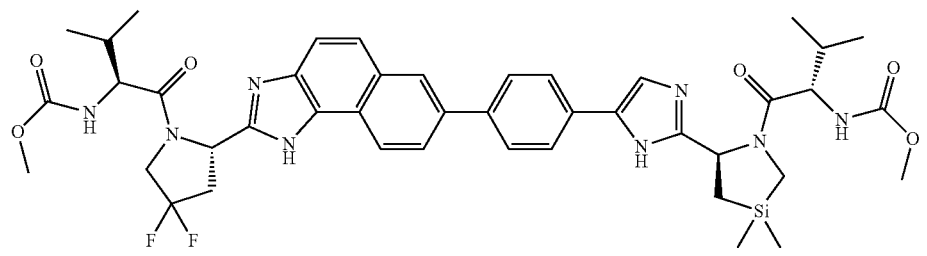
95
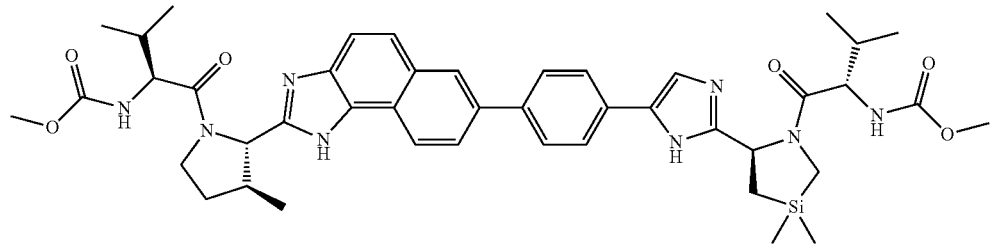

| | |
|---|---|
| 96 | 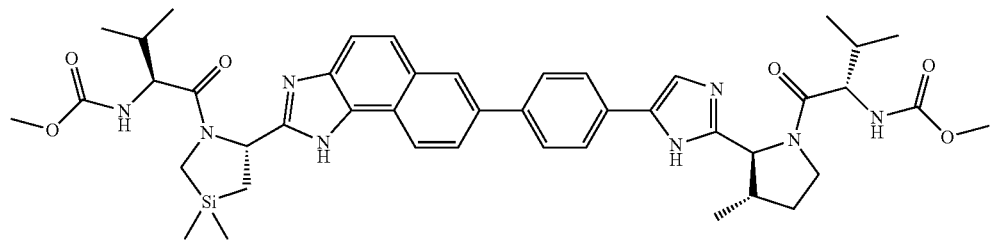 |
| 97 | 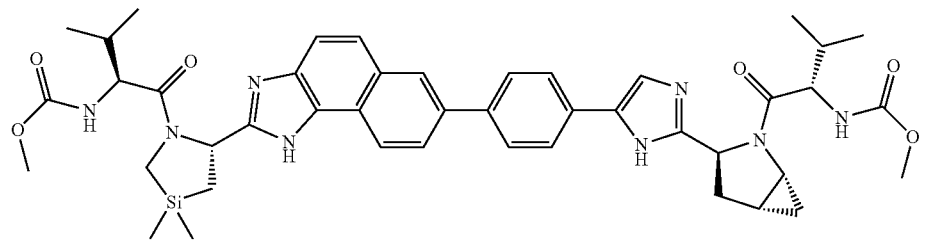 |
| 98 | 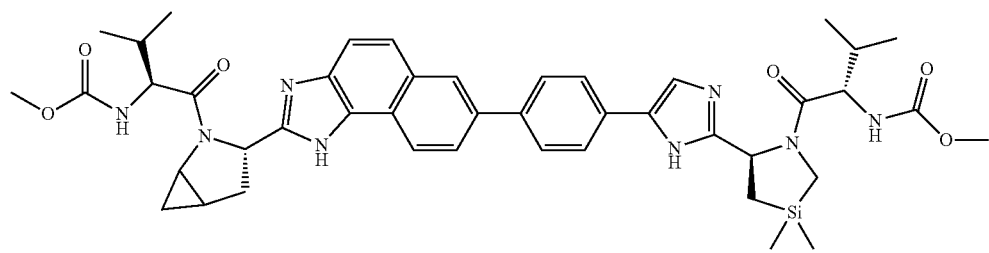 |
| 85 | 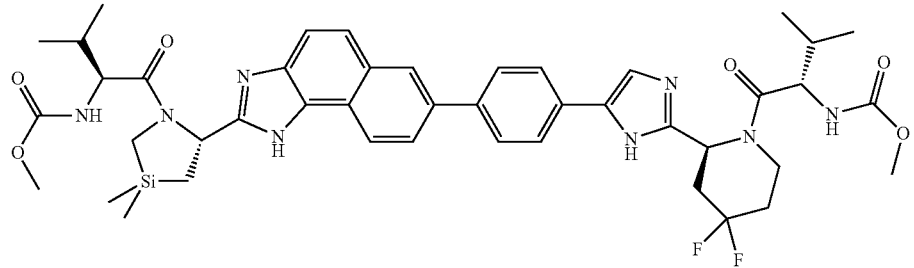 |
| 86 | 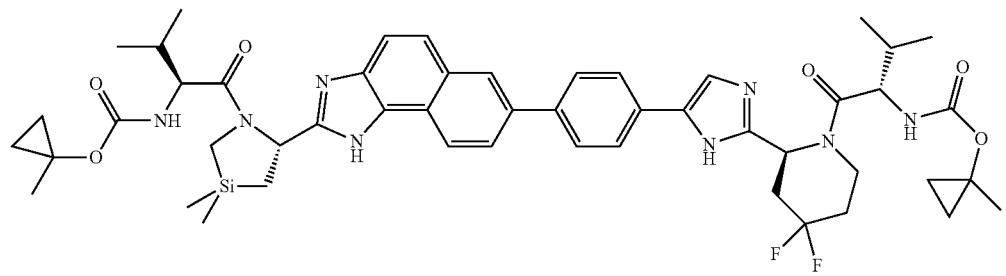 |
| 87 | 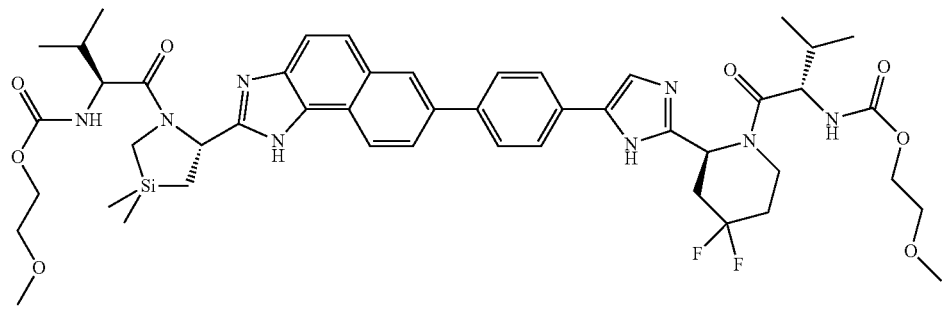 |

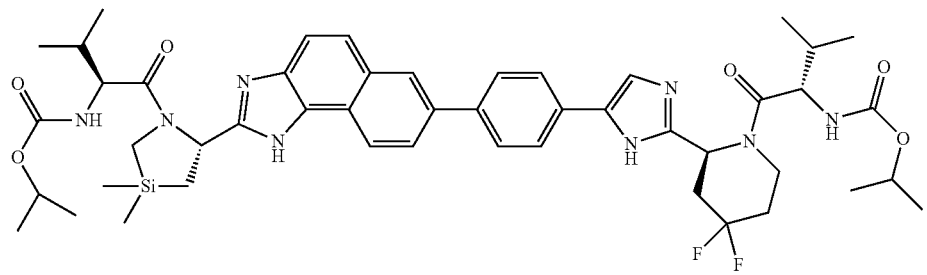
88
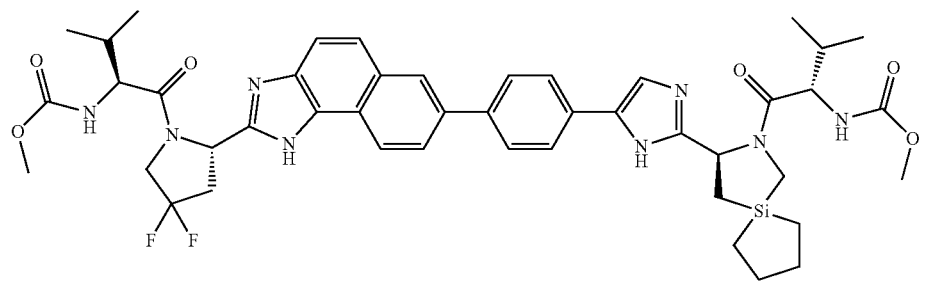
89
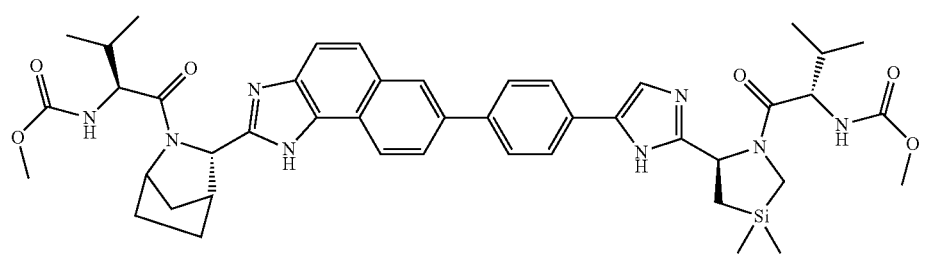
90
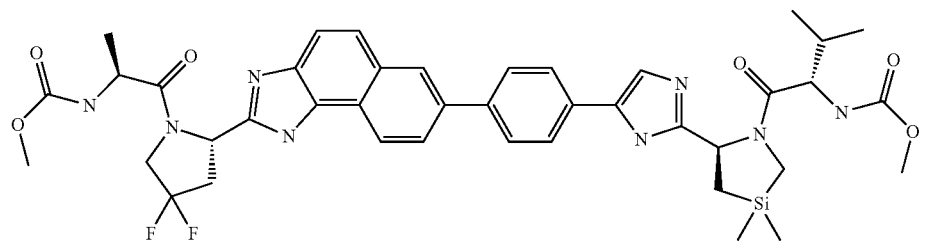
99
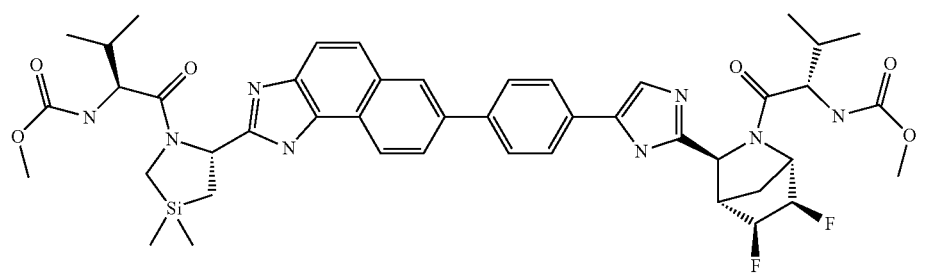
100
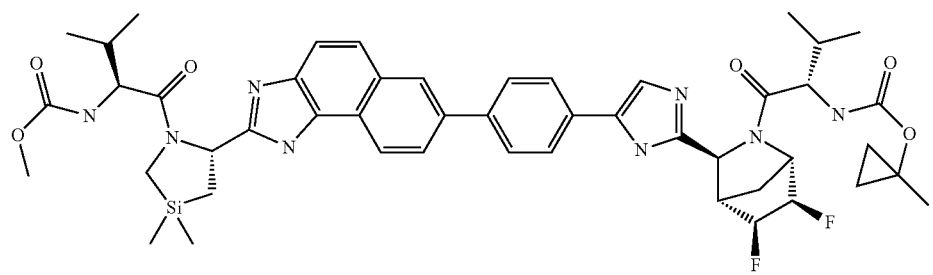
101

-continued

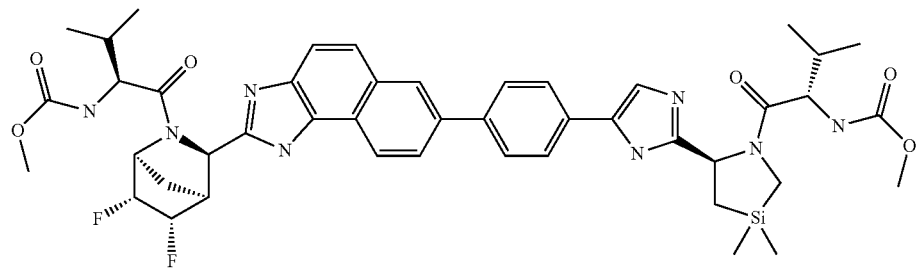
102

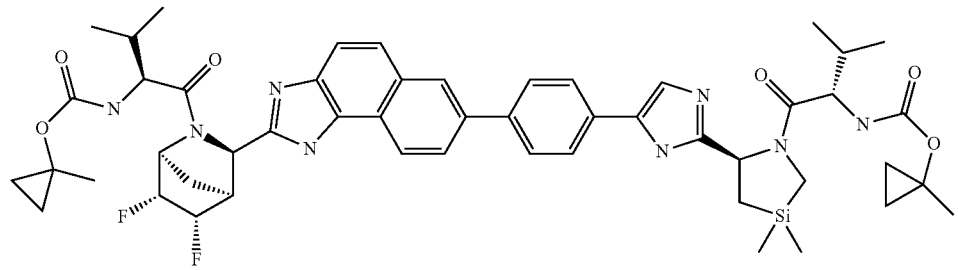
103

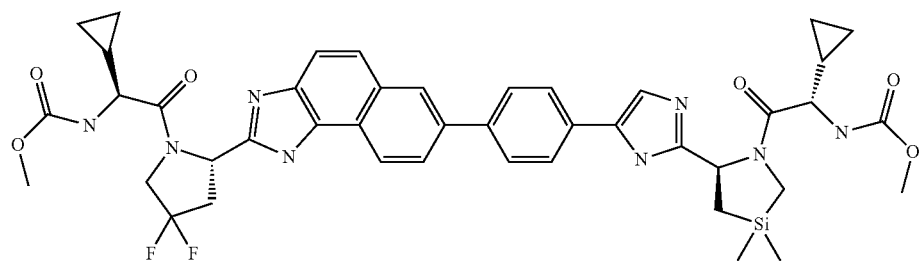
104

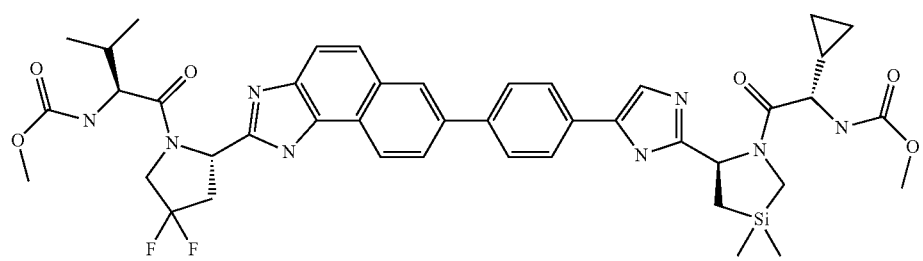
105

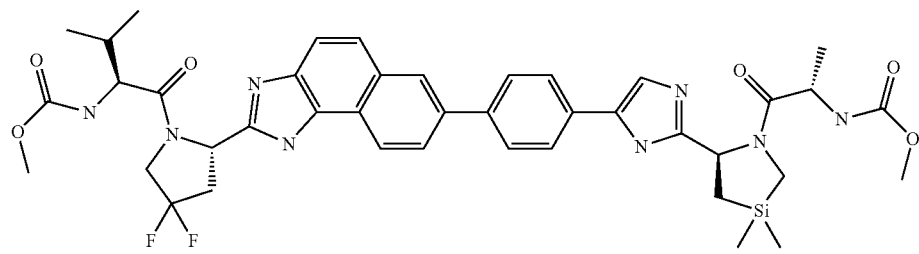
106 and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-8 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available which contain intact fused tricyclic tricyclic ring systems. These starting materials and intermediates are available from commercial suppliers such as Sigma-Aldrich (St. Louis, Mo.) and Acros Organics Co. (Fair Lawn, N.J.). Such starting materials and intermediates compounds are used as received. When such fused tricyclic moieties are not commercially available, they can be prepared using methods well-known to those skilled in the art of organic synthesis. Such synthetic methods include, but are not limited to, those described in Kricka et al., *J. Chem. Soc. Perkin Trans I*, 859-863 (1973); Kricka et al., *Chem. Rew.*, 74, 101-123, (1974); Kurfuerst et al., *Coll. Czech. Chem. Comm.*, 54, 1705-1715, (1989); Saroja et al., *J. Org. Chem.* 69, 987-990, (2004); Fanta et al., *Synth.* 9-21, (1974), U.S. Patent Publication No. US2005038037; and International Publication No. WO2004039859.

Scheme 1 shows a method useful for making the naphthyl imidazole compounds of formula A7 and A8, which are useful intermediates for making the Compounds of Formula (I).

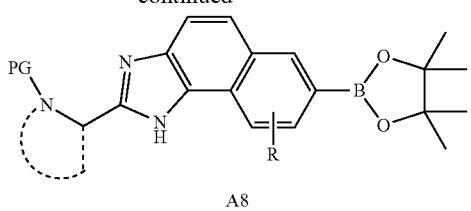

Nitration of bromonaphthyl acetamide A1 provides nitro analog A2 (*J. Am. Chem. Soc*, 73:4297 (1997)). The removal of acetyl group under acidic conditions followed by reduction of the nitro group should afford diaminonaphthalene A4. Coupling of the aniline to a cyclic or acyclic N-protected-α-amino acid A5 gives an amide of formula A6, which upon heating in acetic acid will cyclize to provide tricyclic bor-monaphthylimidazole A7. The bromide could be converted to a boronate A8 with a palladium catalyst.

Scheme 2 shows a method useful for making the quinolineimidazole compounds of formula B6, which are useful intermediates for making the Compounds of Formula (I).

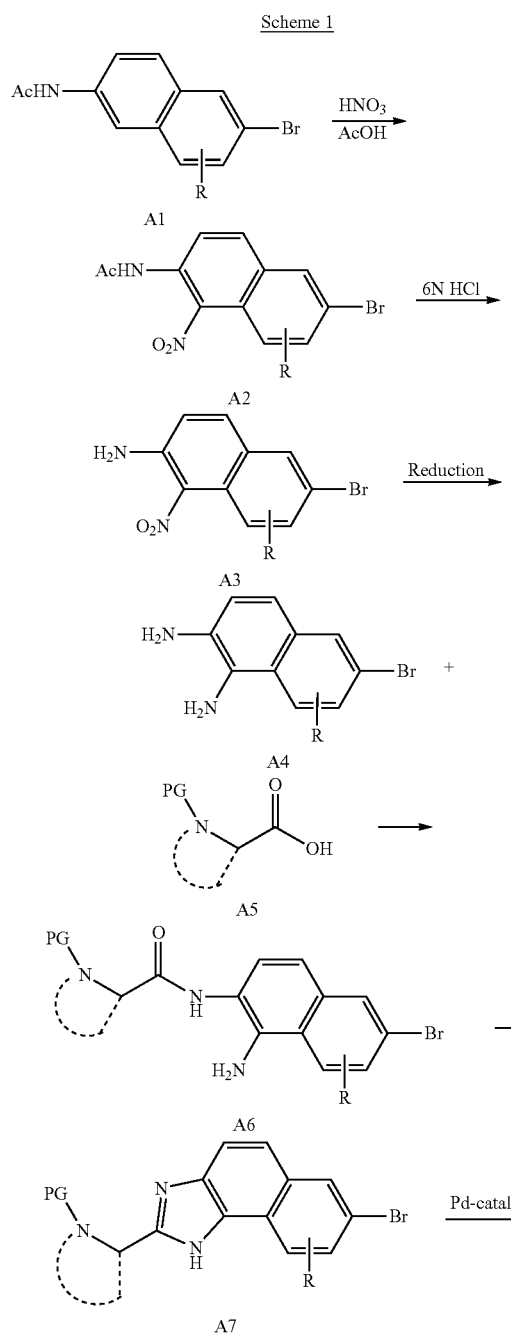

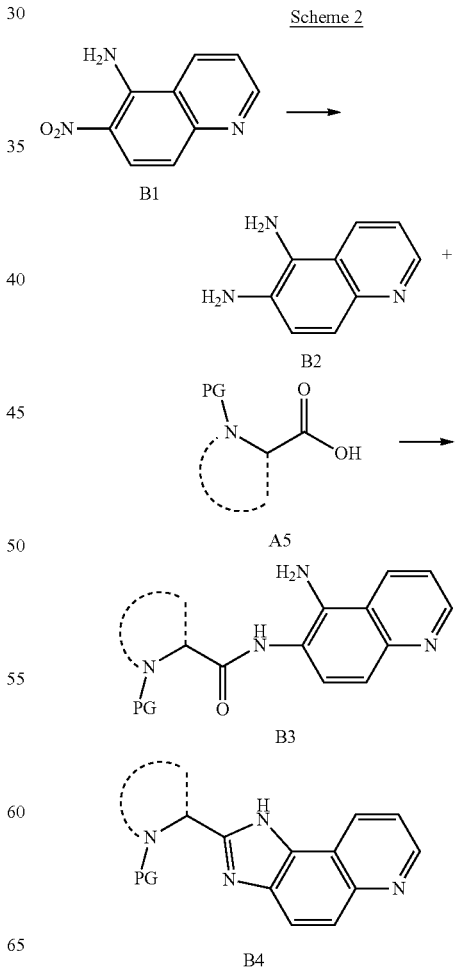

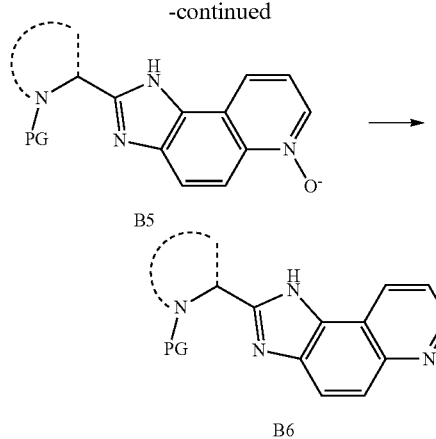

B5

B6

Commercially available aminonitroquinoline B1 can be reduced to diaminoquinoline B2, which is then coupled to a cyclic or acyclic N-protected α-amino acid A5 to provide an amide B3. It can then be cyclized to quinolineimidazole B4 under acidic conditions. N-oxide B5 can then be obtained with m-chloroperbenzoic acid. Upon treatment with phosphorous oxychloride, B5 should give the desired chloroquinoline B6, which can used in Suzuki coupling reactions.

Scheme 3 shows a method useful for making the boronic acid compounds of formula C4, which are useful intermediates for making the Compounds of Formula (I), where in "C" is a monocyclic 5 to 6-membered heteroaryl (examples: thiophene or pyridine).

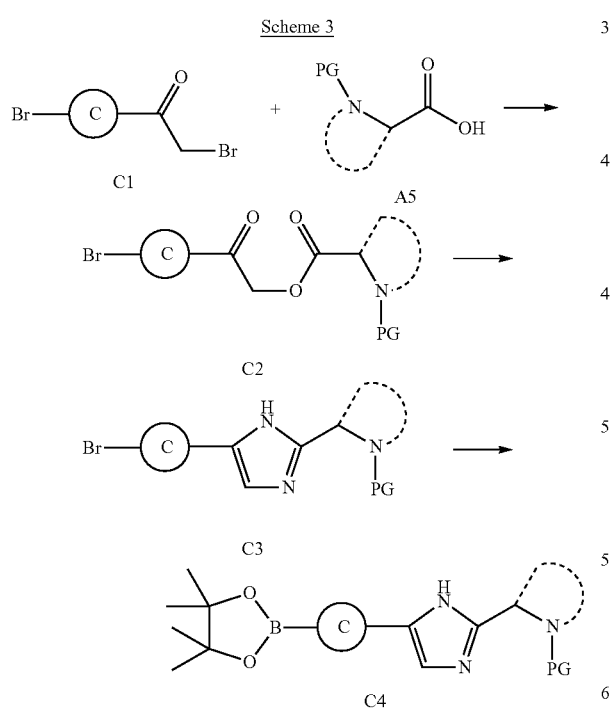

The Suzuki coupling partner C3 or C4 can be prepared from commercially available heteroaryl bromoacetyl compound of formula C1. (Scheme 3). When treated with an N-protected amino acid (PG-AA-OH) in the presence of an amine base, e.g., DIPEA, a ketoester C2 is formed. If heated together with ammonium acetate, the ketoester is converted to the desired imidazole derivative C3. The bromide can then be converted to a boronate C4 with a palladium catalyzed reaction.

Scheme 4 shows methods useful for making the compounds of formula C1 and C3, which are useful intermediates for making the Compounds of Formula (I), wherein variable C is other than a bond and B is an imidazole ring.

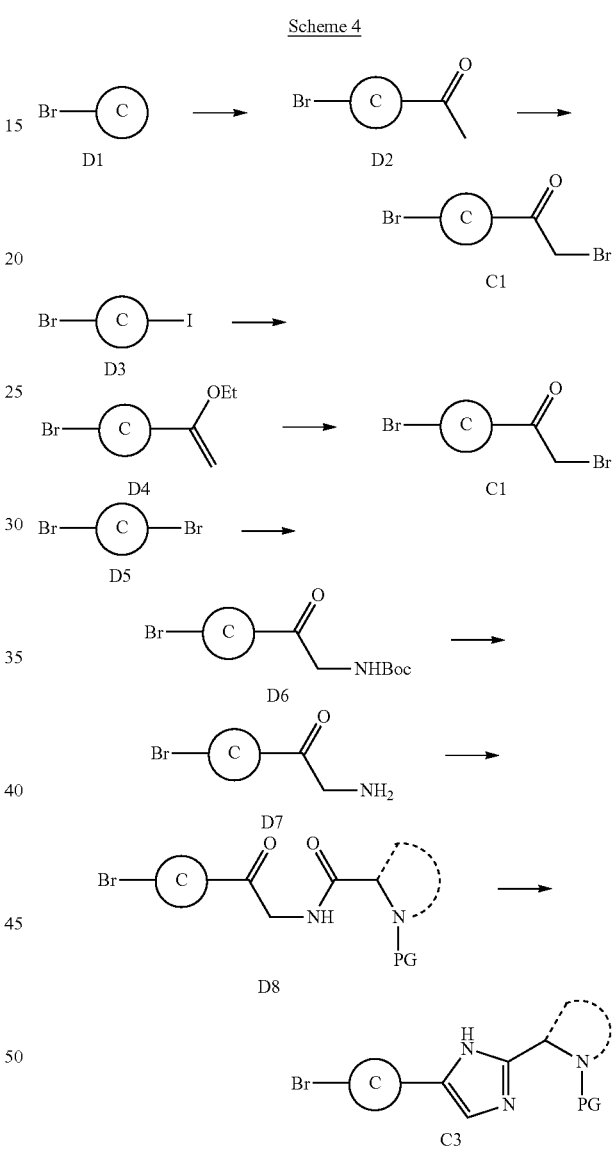

When heteroaryl bromoacetyl C1 is not commercially available, it can be prepared by performing Friedel-Crafts acylation on a heteroaryl bromide of formula D1 using well-known methods, (e.g., those described in Kricka et al., *J. Chem. Soc. Perkin Trans I,* 859-863 (1973), and Kricka et al, *Chem. Rew.,* 74, 101-123, (1974)) to provide the acylated products of formula D2. A compound of formula D2 can then be brominated using bromine, for example, to provide the compounds of formula C1.

On the other hand, bromo-iodo substituted heteroaromatic rings D3 can undergo a Stille coupling with (α-ethoxyvinyl) tributylstannane in the presence of a palladium catalyst using the methods including, but not limited to those described in Choshi et al., *J. Org. Chem.*, 62:2535-2543 (1997), and Scott et al., *J. Am. Chem. Soc.*, 106:4630 (1984)), to provide the ethyl-vinyl ether intermediate D4. Treating D4 with N-bromosuccimide gives the desired bromoacetyl intermediate C1, which can then be elaborated to advanced intermediates C3 or C4 for Suzuki coupling.

Alternatively, a heteroaromatic dibromide of formula D5 can be lithiated using n-butyl lithium and then quenched with N-Boc-glycine Weinreb amide to provide a Boc-protected β-keto amino compound of formula D6. Removal of the Boc group using TFA, for example, provides an amine compound of formula D7, which can then be coupled with an N-protected amino acid using typical amide bond forming reagents such as HATU to provide a ketoamide compound of formula D8. Upon heated in the presence of ammonium acetate, compound D8 can be cyclized to the imidazole analog of formula C3.

Scheme 5 shows a method useful for making the boronic acid compounds of formula E4, which are useful intermediates for making the Compounds of Formula (I).

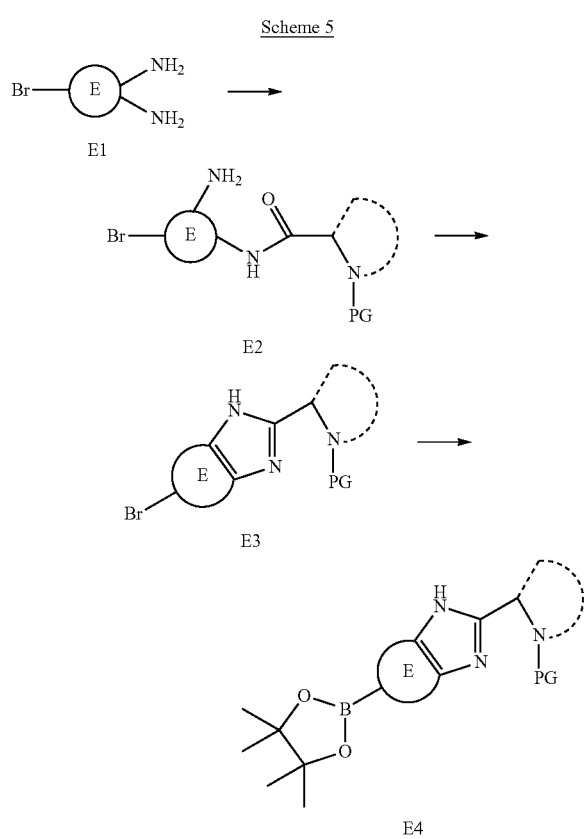

A heteroaromatic diamine E1 could be converted to a bicyclic imidazole E3 using the two step coupling-cyclization procedure described, for example, in Scheme 3. The corresponding boronate E4 can then easily be obtained from bromide E3 via well-known chemistry. Both E3 and E4 can be used as intermediate coupling partners in a Suzuki coupling process to provide the Compound of Formula (I).

Scheme 6 shows methods useful for making the Compounds of Formula (I) via a Suzuki Coupling process.

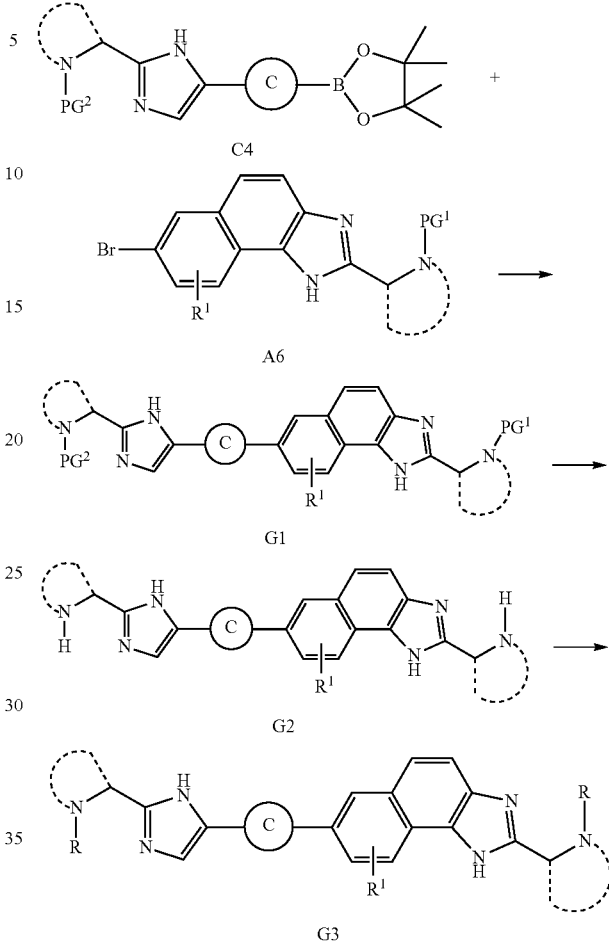

A Suzuki coupling between protected imidazole boronate C4 (or boronic acid, not shown) and the fused bi-aryl tricyclic bromide A6 using, for example, the methods described in *Angew Chem. Int. Ed. Engl.*, 40, 4544 (2001) provide the compounds of formula G1. Compounds of formula G1 can then be used to provide compounds of formula G2 by removal of the nitrogen protecting groups of G1. An appropriate cap of group R can be added to the deprotected amino groups of G2 using reactions including, but not limited to acylation (with an acyl chloride or amino acid coupling reagent such as HATU or HOBt/EDCI), sulfonylation (with a sulfonyl chloride) or alkylation (with alkyl halide or reductive amination) to provide the desired Compounds of Formula (I).

Scheme 7 shows alternative methods useful for making the Compounds of Formula (I) via a Suzuki Coupling process.

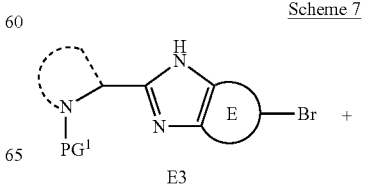

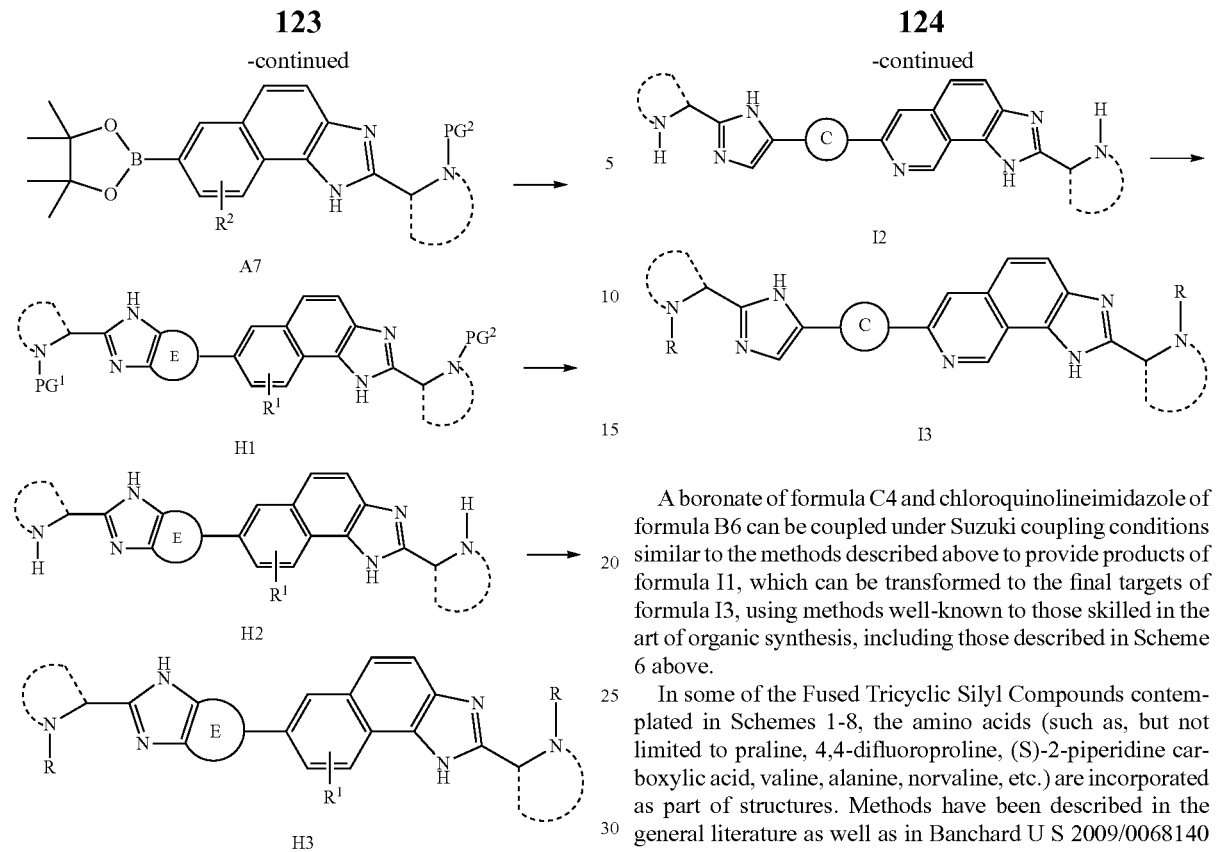

Similarly, a bicyclic bromide of formula E3 and fused tricyclic boronate of formula A7 can be joined using the methods described in Scheme 6 above, to provide coupled intermediates of formula H1. The compounds of formula H1 can then be further elaborated using, for example, the methods described in Scheme 6 above, to provide the Compounds of Formula (I), wherein C is a bond and B is a bicyclic heteroarylene group.

Scheme 8

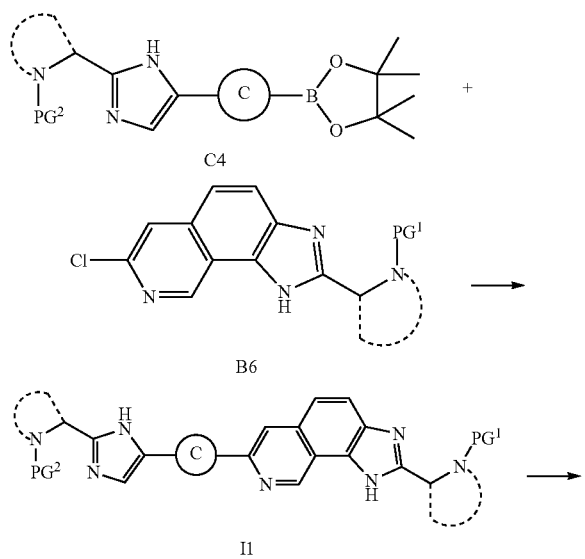

A boronate of formula C4 and chloroquinolineimidazole of formula B6 can be coupled under Suzuki coupling conditions similar to the methods described above to provide products of formula I1, which can be transformed to the final targets of formula I3, using methods well-known to those skilled in the art of organic synthesis, including those described in Scheme 6 above.

In some of the Fused Tricyclic Silyl Compounds contemplated in Schemes 1-8, the amino acids (such as, but not limited to praline, 4,4-difluoroproline, (S)-2-piperidine carboxylic acid, valine, alanine, norvaline, etc.) are incorporated as part of structures. Methods have been described in the general literature as well as in Banchard U S 2009/0068140 for the preparation of such amino acid-derived intermediates.

One skilled in the art of organic synthesis will recognize that the synthesis of fused tricyclic cores in Formula (I) may require protection of certain functional groups (i.e., derivatization for the purpose of chemical compatibility with a particular reaction condition). Suitable protecting groups for the various functional groups of these compounds and methods for their installation and removal can be found in Greene et al., *Protective Groups in Organic Synthesis*, Wiley-Interscience, New York, (1999).

One skilled in the art of organic synthesis will also recognize that one route for the synthesis of fused bi-aryl tricyclic cores in Formula (I) may be more desirable depending on the choice of appendage substituents. Additionally, one skilled in the art will recognize that in some cases the order of reactions may differ from that presented herein to avoid functional group incompatibilities and can amend the synthetic route accordingly.

One skilled in the art of organic synthesis will recognize that the synthesis of certain fused tricyclic cores in Formula (I) require the construction of an amide bond. Methods useful for making such amide bonds, include but are not limited to, the use of a reactive carboxy derivative (e.g., an acid halide, or ester at elevated temperatures) or the use of an acid with a coupling reagent (e.g. HOBt, EDCI, DCC, HATU, PyBrop) with an amine.

The preparation of ring systems contemplated in this invention have been described in the literature and in compendia such as "Comprehensive Heterocyclic Chemistry" editions I, II and III, published by Elsevier and edited by A. R. Katritzky & R J K Taylor. Manipulation of the required substitution patterns have also been described in the available chemical literature as summarized in compendia such as "Comprehensive Organic Chemistry" published by Elsevier and edited by D H R, Barton and W. D. Ollis; "Comprehensive Organic Functional Group Transformations" edited by edited by A. R. Katritzky & R J K Taylor and "Comprehensive Organic Transformation" published by Wily CVH and edited by R. C. Larock.

The starting materials used and the intermediates prepared using the methods set forth in the Schemes above may be isolated and purified if desired using conventional techniques, including but not limited to filtration, distillation, crystallization, chromatography and alike. Such materials can be characterized using conventional means, including physical constants and spectral data.

Uses of the Fused Tricyclic Silyl Compounds

The Fused Tricyclic Silyl Compounds are useful in human and veterinary medicine for treating or preventing a viral infection in a patient. In one embodiment, the Fused Tricyclic Silyl Compounds can be inhibitors of viral replication. In another embodiment, the Fused Tricyclic Silyl Compounds can be inhibitors of HCV replication. Accordingly, the Fused Tricyclic Silyl Compounds are useful for treating viral infections, such as HCV. In accordance with the invention, the Fused Tricyclic Silyl Compounds can be administered to a patient in need of treatment or prevention of a viral intention.

Accordingly, in one embodiment, the invention provides methods for treating a viral infection in a patient comprising administering to the patient an effective amount of at least one Fused Tricyclic Silyl Compound or a pharmaceutically acceptable salt thereof.

Treatment or Prevention of a Flaviviridae Virus

The Fused Tricyclic Silyl Compounds can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Fused Tricyclic Silyl Compounds are useful in the inhibition of HCV (e.g., HCV NS5A), the treatment of HCV infection and/or reduction of the likelihood or severity of symptoms of HCV infection and the inhibition of HCV viral replication and/or HCV viral production in a cell-based system. For example, the Fused Tricyclic Silyl Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Fused Tricyclic Silyl Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Fused Tricyclic Silyl Compounds are also useful in the preparation and execution of screening assays for antiviral compounds. For example the Fused Tricyclic Silyl Compounds are useful for identifying resistant HCV replicon cell lines harboring mutations within NS5A, which are excellent screening tools for more powerful antiviral compounds. Furthermore, the Fused Tricyclic Silyl Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Fused Tricyclic Silyl Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Fused Tricyclic Silyl Compound, or a pharmaceutically acceptable salt thereof, and (ii) at least one additional therapeutic agent that is other than a Fused Tricyclic Silyl Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Fused Tricyclic Silyl Compound and an additional therapeutic agent may be present in fixed amounts (dosage amounts) in a single dosage unit (e.g., a capsule, a tablet and the like).

In one embodiment, the at least one Fused Tricyclic Silyl Compound is administered during a time when the additional therapeutic agent(s) exert their prophylactic or therapeutic effect, or vice versa.

In another embodiment, the at least one Fused Tricyclic Silyl Compound and the additional therapeutic agent(s) are administered in doses commonly employed when such agents are used as monotherapy for treating a viral infection.

In another embodiment, the at least one Fused Tricyclic Silyl Compound and the additional therapeutic agent(s) are administered in doses lower than the doses commonly employed when such agents are used as monotherapy for treating a viral infection.

In still another embodiment, the at least one Fused Tricyclic Silyl Compound and the additional therapeutic agent(s) act synergistically and are administered in doses lower than the doses commonly employed when such agents are used as monotherapy for treating a viral infection.

In one embodiment, the at least one Fused Tricyclic Silyl Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Fused Tricyclic Silyl Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Fused Tricyclic Silyl Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/

Vertex), VCH-916 (ViroChem), VCH-716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the faun of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flannel Technologies), belerofon (Nautilus) and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillion), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31): 9340-9348 (1997); Ingallinella et al., *Biochemistry*, 37(25): 8906-8914 (1998); Llinàs-Brunet et al., *Bioorg Med Chem Lett*, 8(13): 1713-1718 (1998); Martin et al., *Biochemistry*, 37(33):11459-11468 (1998); Dimasi et al., *J Virol*, 71(10): 7461-7469 (1997); Martin et al., *Protein Eng*, 10(5):607-614 (1997); Elzouki et al., *J Hepat*, 27(1):42-48 (1997); *Bio World Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

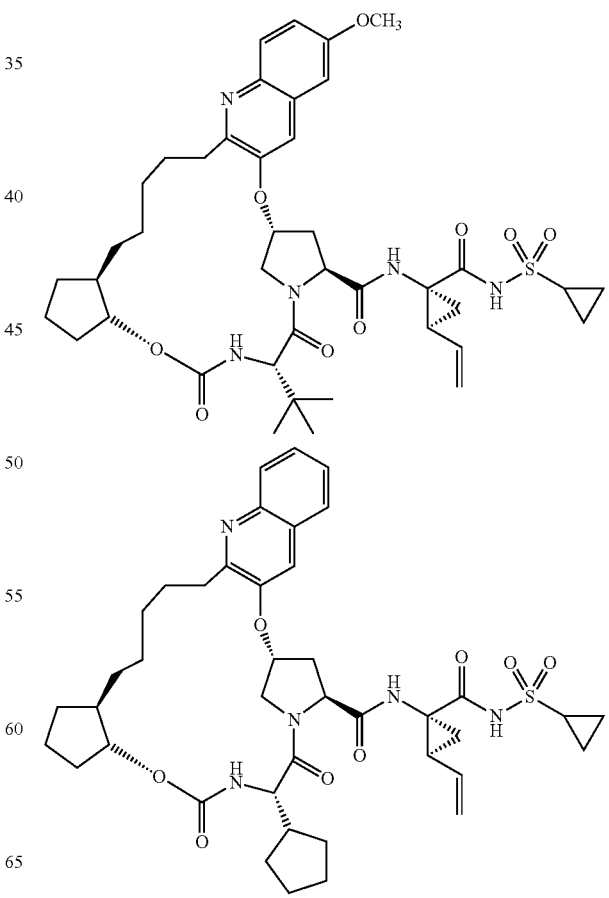

131
-continued
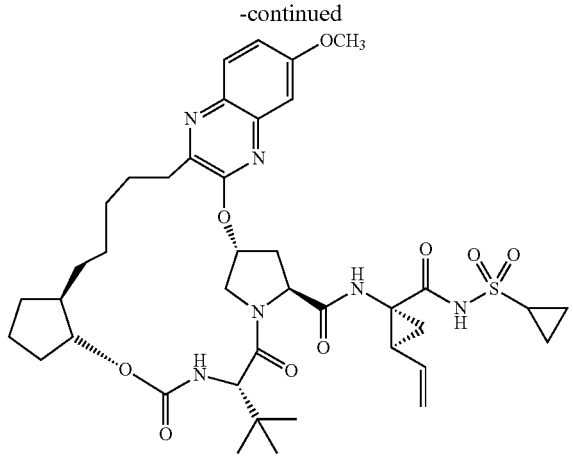
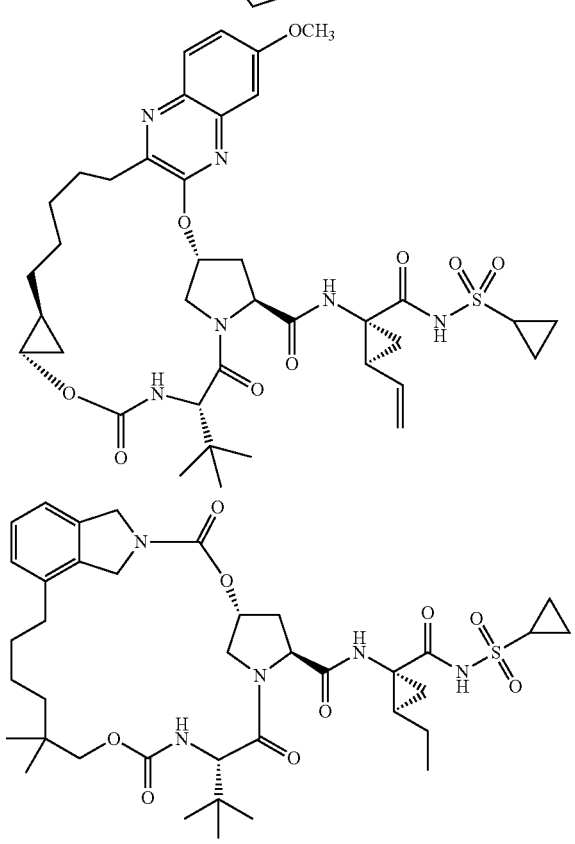
132
-continued
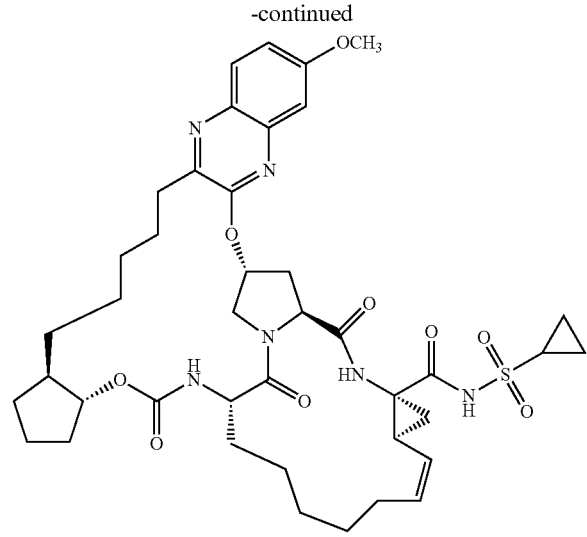
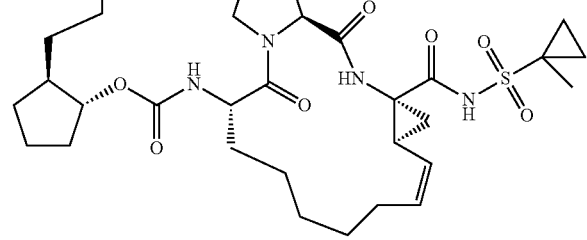
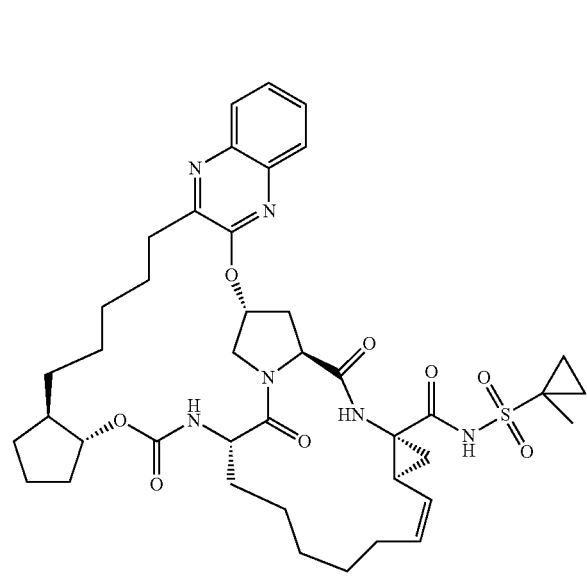

133
-continued
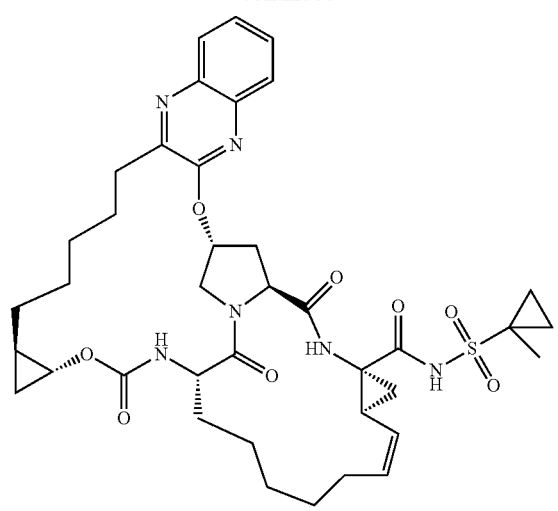
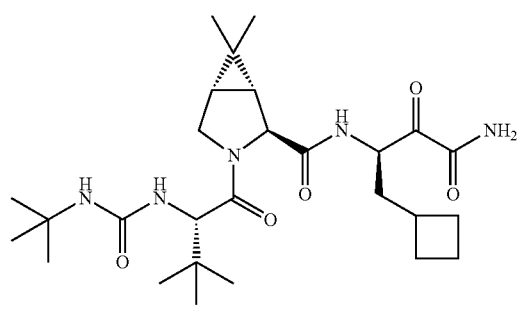
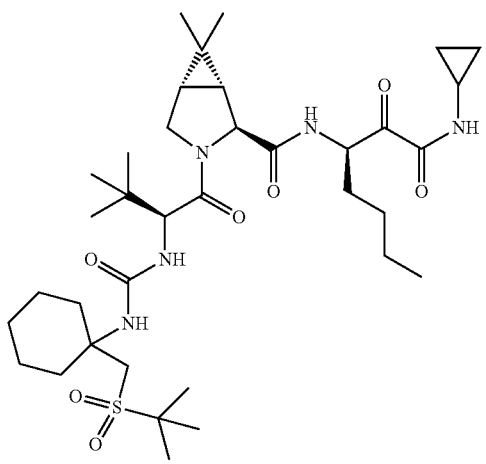
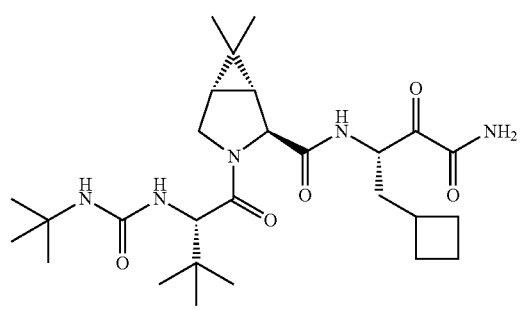
134
-continued
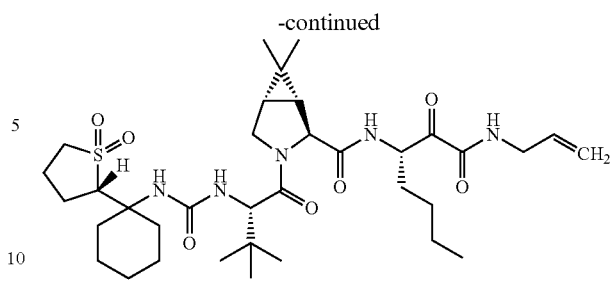
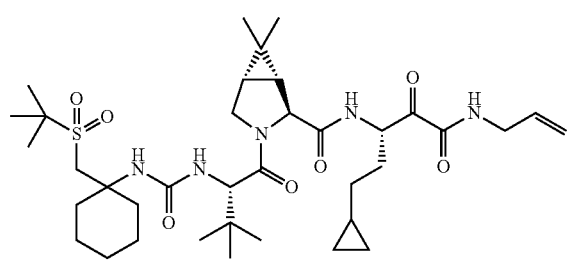
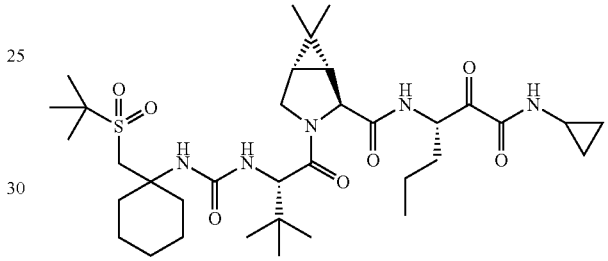
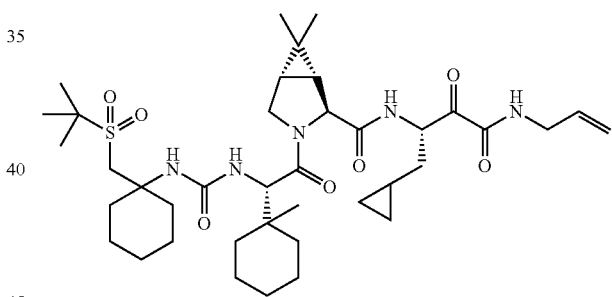
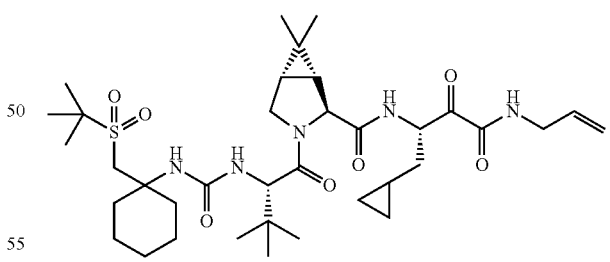
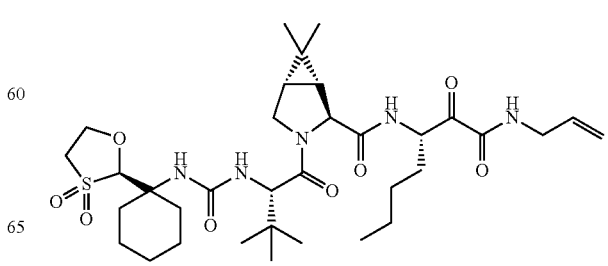

-continued
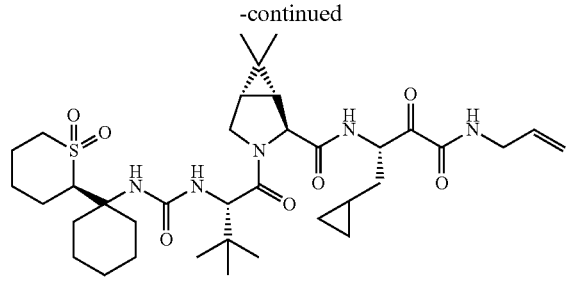
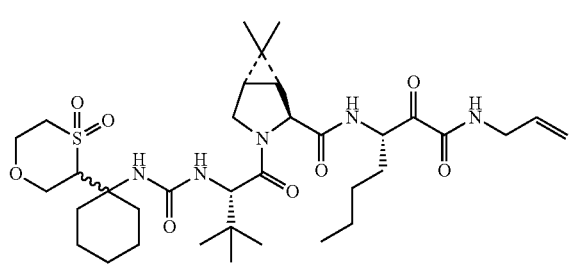
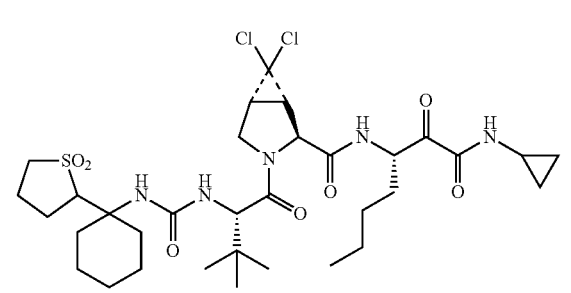
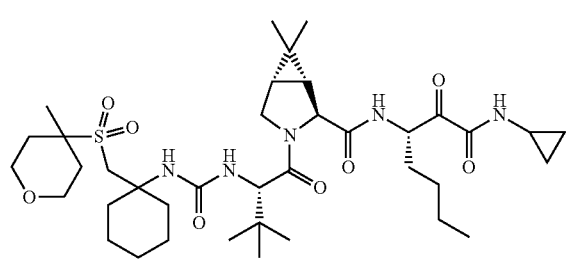
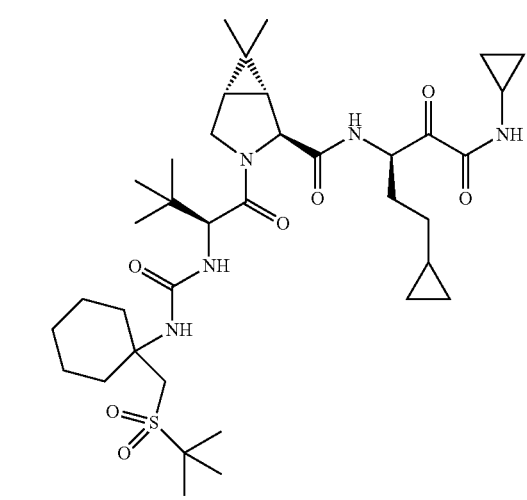
-continued
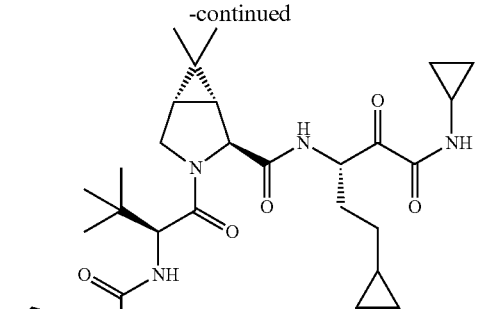
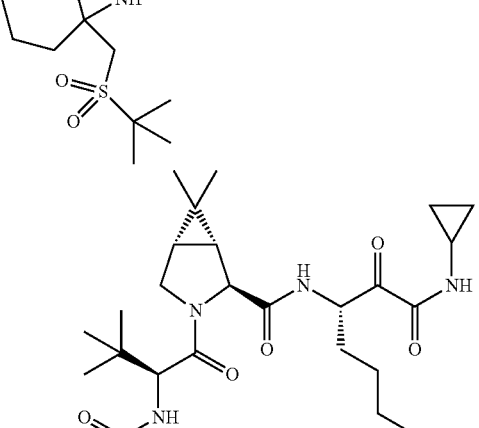
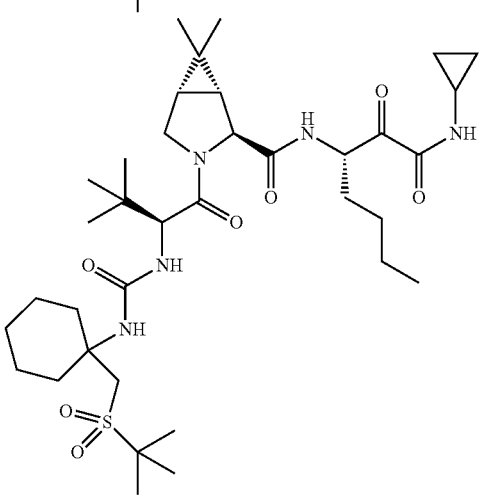
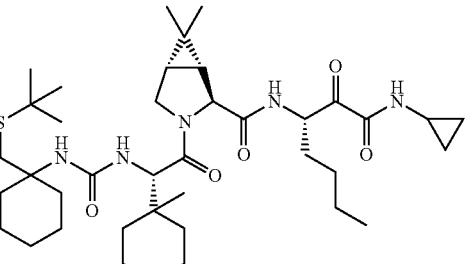
and
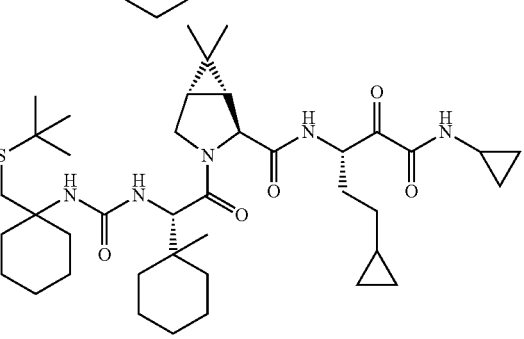
and pharmaceutically acceptable salts thereof.
Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

Viral entry inhibitors useful as second additional therapeutic agents in the present compositions and methods include, but are not limited to, PRO-206 (Progenies), REP-9C (REPICor), SP-30 (Samaritan Pharmaceuticals) and ITX-5061 (iTherx).

HCV NS4A inhibitors useful in the useful in the present compositions and methods include, but are not limited to, those disclosed in U.S. Pat. Nos. 7,476,686 and 7,273,885; U.S. Patent Publication No, US20090022688; and International Publication Nos. WO 2006/019831 and WO 2006/019832. Additional HCV NS4A inhibitors useful as second additional therapeutic agents in the present compositions and methods include, but are not limited to, AZD2836 (Astra Zeneca), ACH-1095 (Achillion) and ACH-806 (Achillion).

HCV NS5A inhibitors useful in the present compositions and methods include, but are not limited to, A-832 (Arrow Therpeutics), PPI-461 (Presidio), PPI-1301 (Presidio) and BMS-790052 (Bristol-Myers Squibb).

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis), MBL-HCV1 (MassBiologics), GI-5005 (GlobeImmune), CT-011 (CureTech/Teva) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenies), HepaCide-I (Nano Virocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Fused Tricyclic Silyl Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Fused Tricyclic Silyl Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3 MIU(12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3 MIU (11.1 mcg/mL)/TIW for at least 48 to 52 weeks, or alternatively 6 MIU/TIW for 12 weeks followed by 3 MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the Fused Tricyclic Silyl Compounds are useful in veterinary and human medicine. As described above, the Fused Tricyclic Silyl Compounds are useful for treating or preventing HCV infection in a patient in need thereof.

When administered to a patient, the Fused Tricyclic Silyl Compounds can be administered as a component of a composition that comprises a pharmaceutically acceptable carrier or vehicle. The present invention provides pharmaceutical compositions comprising an effective amount of at least one Fused Tricyclic Silyl Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tricyclic Silyl Compounds are administered orally.

In another embodiment, the one or more Fused Tricyclic Silyl Compounds are administered intravenously.

In one embodiment, a pharmaceutical preparation comprising at least one Fused Tricyclic Silyl Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Silyl Compound(s) by weight or volume. In various embodiments, the present compositions can contain, in one embodiment, from about 1% to about 70% or from about 5% to about 60% of the Fused Tricyclic Silyl Compound(s) by weight or volume.

The quantity of Fused Tricyclic Silyl Compound in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tricyclic Silyl Compounds will be regulated according to the judgment of the attending clinician considering such factors as age, condition and size of the patient as well as severity of the symptoms being treated. Generally, a total daily dosage of the Fused Tricyclic Silyl Compounds range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Fused Tricyclic Silyl Compound or a pharmaceutically acceptable salt thereof; (ii) one or more additional therapeutic agents that are not a Fused Tricyclic Silyl Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and two additional therapeutic agents, each of which are independently selected from the group consisting of HCV antiviral agents, immunomodulators, and anti-infective agents.

Kits

In one aspect, the present invention provides a kit comprising a therapeutically effective amount of at least one Fused Tricyclic Silyl Compound, or a pharmaceutically acceptable salt, solvate, ester or prodrug of said compound and a pharmaceutically acceptable carrier, vehicle or diluent.

In another aspect the present invention provides a kit comprising an amount of at least one Fused Tricyclic Silyl Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Fused Tricyclic Silyl Compounds and the one or more additional therapeutic agents are provided in the same container. In one embodiment, the one or more Fused Tricyclic Silyl Compounds and the one or more additional therapeutic agents are provided in separate containers.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Intermediate Compound Int-1a

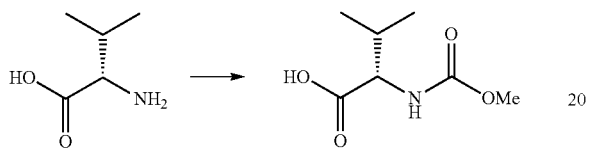
Int-1a

To a solution of L-valine (10.0 g, 85.3 mmol) in 1M aqueous NaOH solution (86 mL) at room temperature was added solid sodium carbonate (4.60 g, 43.4 mmol). The reaction mixture was cooled to 0° C. (ice bath) and then methyl chloroformate (7.20 mL, 93.6 mmol) was added dropwise over 20 minutes. The reaction mixture was then allowed to warm to room temperature, and allowed to stir at room temperature for an additional 4 hours. The reaction mixture was then diluted with diethyl ether (100 mL), the resulting solution was cooled to at 0° C., and then concentrated hydrochloric acid (18 mL, 216 mmol) was added slowly. The reaction was extracted with EtOAc (3×100 mL) and the combined organics were dried over MgSO₄, filtered and concentrated in vacuo to provide Compound Int-1a (13.5 g, 90%), which was used without further purification.

The following intermediates can be prepared by the reaction of L-valine with isopropyl chloroformate (Aldrich Inc.), 2-methoxyethyl chloroformate (Aldrich) or with 1-methylcyclopropyl hydroxysuccinimide respectively, using the method described above:

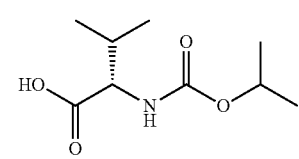
Int-1b

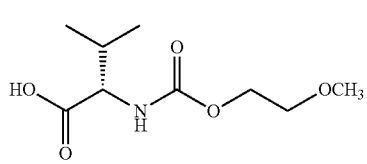
Int-1c

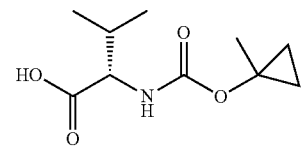
Int-1d

Example 2

Preparation of Intermediate Compound Int-2a

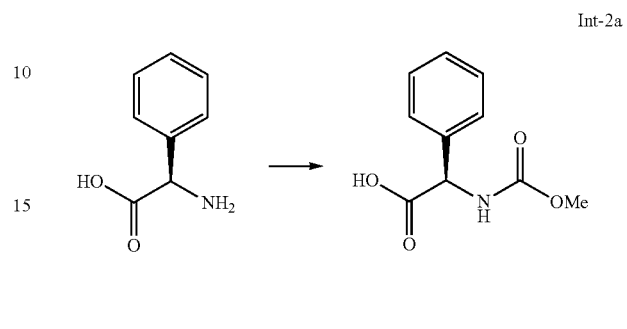
Int-2a

To a solution of D-phenylglycine (10.0 g, 66.1 mmol) and NaOH (21.2 g, 265 mmol) in water (60 mL) at 0° C. was added methyl chloroformate (10.2 mL, 133 mmol) dropwise over 20 minutes. The resulting mixture was allowed to stir at 0° C. for 1 hour, then was acidified using concentrated hydrochloric acid (25 mL, 300 mmol). The acidic solution was extracted with EtOAc (3×100 mL) and the combined organics were dried over MgSO₄, filtered and concentrated in vacuo to provide Compound Int-2a (12.6 g, 91%), which was used without further purification.

The following intermediates can be prepared by the reaction of glycine, L-Alanine and 4-F phenylglycine, respectively with methyl chloroformate (Aldrich Inc.) using the method described above:

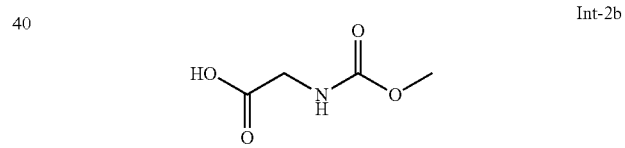
Int-2b

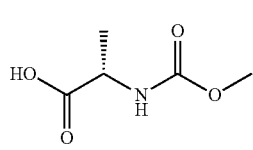
Int-2c

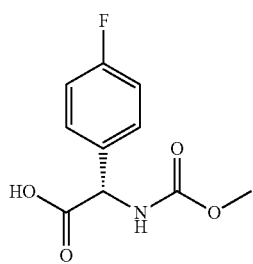
Int-2d

Example 3

Preparation of Intermediate Compound Int-3a

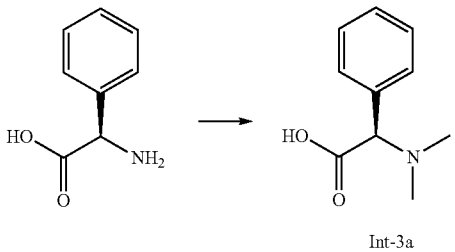

Int-3a

A solution of D-phenylglycine (20.0 g, 132 mmol), 37% aqueous formaldehyde (66 mL, 814 mmol) and 5% Pd on carbon (8.0 g, mmol) in a mixture of methanol (80 mL) and 1 N HCl (60 mL) was placed on a hydrogenation shaker and shook under an atmosphere of 35-40 psi hydrogen for 4 hours. The reaction was then flushed with nitrogen, filtered through a celite pad and concentrated in vacuo to provide Compound Int-3a (29.7 g, quant.) as a white solid, which was used without further purification.

Example 4

Preparation of Intermediate Compound Int-4-e

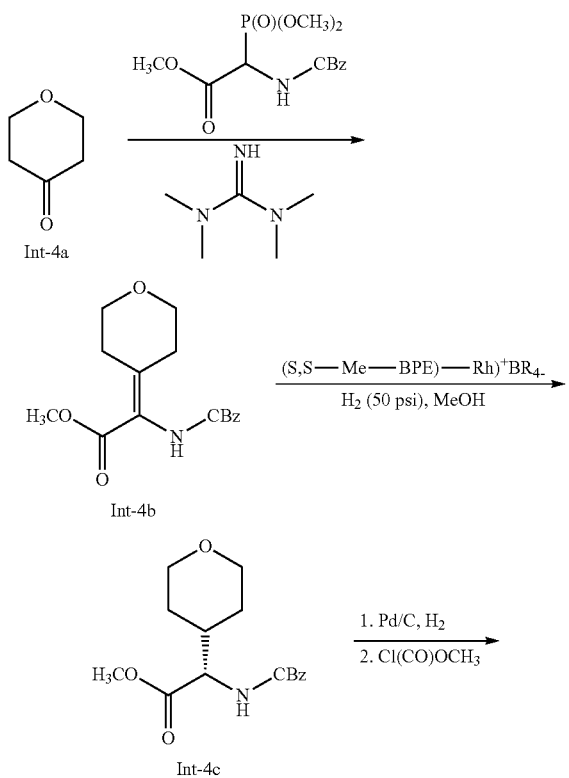

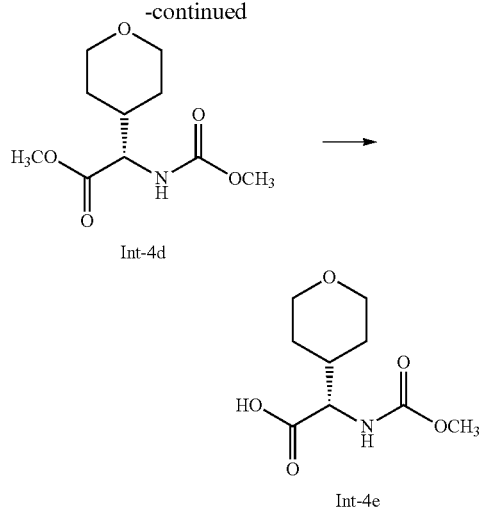

Int-4d

Int-4e

Step A—Synthesis of Intermediate Compound Int-4-b

To a solution of methyl 2-(benzyloxycarbonylamino)-2-(dimethoxyphosphoryl)acetate (10.0 g, 30.2 mmol, made as described in Hamada et al., Organic Letters; English; 20: 4664-4667 (2009)) in THF (100 mL) at −20° C. was added tetramethylguanidine (4.20 mL, 33.2 mmol). The reaction mixture was allowed to stir at −20° C. for 1 hour then dihydro-2H-pyran-4(3H)-one (Int-4a) was added (3.1 mL, 33.2 mmol) in THF (5 mL) and the reaction mixture was warmed to room temperature and stirred for about 15 hours. EtOAe (200 mL) was added and the organic mixture was washed with water (3×50 mL) and brine (50 mL). The organic layers were combined and dried with $Na_2SO_4$, filtered and concentrated in vacuo. The crude product was purified using flash chromatography on an ISCO 330 g Redi-Sep column using 0-35% EtOAc/hexanes as the eluent to provide Compound Int-4-b as a white solid (615 mg, 45%). $^1$H NMR ($CDCl_3$) δ 7.40-7.30 (m, 5H), 6.00 (br s, 1H), 5.12 (s, 2H), 3.80-3.65 (m, 7H), 2.92 (m, 2H), 2.52-2.48 (m, 2H).

Step B—Synthesis of Intermediate Compound Int-4c

To a solution of Int-4b (2.43 g, 7.96 mmol) in methanol (160 mL) previously purged with $N_2$ was added (−)-1,2-Bis ((2S,5S)-2,5-dimethylphospholano)ethane (cyclooctadiene) rhodium(I) tetrafluoroborate (487 mg, 0.880 mmol) under $N_2$. The mixture was shaken in a Parr shaker apparatus for 18 hours at 50 psi of $H_2$. After evacuating the hydrogen, the suspension was filtered and the filtrate was concentrated to provide Compound Int-4c as a white solid (1.30 g, 53%). $^1$H NMR ($CDCl_3$) δ 7.40-7.30 (m, 5H), 532 (br s, 1H), 5.12 (s, 2H), 4.40-4.30 (m, 1H), 4.00-3.95 (m, 2H), 3.75 (s, 3H), 3.40-3.25 (m, 2H), 2.10-1.95 (m, 1H), 1.50-1.45 (m, 4H).

Step C—Synthesis of Intermediate Compound Int-4d

To a suspension of 50% palladium on carbon (10% wet, 200 mg) in absolute ethanol (20 mL) under nitrogen was added Int-4c (1.06 g, 3.45 mmol). With stirring, the solution was placed under vacuum for 30 seconds and then was opened to a hydrogen gas balloon for 2 hours. After evacuating the hydrogen, the suspension was filtered through a Celite pad and the pad washed with ethanol (2×20 mL). The filtrate was concentrated to provide a colorless oil (585 mg, 98%). $^1$H NMR ($CDCl_3$) δ 4.06-3.96 (m, 2H), 3.73 (s, 3H), 3.48-3.28 (m, 3H), 1.92-1.78 (m, 1H), 1.61-1.47 (m, 6H).

To a solution of the colorless oil (585 mg, 3.37 mmol) and triethylamine (0.710 mL, 5.09 mmol) in $CH_2Cl_2$ (6 mL) was added methyl chloroformate (0.290 mL, 3.76 mmol). The reaction mixture was allowed to stir at room temperature for about 15 hours. Water (15 mL) was added and the aqueous mixture was extracted with CH$_2$Cl$_2$ (3×20 mL). The combined organic layers were dried over Na$_2$SO$_4$, filtered and concentrated in vacuo. The crude product was purified using flash chromatography on an ISCO 24 g Redi-Sep column using 0-3% MeOH/CH$_2$Cl$_2$ as the eluent to provide Compound Int-4d as a colorless oil (600 mg, 77%). $^1$H NMR (CDCl$_3$) δ 5.27-5.18 (m, 1H), 4.38-4.28 (m, 1H), 4.06-3.96 (m, 2H), 3.75 (s, 3H), 3.69 (s, 3H), 3.39-3.30 (m, 2H), 2.09-1.94 (m, 1H), 1.59-1.48 (m, 4H).

Step D—Synthesis of Intermediate Compound Int-4e

To a solution of compound Int-4d (600 mg, 2.59 mmol) in THF (5 mL) was added lithium hydroxide monohydrate (218 mg, 5.19 mmol) in water (5 mL). The reaction mixture was allowed to stir at room temperature for 2 hours then concentrated to half volume. The aqueous mixture was then acidified with 6N HCl and extracted with EtOAc (7×50 mL). The combined organic layers were dried over Na$_2$SO$_4$, filtered and concentrated to provide Compound Int-4e as an off-white solid (485 mg, 86%). $^1$H NMR (CD$_3$OD) δ 4.09-4.07 (m, 1H), 3.96-3.92 (m, 2H), 3.65 (s, 3H), 3.40-3.34 (m, 2H), 2.10-1.99 (m, 1H), 1.56-1.47 (m, 4H).

Example 5

Preparation of Intermediate Compound 5f

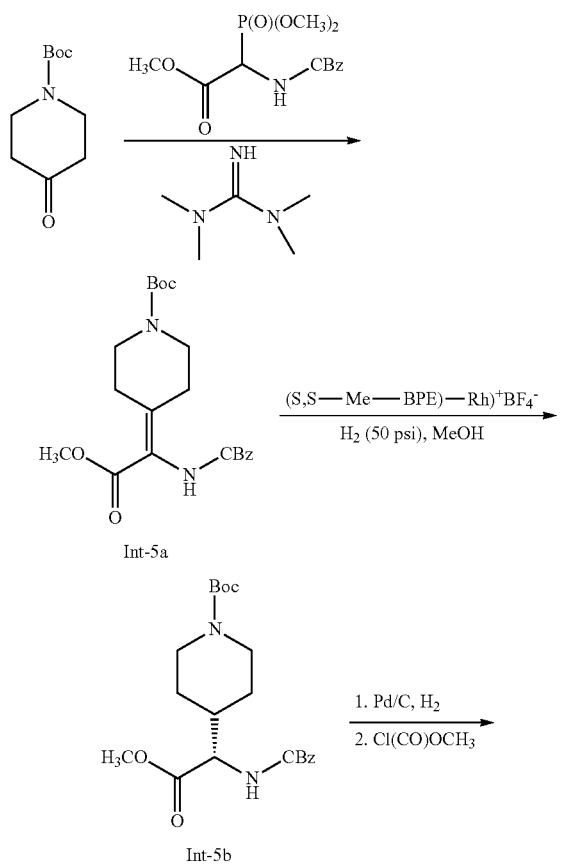

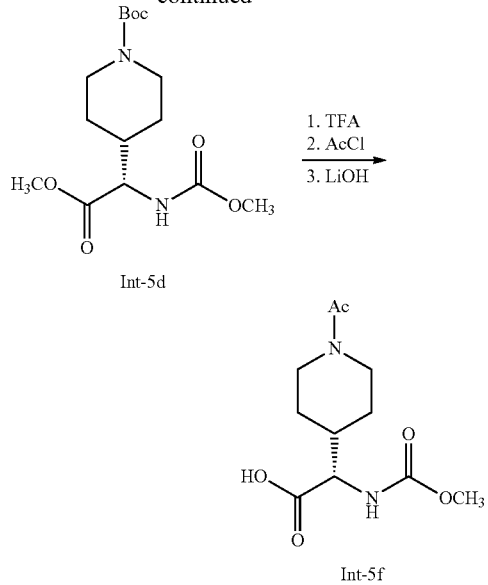

Step A—Synthesis of Intermediate Compound Int-2a

To a solution of methyl 2-(benzyloxycarbonylamino)-2-(dimethoxyphosphoryl)acetate (1.50 g, 4.52 mmol) in THF (5 mL) at −20° C. was added tetramethylguanidine (625 μL, 4.98 mmol). The reaction mixture was allowed to stir at −20° C. for 1 hour then tert-butyl 4-oxopiperidine-1-carboxylate was added (992 mg, 4.97 mmol) in THF (2 mL) and the reaction mixture was warmed to room temperature and stirred for about 15 hours. EtOAc (90 mL) was added and the organic mixture was washed with water (3×20 mL) and brine (25 mL). The combined organic layers were dried over Na$_2$SO$_4$, filtered and concentrated in vacuo. The crude product was purified using flash chromatography on an ISCO 40 g Redi-Sep column using 0-35% EtOAc/hexanes as the eluent to provide Compound Int-5a as a white semi-solid (1.1 g, 61%). $^1$H NMR (CDCl$_3$) δ 7.40-7.30 (m, 5H), 6.02 (br s, 1H), 5.12 (s, 2H), 3.80-3.40 (m, 7H), 2.90-2.80 (m, 2H), 2.45-2.35 (m, 2H), 1.45 (s, 9H).

Step B—Synthesis of Intermediate Compound Int-5b

To a solution of Int-5a (1.30 g, 3.21 mmol) in methanol (90 mL) previously purged with N$_2$ was added (−)-1,2-Bis((2S,5S)-2,5-dimethylphospholano)ethane (cyclooctadiene)rhodium(I) tetrafluoroborate (197 mg, 0.354 mmol) under N$_2$. The mixture was shaken in a Parr shaker apparatus for 18 hours at 50 psi of H$_2$. After evacuating the hydrogen, the suspension was filtered and the filtrate was concentrated to provide Compound Int-5b as a colorless oil (1.00 g, 77%). $^1$H NMR (CDCl$_3$) δ 7.40-7.30 (m, 5H), 5.35-5.25 (m, 1H), 5.10 (s, 2H), 4.40-4.35 (m, 1H), 4.20-4.10 (m, 2H), 3.70 (s, 3H), 2.70-2.55 (m, 2H), 2.00-1.90 (m, 1H), 1.65-1.40 (m, 1H), 1.30-1.20 (m, 2H).

Step C—Synthesis of Intermediate Compound Int-5c

To a solution of 50% palladium on carbon (10% wet, 250 mg) in absolute ethanol (20 mL) under nitrogen was added Int-5b (1.00 g, 2.46 mmol). With stirring, the solution was placed under vacuum for 30 seconds and then was opened to a hydrogen gas balloon for 2 hours. After evacuating the hydrogen, the suspension was filtered through a Celite pad and the pad washed with ethanol (2×20 mL). The filtrate was concentrated to provide Compound Int-5c as a colorless oil (670 mg, quant.). $^1$H NMR (CDCl$_3$) δ 4.21-4.08 (m, 2H), 3.73

(s, 3H), 3.31 (d, J=6.0 Hz, 1H), 2.75-2.57 (m, 2H), 1.84-1.70 (m, 1H), 1.68-1.56 (m, 1H), 1.45 (s, 9H), 1.45-1.20 (m, 5H).

Step D—Synthesis of Intermediate Compound Int-5d

To a solution of compound Int-5c (670 mg, 2.46 mmol) and triethylamine (0.520 mL, 3.73 mmol) in CH$_2$Cl$_2$ (10 mL) was added methyl chloroformate (0.210 mL, 2.72 mmol). The reaction mixture was allowed to stir at room temperature for about 15 hours. Water (20 mL) was added and the aqueous mixture was extracted with CH$_2$Cl$_2$ (2×15 mL). The combined organic layers were dried over Na$_2$SO$_4$, filtered and concentrated in vacuo. The crude product was purified using flash chromatography on an ISCO 24 g Redi-Sep column using 0-3% MeOH/CH$_2$Cl$_2$ as the eluent to provide Compound Int-5d as an off-white solid (515 mg, 63%). $^1$H NMR (CDCl$_3$) δ 5.26-5.17 (m, 1H), 4.38-4.30 (m, 1H), 4.20-4.07 (m, 2H), 3.75 (s, 3H), 3.68 (s, 3H), 2.71-2.57 (m, 2H), 2.00-1.85 (m, 1H), 1.87-1.48 (m, 2H), 1.44 (s, 9H), 1.35-1.18 (m, 2H).

Step E—Synthesis of Intermediate Compound Int-5e

Compound Int-5d (300 mg, 0.908 mmol) was dissolved in a mixture of TFA (2 mL) and CH$_2$Cl$_2$ (10 mL) and the solution was allowed to stir at room temperature for 1 hour before it was concentrated in vacuo to provide a solid. To this residue triethylamine (0.760 mL, 5.45 mmol) in CH$_2$Cl$_2$ (10 mL) was added followed by acetic anhydride (0.086 mL, 0.915 mmol). The reaction mixture was allowed to stir at room temperature for about 15 hours then concentrated in vacuo. The crude product was purified using flash chromatography on an ISCO 12 g Redi-Sep column using 0-4% MeOH/CH$_2$Cl$_2$ as the eluent to provide Compound Int-5e as a colorless oil (247 mg, 99%). $^1$H NMR (CDCl$_3$) δ 5.27-5.21 (m, 1H), 4.73-4.62 (m, 1H), 4.42-4.32 (m, 1H), 3.69 (s, 3H), 3.18 (s, 3H), 3.18-3.09 (m, 1H), 3.07-2.95 (m, 1H), 2.55-2.41 (m, 1H), 2.07 (s, 3H), 1.78-1.49 (m, 3H), 1.38-1.21 (m, 2H).

Step F—Synthesis of Intermediate Compound Int-5f

To a solution of compound Int-5e (247 mg, 2.59 mmol) in THF (3 mL) was added lithium hydroxide monohydrate (77 mg, 1.83 mmol) in water (3 mL). The reaction mixture was allowed to stir at room temperature for about 15 hours then concentrated to half volume. The aqueous mixture was then acidified with 1N HCl to pH 4 and extracted with EtOAc (7×15 mL). The combined organics were dried over Na$_2$SO$_4$, filtered and concentrated to provide Compound Int-5f as an off-white solid (106 mg, 45%). $^1$H NMR (CD$_3$OD) δ 5.52-5.43 (m, 1H), 4.71-4.62 (m, 1H), 4.44-4.31 (m, 1H), 3.91-3.81 (M, 1H), 3.70 (s, 3H), 3.12-2.99 (m, 1H), 2.58-2.46 (m, 1H), 2.10 (m, 4H), 1.86-1.54 (m, 2H), 1.50-1.21 (m, 3H).

Example 6

Preparation of Intermediate Compound Int-6f

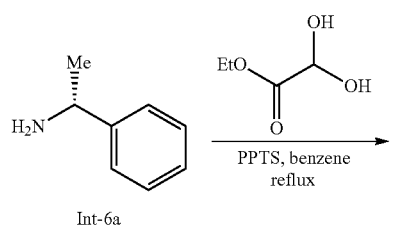

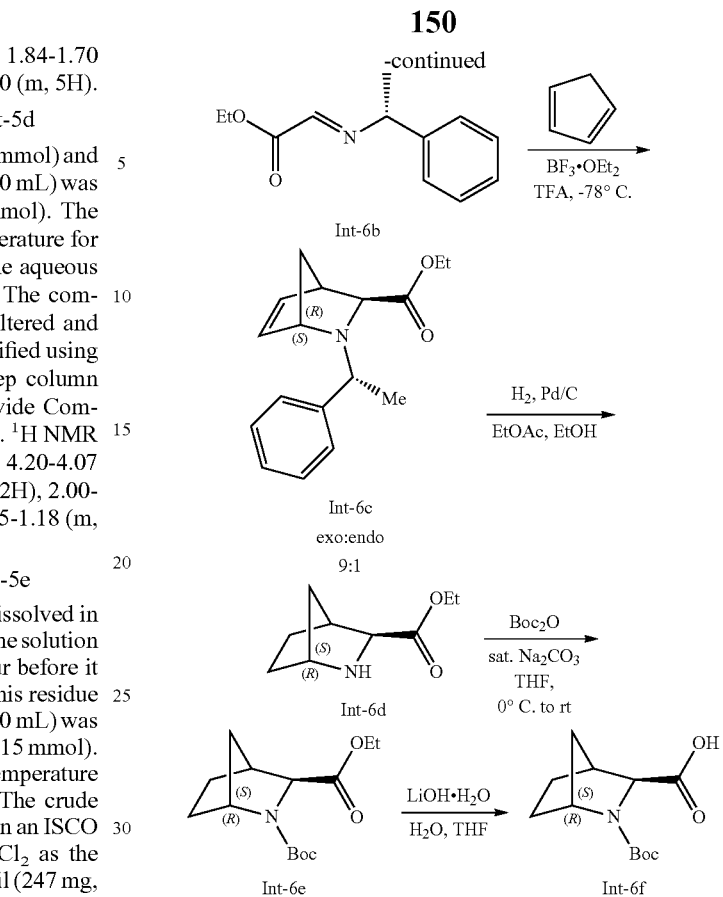

Step A—Synthesis of Intermediate Compound Int-6b

A stirred mixture of Int-6a (50.0 g, 0.412 mol), ethyl glyoxylate (81.5 mL, 50% in toluene, 0.412 mol) and PPTS (0.50 g, 2.00 mmol) in benzene (600 mL) was heated to reflux in a Dean-Stark apparatus until no further water (~8 mL) azeotroped from the reaction (~4 h). The resulting mixture was concentrated in vacuo. The crude residue Int-6b was used without purification: $^1$H NMR (300 MHz, CDCl$_3$) δ 7.72 (s, 1H), 7.36-7.24 (m, 5H), 4.61 (q, J=6.9 Hz, 1H), 4.35 (q, J=7.2 Hz, 2H), 1.62 (d, J=6.6 Hz, 3H), 1.34 (t, 7.2 Hz, 3H).

Step B—Synthesis of Intermediate Compound Int-6c

To a stirred solution of crude Int-6b in methylene chloride (600 mL) at −78° C. were added the following in 10 minute intervals: TFA (31.0 mL, 0.416 mol), boron trifluoride etherate (51.3 mL, 0.416 mol) and freshly distilled cyclopentadiene (32.7 g, 0.494 mol). After less than 2 minutes the reaction forms a thick brown mass. After 6 hours at −78° C. the reaction was allowed to slowly warm to room temperature for about 15 hours, at which time the reaction had formed a dark brown solution. The reaction was quenched with saturated aqueous Na$_2$CO$_3$ (~900 mL) and stirred for 30 minutes. The resultant solids were removed by filtration through Celite®. The aqueous filtrate was extracted with methylene chloride (3×100 mL). The combined extracts were washed with saturated aqueous NaCl (2×75 mL), dried over Na$_2$SO$_4$, filtered and concentrated in vacuo. The crude product was purified using flash column chromatography (silica; 8×18 cm) using 10% to 25% ethyl acetate/hexanes as the eluent to provide endo Int-6c (10.9 g, 9%) as a brown oil: $^1$H NMR (300 MHz, CDCl$_3$) δ 7.34-7.19 (m, 5H), 6.00-5.95 (m, 1H), 4.18 (q, J=7.1 Hz, 3H), 3.47 (s, 1H), 3.03 (s, 1H), 2.97 (q, J=6.5 Hz, 1H), 2.41 (s, 1H), 1.86 (d, J=8.2 Hz, 1H), 1.26 (t, J=6.6 Hz, 3H), 1.17 (t, J=6.6 Hz, 3H). Exo Int-6c (84.3 g, 74%) was collected as a brown oil: $^1$H NMR (300 MHz, CDCl$_3$) δ 7.34-7.19 (m, 5H), 6.36-6.33 (m, 1H), 6.22-6.18 (m, 1H), 4.37 (s, 1H), 3.87 (q, J=6.8 Hz, 2H), 3.10 (q, J=6.5 Hz, 1H), 2.96 (s, 1H), 2.27 (s, 1H), 2.20 (d, J=8.4 Hz, 1H), 1.48 (d, J=6.5 Hz, 3H), 1.01 (d, J=7.0 Hz, 3H), 1.00 (m, 1H).

Step C—Synthesis of Intermediate Compound Int-6d

A mixture of exo-Int-6c (15.8 g, 0.582 mol) and 10% Pd/C (4.07 g, 50% wet) in a 1:2 mixture of EtOH/EtOAc (150 mL) was shaken in a Parr hydrogenation apparatus under an atmosphere of H$_2$ (50 psi). After 23 hours the mixture was filtered through Celite® and the filtrate concentrated in vacuo. $^1$H NMR analysis of the resulting residue (10.8 g) showed some aromatic resonances present. Repetition of the hydrogenation procedure using 10% Pd/C (2.0 g) afforded Int-6d (10.0 g, quant.) as a brown oil: $^1$H NMR (300 MHz, CDCl$_3$) δ 4.18 (q, J=7.2 Hz, 3H), 3.54 (s, 1H), 3.32 (s, 1H), 2.62 (s, 1H), 2.23 (s, 1H), 1.64-1.39 (m, 5H), 1.31-1.20 (m, 4H).

Step D—Synthesis of Intermediate Compound Int-6e

To a stirred mixture of Int-6d (36.6 g, 0.236 mol) and saturated aqueous Na$_2$CO$_3$ (300 mL) in THF (600 mL) at 0° C. was added di-tert-butyl dicarbonate (59.0 g, 0.270 mol). The reaction mixture was allowed to slowly warm to room temperature over 6 hours. After 68 hours the reaction mixture was diluted with EtOAc (250 mL) and water (250 mL). The aqueous layer was extracted with EtOAc (2×200 mL) and the combined extracts were washed with saturated aqueous NaCl (2×75 mL), dried over Na$_2$SO$_4$, filtered and concentrated in vacuo. The resulting residue was purified using flash column chromatography (silica; 16×10 cm) using 10-20% ethyl acetate/hexanes as the eluent to provide Compound Int-6e (49.0 g, 84%) as a pale yellow oil: $^1$H NMR (300 MHz, CDCl$_3$) δ 4.35 (s, 0.6H), 4.22-4.10 (m, 2.4H), 3.81 (s, 0.45H), 3.71 (s, 0.55H), 2.66 (s, 1H), 1.96-1.90 (m, 1H), 1.76-1.50 (m, 3H), 1.55-1.45 (m, 5H), 1.39 (s, 5H), 1.30-1.23 (m, 4H).

Step E—Synthesis of Intermediate Compound Int-6f

To a stirred mixture of Int-6e (49.0 g, 0.182 mmol) in 1:1 THF/water (600 mL) was added LiOH.H$_2$O (15.3 g, 0.364 mol). The reaction mixture was warmed to 60° C. for 47 hours, cooled to room temperature and concentrated in vacuo to remove excess THF. The resulting residue was diluted with CH$_2$Cl$_2$ (200 mL) then acidified with 2N HCl until pH~4. The aqueous layer was extracted with CH$_2$Cl$_2$ (4×100 mL) and the combined extracts were washed with saturated aqueous NaCl (25 mL), dried over Na$_2$SO$_4$, filtered and concentrated in vacuo to provide Compound Int-6f (41.2 g, 93%) as an off white solid: $^1$H NMR (400 MHz, DMSO-d$_6$) δ 12.44 (s, 1H), 4.13 (s, 56H), 4.06 (s, 0.47H), 3.61 (d, J=4.0 Hz, 1H), 2.59 (s, 1H), 1.75-1.45 (m, 5H), 1.39 (s, 4H), 1.32 (s, 5H), 1.23 (t, J=8.4 Hz, 1H); Optical Rotation: $[\alpha]^D_{25}$ −169.0° (c=1.1, CHCl$_3$).

Example 7

Preparation of Intermediate Compound Int-7d

Step A—Synthesis of Intermediate Compound Int-7b

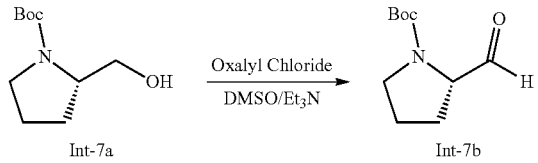 [SMILES: CC(C)(C)OC(=O)N1CCC[C@H]1CO ; CC(C)(C)OC(=O)N1CCC[C@H]1C=O]

A 2 L, 3-necked round bottomed flask equipped with an overhead stirrer and a N$_2$ inlet was charged with a solution of oxalyl chloride (130 mL, 0.26 mol) in dichloromethane (250 mL). The solution was cooled to −78° C., and a solution of DMSO (20 mL, 0.28 mol) in dichloromethane (30 mL) was added dropwise. After 30 minutes, a solution of (S)—N-Boc-prolinol (Int-7a, 40 g, 0.2 mol) in dichloromethane (200 mL) was added dropwise. After 30 minutes, triethylamine (140 mL, 1.0 mol) was added to the solution, and the flask was transferred to an ice/water bath and stirred for another 30 minutes. The reaction mixture was diluted with dichloromethane (200 mL) and washed successively with H$_2$O, 1M HCl, saturated NaHCO$_3$, and brine. The organic layer was dried over Na$_2$SO$_4$, filtered, and concentrated to provide Compound Int-7b (40 g) as an oil, which was used without further purification.

Step B—Synthesis of Intermediate Compound Int-7c

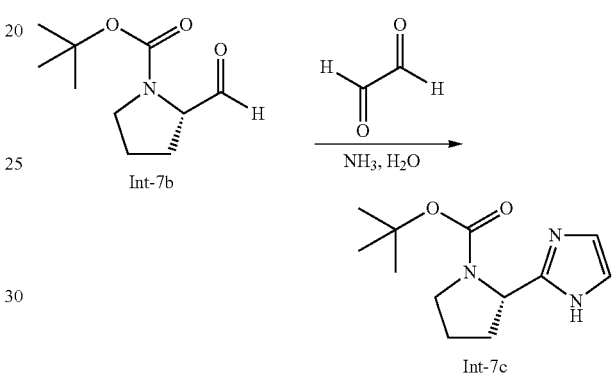

To Int-7b (80 g, 0.4 mol) was added a solution of ammonia in MeOH (prepared from 150 mL of 7 N ammonia/MeOH and 200 mL MeOH, 1.05 mol, 260 mol %). An exotherm was noted and the internal reaction temperature increased to about 30° C. The resulting reaction was allowed to stir for 30 minutes at room temperature, then glyoxal (76 g, 0.52 mol, 130 mole %) was added portionwise over a 5 minute period, during which time the internal reaction temperature increased to about 60° C. The reaction was allowed to stir for about 15 hours at room temperature, then the reaction mixture was concentrated in vacuo and to the resulting residue was added dichloromethane (1 L) and water (0.5 L). The organic layer was separated, washed water (0.25 L), dried over MgSO$_4$, filtered and concentrated in vacuo. The residue obtained was slurried with hot ethyl acetate (100 mL) and hexanes (100 mL) and the slurry was allowed to cool to room temperature. The cooled slurry was then filtered and the collected solid was washed with 30% ethyl acetate/hexanes, then dried under vacuum to provide Compound Int-7c (66.2 g, 70% yield). $^1$H NMR (DMSO) δ: 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H).

Step C—Synthesis of Intermediate Compound Int-7d

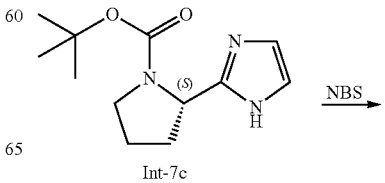

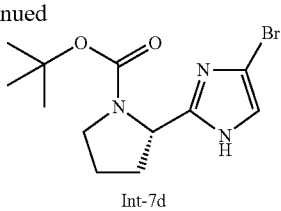

Int-7d

N-Bromo succinimide (838.4 mg, 4.71 mmol) was added in portions over 15 minutes to a cooled (ice/water) CH$_2$Cl$_2$ (20 mL) solution of Int-7c (1.06 g, 4.50 mmol). The reaction mixture was allowed to stir for 75 minutes and concentrated in vacuo to an oil. The crude product was purified using silica-gel RPLC (Acetonitrile/water/0.1% TFA) to separate the mono bromide from its dibromo analog (over bromination) and the starting material. The RPLC elute was neutralized with excess NH$_3$/MeOH, and the volatile component was removed in vacuo. The resulting residue was partitioned between CH$_2$Cl$_2$ and water, and the aqueous layer was extracted with water. The combined organic phase was dried (MgSO$_4$), filtered, and concentrated to provide Compound Int-7d as a white solid (374 mg). $^1$H NMR (DMSO) δ: 12.12 (br s, 1H), 7.10 (m, 1H), 4.70 (m, 1H), 3.31 (m, 1H; overlapped with water signal), 2.25-1.73 (m, 4H), 1.39/1.17 (s, 3.8H+5.2H).

Alternative Synthesis of Int-7d

Step D—Synthesis of Intermediate Compound Int-7e

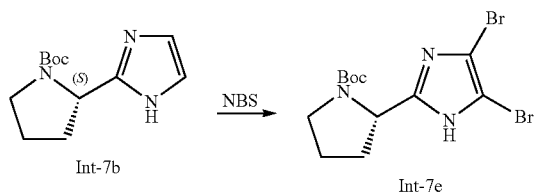

Int-7b → Int-7e

To a suspension of Int-7b (140 g, 0.59 mol) in THF (2000 mL) was added N-bromosuccinimide (200 g, 1.1 mol). The mixture was allowed to stir at room temperature under N$_2$ gas for about 15 hours. The solvent was then removed in vacuo, and the resulting residue was purified using silica-gel chromatography (ethyl acetate eluent) to provide 230 g of Compound Int-7e. MS (ESI) m/e (M+H$^+$): 396.

Step E—Synthesis of Intermediate Compound Int-7d

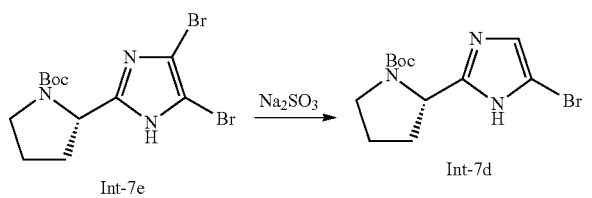

Int-7e → Int-7d

To a suspension of Int-7e (230 g, 0.58 mol) in EtOH/H$_2$O (1:1 ratio, 3000 mL) was added Na$_2$SO$_3$ (733 g, 5.8 mol). The resulting mixture was allowed to stir at mild reflux for about 15 hours. After cooling to room temperature, the mixture was extracted with dichloromethane twice and the combined organic layers were concentrated under vacuum to a semi-solid. The resulting residue was purified using chromatography on silica gel to provide Compound Int-7d. MS (ESI) ink (M+H$^+$): 317.

Step F—Synthesis of Intermediate Compound Int-7f

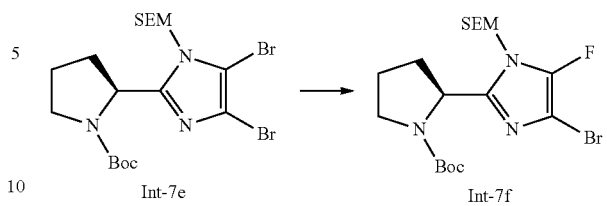

Int-7e → Int-7f

Compound Int-7e (2.63 g, 5.0 mmol) was dissolved in THF (30 mL) and the resulting solution was cooled to −78° C., then n-BuLi (1M in hexane, 2.2 mL, 5.5 mmol) was added and the reaction was allowed to stir for 20 minutes. N-fluorodibenzenesulfonimide (1.6 mL, 5.0 mmol) was added at −78° C. and the mixture was allowed to warm slowly to room temperature again. The reaction was quenched with aq. NH$_4$Cl then partitioned between water and EA. The organic layer was dried over Na$_2$SO$_4$ and concentrated in vacuo. The resulting residue was purified using flash column chromatography (Gradient of EtOAc:petroleum ether from 0-20% EtOAc) to provide Compound Int-7f. (63% yield). MS (ESI) m/z (M+H)$^+$: 464, 466. $^{19}$F NMR=−151.8 ppm Example 8

Preparation of Intermediate Compound Int-8g

Step A—Synthesis of Intermediate Compound Int-8b

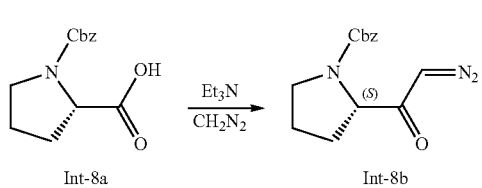

Int-8a → Int-8b

To a solution of compound CBz-proline (50 g, 0.2 mol) in THF (500 mL) and Et$_3$N (20 mL) was added dropwise isopropyl chloroformate (25 g, 0.22 mol) at ice water bath. Then the resulting solution was allowed to warm to room temperature and stirred for 1 h. Then a solution of CH$_2$N$_2$ (0.22 mol) in ether was added slowly until no N$_2$ gas evolution was noted. Acetic acid (4 mL) was added and the reaction mixture was allowed to stir for 10 minutes. NaHCO$_3$ solution was then added and the reaction mixture extracted three times with ethyl acetate. The organic layers were combined, dried over Na$_2$SO$_4$, and concentrated to provide crude product. The crude product was then purified using column chromatography on silica gel (Pet Ether:E.Acetate=3:1) to provide Compound Int-8b (38 g, 70% yield).

Step B—Synthesis of Intermediate Compound Int-8c

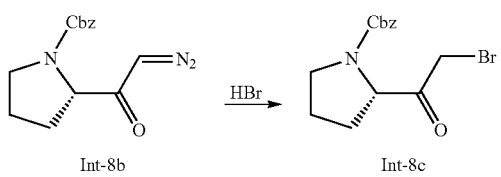

Int-8b → Int-8c

To a solution of Int-8b (38 g, 0.14 mol) in acetic acid (20 mL) was added dropwise an aqueous HBr solution (112 g, 0.14 mol). After 10 min, the mixture was poured into an aqueous NaHCO₃ solution and extracted three times with ethyl acetate. The combined organic layers were washed with brine, water, dried over Na₂SO₄ and concentrated in vacuo to provide Compound Int-8c (30 g, 68% yield).

Step C—Synthesis of Intermediate Compound Int-8e

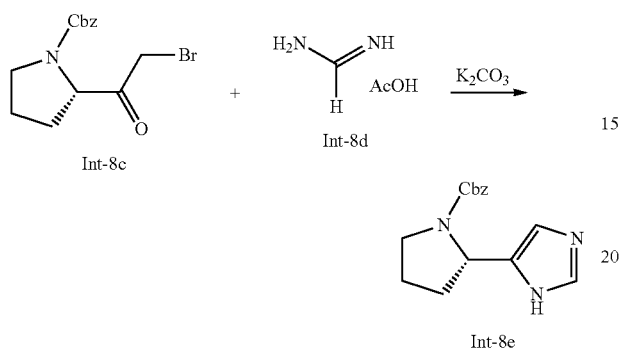

To a solution of Int-8c (10 g, 32 mmol) and compound Int-8d (8.4 g, 64 mmol) in DMF (70 mL) was added K₂CO₃ (18 g, 126 mmol). The mixture was allowed to stir at 100° C. in a sealed tube for about 15 hours. The solvent was removed and the resulting residue was purified using column chromatography on silica gel (DCM:MeOH 20:1) to provide Compound Int-8e. (6 g, 59% yield).

Step D—Synthesis of Intermediate Compound Int-8f

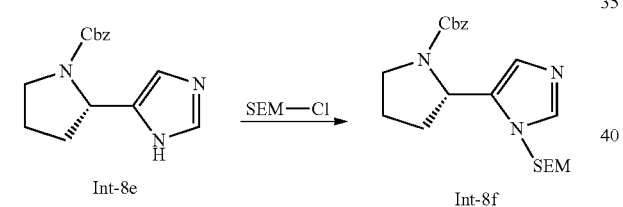

To a solution Int-8e (4 g, 14.7 mmol) in THF (40 mL) was added NaH (6.6 g, 60% content, 16.17 mmol) at 0° C. The mixture was allowed to stir at room temperature for 30 minutes and then cooled to 0° C., and SEM-Cl (2.4 g, 14.7 mmol) added dropwise. The resulting mixture was allowed to stir at 0° C. for 2 hours. The solvent was removed under vacuum and the resulting residue was purified using column chromatography on silica gel (DCM:MeOH=20:1) to provide Compound Int-8f. (2 g, 34% yield).

Step E—Synthesis of Intermediate Compound Int-8g

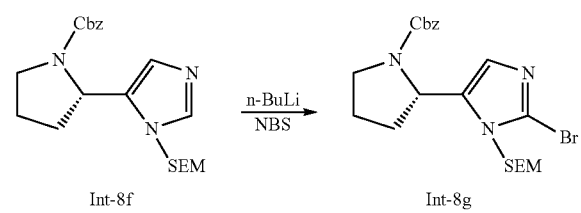

To a solution of Int-8f (2 g, 5 mmol) in THF (20 mL) was added dropwise n-BuLi (2.5 mL, 6.3 mmol) at −78° C. (bath) under N₂ protection. The resulting solution was allowed to stir at this temperature for 30 minutes, then a solution of NBS (0.89 g, 5 mmol) in THF (10 mL) was added dropwise at −78° C. The mixture was allowed to stir at −78° C. for 1 hour and then aqueous NH₄Cl solution was added. The organic layer was separated and concentrated in vacuo off to provide a crude residue, which was purified using column chromatography on silica gel (pet. ether:EtOAc=3:1 as the eluent) to provide Int-8g (400 mg, 16.5% yield).

Example 9

Preparation of Intermediate Compound Int-9e

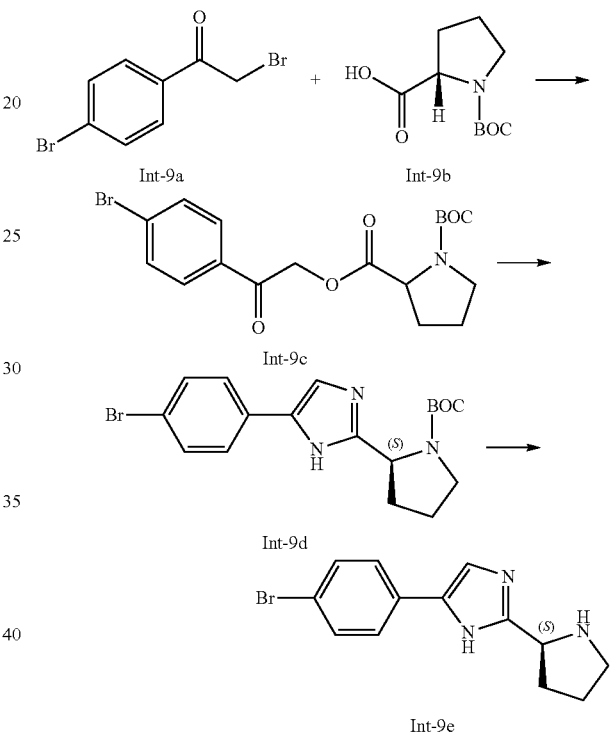

Step A—Synthesis of Intermediate Compound Int-9c

A mixture of compound Int-9a (50.0 g, 179.9 mmol), compound Int-9b (43.0 g, 199.8 mmol), and triethylamine (30 mL, 215.5 mmol) in DMF (100 mL) was allowed to stir at room temperature for about 4 days. Ethyl acetate (600 mL) was then added to the reaction mixture and the resulting solution was washed with brine (3×100 mL), dried over sodium sulfate and concentrated in vacuo to provide Compound Int-9c as a brown gel (74.5 g, ~100% yield), which was used without further purification.

Step B—Synthesis of Intermediate Compound Int-9d

Compound Int-9c (20 g, crude, ~48.5 mmol), ammonium acetate (20.0 g, 256.6 mmol), and o-xylene (100 mL) were added to a 500 mL pressure vessel. The resulting mixture was allowed to stir at 140° C. for 2.5 hours, then cooled to room temperature and concentrated in vacuo. The resulting residue was taken up in ethyl acetate (400 mL), washed with saturated sodium carbonate solution, dried over sodium sulfate, and concentrated in vacuo. The resulting residue was purified using a 330 g ISCO silica column/Combi-Flash system (20-50% ethyl acetate in hexanes) to provide Compound Int-9d as an orange solid (15.5 g, 81% yield).

Step C—Synthesis of Intermediate Compound Int-9e

A solution of compound Int-9d (4.0 g, 10.2 mmol), trifluoroacetic acid (10 mL, 130.6 mmol), and dichloromethane (10 mL) was allowed to stir at room temperature for about 15 hours, then was concentrated in vacuo. The resulting residue was taken up in dichloromethane (60 mL), washed with saturated sodium carbonate, dried over sodium sulfate, and concentrated in vacuo to provide Compound Int-9e as an off-white solid (3 g, ~100% yield), which was used without further purification.

Int-9f was prepared from N-BOC-trans-fluoro-L-proline, (available from Alfa) using the method described above.

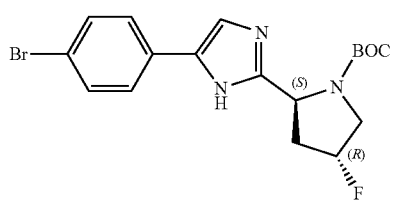

Int-9g was prepared from N-Boc-4,4-difluoro-L-proline, (Aldrich) using the method described above.

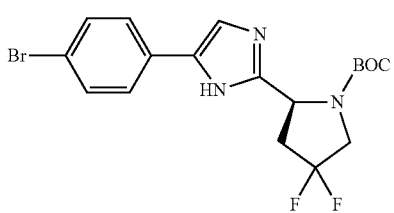

Int-9h was prepared from BOC-HYP-OH, (available from Aldrich) using the method described above.

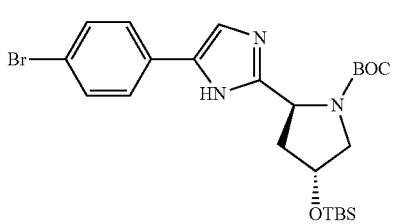

Int-9i was prepared from commercially available BOC-4-amino-pyrrolidine-2-carboxylic acid using the method described above.

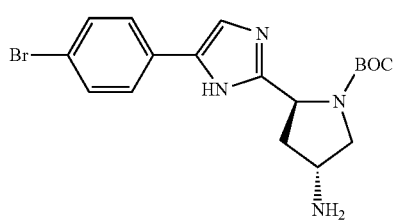

Int-9j was prepared from commercially available BOC-4-amino-pyrrolidine-2-carboxylic acid using the method described above, with appropriate functionalization with methyl chloroformate as in example 1.

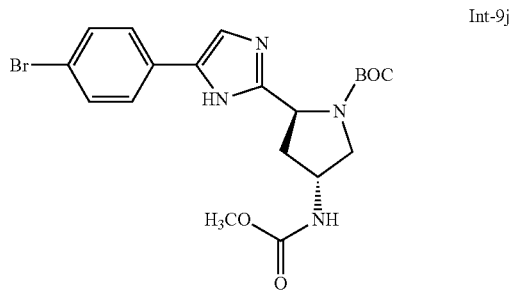 [SMILES: COC(=O)N[C@@H]1C[C@@H](c2ncc(-c3ccc(Br)cc3)[nH]2)N(C(=O)OC(C)(C)C)C1]

Int-9k was prepared from 2S-carboxy piperidine (prepared according to method described in Gudasheva et al., *J. Med. Chem Ther.* 1996, 31, 151).

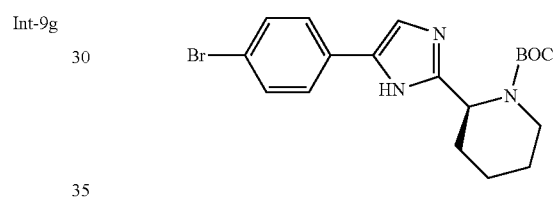

Int-9l was prepared from 2S-carboxy-4,4-F piperidine (prepared according to the method described in Chinese Patent No. CN 101462999).

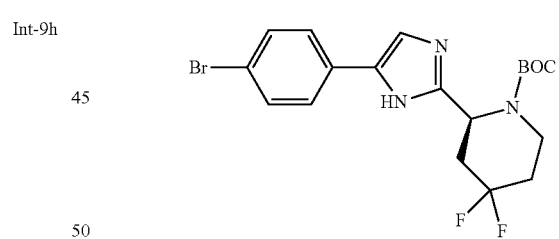

Int-9m was prepared from 2S-carboxy morpholine, using the method described above.

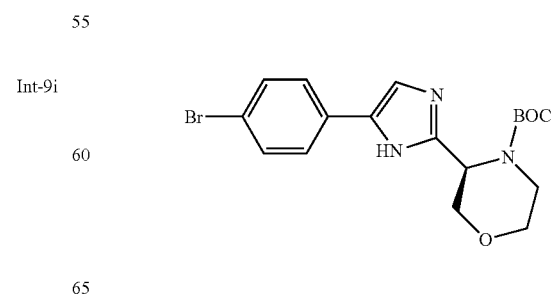

Int-9q was prepared from commercially available Int-9o using the method described above

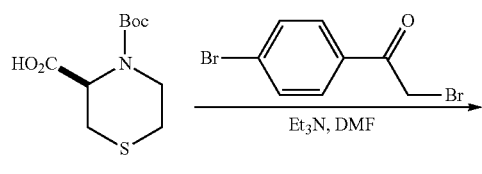

Int-9o

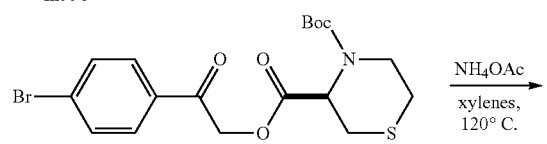

Int-9p

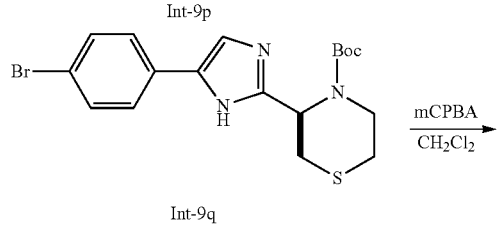

Int-9q

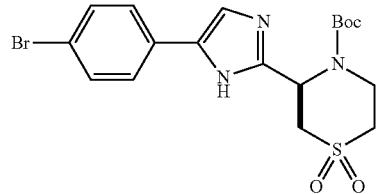

Int-9r

Synthesis of Int-9r

Compound Int-9q (712 mg, 1.68 mmol) was dissolved in DCM (17 mL), solid mCPBA (839 mg, 8.39 mmol) was added and the reaction was stirred for about 15 hours at room temperature. The reaction mixture was then diluted with DCM (150 mL) and quenched by the addition of 1 N aq. sodium bisulfate (40 mL). The organic phase was separated and then washed with saturated aqueous sodium bicarbonate (2×60 mL), brine (60 mL), dried over anhydrous MgSO₄, filtered, and concentrated in vacuo. The resulting crude Int-9r was purified using silica gel chromatography (80 g RediSep® SiO₂ cartridge; 1-9% MeOH/EtOAc gradient) to provide Compound Int-9r (458 mg, 60% yield) as a yellow solid.

Int-9s was prepared from (1R,3S,4S)—N-BOC-2-azabicyclo[2.2.1]-heptane-3-carboxylic acid using the method described above for the synthesis of compound Int-9r.

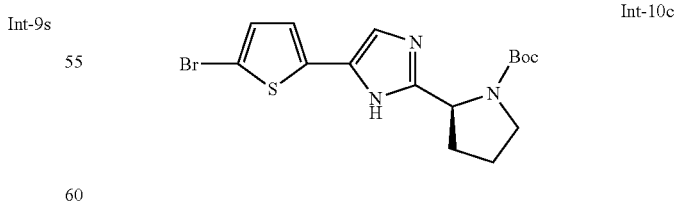

Int-9t was prepared from 15 g of 2(S)-azabicyclo[2.2.2]-octane-2,3-dicarboxylic acid 2-tort-butyl ester (commercially available from Wuxi Apptech Co) using the method described above for the synthesis of compound Int-9r, to provide 10.1 g of Int-9t.

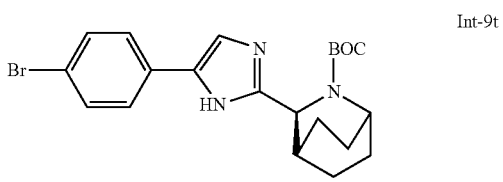 [SMILES: CC(C)(C)OC(=O)N1C2CCC(CC2)[C@H]1c1ncc(-c2ccc(Br)cc2)[nH]1]

Example 10

Preparation of Intermediate Compound Int-10c

Step A—Synthesis of Intermediate Compound Int-10a

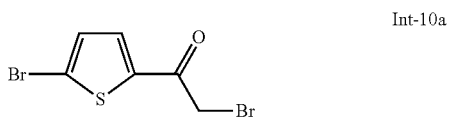

To a solution of 2-acetyl-5-bromothiophene (10.0 g, 48.8 mmol) in anhydrous CH₂Cl₂ (120 mL) at room temperature was added bromine (7.79 g, 48.8 mmol). The resulting reaction was allowed to stir at room temperature for 20 hours, then was concentrated in vacuo to provide Int-10a as a yellow solid (14.0 g, quant.), which was used without further purification.

Step B—Synthesis of Intermediate Compound Int-10b

Int-10b

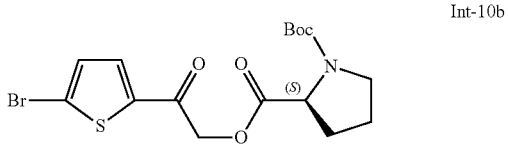 [SMILES: CC(C)(C)OC(=O)N1CCC[C@H]1C(=O)OCC(=O)c1ncc(Br)s1]

To a solution of Int-10a (13.9 g, 48.8 mmol) and N-Boc-proline (22.1 g, 103 mmol) in anhydrous acetonitrile (250 mL) at room temperature was added diisopropylethylamine (18.0 mL, 101 mmol). The reaction was allowed to stir at room temperature for 16 hours, then EtOAc (500 mL) and water (500 mL) were added and the layers were separated. The organic solution was washed with saturated aqueous sodium bicarbonate solution (500 mL), dried over MgSO₄, filtered and concentrated in vacuo to provide Int-10b (21.2 g, quant.), which was used without further purification.

Step C—Synthesis of Intermediate Compound Int-10c

A suspension of Int-10b (11.7 g, 28.0 mmol) and NH₄OAc (43 g, 559 mmol) in anhydrous toluene (200 mL) was heated to 100° C. and allowed to stir at this temperature for 12 hours. The reaction mixture was then cooled to room temperature, and EtOAc (500 mL) and water (500 mL) were added. The layers were separated and the aqueous layer was extracted with EtOAc (2×200 mL). The combined organics were dried over MgSO₄, filtered and concentrated in vacuo and the resulting residue was purified using flash chromatography on an ISCO 330 g Redi-Sep column (10-80% EtOAc/hexanes as eluent) to provide Int-10c (6.18 g, 56%). LRMS: (M+H)⁺=398.1, 400.1.

Example 11

Preparation of Intermediate Compound Int-11f

Step A—Synthesis of Intermediate Compound Int-11a

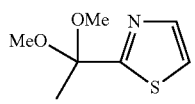

To a solution of 2-acetylthiazole (10.0 g, 78.6 mmol) in anhydrous MeOH (150 mL) at room temperature was added trimethyl orthoformate (52.0 g, 488 mmol) and p-toluenesulfonic acid (14.2 g, 74.7 mmol). The resulting reaction was heated to 50° C. and was allowed to stir at this temperature for 12 hours. EtOAc (600 mL) was then added and the resulting solution was washed with saturated aqueous sodium bicarbonate solution (600 mL) and brine (600 mL). The organic layer was dried over MgSO₄, filtered and concentrated in vacuo to provide Compound Int-11a (12.1 g, 90%), which was used without further purification.

Step B—Synthesis of Intermediate Compound Int-11b

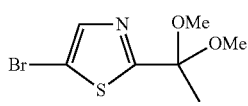

To a solution of Int-11a (8.0 g, 46.2 mmol) in anhydrous THF (150 mL) at −78° C. under nitrogen was added n-butyl lithium (23.1 mL, 2.0 M, 46.2 mmol) over 10 minutes. The reaction mixture was allowed to stir at −78° C. for 45 minutes, then a solution of carbon tetrabromide (15.9 g, 48.0 mmol) in anhydrous THF (50 mL) was added dropwise over 10 minutes. The cooling bath was removed and the reaction mixture was then allowed to warm to 0° C. on its own. The reaction mixture was then quenched with saturated ammonium chloride solution (50 mL). The reaction mixture was then diluted with water (150 mL) and diethyl ether (150 mL) and separated. The organic phase was washed with brine (200 mL), dried over MgSO₄, filtered and concentrated in vacuo. The resulting residue was purified using flash chromatography on an ISCO 330 g Redi-Sep column (0-20% EtOAc/hexanes as eluent) to provide Compound Int-11b (7.47 g, 65%).

Step C—Synthesis of Intermediate Compound Int-11c

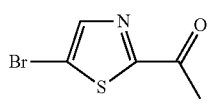

To a solution of Int-11b (7.47 g, 29.6 mmol) in anhydrous CH₂Cl₂ (100 mL) at room temperature was added TFA (64 mL) and water (2.0 mL). The resulting reaction was allowed to stir at room temperature for 17 hours, and then was con-centrated in vacuo. The resulting residue was taken up in diethyl ether (300 mL) and 10% aqueous NaHCO₃ solution (300 mL) and separated. The organic phase was washed with water and brine, dried over MgSO₄, filtered and concentrated in vacuo to provide Compound Int-11c (5.63 g, 92%), which was used without further purification.

Step D—Synthesis of Intermediate Compound Int-11d

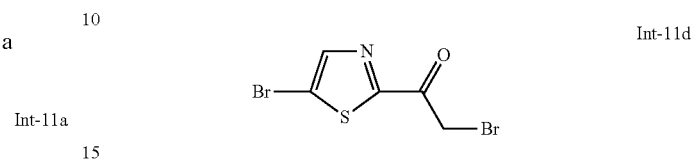

To a solution of 2-acetyl-5-bromothiazole (5.63 g, 27.3 mmol) in anhydrous CH₂Cl₂ (100 mL) at room temperature was added bromine (4.39 g, 27.3 mmol). The reaction mixture was allowed to stir at room temperature for about 15 hours for 48 hours, then was concentrated in vacuo to provide Compound-Int-11d as a yellow solid (8.63 g, quant.), which was used without further purification.

Step E—Synthesis of Intermediate Compound Int-11e

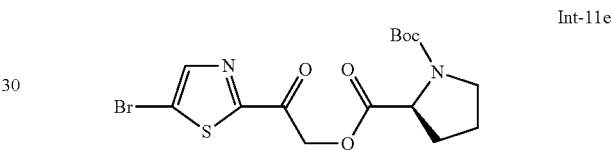

Compound Int-11e was prepared from compound Int-11d using the method described in Example 3, Step B.

Step F—Synthesis of Intermediate Compound Int-11f

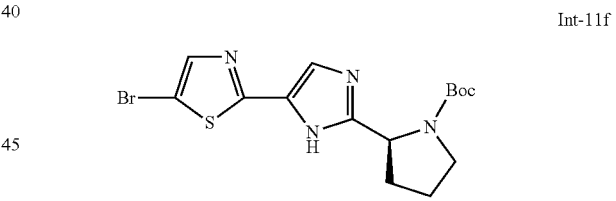

Compound Int-11f was prepared from compound Int-11e using the method described in Example 8, Step C. LRMS: (M+H)⁺=399.0, 401.0.

Example 12

Preparation of Intermediate Compound Int-12c

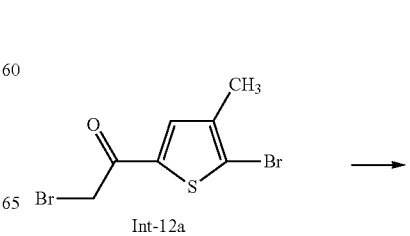

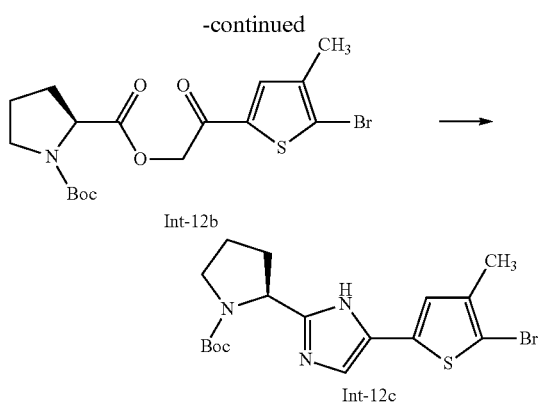

Int-12b

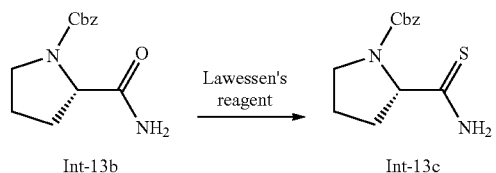 [SMILES: NC(=O)[C@@H]1CCCN1C(=O)OCc1ccccc1 ; NC(=S)[C@@H]1CCCN1C(=O)OCc1ccccc1]

Step A—Synthesis of Intermediate Compound Int-12a

To a solution of 5-bromothiophene-2-carboxylic acid (7.6 g, 34.4 mmol) in anhydrous $CH_2Cl_2$ (270 mL) at room temperature was added oxalyl chloride (3.80 mL, 44.5 mmol) dropwise. The resulting reaction was allowed to stir at room temperature for 1.5 hours, then heated to reflux and allowed to stir at this temperature for 1 hour. The reaction mixture was cooled to room temperature, concentrated in vacuo, and the resulting residue was dissolved in anhydrous acetonitrile (180 mL) and cooled to −15° C. (Trimethylsilyl)diazomethane solution in hexane (25.8 mL, 2 M, 51.6 mmol) was added dropwise over 20 minutes and the resulting reaction was allowed to stir at −15° C. for 1 hour. A hydrobromide solution in acetic acid (7.2 mL, 33 wt %, 41.6 mmol) was then added to the cooled reaction mixture dropwise and the resulting reaction was allowed to stir at −15° C. for additional 20 minutes. The reaction mixture was concentrated in vacuo and the resulting residue was dissolved in ethyl acetate (300 mL) and washed with water, saturated aqueous sodium bicarbonate solution and brine (200 mL each). The organic phase was dried over $MgSO_4$, filtered and concentrated in vacuo to provide Compound Int-12a as a light yellow solid (6.5 g, 63%), which was used without further purification.

Step B—Synthesis of Intermediate Compound Int-12c

Compound Int-12c was synthesized from Int-12a according to the methods described in Example 10, Steps B and C. Int-1c2: LRMS: $(M+H)^+=414.2$.

Example 13

Preparation of Intermediate Compound Int-13d

Step A—Synthesis of Intermediate Compound Int-13b

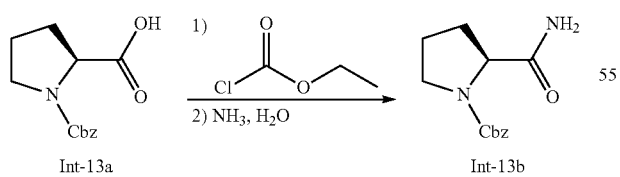

Ethyl chloroformate (12 mL, 125 mmol) in 180 mL of THF was added drop-wise to a cooled solution (−5° C.) of compound Z-Pro-OH (13.8 g, 55.5 mmol), TEA (7.71 mL, 55.5 mmol). The resulting slurry was allowed to stir for 20 minutes at −5° C. before saturated $NH_4OH$ (15 mL) was added. The solution was allowed to stir at room temperature for 18 hours, volatiles were removed, and the resulting residue was taken up in EtOAc (180 mL). The undissolved white precipitate was filtered off and rinsed with EtOAc (100 mL). The organic layers were dried over $Na_2SO_4$ and concentrated in vacuo to provide the desired product (13.5 g) as off-white amorphous solid (Int-13b). MS (ESI) m/e $(M+H^+)$: 249.

Step B—Synthesis of Intermediate Compound Int-13c

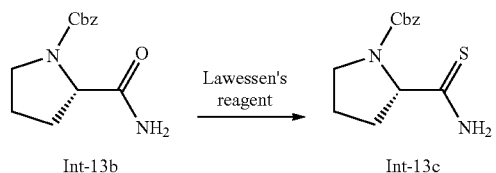 [SMILES: NC(=O)[C@@H]1CCCN1C(=O)OCc1ccccc1 ; NC(=S)[C@@H]1CCCN1C(=O)OCc1ccccc1]

Lawesson's reagent (16.1 g, 39.9 mmol) was added to a stirred slurry of the amide Int-13b (18 g, 72.6 mmol) in PhMe (200 mL) at room temperature. The reaction mixture was heated to 100° C. for 3 hours before the solvent was removed. The resulting residue was purified using flash chromatography on silica gel (DCM/MeOH=1:0-20:1) to provide Compound Int-13e (18 g). MS (ESI) m/e $(M+H^+)$: 265.

Step C—Synthesis of Intermediate Compound Int-13d

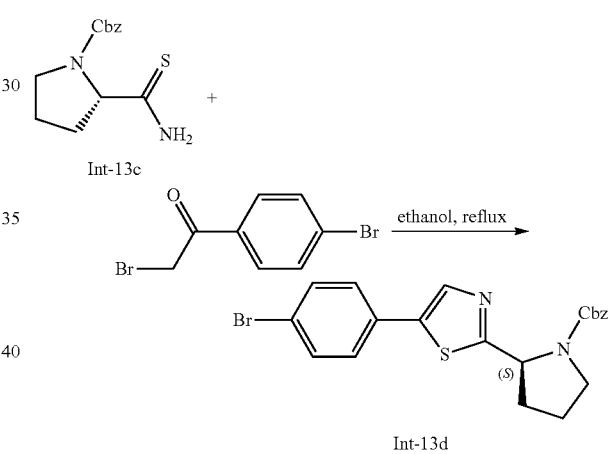

A mixture of Int-13c (10.0 g, 37.8 mmol) and the bromoacetophenone (10.0 g, 35.9 mmol) in EtOH (100 mL) was heated at 90° C. for 3 hours. The reaction mixture was cooled and concentrated in vacuo, and the resulting residue was purified using flash chromatography on silica gel to provide Compound Int-13d (11 g). MS (ESI) m/e $(M+H^{30})$: 444.

Example 14

Preparation of Intermediate Compound Int-14b

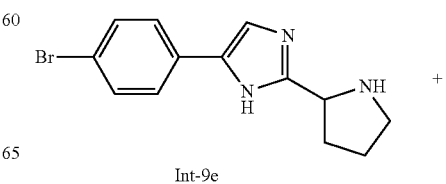

-continued

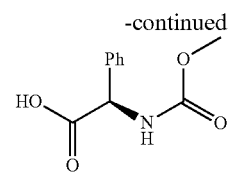
Int-14a

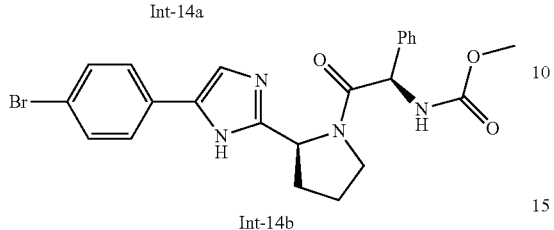
Int-14b

A solution of compound Int-9e (1.0 g, 3.42 mmol), compound Int-14a (0.95 g, 4.54 mmol), HATU (1.3 g, 3.42 mmol), and DMF (10 mL) was allowed to stir at room temperature for about 15 hours. The solution was then diluted with ethyl acetate (100 mL), washed with brine (3×40 mL), dried over sodium sulfate, and concentrated in vacuo. The resulting residue was purified using an 80 g silica gel column/Combi-Flash system (0-5% methanol in dichloromethane) to provide Compound Int-14b as a gel (1.12 g, 68%).

Example 15

Preparation of Intermediate Compound Int-15e

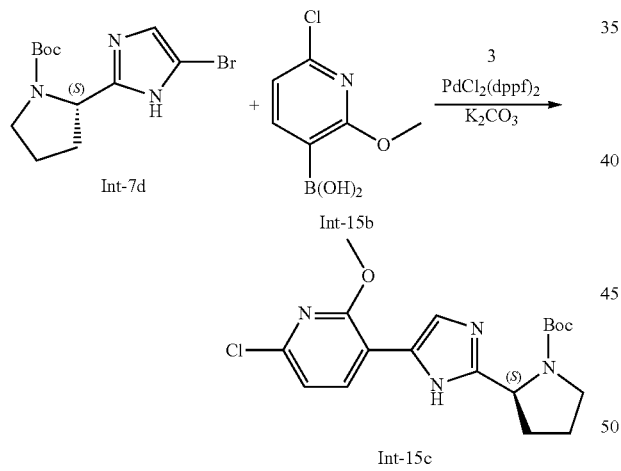

To a solution of compound Int-7d (0.5 g, 1.58 mmol) in DME (15 mL) at room temperature under N₂ was added PdCl₂(dppf)₂ (258 mg, 0.30 mmol). The reaction mixture was allowed to stir at 100° C. for 5 minutes, then a solution of compound Int-15b (592 mg, 3.16 mmol) and K₂CO₃ (654 mg, 4.74 mmol) in 15 mL H₂O was added to the reaction mixture in 3 portions over 10 minutes. The resulting reaction was allowed to stir for an additional 30 minutes, after which time thin-layer chromatography analysis indicated consumption of compound Int-7a. The reaction was allowed to stir for an additional 30 minutes, then was concentrated in vacuo, and the resulting residue was taken up in 150 mL ethyl acetate. The organic phase was separated, washed with water (50 mL), brine and dried over sodium sulfate. After filtration, the organic layer was concentrated in vacuo and the resulting residue was purified using flash liquid chromatography (0% to 100% EtOAc/Hexane) to provide 600 mg of compound Int-15c (>85% purity, theory 597 mg). HPLC (C18 column Gemini 5u 110A, 150×21.2 mm, 5 micron). FABMS: MH⁺=379

Example 16

Preparation of Intermediate Compound Int-16b

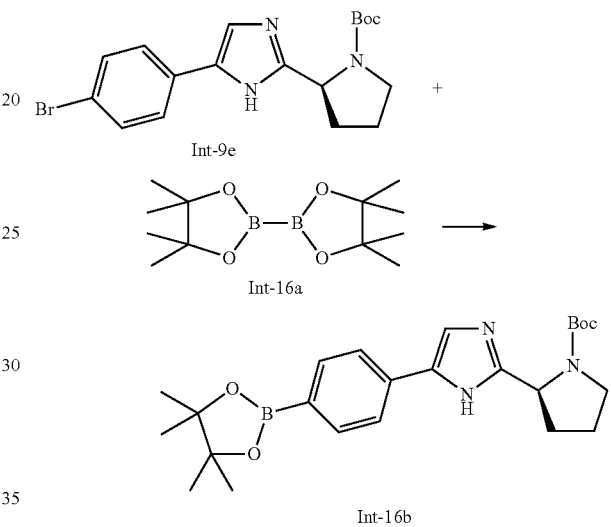

Compound Int-9e (4.2 g, 12.24 mmol), bis(pinacolato) diboron (Compound Int-16a, 6.5 g, 25.6 mmol), Pd(PPh₃)₄ (0.563 g, 0.49 mmol), potassium acetate (3.1 g, 31.58 mmol) and 1,4-dioxane (100 mL) were added to a 350 mL pressure vessel. The resulting mixture was degassed and allowed to stir at 80° C. for 20 hours. The reaction mixture was then cooled to room temperature and filtered. The filtrate was concentrated in vacuo and the residue obtained was purified using flash column chromatography on silica gel (0-2% methanol in dichloromethane) to provide Compound Int-16b as a white wax (2.5 g, 46.5%).

Example 16a

Preparation of Intermediate Compound Int-16c

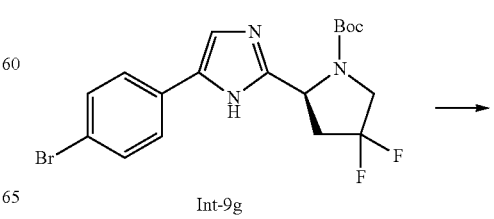
Int-9g

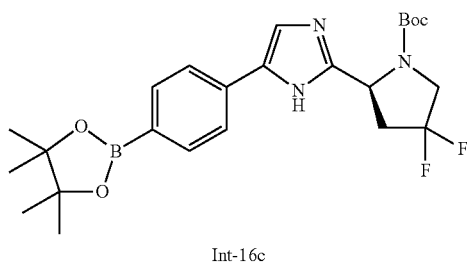

Int-16c

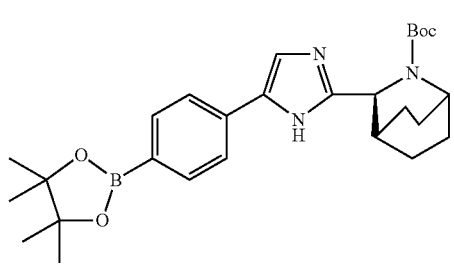

Int-16g

Compound Int-9g (5.7 g, 13.31 mmol), bis(pinacolaton) diboron (6.8 g, 26.78 mmol), Pd(PPh$_3$)$_4$ (0.76 g, 0.66 mmol), potassium acetate (2.0 g, 20.37 mmol) and 1,4-dioxane were added to a 500 mL flask. The resulting suspension was degassed and allowed to stir at 80° C. for about 15 hours. The reaction mixture was then cooled to room temperature and filtered. The filtrate was concentrated in vacuo and the residue obtained was purified using a 220 g ISCO silica column on Combi-Flash Rf with elution of 0-4% methanol in dichloromethane to provide Compound Int-16c as a wax (5.4 g, 85%).

Int-16d, Int-16e, Int-16f and Int-16g were prepared from Int-9h, Int-9f, Int-9s and Int-9t, respectively, using the method described above.

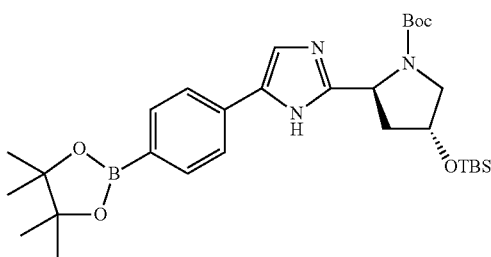

Int-16d

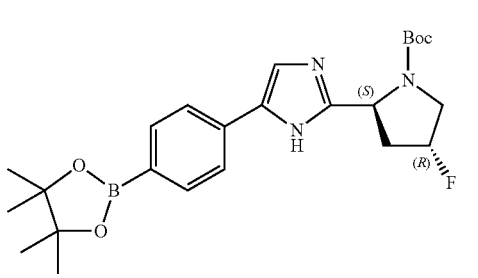

Int-16e

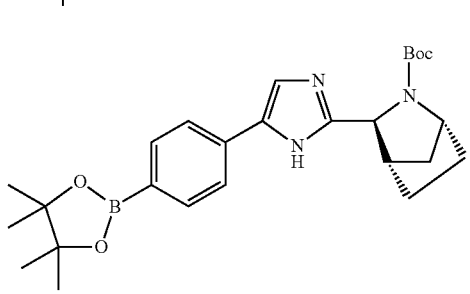

Int-16f

Example 17

Preparation of Intermediate Compound Int-17

Step A—Synthesis of Intermediate Compound Int-17a

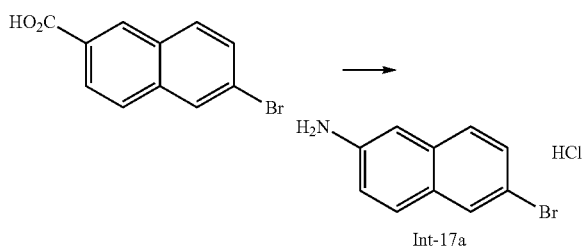

Int-17a

A mixture of 6-bromo-2-naphthoic acid (80.3 g, 319 mmol), diphenylphosphoryl azide (71 mL, 352 mmol) and triethylamine (50 mL, 358 mmol) in tert-butanol (400 mL) was heated to reflux and allowed to stir at this temperature for 15 hours. The reaction mixture was then cooled to room temperature and poured over saturated aqueous NaHCO$_3$ solution (600 mL) and stirred vigorously for 30 minutes. The resulting suspension was filtered, washed with water (200 mL) and dried in vacuo at 65° C. The resulting white solid was suspended in MeOH (500 mL) and cooled to −78° C., then HCl gas was bubbled into the mixture until saturated. The reaction mixture was then allowed to stir at room temperature for 15 hours, after which time the resulting solids were collected by filtration, then washed with ice-cold MeOH (100 mL) to provide Compound Int-17a as an off-white solid (74.8 g, 91%), which was used without further purification. $^1$H NMR (DMSO-d$_6$) δ 10.5-10.0 (br s, 3H), 8.23 (s, 1H), 7.99 (d, J=9.0 Hz, 1H), 7.92 (d, J=9.0 Hz, 1H), 7.84 (s, 1H), 7.68-7.65 (m, 1H), 7.56-7.51 (m, 1H). LRMS: (M+2H)$^+$=223.

Step B—Synthesis of Intermediate Compound Int-17b

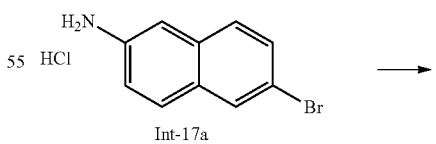

Int-17a

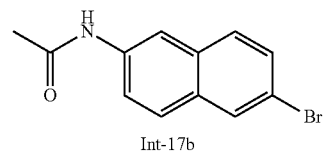

Int-17b

To a solution of Compound Int-17a (74.8 g, 289 mmol) and triethylamine (120 mL, 860 mmol) in CH$_2$Cl$_2$ (500 mL) at 0°

C. was added acetic anhydride (27.5 mL, 292 mmol). The resulting reaction was warmed to room temperature and allowed to stir at this temperature for 1.5 hours. The reaction mixture was filtered and the filtrate concentrated in vacuo. The resulting residue was triturated with hexanes (500 mL) and the resulting solids were filtered, washed with hexanes (100 mL) and dried in vacuo at 55° C. for 1 hour to provide Compound Int-17b as an off-white solid (60.6 g, 79%), which was used without further purification. $^1$H NMR (DMSO-d$_6$) δ 10.1 (s, 1H), 8.30 (s, 1H), 8.09 (s, 1H), 7.85-7.76 (m, 2H), 7.62-7.53 (m, 2H), 2.10 (s, 3H). LRMS: (M+H)$^+$=265.

Step C—Synthesis of Intermediate Compound Int-17c

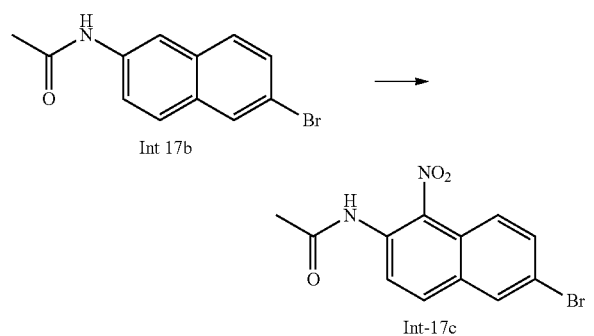

To a solution of Compound Int-17b (60.6 g, 229 mmol) and acetic anhydride (120 mL) in acetic acid (500 mL) at 0° C. was added a solution of fuming nitric acid (36 mL) in Acetic acid (84 mL) dropwise over 2 hours. The resulting reaction was warmed to room temperature and stirred vigorously at this temperature for 4.5 hours. The reaction mixture was filtered and the collected solids were washed with water (100 mL), then recrystallized from EtOH (1.4 L) to provide Compound Int-17c as an off-white solid (58.5 g, 83%), which was used without further purification. $^1$H NMR (DMSO-d$_6$) δ 8.95 (br s, 1H), 8.46 (d, J=9.0 Hz, 1H), 8.00 (s, 1H), 7.92-7.87 (m, 2H), 7.72-7.67 (m, 1H), 2.28 (s, 3H).

Step D—Synthesis of Intermediate Compound Int-17d

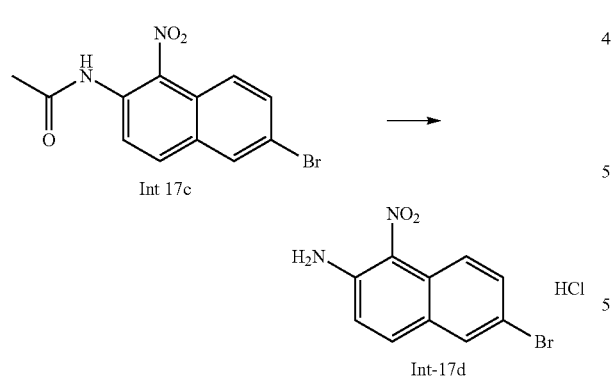

To a solution of Compound Int-17c (58.5 g, 189 mmol) in MeOH (150 mL) was added 6 N HCl (150 mL) and the resulting reaction was heated to 75° C. and allowed to stir at this temperature for 6 hours, then cooled to room temperature. The reaction mixture was filtered and the collected solids were rinsed with water (100 mL) and dried in vacuo at 55° C. for 2 hours to provide Compound Int-17d as a yellow solid (47.9 g, 95%), which was used without further purification.

$^1$H NMR (DMSO-d$_6$) δ 8.45 (d, J=9.6 Hz, 1H), 8.09-8.00 (m, 3H), 7.84 (d, J=9.6 Hz, 1H), 7.73-7.67 (m, 1H), 7.21 (d, J=9.6 Hz, 1H), 3.33 (br s, 1H).

Step E—Synthesis of Intermediate Compound Int-17e

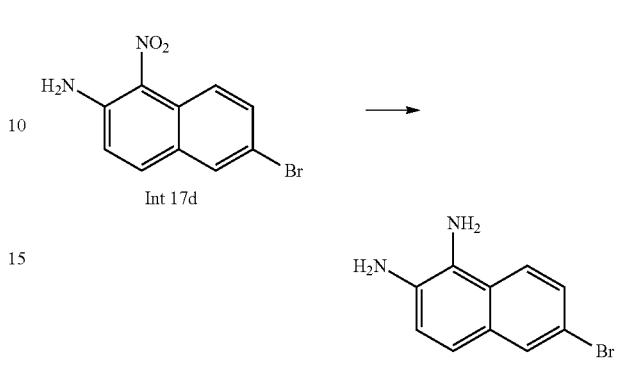

To a solution of Compound Int-17d (47.9 g, 179 mmol) and ammonium chloride (14.4 g, 269 mmol) in water (100 mL) and THF (250 mL) was added iron powder (50 g, 895 mmol). The resulting reaction was heated to 60° C. and allowed to stir vigorously at this temperature for 3 hours, then cooled to room temperature. The reaction mixture was filtered through a Celite® pad and rinsed with MeOH until the Celite was colorless. The combined filtrate and rinsings were concentrated in vacuo and the resulting residue was purified immediately on a silica gel plug (17 cm L×14 cm W) eluting with 1% MeOH/CH$_2$Cl$_2$ (7 L) to provide Compound Int-17e as a brown solid (40.5 g, 95%). $^1$H NMR (DMSO-d$_6$) δ 7.85-7.79 (m, 2H), 7.32-7.29 (m, 1H), 7.03-6.96 (m, 2H), 4.86 (br s, 4H). LRMS: (M+H)$^+$=238.

Step F—Synthesis of Intermediate Compound Int-17f

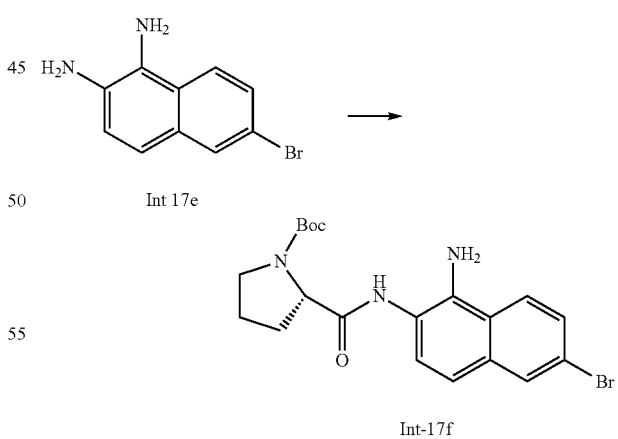

To a solution of Compound Int-17e (401 g, 171 mmol), N-Boc-proline (45.0 g, 209 mmol) and diisopropylethylamine (90 mL, 517 mmol) in anhydrous DMF (1 L) at 0° C. was added HATU (78 g, 205 mmol). The resulting reaction was warmed to room temperature then allowed to stir at this temperature for 9 hours. Water (1.5 L) was added to the reaction mixture and the resulting solution was extracted with MTBE (3×1.5 L). The combined organic extracts were washed with brine (3×1 L), dried over $Na_2SO_4$, filtered and concentrated in vacuo. The resulting residue was dissolved in MeOH (75 mL) and water (1.5 L) was added. The resulting heterogeneous mixture was allowed to stir vigorously for 2 hours, then filtered. The filter cake was washed with water (1 L) and dried in vacuo at 55° C. to provide Compound Int-17f as an off-white solid (66.5 g, 90%), which was used without further purification. $^1$H NMR (DMSO-$d_6$) δ 9.45-9.42 (m, 1H), 8.12-8.09 (m, 1H), 8.00 (s, 1H), 7.52-7.47 (m, 1H), 7.36-7.33 (m, 1H), 7.19-7.08 (m, 1H), 5.58 (s, 1H), 5.45 (s, 4.35-4.21 (m, 1H), 3.45-3.31 (m, 2H), 2.33-2.13 (m, 1H), 2.0-1.75 (m, 3H), 1.46-1.38 (m, 9H).

Step G—Synthesis of Intermediate Compound Int-17

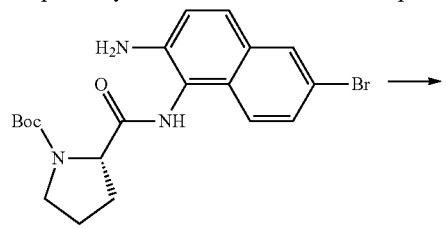

Int 17f

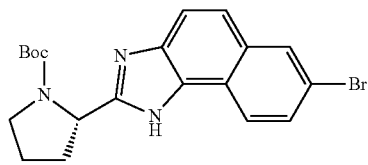

Int-17

A solution of Compound Int-17f (66.5 g, 153 mmol) and Acetic acid (500 mL) was heated to 60° C. and allowed to stir at this temperature for 1 hour. The reaction mixture was cooled to room temperature, water (1 L) was added and the mixture was adjusted to pH 8 using solid sodium carbonate. The aqueous mixture was extracted with $CH_2Cl_2$ (2×1 L) and the combined organic extracts were dried over $Na_2SO_4$, filtered and concentrated in vacuo to provide Compound Int-17 as a crude brown solid (63.7 g, quant.), which was used without further purification. $^1$H NMR (DMSO-$d_6$) δ 13.0-12.5 (m, 1H), 8.34 (d, J=9.0 Hz, 1H), 8.25-8.23 (m, 1H), 7.78-7.60 (m, 3H), 5.11-4.93 (m, 1H), 3.70-3.56 (m, 1H), 3.51-3.39 (m, 1H), 2.45-2.24 (m, 1H), 2.13-1.85 (m, 3H), 1.49-0.95 (m, 9H). LRMS: (M+H)$^+$=416.

Compound Int-17g was prepared from N-BOC-trans-fluoro-L-proline, using the method described above.

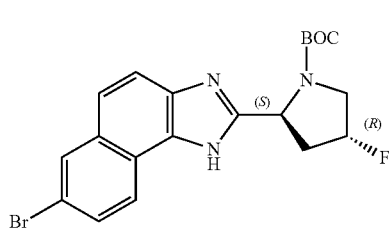

Compound Int-17h was prepared from N-Boc-4,4-difluoro-L-proline, using the method described above.

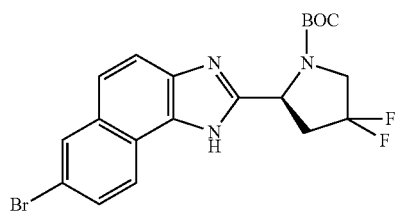

Compound Int-17i was prepared from BOC-HYP-OH, using the method described above.

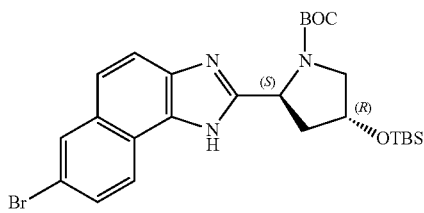

Compound Int-17j was prepared from L-pipecolic acid, using the method described above.

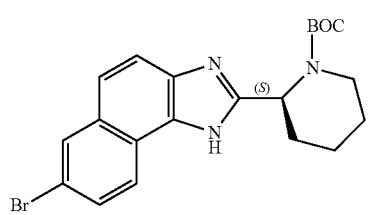

Compound Int-17k was prepared from 2S-carboxy morpholine, using the method described above.

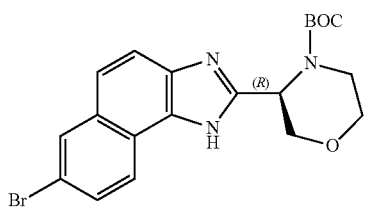

Compound Int-17l was prepared from (1R,3S,4S)—N-BOC-2-azabicyclo[2.2.1]-heptane-3-carboxylic acid, using the method described above.

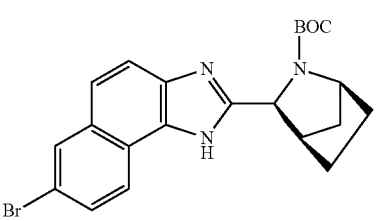

Compound Int-17m was prepared from 2(S)-azabicyclo[2.2.2]-octane-2,3-dicarboxylic acid 2-tert-butyl ester, using the method described above.

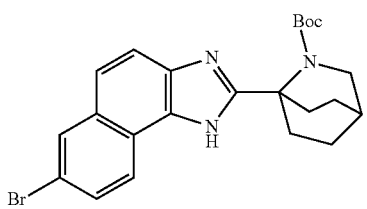

Int-17m

Example 18

Preparation of Intermediate Compound Int-18

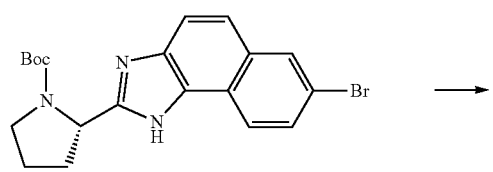

Int-17

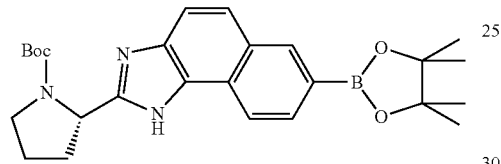

Int-18

To a solution of Compound Int-17 (21 g, 50.4 mmol), bis(pinacolato)diboron (14.1 g, 55.5 mmol) and KOAc (7.5 g, 76.4 mmol) in 1,4-dioxane (20 mL) was added a premixed solution of Pd(dba)$_2$ (1.16 g, 2.01 mmol) and tricyclohexylphosphine (1.14 g, 4.06 mmol) in 1,4-dioxane (10 mL). The resulting reaction was heated to 100° C. and allowed to stir at this temperature for 4 hours, then cooled to room temperature. The reaction mixture was filtered through Celite, and the Celite was rinsed with CH$_2$Cl$_2$ (100 mL) and the combined filtrate and washing was concentrated in vacuo. The resulting residue was purified using flash chromatography on an ISCO 330 g Redi-Sep column using a gradient of 0-70% EtOAc/hexanes as eluent to provide Compound Int-18 as a yellow solid (19 g, 82%). $^1$H NMR (DMSO-d$_6$) δ 13.0-12.5 (m, 1H), 8.40-8.36 (m, 2H), 7.84-7.63 (m, 3H), 5.13-4.93 (m, 1H), 3.73-3.57 (m, 1H), 3.51-3.41 (m, 1H), 2.44-2.25 (m, 1H), 2.18-1.95 (m, 3H), 1.40-1.02 (m, 21H). LRMS: (M+H)$^+$=464.

Example 19

Preparation of Intermediate Compound Int-19e

Step A—Synthesis of Intermediate Compound Int-19a

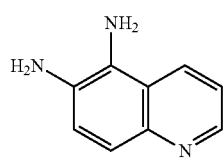

Int-19a

To a solution of 50% palladium on carbon (10% wet, 250 mg) in absolute ethanol (100 mL) under nitrogen atmosphere, was added 5-amino-6-nitroquinoline (5.00 g, 26.4 mmol). With stirring, the solution was placed in vacuo for 30 seconds and then was put under H$_2$ atmosphere using a hydrogen gas-filled balloon. The reaction was allowed to stir for 2 hours, then the reaction flask was evacuated in vacuo and placed under nitrogen atmosphere. The reaction mixture was then sonicated for 10 minutes and methanol (50 mL) was added. The resulting solution was then placed under H$_2$ atmosphere again and allowed to stir for 2 hours. After evacuating the flask of hydrogen, the reaction mixture was filtered through a Celite pad and the pad was washed with methanol (2×200 mL). The combined filtrate and washings were concentrated in vacuo and the resulting residue was dissolved in CH$_2$Cl$_2$ (75 mL). The resulting solution was purified using an ISCO 330-g Redi-Sep column (0-10% methanol/CH$_2$Cl$_2$ as eluent) to provide Compound Int-19a as a yellow solid (3.76 g, 89%).

Step B—Synthesis of Intermediate Compound Int-19b

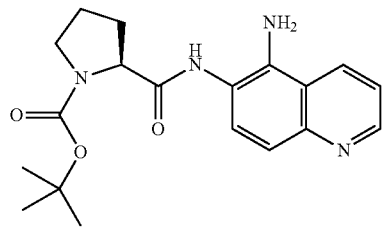

Int-19b

To a solution of Compound Int-19a (1.00 g, 6.28 mmol), HATU (2.63 g, 6.91 mmol) and diisopropylethylamine (3.28 mL, 18.8 mmol) in anhydrous DMF (20 mL) was added Boc-Pro-OH (1.49 g, 6.91 mmol). The resulting reaction was placed under nitrogen atmosphere and was allowed to stir at room temperature for 17 hours. The reaction mixture was then partitioned between EtOAc (100 mL) and saturated aqueous NaCl solution (100 mL). The aqueous layer was extracted with EtOAc (4×100 mL) and the combined organic extracts were washed with brine (4×100 mL). The resulting solution was dried over Na$_2$SO$_4$, filtered and concentrated in vacuo. The resulting residue was dissolved in CH$_2$Cl$_2$ (10 mL) and was purified via chromatography using an ISCO 80-g Redi-Sep column (0-5% methanol/CH$_2$Cl$_2$ as eluent) to provide Compound Int-19b as an orange oil (0.713 g, 32%). ESI-LRMS: (M+H—C$_4$H$_9$O$_2$)$^+$=257.

Step C—Synthesis of Intermediate Compound Int-19c

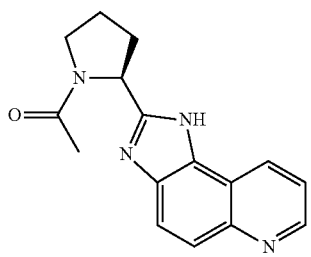

Int-19c

A solution of compound Int-19b (3.00 g, 8.41 mmol) in CH$_3$COOH (70 mL) was places under nitrogen atmosphere, heated to reflux and allowed to stir at this temperature for 18 hours. The reaction mixture was cooled to room temperature, then was concentrated in vacuo. The oily residue obtained was diluted with CH$_2$Cl$_2$ and the solution was neutralized using saturated aqueous NaHCO$_3$ solution (125 mL). The resulting biphasic mixture was allowed to stir for 1 hour and then separated. The aqueous layer was extracted with CH$_2$Cl$_2$ (2×200 mL) and the combined organic extracts were concentrated in vacuo to provide Compound Int-19c as an orange foam (2.04 g, 86%), which was used without further purification. $^1$H NMR (CDCl$_3$) δ 11.61 (br s, 0.32H), 11.04 (br s, 0.68H), 8.93-8.85 (m, 1.68H), 8.38-8.30 (m, 0.32H), 8.08-7.70 (m, 2H), 7.53-7.40 (m, 1H), 5.51-5.43 (m, 1H), 3.64-3.51 (m, 2H), 3.34-3.13 (m, 1H), 2.5.1-2.11 (m, 6H). LCMS: (M+H)$^+$=281.

Step D—Synthesis of Intermediate Compound Int-19d

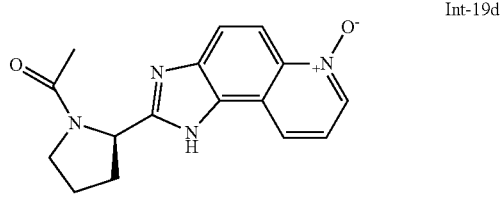 [SMILES: CC(=O)N1CCC[C@@H]1c1nc2ccc3c(ccc[n+]3[O-])c2[nH]1]

Int-19d

To a 0° C. solution of Compound Int-19c (2.03 g, 7.24 mmol) in CH$_2$Cl$_2$ (75 mL) under nitrogen, was added 3-chloroperoxybenzoic acid (1.50 g, 8.69 mmol). The resulting reaction was allowed to warm to room temperature while stirring for 18 hours, then the reaction mixture was cooled to 0° C. and quenched by adding 10% Na$_2$SO$_3$ solution (25 mL). The organic solvent was removed in vacuo and the remaining aqueous solution was directly purified using an ISCO 80 g Redi-Sep column (0-10% CH$_3$OH/CH$_2$Cl$_2$ as the eluent) to provide a bright yellow foam product. This material underwent a second flash chromatography purification using an ISCO 80 g Redi-Sep column (0-10% CH$_3$OH/CH$_2$Cl$_2$ as the eluent) to provide Compound Int-19d as a light yellow foam (1.85 g, 86%). $^1$H NMR (CDCl$_3$) δ 11.69 (br s, 0.17H), 11.12 (br s, 0.83H), 8.59-8.38 (m, 2.83H), 8.04-7.96 (d, J=9.5 Hz, 0.17H), 7.88-7.81 (d, J=8.2 Hz, 0.17H), 7.75-7.67 (d, J=9.4 Hz, 0.83H), 7.36-7.23 (m, 1H), 5.43-5.34 (m, 1H), 3.56-3.48 (m, 2H), 3.24-3.06 (m, 1H), 2.43-2.06 (m, 6H).

Step E—Synthesis of Intermediate Compound Int-19e

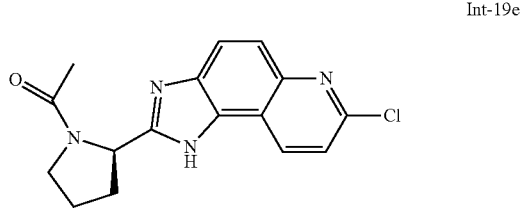 [SMILES: CC(=O)N1CCC[C@@H]1c1nc2ccc3nc(Cl)ccc3c2[nH]1]

Int-19e

A solution of Compound Int-19d (1.84 g, 6.20 mmol) in CH$_2$Cl$_2$ (20 mL) was placed under nitrogen atmosphere, cooled to 0° C., and to the resulting cooled solution was added triethylamine (1.04 mL, 7.45 mmol). The resulting reaction was allowed to stir for 10 minutes, then a solution of phosphoryl chloride (1.14 g, 7.45 mmol) in CH$_2$Cl$_2$ (10 mL) was added dropwise over 10 minutes. The reaction was allowed to stir for an additional 1.75 hours at 0° C. then was quenched by the dropwise addition of water (3.0 mL). The resulting reaction mixture was neutralized to pH 7 using 2N NaOH (~15 mL), then loaded directly onto a 120 g Redi-Sep column and purified using 0-10% CH$_3$OH/CH$_2$Cl$_2$ as the eluent to provide a yellow solid product. The yellow solid product (containing both isomers of Compound Int-19e) was then separated into individual isomers using semi-preparative HPLC (Luna C18, CH$_3$CN/water with 0.05% TFA). The isomerically clean fractions were combined with saturated NaHCO$_3$ solution (10 mL) and the organic solvent was removed in vacuo. The remaining aqueous portion was extracted with EtOAc (3×100 mL) and the combined organic extracts were dried over Na$_2$SO$_4$, filtered and concentrated in vacuo. The resulting residue was dissolved in a mixture of CH$_3$CN and water and the solution was freeze-dried for about 15 hours to provide Compound Int-19e as an off-white solid (463 mg, 23%). $^1$H NMR (CDCl$_3$) δ 11.10 (br s, 1H), 8.87 (br s, 1H), 7.89-7.68 (m, 2H), 7.53-7.42 (d, J=8.6 Hz, 1H), 5.52-5.40 (d, J=8.0 Hz, 1H), 3.69-3.53 (m, 2H), 3.26 (br s, 1H), 2.52-2.11 (m, 6H).

Example 20

Preparation of Intermediate Compound Int-20e

Step A—Synthesis of Intermediate Compound Int-20b

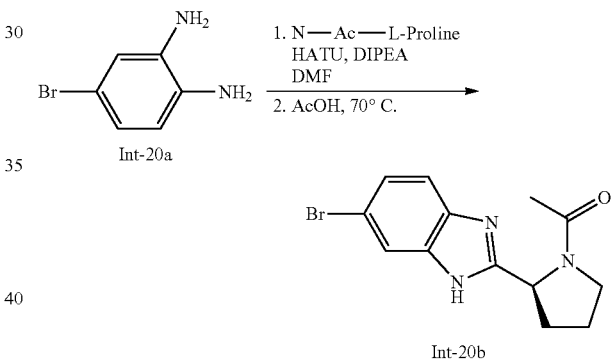

To a solution of Int-20a (6.1 g, 321 mmol), N-acetyl-L-proline (5.4 g, 34.35 mmol) and HATU (13.7 g, 34.35 mmol) in anhydrous DMF (100 mL) was added diisopropylethylamine (16.91 mL, 96.9 mmol) dropwise over 15 minutes at ice temperature The reaction was warmed to room temperature and allowed to stir for 3 hours. The reaction was then diluted with EtOAc (500 mL) and the organic layer washed with water (200 mL×2). The aqueous layer was back-extracted with EtOAc (100 mL×2). The combined organic layers were washed with brine, dried over MgSO$_4$, filtered and concentrated in vacuo. The crude product was purified using flash chromatography using a 1%-2% MeOH/CH$_2$Cl$_2$ as eluent to provide the intermediate amide (4.1 g). The amide was dissolved in glacial acetic acid and was heated at 60-70° C. for 1 hour. The reaction mixture was diluted with EtOAc (100 mL) and cooled in ice bath. Saturated Na$_2$CO$_3$ solution was added slowly until the pH=8. The organic layer was separated and the aqueous layer was extracted with EtOAc (250 mL×2). The combined organic layers were washed with water and brine, dried over MgSO$_4$, filtered and concentrated in vacuo to provide Compound Int-20b (3.75 g, 38%). LCMS: M$^+$=308

Step B—Synthesis of Intermediate Compound Int-20c

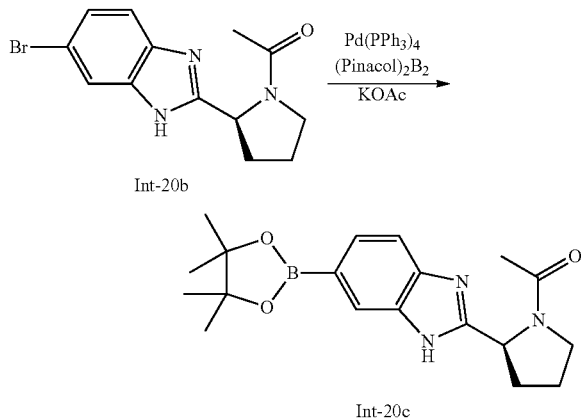

Int-20b (925 mg, 3 mmol), (Pinacol)₂B₂ (1.6 g, 6.3 mmol), Pd(PPh₃)₄ (174 mg, 0.15 mmol), potassium acetate (736 mg, 7.5 mmol) and 1,4-dioxane (100 mL) were added to 350 mL pressure vessel. The resulting mixture was degassed, purged with nitrogen and allowed to stir at 80° C. for 17 hours. After the reaction was cooled to room temperature the solution was diluted with CH₂Cl₂ (300 mL) and filtered through a celite plug. The filtrate was washed with NaHCO₃ solution (50 mL) and water (50 mL). The combined organic layers were washed with brine, dried over MgSO₄, filtered and concentrated in vacuo. The crude product was purified using flash chromatography using a 0-5% MeOH/CH₂Cl₂ as eluent to provide Compound Int-20c (750 mg, 70%, contains some pinacol). MS: MH$^+$=356.2; $^1$H NMR (500 MHz, CD₃OD): δ 8.1-7.4 (m, 3H), 5.3 (m, 1H), 3.9 (m, 1H), 3.7 (m, 1H), 2.4 (m, 1H), 2.0-2.2 (m, 6H), 1.39 (bs, 12H).

Example 21

Preparation of Intermediate Compound Int-21d

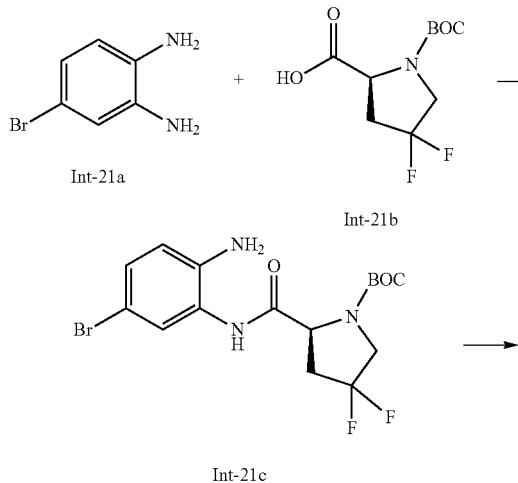

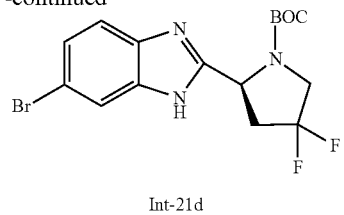

Step A—Synthesis of Intermediate Compound Int-21c

A solution of Compound Int-21a (7.35 g, 39.3 mmol), Compound Int-21b (9.88 g, 39.3 mmol) and diisopropylethylamine (10 mL, 57.5 mmol) in DMF (40 mL) was cooled to 0° C. HATU (15.0 g, 39.45 mmol) was added slowly to the cooled solution and the resulting reaction was allowed to warm to room temperature on its own, then stirred at room temperature for 19 hours. The reaction mixture was then diluted with ethyl acetate (300 mL) and washed with brine (3×100 mL), and the organic phase was dried over sodium sulfate, filtered and concentrated in vacuo. The residue obtained was purified using a 330 g ISCO silica column (0-5% methanol in dichloromethane as eluent) to provide Compound Int-21c as a brown gel (15.1 g, 91%).

Step B—Synthesis of Intermediate Compound Int-21d

Compound Int-21c (15.1 g, 35.9 mmol) was dissolved in acetic acid (50 mL) in a 500 mL flask. The resulting solution was heated to 60° C. and allowed to stir at this temperature for 4 hours, then cooled to room temperature and concentrated in vacuo. The resulting residue was dissolved in dichloromethane (200 mL), dried (sodium sulfate and sodium carbonate), filtered and concentrated in vacuo to provide Compound Int-21d as a brown solid (11.0 g, 76%), which was used without further purification. LCMS anal. calcd. for: C₁₆H₁₈BrF₂N₃O₂ 401.1. Found: 402.2 (M+H)⁺.

Example 22

Preparation of Intermediate Compound Int-22e

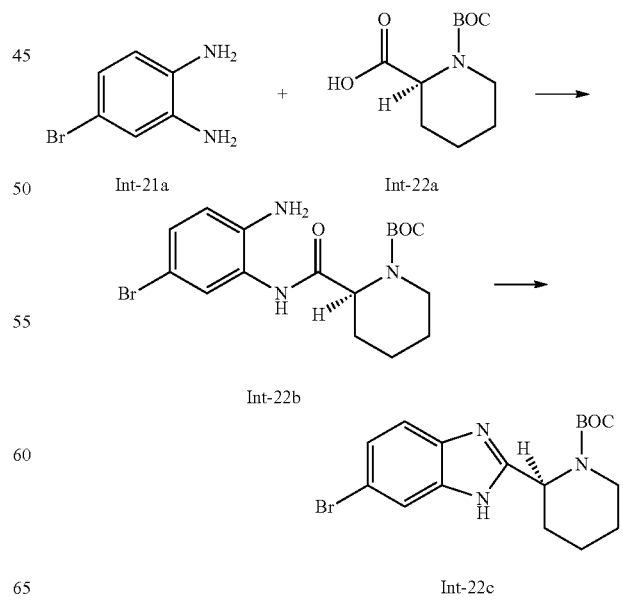

Step A—Synthesis of Intermediate Compound Int-22b

Using the method described in Example 21, Step A, Compounds Int-21a and Int-22a were coupled to provide Compound Int-22b as a brown gel (12.5 g, 81%).

Step B—Synthesis of Intermediate Compound Int-22c

Using the method described in Example 29, Step B, Compound Int-22b was converted to Compound Int-22c as a brown solid (11.20 g, 93%), which was used without purification.

Example 23

Preparation of Intermediate Compound Int-23e

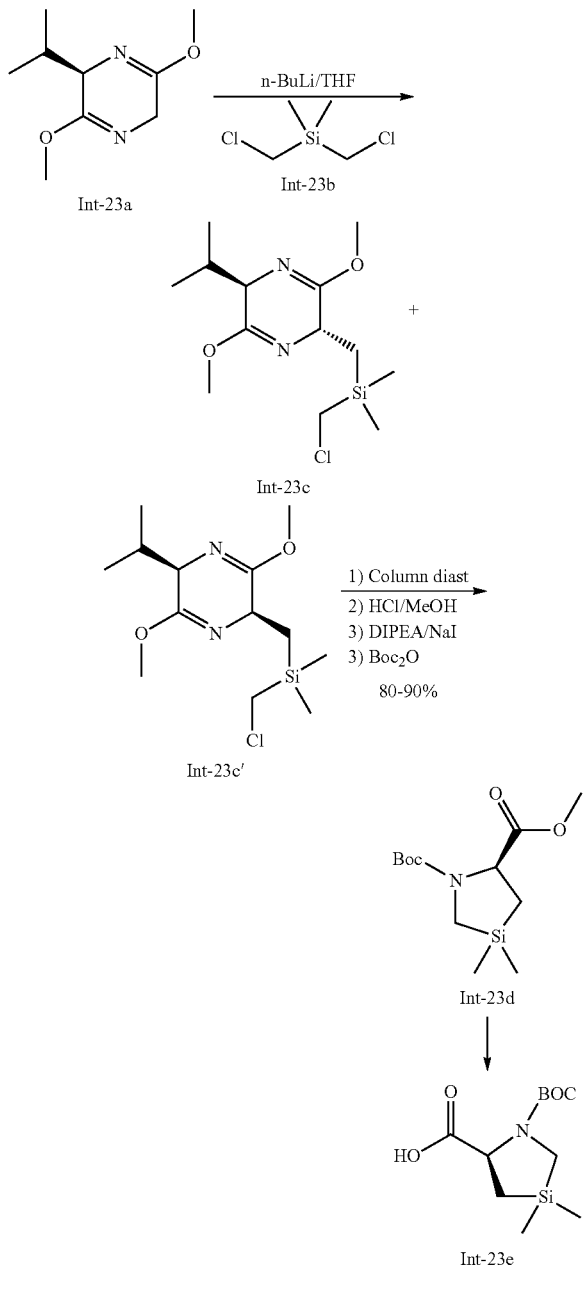

Step A—Synthesis of Intermediate Compound Int-23e

A 5 L-3 necked round bottomed flask, equipped with a mechanical stirrer, temperature probe, addition funnel and $N_2$ inlet, was charged with the Schollkopf chiral auxiliary-(Int-23a, 200 g, 1.09 mol, 1.0 eq), bis(chloromethyl)dimethylsilane (Int-23b, 256 g, 1.63 mol, 1.5 eq), and THF (2 L, Aldrich anhydrous). The flask was cooled in a dry ice/2-propanol bath until the internal temperature reached −75° C. n-Butyl lithium (Aldrich 2.5 M in hexanes, 478 mL, 1.19 mol, 1.09 eq) was added via a dropping funnel over 1 hour while maintaining the internal reaction temperature between −67° C. and −76° C. The resulting orange-red solution was allowed to gradually warm to room temperature for about 15 hours. The reaction mixture was then re-cooled to 0° C. and quenched with 500 mL of water. Diethyl ether (2 L) was added and the layers were separated. The aqueous layer was extracted with 1 L of diethyl ether. The combined organic layers was washed with water and brine, dried with $MgSO_4$, filtered, and concentrated in vacuo to provide 480 g of an orange oil. This material was left under vacuum for about 15 hours to provide 420 g of oil (mixture of Int-23c and Int-23c'). The crude product was split into two batches and purified via silica gel chromatography on a 1.6 Kg flash column. The column was eluted with gradient of 0-4% $Et_2O$ in hexanes. The product fractions were concentrated in vacuo at a bath temperature at or below 40° C. to provide 190 grams of Compound Int-25c-(60% yield).

Step B—Synthesis of Intermediate Compound Int-23d

A 5 L, 3-necked round bottomed flask equipped with a mechanical stirrer, addition funnel, temperature probe, external water bath and $N_2$ inlet was charged with compound Int-23c (196 g, 0.643 mol, 1.0 eq) and methanol (1.5 L). Aqueous HCl (500 mL of 10% by volume) was added at room temperature over 30 minutes, with a mild exotherm observed. The temperature increased to 37° C. then dropped back down. The reaction mixture was allowed to stir at room temperature for 3 hours and was monitored by TLC and LCMS. The reaction mixture was then concentrated in vacuo to an oil. Additional methanol (3×200 mL) was added and the reaction mixture was concentrated in vacuo again. The resulting crude product was dried under house vacuum for about 15 hours. The crude product was then dissolved in $CH_2Cl_2$ (750 mL) and $Et_2O$ (1250 mL) and sodium iodide (96.4 g, 0.643 mol, 1.0 eq) was added. Diisopropylethylamine (336 mL, 1.929 mol, 3.0 eq) was added slowly over 25 minutes with efficient stirring, causing the temperature to increase to 35° C. then decrease again. The reaction mixture was allowed to stir at room temperature for 2 hours, at which time the MS of an aliquot indicated consumption of the starting material. The reaction mixture was allowed to stir for an additional 2 hours and then Boc-anhydride (281 g, 1.286 mol, 2.0 eq) was added. The reaction mixture was then allowed to stir at room temperature. After two days, the reaction mixture was diluted with EtOAc (2 L) and water (1 L), and the layers were separated. The aqueous phase was extracted with 500 mL of EtOAc. The combined organic layers were washed with water (500 mL), and brine (500 mL), dried with $MgSO_4$, filtered, and concentrated in vacuo to a yellow oil (380 g). The crude product was split into two 180 g portions for convenience and each portion was purified via flash silica gel chromatography. Column conditions for a 180 g portion of crude product are as follows. The 180 gram sample of crude product was loaded onto a 191 g $SiO_2$ cartridge and purified on a 1.5 Kg $SiO_2$ column. The column was eluted using a 0%-20% EtOAc/hexanes gradient as the mobile phase to provide 52 grams of pure Int-23d and additional fractions of Int-23d that contained a small amount of a Boc-valine impurity. The impure fractions from the two columns were recombined and re-purified. After chromatography, compound Int-23d was obtained as an oil which solidified to a white solid on standing (128 g, 65% yield over the three steps.)

Step C—Synthesis of Intermediate Compound Int-23e

A solution of Int-23d (8.5 g, 31.1 mmol) in methanol (100 mL) and 1.0 M aqueous KOH solution (48 mL, 48 mmol) was allowed to stir at room temperature for about 15 hours, neutralized with 48 ml of 1.0 M aqueous HCl solution to pH~5, and concentrated in vacuo to an oil. The resulting residue was extracted with dichloromethane (2×100 mL) and the combined organic layers were concentrated in vacuo to provide Compound Int-23e as a gel (7.74 g, 96%). Chiral purity was determined using a Chiralcell AD-H column, SFC mode, $CO_2$/MeOH 90/10.

Example 24

Preparation of Intermediate Compound Int-24g

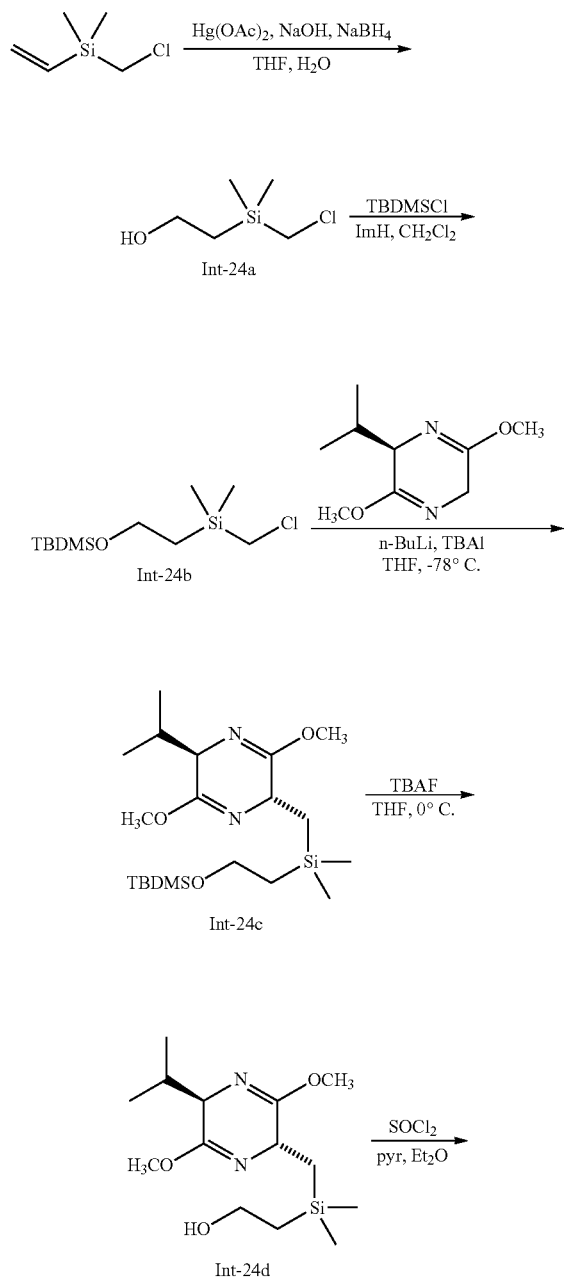

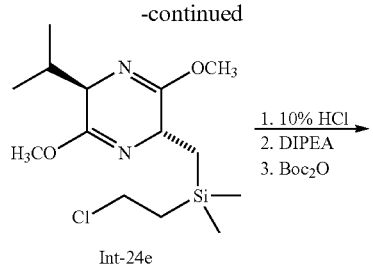

Step A—Synthesis of Intermediate Compound Int-24a

Mercuric acetate (14.3 g, 44.8 mmol) was dissolved in water (45 mL), and THF (45 mL) was added. To this yellow solution at room temperature was added (chloromethyl)-dimethylvinylsilane (5.65 g, 41.9 mmol) which became homogeneous in 30 seconds. The resulting solution was allowed to stir for 5 minutes, then aqueous NaOH (3M, 45 mL) was added, followed by a solution (45 mL) of $NaBH_4$ (0.5M) in 3M NaOH. Diethyl ether (160 mL) was added and the mixture stirred at room temperature for and additional 1 hr. The mixture was then saturated with NaCl and the layers separated. The organic layer was washed with brine (100 mL), dried with $Na_2SO_4$, and concentrated in vacuo to provide Compound Int-24a as a colorless oil (5.72 g, 89%). $^1$H NMR ($CDCl_3$) δ 3.84-3.75 (m, 2H), 2.81 (s, 2H), 1.34-1.31 (m, 1H), 1.10-1.05 (m, 2H), 0.148 (s, 6H).

Step B—Synthesis of Intermediate Compound Int-24b

To a solution of Int-24a (5.72 g, 37.4 mmol) in $CH_2Cl_2$ (50 mL) was added imidazole (3.82 g, 56.1 mmol). The mixture was allowed to stir at 0° C. and tert-butyldimethylsilyl chloride (8.46 g, 56.1 mmol) was slowly added over 10 minutes and the reaction mixture was warmed to room temperature and stirred for about 15 hours. Water (50 mL) was added and the layers separated. The aqueous layer was extracted with $CH_2Cl_2$ (3×30 mL) and the combined organic layers were dried over $Na_2SO_4$, filtered and concentrated in vacuo at 80° C. to remove residual tert-butyldimethylsilyl chloride and afford the desired product Int-24b as a colorless oil (9.82 g, 98%). $^1$H NMR ($CDCl_3$) δ 3.75 (t, J=7.4 Hz, 2H), 2.78 (s, 2H), 0.99 (t, J=7.4 Hz, 2H), 0.87 (s, 9H), 0.011 (s, 6H), 0.02 (s, 6H).

Step C—Synthesis of Intermediate Compound Int-24c

To a solution of (R)-2-isopropyl-3,6-dimethoxy-2,5-dihydropyrazine (6.16 g, 33.4 mmol) in THF (60 mL) was added TBAI (617 mg, 1.67 mmol). The mixture was cooled to −78° C. and a solution of n-BuLi (14.7 mL, 2.5M in hexanes, 36.75 mmol) was slowly added over 10 minutes. The reaction mixture was allowed to stir at −78° C. for 30 minutes, then Int-24b in THF (20 mL) was slowly added over 10 minutes. The reaction was allowed to stir at −78° C. for 2 hours then allowed to warmed to room temperature and stirred for about 15 hours. The reaction was quenched by addition of MeOH (5 mL), concentrated in vacuo, water added (50 mL) followed by diethyl ether (50 mL) and the layers were separated. The organic layer was washed with water (2×50 mL) then dried over $Na_2SO_4$, filtered and concentrated in vacuo to provide the crude product. Further purification by column chromatography on a 330 g ISCO Redi-Sep silica gel column using a eluent of $CH_2Cl_2$ with a gradient of 0-10% EtOAc/hexanes afforded the desired product Int-24e as a light amber oil (8.65 g, 63%). $^1$H NMR (CDCl$_3$) δ 4.07-3.99 (m, 1H), 3.94-3.89 (m, 1H), 3.79-3.71 (m, 2H), 3.68-3.63 (m, 6H), 2.32-2.17 (m, 1H), 1.25-1.21 (m, 1H), 1.06-0.95 (m, 5H), 0.88 (s, 10H), 0.74-0.68 (m, 1H), 0.69-0.66 (m, 2H), 0.12-0.02 (m, 12H).

Step D—Synthesis of Intermediate Compound Int-24d

To a THF solution (60 mL) of Int-24c (8.65 g, 20.8 mmol) cooled to 0° C. was slowly added a solution of tetrabutylammonium fluoride (31.3 mL, 1.0M in THF, 31.0 mmol) over 5 minutes. The reaction mixture was allowed to warm to room temperature for about 15 hours with stirring. The reaction was then concentrated in vacuo, and the crude product chromatographed on a 120 g ISCO Redi-Sep silica gel column using a $CH_2Cl_2$ with gradient of 0-3% MeOH/$CH_2Cl_2$ as the eluent to provide Compound Int-24d as a colorless oil (4.69 g, 99%). $^1$H NMR (CDCl$_3$) δ 4.15-4.05 (m, 1H), 3.98-3.91 (m, 1H), 3.84-3.73 (m, 2H), 3.69 (s, 6H), 2.39-2.32 (m, 1H), 2.30-2.18 (m, 1H), 1.37-1.29 (m, 1H), 1.10-1.01 (m, 5H), 0.93-0.85 (m, 2H), 0.74-0.68 (m, 2H), 0.14-0.08 (m, 6H).

Step F—Synthesis of Intermediate Compound Int-24e

To a $Et_2O$ (30 mL) solution of Int-24d (2.12 g, 267 mmol) was added pyridine (720 µL, 8.82 mmol). The mixture was cooled to 0° C. and thionyl chloride (575 µL, 7.90 mmol) in $Et_2O$ (2 mL) was slowly added over 5 minutes. The reaction mixture was allowed to warm to room temperature for about 15 hours with stirring. The reaction mixture was filtered and the filtrate concentrated in vacuo to provide the crude product. Further purification by column chromatography using a 80 g ISCO Redi-Sep silica gel column with $CH_2Cl_2$ and a gradient of 0-3% MeOH as the eluent afforded the desired product Int-24e as an amber oil (417 mg, 16%). $^1$H NMR (CDCl$_3$) δ 4.22-3.62 (m, 7H), 2.50-2.13 (m, 4H), 1.58-1.41 (m, 1H), 1.32-0.65 (m, 9H), 0.24-0.04 (m, 6H).

Step G—Synthesis of Intermediate Compound Int-24f

To a solution of Int-24e (417 mg, 1.40 mmol) in MeOH (10 mL) was added a 10% aqueous HCl solution (10 mL). The resulting mixture was allowed to stir at room temperature for about 15 hours and concentrated in vacuo. The resulting residue was coevaporated with MeOH (3×30 mL) and then dissolved in $CH_2Cl_2$ (3 mL) and $Et_2O$ (6 mL). To this solution was added diisopropylethylamine (750 µL, 4.30 mmol) and the reaction allowed to stir at room temperature After 7 hours di-tert-butyl dicarbonate (703 mg, 3.22 mmol) was added and the reaction was stirred for about 15 hours at room temperature and then concentrated in vacuo. The crude product was further purified using column chromatographed using a 12 g ISCO Redi-Sep silica gel column with $CH_2Cl_2$ and gradient of 0-50% EtOAc/hexanes mixture as the eluent to provide Compound Int-24f as an amber oil (94 mg, 23%). $^1$H NMR (CDCl$_3$) δ 4.22-4.01 (m, 1H), 4.10-3.94 (m, 1H), 3.85-3.70 (m, 3H), 2.32-2.09 (m, 1H), 1.44 (s, 7H), 1.24-0.88 (m, 6H), 0.16-0.05 (m, 6H).

Step H—Synthesis of Intermediate Compound Int-24g

To a solution of compound Int-24f (218 mg, 0.758 mmol) in THF (3 mL) was added lithium hydroxide monohydrate (64 mg, 1.52 mmol) in water (3 mL). The reaction mixture was allowed to stir at room temperature for about 15 hours then concentrated in vacuo to half volume. The aqueous mixture was then acidified with 1N HCl to pH 4 and extracted with EtOAc (5×30 mL). The combined organic layers were dried over $Na_2SO_4$, filtered and concentrated in vacuo to provide Compound Int-24g as an off-white solid (157 mg, 87%). $^1$H NMR (CDCl$_3$) δ 1.44 (s, 8H), 1.34-0.78 (m, 9H), 0.17-0.03 (m, 6H).

Example 25

Preparation of Intermediate Compound Int-25d

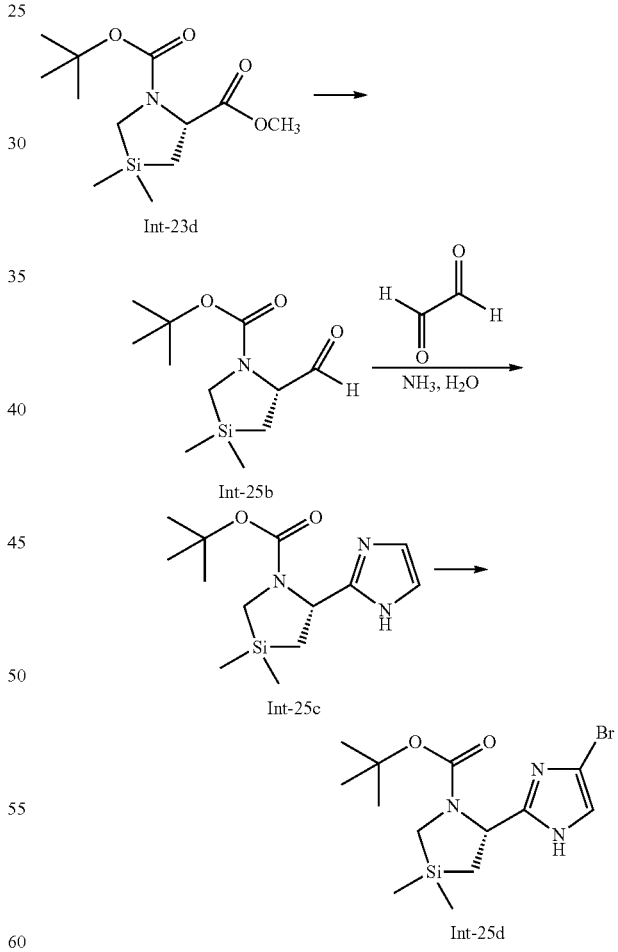

Int-25c was prepared from Int-23d using the methods described in Examples 7 and 8. Int-25d was prepared from Int-25c using the methods described in Example 7.

Example 26

Preparation of Intermediate Compound Int-26b

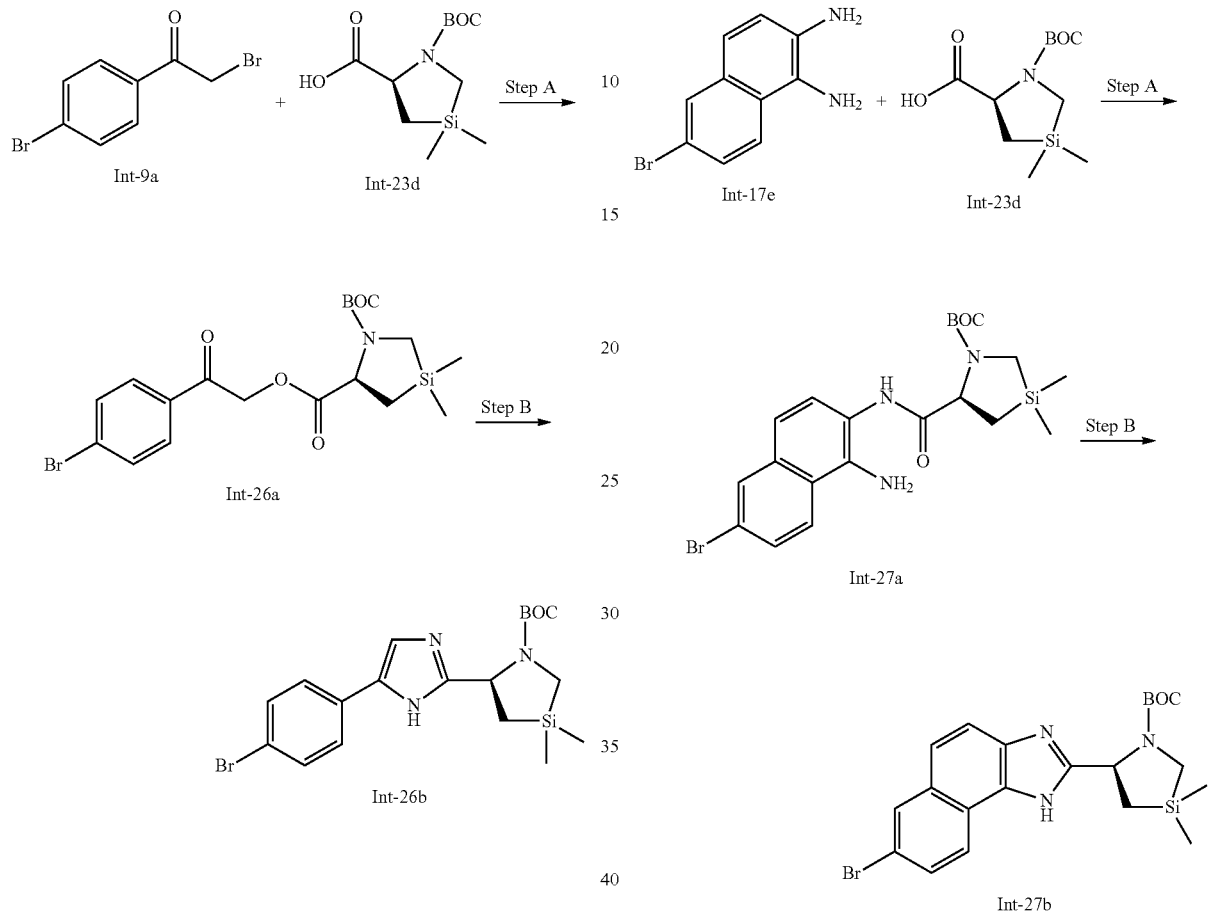

Example 27

Preparation of Intermediate Compound Int-27b

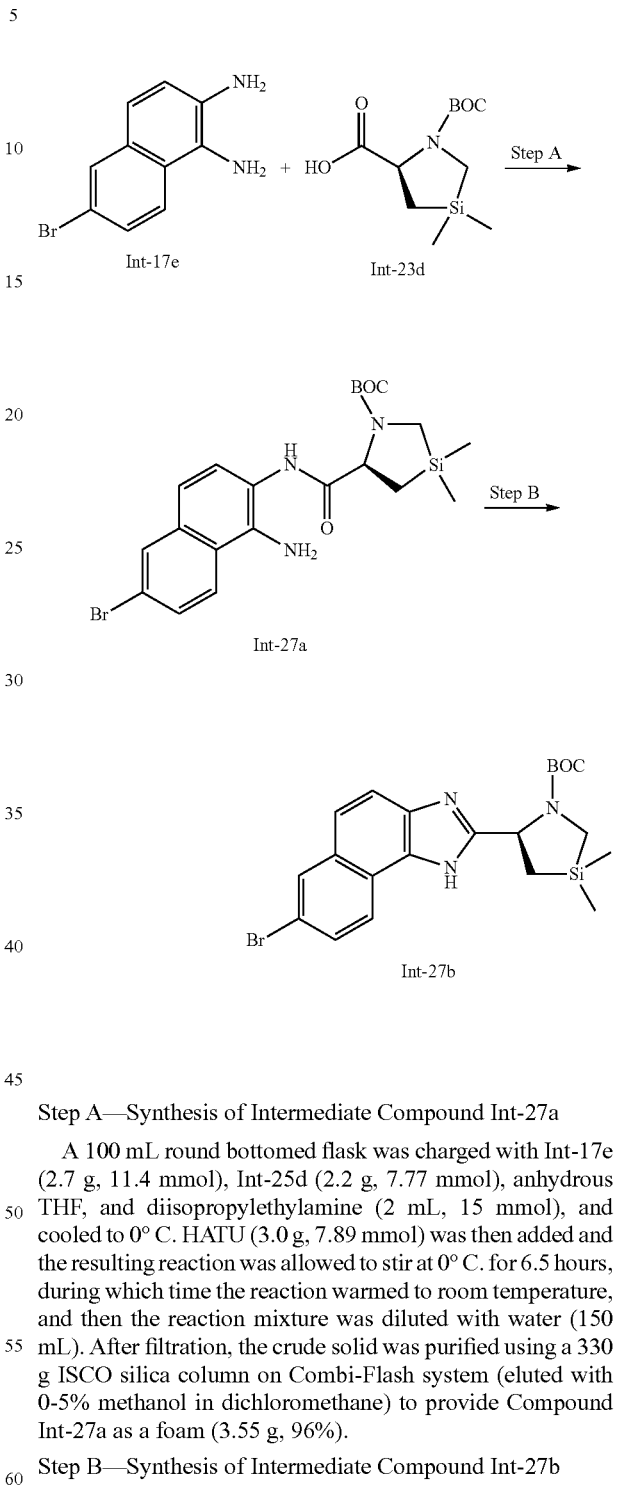

Step A—Synthesis of Intermediate Compound Int-26a

Int-9a (Aldrich, 9.0 g, 32.4 mmol) and Int-23d (7.74 g, 29.85 mmol) were dissolved in DMF (50 mL). Triethylamine (10 mL, 71.83 mmol) was then added slowly at room temperature and the mixture was stirred for about 15 hours. Ethyl acetate (500 mL) was added, and the organic layer was washed with brine (3×100 mL), dried over sodium sulfate, and concentrated in vacuo to an oil. The resulting residue was purified using a 220 g ISCO silica column with gradient of 0-20% ethyl acetate in hexanes as the eluent to provide Compound Int-26a as a gel (12.3 g, 83%).

Step B—Synthesis of Intermediate Compound Int-26b

A 350 ml pressure vessel was charged with Int-26a (12.3 g, 26.96 mmol), ammonium acetate (18.0 g, 233.7 mmol), xylenes (50 mL), sealed and stirred at 120° C. for two hours. After cooling to room temperature, the suspension was concentrated in vacuo. The resulting residue was dissolved in ethyl acetate (300 mL), washed with water (100 mL) 1-0 and saturated sodium carbonate solution (100 mL). the combined organic layer was dried over sodium sulfate, and concentrated in vacuo. The resulting residue was further purified using a 330 g ISCO silica column with gradient of 10-50% ethyl acetate in hexanes as an eluent to provide Compound Int-26b as a pale solid (8.5 g, 72%).

Step A—Synthesis of Intermediate Compound Int-27a

A 100 mL round bottomed flask was charged with Int-17e (2.7 g, 11.4 mmol), Int-25d (2.2 g, 7.77 mmol), anhydrous THF, and diisopropylethylamine (2 mL, 15 mmol), and cooled to 0° C. HATU (3.0 g, 7.89 mmol) was then added and the resulting reaction was allowed to stir at 0° C. for 6.5 hours, during which time the reaction warmed to room temperature, and then the reaction mixture was diluted with water (150 mL). After filtration, the crude solid was purified using a 330 g ISCO silica column on Combi-Flash system (eluted with 0-5% methanol in dichloromethane) to provide Compound Int-27a as a foam (3.55 g, 96%).

Step B—Synthesis of Intermediate Compound Int-27b

A mixture of Int-27a (2.0 g, 4.18 mmol) and acetic acid (20 mL) was allowed to stir at 60° C. for 5 hours and was then cooled to room temperature. The acetic acid was then removed in vacuo and the resulting residue was purified using a 120 g ISCO silica column on Combi-Flash RF system (0-5% methanol in dichloromethane) to provide Compound Int-27b as a solid (1.56 g, 81%).

Example 28

Preparation of Compound 2

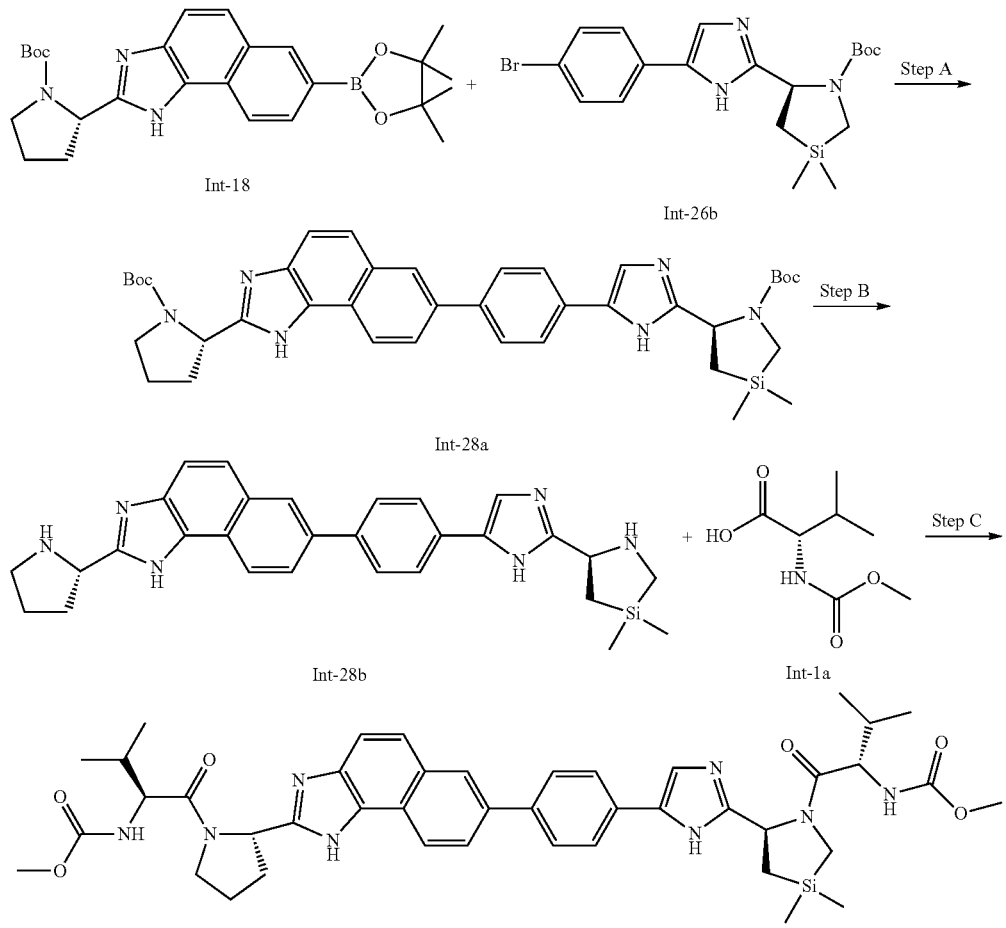

Step A—Synthesis of Intermediate Compound Int-28a

A 200 mL flask was charged with boronic acid Int-18 (0.55 g, 1.19 mmol), bromide Int-26b (0.35 g, 0.80 mmol), $PdCl_2$·dppf-dichloromethane complex (65 mg, 0.08 mmol), a solution of sodium carbonate (1.5M, 1.0 mL, 1.5 mmol), and 1,4-dioxane (10 mL). The resulting mixture was degassed and refluxed at approximately 80° C. under nitrogen atmosphere for about 15 hours. The reaction was then cooled and concentrated in vacuo to provide crude product as an oil. Further purification was accomplished using a 80 g ISCO silica column on Combi-Flash-RF system with a gradient of 0-4% methanol in dichloromethane as the eluent to provide Compound Int-28a as a pale foam (320 mg, 58%). LCMS anal. calcd. For: $C_{39}H_{48}N_6O_4Si$ 692.4. Found: 693.4 $(M+H)^+$.

Step B—Synthesis of Intermediate Compound Int-28b

Compound Int-28a (320 mg, 0.462 mmol) was dissolved in dichloromethane (3 mL) and trifluoroacetic acid (3 mL) was added. The resulting solution was allowed to stir at room temperature for 5 hours and then concentrated in vacuo to provide Compound Int-28b as a solid (225 mg), which was used for the next reaction without purification.

Step C—Synthesis of Compound 2

A 100 mL flask was charged with diamine Int-28b (225 mg, ~0.46 mmol), acid Int-1a (200 mg, 1.14 mmol), diisopropylethylamine (0.5 mL, 3.75 mmol), DMF (5 mL) and cooled to 0° C. HATU (435 mg, 1.14 mmol) was then added and the resulting solution was allowed to warm to room temperature After 2.5 hours the reaction was partially concentrated in vacuo and purified using reverse phase chromatography (0-90% acetonitrile in water with 0.1% TFA as an eluent) provided Compound 2 as a white solid (180 mg, 49%). LCMS anal. calcd. for: $C_{43}H_{54}N_8O_6Si$ 806.4. Found: 807.4 $(M+H)^+$.

The compounds set forth in the table below were made using the method described above and substituting the appropriate reactants and reagents:

| Compound No. | MS (M + H) |
|---|---|
| 1 | 808.3 |
| 15 | 833.4 |
| 16 | 833.4 |
| 55 | 825.2 |
| 56 | 843.3 |
| 65 | 823.4 |
| 70 | 868.2 |
| 71 | 862.0 |

189
-continued

| Compound No. | MS (M + H) |
|---|---|
| 72 | 845.0 |
| 73 | 808.0 |
| 74 | 907.2 |
| 76 | 794 |
| 77 | 924.2 |
| 78 | 836.1 |
| 79 | 836.1 |
| 80 | 916.2 |
| 81 | 900.1 |
| 83 | 924.2 |
| 84 | 900.1 |

190
-continued

| Compound No. | MS (M + H) |
|---|---|
| 102 | 870.1 |
| 103 | 950.2 |
| 104 | 840.0 |
| 105 | 842.0 |
| 106 | 816.0 |

Example 29

Preparation of Compound 54

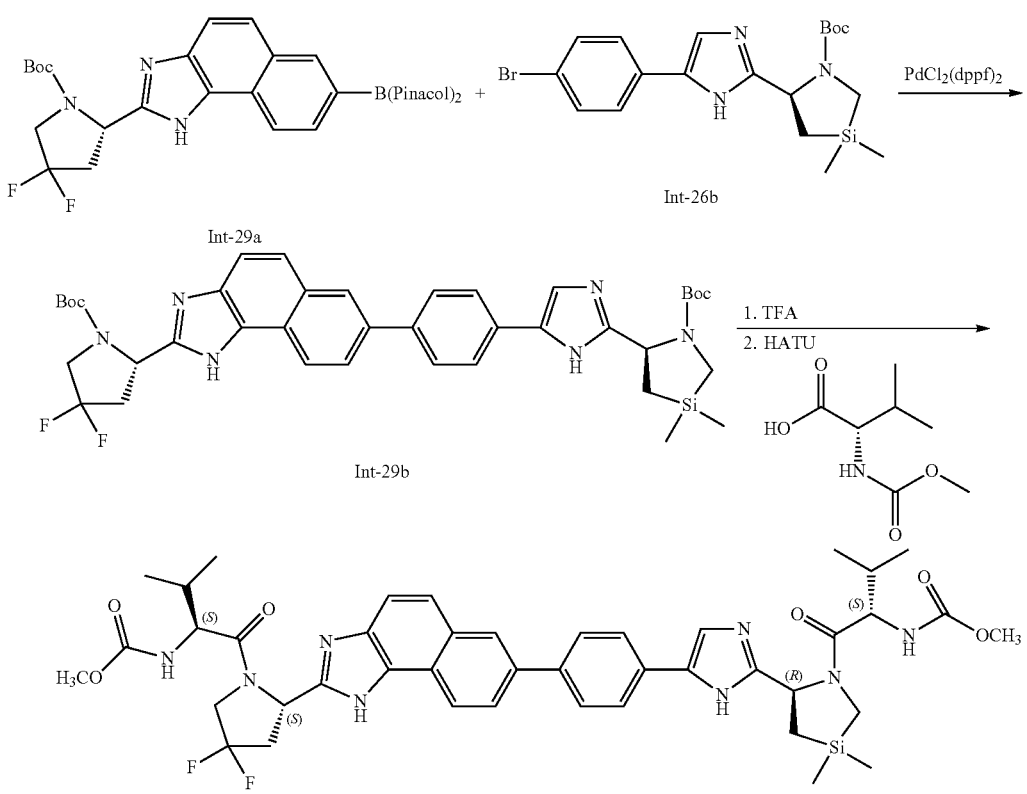

54

-continued

| Compound No. | MS (M + H) |
|---|---|
| 85 | 858.1 |
| 86 | 938.2 |
| 87 | 946.2 |
| 88 | 914.2 |
| 89 | 870.1 |
| 90 | 834.1 |
| 91 | 777 |
| 92 | 844.0 |
| 93 | 834 |
| 94 | 844.0 |
| 95 | 822.1 |
| 96 | 822.1 |
| 97 | 820.1 |
| 99 | 816.0 |
| 100 | 870.1 |
| 101 | 910.1 |

Step A—Synthesis of Intermediate Compound Int-29a

A mixture of Int-17h (9.54 g, 21.1 mmol), bis(pinacolato) diboron (5.89 g, 23.2 mmol), $PdCl_2(dppf)$ (1.54 g, 2.11 mmol) and potassium acetate (6.21 g, 63.3 mmol) in dioxane (120 mL) in a sealed tube was degassed via alternate vacuum and argon flushes. The reaction was then heated to 100° C. and allowed to stir at this temperature for about 4 hours. The reaction mixture was cooled to room temperature and diluted with EtOAc (200 mL), filtered through Celite®, and the collected solids were washed with EtOAc until the filtrate was colorless. The layers were separated and the organic phase was washed sequentially with saturated aqueous $NaHCO_3$ (2×25 mL) and saturated aqueous NaCl (3×25 mL), dried over $Na_2SO_4$, filtered and concentrated in vacuo. The resulting residue (16.3 g) was taken up in $CH_2Cl_2$ and purified using flash chromatography on an ISCO 330-g Redi-Sep column using 0-30% EtOAc/hexanes then 30% EtOAc/hexanes as the eluent to provide Compound Int-29a (9.02 g, 85%) as a light brown solid. ESI-LCMS 2.14 min; [M+H]⁺=500. ¹H NMR (CDCl₃): δ 11.33 (br s, 0.32H), 10.79 (br s, 0.48H), 8.58 (d, J=8.1 Hz, 0.60H), 8.45 (d, J=6.6 Hz, 1H), 7.99 (dd, J=8.4, 0.6 Hz, 0.60H), 7.93 (s, 0.80H), 7.82 (d, J=9.0 Hz, 0.52H), 7.75-7.68 (m, 1H), 7.55 (d, J=8.7 Hz, 0.60H), 5.45-5.38 (m, 1H), 4.08-3.60 (m, 3H), 3.00-2.80 (m, 1H), 1.51 (s, 9H), 1.40 (s, 12H).

Step B—Synthesis of Intermediate Compound Int-29b

A mechanically stirred mixture of Int-29a (9.25 g, 18.5 mmol), Int-26b (8.89 g, 20.3 mmol), PdCl₂(dppf) (2.03 g, 2.78 mmol) and sodium carbonate (5.89 g, 55.6 mmol) in 1:2 water/dioxane (600 mL) at room temperature was purged with dry N₂ for 10 minutes then argon gas for 5 minutes. The reaction mixture was then heated to 85° C. and allowed to stir at this temperature for 3 hours. The reaction mixture was cooled to room temperature then filtered through Celite® and the collected solids were washed with EtOAc until the filtrate was colorless. The organic layer of the filtrate was separated and washed with saturated aqueous NaCl (3×50 mL), dried over Na₂SO₄, filtered and concentrated in vacuo. The resulting residue (18.8 g) was taken up in CH₂Cl₂ and purified using flash chromatography on an ISCO 330-g Redi-Sep column (0-5% MeOH/CH₂Cl₂ gradient eluent) to provide Compound Int-29b (5.80 g). Compound Int-29b was further purified via chromatography using an ISCO 330-g Redi-Sep column (0-100% EtOAc/hexanes) to provide purified Compound Int-29b (2.81 g, 20%) as an off-white solid. ESI-LCMS 1.70 min; [M+H]⁺=729. ¹H NMR (CDCl₃): δ 11.60-11.40 (m, 0.36H), 11.20-11.00 (m, 0.12H), 10.90-10.40 (m, 0.55H), 10.30-9.90 (m, 0.50H), 8.70-8.58 (m, 1H), 8.20-7.98 (m, 1H), 7.96-7.46 (m, 7H), 7.40-7.28 (m, 0.5H), 7.20-7.08 (m, 0.34H), 5.65-5.38 (m, 2H), 4.10-3.55 (m, 4H), 3.02-2.80 (m, 2H), 2.55-2.37 (m, 1H), 1.60-1.45 (m, 18H), 1.25-1.15 (m, 1H), 0.56-0.25 (m, 6H).

Step C—Synthesis of Compound 54

To a stirred solution of Int-29b (2.80 g, 3.84 mmol) in CH₂Cl₂ (24 mL) at room temperature was added TFA (5 mL) and the resulting solution was allowed to stir at room temperature for 3 hours. The reaction mixture was then concentrated in vacuo to provide a brown oil intermediate, which was used without further purification. Lyophilization of an aliquot from 1:1 MeCN/water (3 mL) at room temperature for 36 hours afforded an off-white solid intermediate. ESI-MS: [M+H]⁺=529. ¹H NMR (DMSO-d₆): δ 9.35 (br s, 1H), 8.96 (br s, 1H), 8.51 (d, J=8.0 Hz, 1H), 8.41 (s, 1H), 8.06 (dd, J=8.5, 1.5 Hz, 1H), 7.97-7.87 (m, 5H), 7.82 (d, J=9.0 Hz, 1H), 7.77 (br s, 1H), 5.34 (t, J=8.5 Hz, 1H), 4.69 (d, J=6.5 Hz, 1H), 3.83 (t, J=12.0 Hz, 3H), 3.22-3.09 (m, 1H), 3.08-2.93 (m, 1H), 1.55 (dd, J=14.5, 6.5 Hz, 1H), 1.21 (dd, J=14.5, 10.5 Hz, 1H), 0.38 (s, 3H), 0.35 (s, 3H).

To a stirred solution of the brown oil intermediate in DMF (60 mL) at 0° C. was added diisopropylethylamine (6.7 mL, 38.4 mmol). The resulting solution was allowed to stir at this temperature for 30 minutes, then (S)-2-(methoxycarbonylamino)-3-methylbutanoic acid (1.48 g, 8.45 mmol) was added and the resulting solution was cooled to −50° C. HATU (3.28 g, 8.64 mmol) was then added and the resulting reaction was allowed to stir at −50° C. for 15 minutes, then the cooling bath was removed and the reaction was allowed to warmly slowly to room temperature on its own. The reaction was then allowed to stir at room temperature for about 14 hours and diluted with water (500 mL). The reaction mixture was filtered and the collected solid was dried in vacuo to provide a crude product (5.4 g) which was dissolved in CH₂Cl₂ and purified using flash chromatography using an ISCO 330-g Redi-Sep column with a 0-10% methanol/CH₂Cl₂ gradient eluent to provide Compound 54 (3.41 g). This compound was further purified using two ISCO 120-g GOLD Redi-Sep columns with a 0-75% EtOAc/hexanes and then 75% EtOAc/Hexanes eluent to provide purified Compound 54 (2.25 g) as an off-white solid. ESI-LCMS 1.54 min; [M+H]⁺=843.

Step D—Synthesis of the Dihydrochloride Salt of Compound 54

To a solution of Compound 54 (2.25 g, 2.67 mmol) in MeOH (24 mL) at room temperature was added 2N HCl in ether (2.66 mL, 5.33 mmol). The resulting reaction was allowed to stand at room temperature for 5 minutes, then was concentrated in vacuo. The resulting residue was dissolved in a 1:2 mixture of acetonitrile:water (15 mL) and the resulting solution was lyophilized at room temperature for 72 hours to provide the dihydrochloride salt of Compound 54 as an off-white solid (2.26 g, 64% over 2 steps). ESI-LRMS [M+H]⁺ 843. ¹H NMR (DMSO-d₆): δ 14.76 (br s, 1H), 14.35 (br s, 1H), 8.70-8.57 (m, 1H), 8.52 (s, 1H), 8.20-8.07 (m, 2H), 8.07-8.02 (m, 2H), 8.02-7.93 (m, 3H), 7.88-7.80 (m, 1H), 7.45 (d, J=8.5 Hz, 1H), 7.15 (d, J=8.5 Hz, 1H), 5.51 (t, J=8.5 Hz, 1H), 5.40-5.29 (m, 1H), 4.64-4.45 (m, 2H), 4.42 (t, J=7.5 Hz, 1H), 4.03 (t, J=8.0 Hz, 1H), 3.56 (s, 3H), 3.53 (s, 3H), 3.32-2.97 (m, 5H), 2.20-2.10 (m, 1H), 2.00-1.90 (m, 1H), 1.65-1.53 (m, 1H), 1.25 (dd, J=15.0, 9.5 Hz, 1H), 0.97-0.81 (m, 7H), 0.79 (d, J=6.5 Hz, 3H), 0.74 (d, J=6.5 Hz, 3H), 0.39 (s, 3H), 0.28 (s, 3H).

Example 30

Preparation of Compound 67

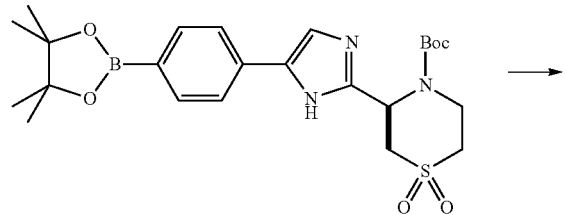

Int-30a

-continued

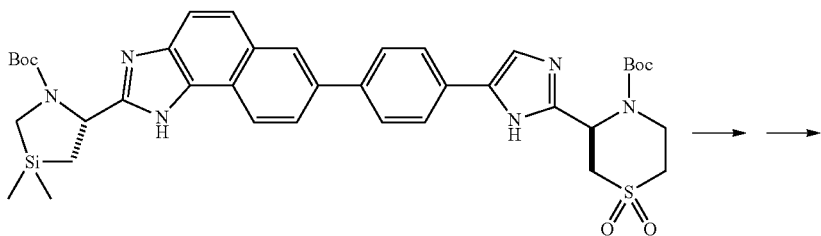

Int-30b

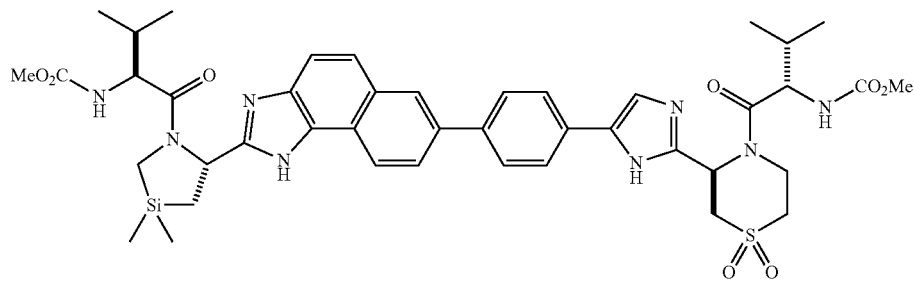

67

Int-30a was converted to the Compound 67 using the method described in Example 29.

Example 31

Preparation of Compound 69

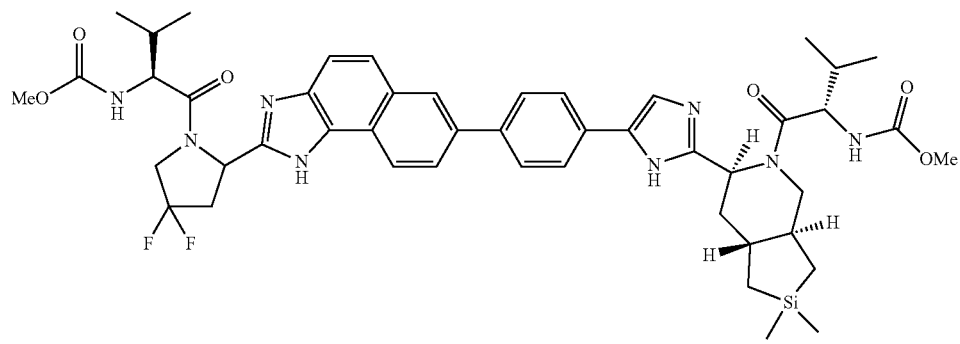

69

Step A—Synthesis of Intermediate Compound Int-31a

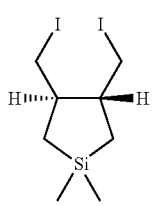

Int-31a

To a solution of dichlorozirconocene ($Cp_2ZrCl_2$) (4.2 g, 14.2 mmol) in 40 mL THF at −78° C. was added n-BuLi (1.6 M in hexane, 18 mL, 28.4 mmol). The resulting reaction was allowed to stir for 1 hour at this temperature, then a −78° C. solution of diphenyldiallylsilane (2 g, 14.2 mmol) in 17 mL of THF was added and the resulting reaction was allowed to stir for 1 hour at −78° C. and for 18 hours at 25° C. The reaction was cooled to −78° C. and a −78° C. solution of iodine (9 g, 35.5 mmol) in 20 mL THF was added at and the reaction was allowed to stir for 1 hour. The reaction was then quenched with 10% aqueous. $H_2SO_4$ and the organic phase was extracted with ether. The organic solution was washed sequentially with saturated aqueous $NaHCO_3$ solution and brine, dried ($Na_2SO_4$), filtered and concentrated in vacuo. The resulting residue was purified using ISCO 120 g column (hexane) to provide Compound Int-31a, 2.75 g (49%). $^1$H NMR ($CDCl_3$) δ 3.44 (dd, J=2.2, 10.0 Hz, 2H), 3.33 (dd, J=4.7, 10.0 Hz, 2H), 1.20 (m, 2H), 0.93 (dd, J=5.9, 14.7 Hz, 2H), 0.63 (dd, J=11.1, 14.2 Hz, 2H), 0.19 (s, 6H).

Step B—Synthesis of Intermediate Compound Int-31b

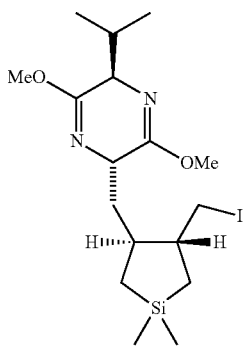

Int-31b

To a −78° C. solution of (2R)-(−)-2,5-dihydro-3,6-dimethoxy-2-isopropylpyrazine (0.61 g, 4.36 mmol) in THF (8 mL) was added n-BuLi (2.5 M in hexane, 1.8 mL, 4.58 mmol). The resulting reaction was allowed to stir for 20 minutes, then Compound Int-31a (2.75 g, 6.98 mmol, in 2 mL of THF) was added and the reaction was allowed to stir at −78° C. for 4 hours. The reaction was quenched with saturated aqueous $NH_4Cl$ solution and the organic layers were extracted with EtOAc. The combined organic solution was washed with brine solution, dried ($Na_2SO_4$), filtered and concentrated in vacuo. The resulting residue was purified using an ISCO 40 g column (gradient from 0% to 2.5% ether in hexane) to provide Compound Int-31b, 783 mg (44%). $^1H$ NMR (CDCl$_3$) δ 4.05 (m, 1H), 3.96 (t, J=3.4 Hz, 1H), 3.72 (s, 3H), 3.71 (s, 3H), 3.49 (dd, J=2.8, 0.4 Hz, 1H), 3.26 (dd, J=6, 9.4 Hz, 1H), 2.30 (m, 1H), 1.96 (m, 1H), 1.60 (m, 2H), 1.37-1.17 (m, 3H), 1.08 (d, J=6.9 Hz, 3H), 0.99-0.86 (m, 2H), 0.72 (d, J=6.6 Hz, 3H), 0.49 (dd, J=11.0, 14.4 Hz, 1H), 0.35 (dd, J=11.0, 14.2 Hz, 1H), 0.16 (s, 6H).

Step C—Synthesis of Intermediate Compound Int-31c

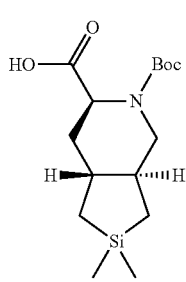

Int-31c

To a 0° C. solution of Compound Int-31b (780 mg, 1.92 mmol) in MeOH (9 mL) was added 10% aqueous HCl (3 mL) and the resulting reaction was allowed to stir at room temperature for 18 hours. The reaction mixture was concentrated in vacuo and the resulting residue was coevaporated with MeOH twice. The resulting white foam was dissolved in a mixture of ether (6 mL) and $CH_2Cl_2$ (9 mL), and to the resulting solution was added diisopropylethylamine (1 mL, 5.7 mmol). The resulting reaction was allowed to stir at room temperature for 18 hours, then di-t-butyl dicarbonate (922 mg, 4.22 mmol) was added and the resulting reaction was allowed to stir at 25° C. for 2 days. The reaction mixture was then poured into cold water and the organic layer was extracted with EtOAc. The combined organic solutions were washed with brine solution, dried ($Na_2SO_4$), filtered and concentrated in vacuo. The resulting residue was dissolved in MeOH (8 mL), cooled to 0° C. and aqueous 1 M KOH solution (3.3 mL, 3.3 mmol) was added. The resulting reaction was allowed to stir at 25° C. for 1 hour, then the reaction mixture was acidified with 10% aqueous HCl and the organic layers were extracted with $CH_2Cl_2$. The combined organic solution was washed with brine solution, dried ($Na_2SO_4$), filtered and concentrated in vacuo to provide Compound Int-31c, which was used without further purification.

Step D—Synthesis of Intermediate Compound Int-31d

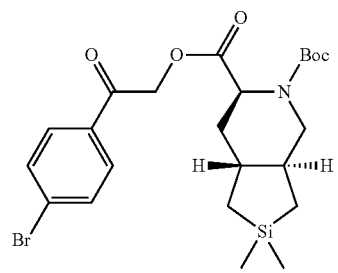

Int-31d

To a solution of Compound Int-31c (ca 320 mg, ca 1 mmol) in DMF (3 mL) were added triethylamine (0.74 mL, 5.3 mmol) and 2,4'-dibromoacetophenone (673 mg, 2.4 mmol). The resulting reaction was allowed to stir for 2 hours at 25° C., then the reaction mixture was poured into cold water and the organic layers were extracted with EtOAc. The combined organic solution was washed with brine solution, dried ($Na_2SO_4$), filtered and concentrated in vacuo. The resulting residue was purified using an ISCO 80 g column (gradient from 0% to 30% EtOAc in hexane) to provide Compound Int-31d (263 mg, 27% from Compound Int-31b). $^1H$ NMR (CDCl$_3$) δ 7.76 (d, J=8.5 Hz, 2H), 7.62 (d, J=8.7 Hz, 2H), 5.50-4.90 (m, 3H), 4.26-4.06 (m, 1H), 3.00-2.45 (m, 2H), 1.75-1.60 (m, 1H), 1.47-1.44 (m, 9H), 1.31-1.13 (m, 3H), 1.00-0.79 (m, 3H), 0.24-0.18 (m, 1H), 0.16-0.12 (m, 6H). LRMS: (M-Boc+H)$^+$=410.

Step E—Synthesis of Intermediate Compound Int-31e

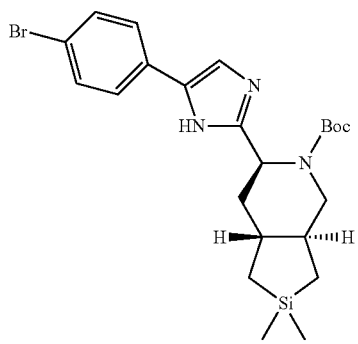 [SMILES: CC(C)(C)OC(=O)N1C[C@H]2C[Si](C)(C)C[C@@H]2C[C@H]1c1ncc(-c2ccc(Br)cc2)[nH]1]

To a solution of Compound Int-31d (263 mg, 0.52 mmol) in o-xylene (2 mL) in a pressure vessel was added ammonium acetate (279 mg, 3.6 mmol). The resulting reaction was heated to 140° C. and allowed to stir at this temperature for 1.5 hours, then cooled to 25° C. The reaction mixture was poured into saturated aqueous NaHCO₃ solution and the organic layer was extracted with EtOAc. The combined organic solution was washed with brine solution, dried (Na₂SO₄), filtered and concentrated in vacuo. The resulting residue was purified using an ISCO 40 g column (gradient from 0% to 30% EtOAc in hexane) to provide Compound Int-31e, 170 mg (67%). ¹H NMR (CDCl₃) δ 7.73-7.20 (m, 4H), 5.50 (br s, 1H), 4.09 (br d, J=12.5 Hz, 1H), 2.9-2.46 (m, 2H), 1.90 (br s, 1H), 1.60-1.47 (m, 9H), 1.31-1.20 (m, 1H), 1.13-1.01 (m, 1H), 0.81 (dd, J=5.3, 13.8 Hz, 1H), 0.26-0.07 (m, 7H). LRMS: (M+H)⁺=490.

Step F—Synthesis of Intermediate Compound Int-31f

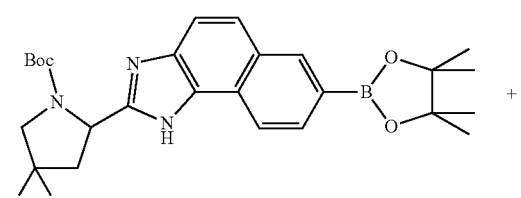

Int-18

Int-31e ⟶

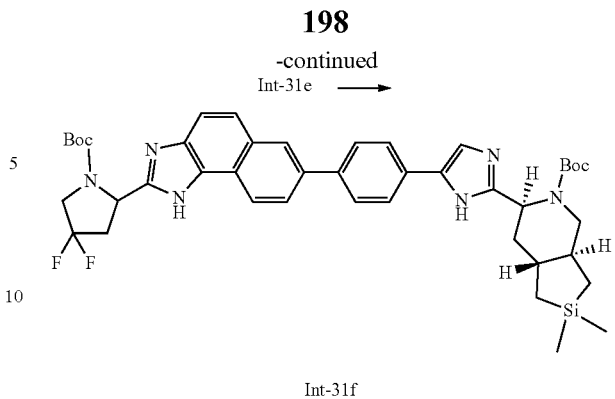

Int-31f

To a solution of Compound Int-Me (170 mg, 0.35 mmol), Compound Int-18 (295 mg, 0.59 mmol) and PdCl₂(dppf)₂·CH₂Cl₂ complex (29 mg, 0.035 mmol) in 1,4-dioxane (4 mL) was added aqueous 2 M Na₂CO₃ solution (0.53 mL, 1.05 mmol). The mixture was degassed, heated to 100° C. and allowed to stir at this temperature for 2.5 hours. The reaction mixture was then cooled to 25° C., diluted with EtOAc and filtered through a celite pad. The filtrate was concentrated in vacuo and the resulting residue was purified using an ISCO 40 g column (gradient from 0% to 55% EtOAc in hexane) to provide Compound Int-31f (212 mg, 78%). LRMS: (M+H)⁺=783.

Step G—Synthesis of Compound 69

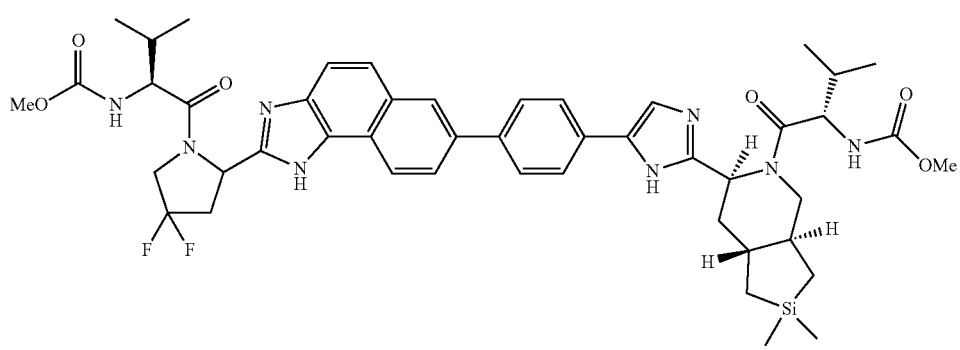

69

A 0° C. solution of Compound Int-31f (212 mg, 0.27 mmol) in CH₂Cl₂ (6 mL) was treated with TFA (2 mL) and the resulting reaction was allowed to stir at 25° C. for 4 hours. The reaction mixture was then concentrated in vacuo and the resulting residue was dissolved in MeOH (10 mL) and treated with 4N HCl in dioxane (1 mL). The mixture was allowed to stir for 5 minutes at 25° C., then was concentrated in vacuo. The resulting residue was dissolved in DMF (3 mL), cooled to −30° C. and treated with Moc-Val-OH (99.4 mg, 0.57 mmol), diisopropylethylamine (0.33 mL, 1.89 mmol), and HATU (221 mg, 0.58 mmol). The resulting reaction was allowed to stir at −30° C. for 1 h, then warmed to 0° C. and stirred at this temperature for an additional 2 hours. The reaction mixture was poured into cold water and the resulting precipitate was collected by filtration and purified using Gilson HPLC (CH₃CN—H₂O, 0.1% TFA) to provide Compound 69. Compound 69 was dissolved in MeOH (10 mL) and treated with 4 N HCl in dioxane (0.3 mL) followed by concentration in vacuo to provide the dihydrochloride salt of Compound 69 (147 mg, 56%). LRMS: (M+H)⁺=897.

Example 32

Preparation of Intermediate Compound Int-32e

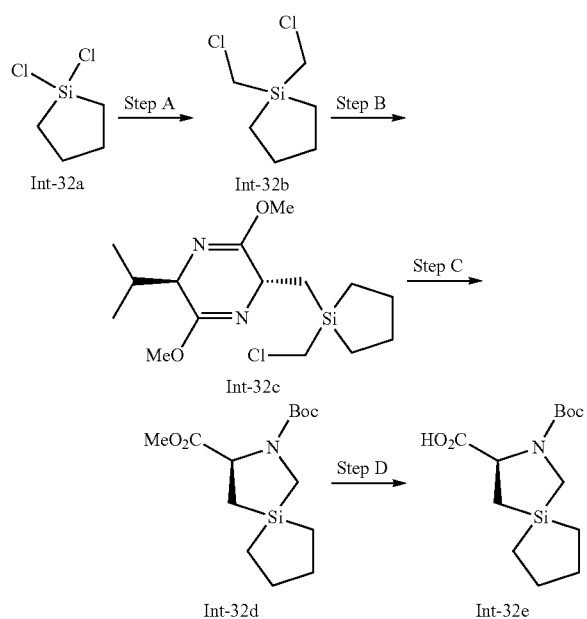

Step A—Synthesis of Intermediate Compound Int-32b

To a 1000 mL flame dried flask was added Int-32a (28.09 g, 181.1 mmol), bromochloromethane (23.5 mL, 362.2 mmol), and anhydrous THF (400 mL). The solution was cooled to −70° C. n-BuLi (2.5M in hexane, 145 mL, 362 mmol) was added slowly over a period of 1 hour. After the solution was allowed to stir at −70 to −60° C. for 20 minutes, it was allowed to warm up to room temperature in an hour. Saturated NH$_4$Cl solution (200 mL) and Et$_2$O (200 mL) were added. The organic layer was separated and the aqueous layer was extracted with Et$_2$O (100 mL) twice. The organic layers were combined, washed with brine, dried over Na$_2$SO$_4$, filtered and concentrated at 25° C. The resulting residue was purified using flash chromatography on silica gel (240 g, eluted with hexane) to provide Compound Int-32b (17.2 g, 51.9%).

Step B—Synthesis of Intermediate Compound Int-32c

To a 500 mL flame dried flask was added (R)-2-isopropyl-3,6-dimethoxy-2,5-dihydropyrazine (10.0 g, 54.3 mmol) and anhydrous THF (200 mL). The solution was cooled to −78° C. n-BuLi (2.5M in hexane, 24.0 mL, 59.7 mmol) was added dropwise. After the solution was allowed to stir at −78° C. for 30 minutes, Int-32b (in 5 mL anhydrous THF) was added dropwise. After the solution was allowed to stir at −78° C. for 1 hour, it was allowed to warm up to room temperature in two hours. Water (100 mL) and Et$_2$O (150 mL) were added. The organic layer was separated and the aqueous layer was extracted with Et$_2$O (100 mL) twice. The organic layers were combined, washed with brine, dried over Na$_2$SO$_4$, filtered and concentrated in vacuo. The resulting residue was purified using flash chromatography on silica gel (40 g, eluted with Et$_2$O in Hexane: 0% to 3%) to provide Compound Int-32c (10.43 g, 58.0%).

Step C—Synthesis of Intermediate Compound Int-32d

To a 500 mL flask was added compound Int-32c (11.5 g, 34.8 mmol) and MeOH (80 mL). 10% HCl (20 mL) was added. The solution was allowed to stir at room temperature for 5 hours and concentrated in vacuo. The resulting residue was dissolved in 20 mL MeOH and concentrated again to remove water and HCl. This process was repeated three times. The resulting residue was dissolved in DCM (50 mL) and Et$_2$O (70 mL). DIPEA (15.4 mL, 86.9 mmol) and NaI (5.2 g, 34.75 mmol) were added. The solution was allowed to stir at room temperature for about 15 hours. Di-tert-butyl dicarbonate (18.9 g, 86.9 mmol) was added. The solution was allowed to stir at room temperature for 4 hours. Water (100 mL) and EtOAc (100 mL) were added. The organic layer was separated and the aqueous layer was extracted with EtOAc (100 mL) twice. The organic layers were combined and washed with brine, dried over anhydrous Na$_2$SO$_4$, filtered, and concentrated in vacuo. The product was purified using flash chromatography on silica gel (220 g, Hexane/EtOAC: 0% to 20%) to provide Compound Int-32d (7.9 g, 75.9%).

Step D—Synthesis of Intermediate Compound Int-32e

Int-32d (7.9 g, 26.4 mmol) was dissolved in MeOH (100 mL) and the resulting solution was cooled to 0° C. KOH (1M in water, 39.6 mL, 39.6 mmol) was added and the resulting reaction was allowed to stir at 0° C. for 2 hours, and then warmed to room temperature and allowed to stir for 3 hours. HCl (2N, 20 mL) was added slowly until the reaction mixture was a pH~4, then the acidified solution was concentrated in vacuo. To the resulting residue was added water (150 mL) and EtOAc (200 mL). The organic layer was separated and the aqueous layer was extracted with EtOAc (2×100 mL). The organic layers were combined, washed with brine, dried over anhydrous Na$_2$SO$_4$, filtered, and concentrated in vacuo. The resulting residue was dried under vacuum for about 72 hours to provide Compound Int-32e (7.45 g, 99%) which was used without further purification.

Example 33

Preparation of Compound 53

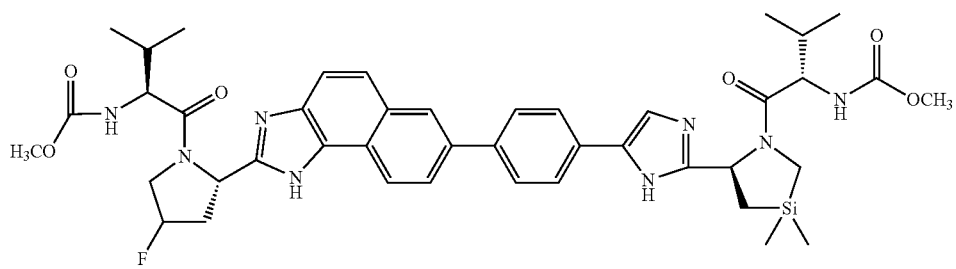

53

Step A—Synthesis of Intermediate Compound Int-33a

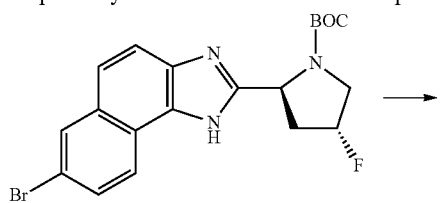

Int-17g

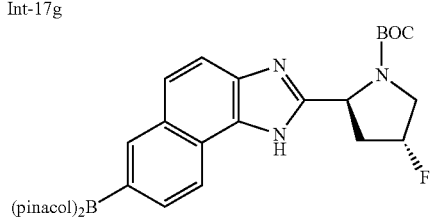

Int-33a

Compound Int-33a was made using the method described in Example 29, Step A and substituting Compound Int-17g for Compound Int-17h.

Step B—Synthesis of Compound 53

Compound 53 was made using the method described in Example 29, Steps B and C and substituting Compound Int-33a for Compound Int-29a.

Step C—Synthesis of the Dihydrochloride Salt of Compound 53

The dihydrochloride salt of Compound 53 was made using the method described in Example 29, Step D and substituting Compound 53 for Compound 54. ESI-LRMS [M+H]$^+$ 825.5. $^1$H NMR (CD$_3$OD): δ 8.25-8.15 (m, 1H), 7.95-7.25 (m, 9H), 5.95-5.75 (m, 1H), 5.6-5.4 (m, 2H), 4.6-4.4 (m, 2H), 4.3-4.1 (m, 2H), 3.7 (s, 6H), 2.9-2.6 (m, 1H), 2.2-2.0 (m, 2H), 1.4-12 (m, 3H), 1.1-0.8 (m, 14H), 0.4 (s, 3H), 0.34 (s, 3H), 0.3-0.2 (m, 2H).

Example 34

Preparation of Compound 56

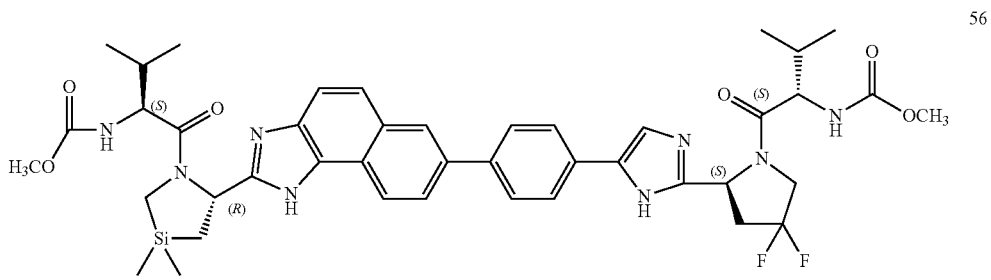

Step A—Synthesis of Compound Int-34a

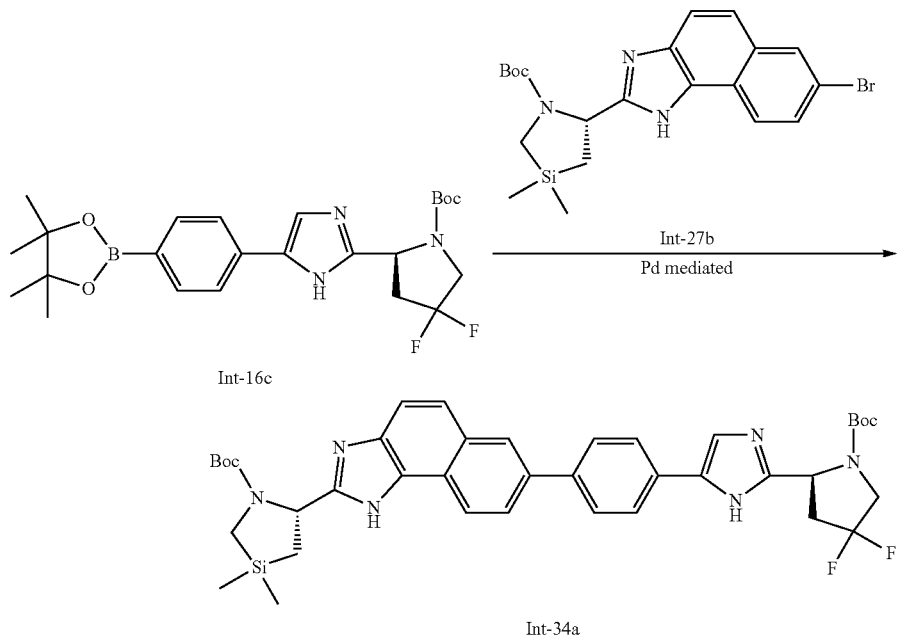

Int-34a

Compound Int-27b (5.0 g, 10.86 mmol), compound Int-16c (5.6 g, 11.78 mmol), PdCl$_2$(dppf) dichloromethane complex (1.7 g, 2.08 mmol), an aqueous solution of sodium carbonate (1.5 M, 12 mL, 18 mmol), and 1,4-dioxane (70 mL) were added to a 500 mL flask. The resulting reaction was degassed, put under nitrogen atmosphere, then heated to 90° C. and allowed to stir at this temperature for 5 hours. The reaction mixture was then cooled to room temperature and concentrated in vacuo and the resulting residue was diluted with dichloromethane (300 mL). The resulting solution was filtered and the filtrate was concentrated in vacuo and the residue obtained was purified using a 330 g ISCO silica column/Combi-Flash system (0-90% ethyl acetate in hexanes as eluent) to provide compound Int-34a as a solid (3.7 g, 46% yield). LCMS anal 729 (M+H)$^+$.

Step B—Synthesis of Compound Int-34b

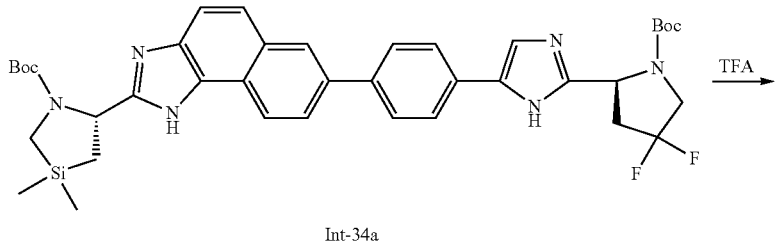

Int-34a

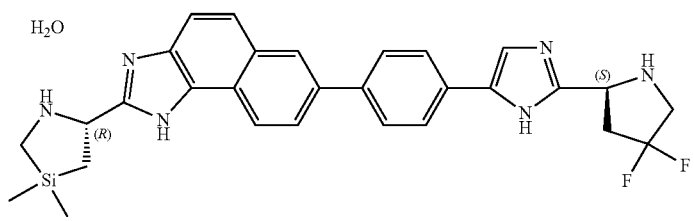

Int-34b

Compound Int-34a (2.9, 3.98 mmol) was taken up in dichloromethane (10 mL) and to the resulting solution was added trifluoroacetic acid (10 mL). The resulting reaction was allowed to stir at room temperature for 5 hours, then the reaction mixture was concentrated in vacuo. The residue obtained was taken up in methanol (100 mL) and to the resulting solution was added HCl in dioxane (4.0 M, 4.5 mL). The resulting solution was concentrated in vacuo to provide compound Int-30 as a solid, which was used without further purification.

Step C—Synthesis of Compound 56

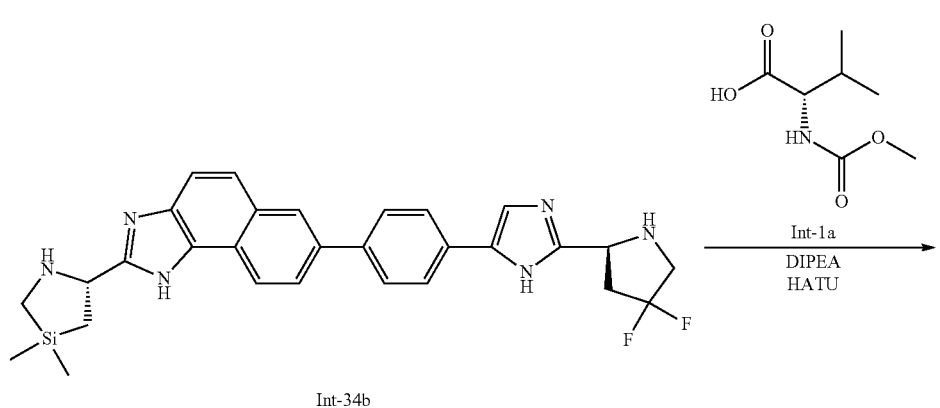

Int-34b

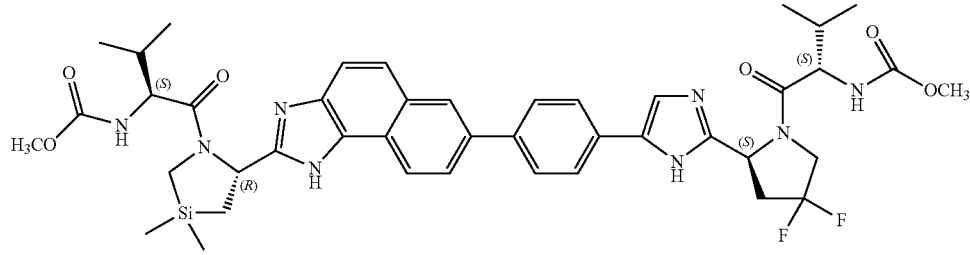

56

A solution of compound Int-34b (3.98 mmol), compound Int-1a (1.6 g, 9.13 mmol) and diisopropylethylamine (6 mL, 45 mmol) in DMF (3 mL) was cooled to −50° C. HATU (3.2 g, 8.42 mmol) was then added slowly to the cooled solution and the resulting reaction was allowed to stir at 10° C. for 2 hours. Water (0.5 mL) was then added to quench the reaction and the resulting solution was added dropwise to 500 mL of water with stirring. The resulting suspension was filtered and the collected solid was purified using a 120 g ISCO silica gold column/Combi-Flash system (0-6% methanol in dichloromethane as eluent) to provide compound 56 as a white solid (1.25 g, 37% yield for 2 steps). 1H (600 MHz, CD$_3$OD) δ 8.58 (1H), 8.46 (1H), 8.18-8.15 (2H), 7.95-8.05 (3H), 7.95 (2H), 7.80 (1H), 5.48-5.42 (2H), 4.5 (2H), 4.45-4.35 (1H), 4.08-4.05 (1H), 3.70-3.60 (6H), 3.60-3.15 (1H), 3.10-2.90 (2H), 2.10-2.00 (2H), 1.90-1.18 (1H), 1.40 (1H), 1.05-0.75 (13H), 0.45 (3H), 0.40 (3H). LCMS anal. calcd. for: C$_{43}$H$_{52}$F$_2$N$_8$O$_6$Si 842.4. Found: 843.4 (M+H)$^+$. HRMS anal calcd. for: C$_{43}$H$_{52}$F$_2$N$_8$O$_6$Si 842.3747. Found: 843.3821.

Preparation of the Dihydrochloride Salt of Compound 56

Compound 56 was taken up in methanol and to the resoling solution was added HCl (1M in ether, 200 mole %). The reaction was allowed to stir for 10 minutes, then the reaction mixture was concentrated in vacuo to provide the dihydrochloride salt of Compound 56 as a white solid, which was used without further purification.

Example 35

Cell-Based HCV Replicon Assay

Measurement of inhibition by compounds of the present invention was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

TaqMan®-Based Assay Protocol:

Compounds of the present invention were assayed for cell-based anti-HCV activity using the following protocol. Replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 μM to 1 μM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (TaqMan® assay). The amplicon was located in 5B. The PCR primers were: 5B.2F, ATGGACAGGCGCCCTGA (SEQ. ID NO. 1); 5B.2R, TTGATGGGCAGCTTGGTTTC (SEQ. ID NO. 2); the probe sequence was FAM-labeled CACGCCAT-GCGCTGCGG (SEQ. ID NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minute. The ΔCT values (CT$_{5B}$-CT$_{GAPDH}$) were plotted against the concentration of test compound and fitted to the sigmoid dose-response model using XLfit4 (MDL). EC$_{50}$ was defined as the concentration of inhibitor necessary to achieve ΔCT=1 over the projected baseline; EC$_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All TaqMan® reagents were from PE Applied Biosystems. Such an assay procedure was described in detail in e.g. Malcolm et al., *Antimicrobial Agents and Chemotherapy* 50: 1013-1020 (2006).

HCV replicon EC$_{50}$ assay data for various replicons and mutants was calculated for selected compounds of the present invention using this method and is provided in the table below. This data indicates that the compounds of the present invention are highly active versus a wide variety of HCV NS5A replicons and mutants.

| No. | 1a (H77) | 1b (Con1) | 2a (JFH) | 2b (AB03090) | 3a (NC00982) | 4a (DQ41878) | 1a (Y93H) | 1a (L31V) |
|---|---|---|---|---|---|---|---|---|
| 1 | 0.003 | 0.003 | 0.003 | NA | 0.26 | 0.067 | NA | NA |
| 2 | 0.01 | 0.004 | 0.019 | NA | 0.05 | NA | NA | NA |
| 15 | 0.088 | 0.011 | 0.12 | NA | 1 | NA | 131 | NA |
| 16 | 0.04 | 0.004 | 0.06 | NA | 0.23 | NA | 146 | NA |

-continued

| No. | 1a (H77) | 1b (Con1) | 2a (JFH) | 2b (AB03090) | 3a (NC00982) | 4a (DQ41878) | 1a (Y93H) | 1a (L31V) |
|---|---|---|---|---|---|---|---|---|
| 20 | 0.14 | 0.004 | 0.3 | NA | 0.26 | NA | 921 | NA |
| 42 | 0.012 | 0.005 | >10 | NA | 11.4 | NA | 103 | NA |
| 44 | >1 | 0.007 | >10 | NA | 31 | NA | 1392 | NA |
| 45 | >1 | 0.009 | >10 | NA | 52 | NA | 2637 | NA |
| 46 | 0.26 | 0.004 | 0.6 | NA | 2.4 | NA | 497 | NA |
| 47 | 0.4 | 0.007 | 1.7 | NA | 5.5 | NA | 1598 | NA |
| 48 | 0.05 | 0.004 | 0.07 | NA | 0.25 | NA | 329 | NA |
| 49 | 0.04 | 0.014 | 0.037 | NA | 0.2 | NA | 185 | NA |
| 50 | 0.505 | 0.008 | 1.62 | NA | 3 | NA | 1148 | NA |
| 51 | >1 | 0.05 | >10 | NA | >100 | NA | 8415 | NA |
| 53 | 0.016 | 0.003 | 0.026 | NA | 0.09 | 0.1 | 10 | 64 |
| 54 | 0.009 | 0.002 | 0.03 | 128 | 0.18 | 0.02 | 65 | 10 |
| 55 | 0.07 | 0.006 | 0.15 | NA | 0.8 | 0.35 | 27 | 62 |
| 56 | 0.016 | 0.003 | 0.027 | 48 | 0.35 | 0.02 | 46 | 16 |
| 57 | 0.068 | <0.05 | 0.069 | NA | 0.798 | 0.652 | 50 | NA |
| 58 | 0.03 | 0.002 | 0.15 | NA | 0.8 | 0.36 | 118 | NA |
| 60 | 0.06 | 0.003 | 0.09 | NA | 2.9 | 0.129 | 96 | NA |
| 61 | 0.06 | 0.005 | 0.005 | NA | 0.2 | 0.076 | 350 | NA |
| 65 | 0.06 | 0.004 | 0.3 | NA | 1.7 | NA | 44 | NA |
| 66 | 0.002 | 0.005 | 0.08 | >100 | 0.15 | NA | 260 | 32 |
| 67 | 0.19 | 0.011 | 0.16 | NA | 5 | 0.5 | 380 | NA |
| 70 | 0.012 | 0.007 | 0.04 | NA | 0.118 | 0.077 | 25 | NA |
| 71 | 0.12 | <0.002 | 0.45 | NA | 0.9 | NA | 188 | NA |
| 72 | 0.1 | 0.004 | 0.496 | NA | 2.411 | NA | 246 | NA |
| 77 | >1 | 85 | >10 | NA | >100 | >100 | >1000 | NA |
| 78 | 0.015 | 0.001 | 0.04 | NA | 0.26 | 0.137 | 90 | NA |
| 79 | 0.127 | 0.012 | 0.315 | NA | 4.4 | 0.45 | 351 | NA |
| 80 | >1 | >1 | >10 | NA | >100 | >100 | >1000 | NA |
| 81 | 0.94 | 0.012 | 0.712 | NA | 9.69 | >10 | >1000 | >100 |
| 83 | >1 | 52 | >10 | NA | >100 | >100 | >1000 | NA |
| 84 | >1 | 2.4 | >10 | NA | >100 | >100 | >1000 | NA |
| 85 | 0.102 | 0.009 | 0.065 | NA | 0.69 | 1.16 | 728 | 89 |
| 86 | >1 | 141 | >10 | NA | >100 | >100 | >1000 | >1000 |
| 87 | >1 | 2.5 | >10 | NA | >100 | >100 | >1000 | >1000 |
| 88 | >1 | 4 | >10 | NA | >100 | >100 | >1000 | >1000 |
| 89 | 0.054 | 0.006 | 0.5 | NA | 0.275 | 0.035 | 211 | NA |
| 92 | 0.015 | 0.003 | 0.02 | 48 | 0.35 | 0.02 | 46 | NA |
| 94 | 0.008 | 0.002 | 0.03 | 129 | 0.2 | 0.02 | 65 | 10 |
| 95 | >0.1 | 0.015 | 0.032 | NA | 0.066 | 1.217 | 210 | 9 |
| 96 | 0.04 | 0.004 | 0.013 | 49.3 | 0.099 | 0.936 | 51 | 1 |
| 97 | 0.005 | 0.002 | 0.005 | 17.11 | 0.09 | 0.029 | 30 | 15 |
| 99 | NA | NA | NA | NA | NA | NA | NA | NA |
| 100 | 0.043 | 0.002 | 0.023 | NA | 7.4 | <0.2 | 204 | 117 |
| 101 | >1 | 0.023 | >10 | NA | 54.6 | >100 | >1000 | >1000 |
| 102 | 0.084 | <2 | 0.097 | NA | 7.5 | 0.3 | 438 | 113 |
| 103 | >1 | 61 | NA | NA | NA | NA | NA | NA |
| 104 | 0.021 | 0.003 | NA | NA | 1.173 | 1.08 | 186.2 | >100 |
| 105 | 0.021 | 0.003 | 0.141 | NA | 0.17 | 0.18 | 151 | 43 |
| 106 | 0.016 | 0.006 | 0.046 | NA | 0.435 | 0.429 | 52.6 | 37.1 |

NA = not available

Wherein gt1a_H77 was prepared as described in Yi et al., *J Virol*. 2004, 78(15):7904-15; gt1b_con1 was prepared as described in Lohmann et al., *Science* 1999, 285(5424):110-3; and gt2a_JFH was prepared as described in Kato et al., *Gastroenterology*. 2003, 125(6):1808-17. Chimeric replicons contain NS5A from patient isolates of genotypes 1a, 1b, 2b, 3a and 4a as indicated.

The study of the HCV life cycle has been difficult due to the lack of a cell-culture system to support the HCV virus. To date, compounds in different structural classes acting on different sites within the HCV polyprotein have demonstrated efficacy in various species, including humans, in reducing HCV viral titers. Furthermore, the subgenomic replicon assay is highly correlated with efficacy in non-humans and humans infected with HCV. See K. del Carmen et al., *Annals of Hepatology*, 2004, 3:54.

It is accepted that the HCV replicon system described above is useful for the development and the evaluation of antiviral drugs. See Pietschmann, T. & Bartenschlager, R., *Current Opinion in Drug Discovery Research* 2001, 4:657-664).

Example 36

Pharmacokinetic Analysis of Compound 56

Various pharmacokinetic parameters for compound 56 were measured in rats, dogs and monkeys as described below.

I. Dosing and Sample Collection

Rats

Male Sprague-Dawley rats (Charles River, Co.) were pre-cannulated (femoral artery) in order to facilitate precise blood sampling times, to increase throughput and to reduce the stress on the animals caused by serial bleedings. Following an overnight fast, rats were dosed with the dihydrochloride salt of compound 56 orally at 5 mg/kg as a suspension in 0.4% hydroxylpropyl methylcellulose (HPMC) or intravenously at 2.5 mg/kg as a solution in 20% hydroxypropyl-β-cyclodextrin (20% HPβCD). Blood was collected into heparin-containing tubes serially from each animal at 0.25, 0.5, 1, 2, 4, 6, 8, 24 and 48 hr (PO), and 0.167, 0.25, 0.5, 1, 2, 4, 6, 8, 24 and 48 hr (IV) post-dosing and centrifuged to generate plasma. The plasma samples were stored at 20° C. until analysis.

Dogs

Following an overnight fast, male beagle dogs were dosed with the dihydrochloride salt of compound 56 orally at 2 mg/kg as a suspension in 0.4% hydroxylpropyl methylcellulose (HPMC) or intravenously at 1 mg/kg as a solution in 20% hydroxypropyl-β-cyclodextrin (20% HPβCD). For oral dosing, the animals were typically restrained by hand and dosed by oro-gastric intubation. Dogs were fed approximately 4 hours after dosing. Blood samples were collected from the jugular or cephalic vein at 0.25, 0.5, 1, 2, 4, 6, 8, 12, 24, 48, 72 and 96 hrs (PO) and 0.167, 0.25, 0.5, 1, 2, 4, 6, 8, 12, 24, 48, 72 and 96 hrs (IV) post-dosing and centrifuged to generate plasma. The plasma samples were stored at 20° C. until analysis.

Monkeys

Following an overnight fast, male cynomolgus monkeys were dosed with the dihydrochloride salt of compound 56 orally at 2 mg/kg as a suspension in 0.4% hydroxylpropyl methylcellulose (HPMC) or intravenously at 1 mg/kg as a solution in 20% hydroxypropyl-β-cyclodextrin (20% HPβCD). For oral dosing, the animals dosed by oro-gastric intubation. Monkeys were fed approximately 1 hour before dosing and 4 hours after dosing. Blood samples were collected from the saphenous and/or cephalic vein at 0.25, 0.5, 1, 2, 4, 6, 8, 12, 24, 48, and 72 (PO), and 0.167, 0.25, 0.5, 1, 2, 4, 6, 8, 12, 24, 48, and 72 hrs (IV) post-dosing and centrifuged to generate plasma. The plasma samples were stored at 20° C. until analysis.

II. Plasma Analysis (for All Species)

Collected plasma samples were analyzed for the presence of compound 56 using LC-MS/MS as described below.

HPLC/API-MS/MS Equipment

The HPLC/API-MS/MS system for the example data consisted of a HPLC pumping system and a auto sampler with the sample tray refrigeration option connected directly to a triple quadrupole mass spectrometer with an API source. Typical HPLC methods for the example data was based on a fast gradient of two solvents: solvent A consisted of 0.1% formic acid in water, and solvent B consisted of 0.1% formic acid in acetonitrile. A fast linear gradient (start at 90% A for 0.2 min, ramp to 95% B from 0.2 to 0.5 min, hold at 95% B until 0.5 min, then ramp back to 90% A from 1.0 to 1.1 min, then hold at, 95% A from 1.1 to 1.2 min) was used. The flow rate for the HPLC system was set to 1 mL/min throughout the HPLC gradient; the HPLC column was a Halo C18 column (2.7 micron particle size, 50×2.1 mm). The example compounds were analyzed by positive ion atmospheric pressure chemical ionization tandem mass spectrometry (APCI-MS/MS). As a general procedure, selected reaction monitoring (SRM) methods were developed for each compound prior to analysis of the plasma samples. Normally, the individual SRM transitions were based on a fragmentation from the protonated molecule ([MH].) to a characteristic product ion.

Using the methods described above, the following pharmacokinetic parameters were calculated in rats, dogs and monkeys and the results are summarized in the table below.

|  | Systemic Clearance (mL/min/kg) | Volume of Distribution (L/kg) | *Oral Bioavailability (%) | Effective Half-Life (hours) |
|---|---|---|---|---|
| Rat (5 mpk/PO 2.5 mpk/IV) | 5.6 | 3.7 | 28 | 7.6 |
| Dog (2 mpk/PO; 1 mpk/IV) | 0.8 | 1.3 | 8.7 | 18 |
| Monkey (2 mpk/PO; 1 mpk/IV) | 1.2 | 1.7 | 11.7 | 17 |

*calculated by dose-normalized area under the concentration-time (AUC) between PO and IV The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound of the formula:

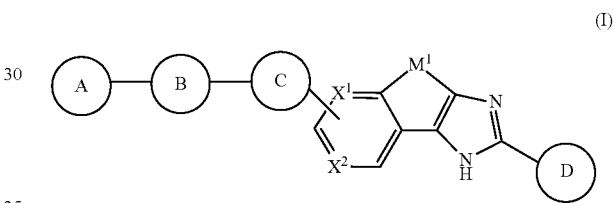

(I)

or a pharmaceutically acceptable salt thereof,
wherein:
A is -alkylene-N($R^7$)($R^{11}$), -alkylene-N($R^{16}$)($R^{11}$), 4 to 7-membered monocyclic heterocycloalkyl, 7 to 11-membered bicyclic heterocycloalkyl or $R^{15}$, wherein said 4 to 7-membered monocyclic heterocycloalkyl group, said 7 to 11-membered bicyclic heterocycloalkyl group or said $R^{15}$ group can be optionally fused to a 3 to 7-membered cycloalkyl group, a 4 to 7-membered heterocycloalkyl group or an aryl group; and wherein said 4 to 7-membered monocyclic heterocycloalkyl group, said 7 to 11-membered bicyclic heterocycloalkyl group or $R^{15}$ group can be optionally and independently substituted on one or more ring nitrogen atoms with $R^4$, and on one or more ring carbon atoms with $R^{12}$, such that two $R^{12}$ groups on the same ring carbon atom, together with the carbon atom to which they are attached, can join to form a spirocyclic 3 to 7-membered cycloalkyl group or a spirocyclic 4 to 7-membered heterocycloalkyl group;
B is 5-membered monocyclic heteroarylene group or a 9-membered bicyclic heteroarylene group containing at least one nitrogen atom, wherein said 5-membered monocyclic heteroarylene group and said 9-membered bicyclic heteroarylene group can be optionally fused to a benzene, pyridine or pyrimidine ring, and wherein said 5-membered monocyclic heteroarylene group or its fused counterpart and said 9-membered bicyclic heteroarylene group or its fused counterpart, can be optionally and independently substituted on one or more ring nitrogen atoms with $R^6$ and on one or more ring carbon atoms with $R^{12}$;

C is a bond, —C(R$^5$)=C(R$^5$)—, —C≡C—, phenylene, monocyclic heteroarylene or bicyclic heteroarylene, wherein said phenylene group, said monocyclic heteroarylene group or said bicyclic heteroarylene group can be optionally and independently substituted on one or more ring nitrogen atoms with R$^6$ and on one or more ring carbon atoms with R$^{12}$;

D is -alkylene-N(R$^7$)(R$^{11}$), -alkylene-N(R$^{16}$)(R$^{11}$), 4 to 7-membered monocyclic heterocycloalkyl, 7 to 11-membered bicyclic heterocycloalkyl or R$^{15}$, wherein said 4 to 7-membered monocyclic heterocycloalkyl group, said 7 to 11-membered bicyclic heterocycloalkyl group or said R$^{15}$ group can be optionally fused to a 3 to 7-membered cycloalkyl group, a 4 to 7-membered heterocycloalkyl group or an aryl group; and wherein said 4 to 7-membered monocyclic heterocycloalkyl group, said 7 to 11-membered bicyclic heterocycloalkyl group or R$^{15}$ group can be optionally and independently substituted on one or more ring nitrogen atoms with R$^4$, and on one or more ring carbon atoms with R$^{12}$, such that two R$^{12}$ groups on the same ring carbon atom, together with the carbon atom to which they are attached, can join to form a spirocyclic 3 to 7-membered cycloalkyl group or a spirocyclic 4 to 7-membered heterocycloalkyl group;

M$^1$ is a bond, —C(R$^7$)$_2$—, —O—, —N(R$^6$)—, —S(O)$_2$— —C(R$^2$)=C(R$^2$)—, —C(R$^2$)=N—, —N=C(R$^2$)—, —C(R$^7$)$_2$—O—, —O—C(R$^7$)$_2$—, —C(R$^7$)$_2$—N (R$^6$)— or —N(R$^6$)—C(R$^7$)$_2$—, such that two geminal R$^7$ groups of M$^1$, together with the carbon atoms to which they are attached, can optionally join to form a 3- to 7-membered cycloalkyl group, a 3- to 7-membered heterocycloalkyl group or a 5- to 6-membered heteroaryl group;

X$^1$ is —C(R$^5$)— or —N—;

X$^2$ is —C(R$^5$)— or —N—;

each occurrence of R$^1$ is independently C$_1$-C$_6$ alkyl, -alkylene-O—(C$_1$-C$_6$ alkyl), C$_1$-C$_6$ haloalkyl, 3- to 7-membered cycloalkyl, 4- to 7-membered heterocycloalkyl, aryl or heteroaryl, wherein said 3- to 7-membered cycloalkyl group, said 4- to 7-membered heterocycloalkyl group, said aryl group or said heteroaryl group can be optionally substituted with up to three groups, which can be the same or different, and are selected from C$_1$-C$_6$ alkyl, 3- to 7-membered cycloalkyl, 4- to 7-membered heterocycloalkyl, aryl, heteroaryl, halo, C$_1$-C$_6$ haloalkyl, —Si(R$^{13}$)$_3$, —CN, —OR$^3$, —N(R$^3$)$_2$, —C(O)R$^{10}$, —C(O)OR$^3$, —C(O)N(R$^3$)$_2$, —NHC(O)R$^{10}$, —NHC(O)NHR$^3$, —NHC(O)OR$^3$, —OC(O)R$^{10}$, —SR$^3$ and —S(O)$_2$R$^{10}$;

each occurrence of R$^2$ is independently H, C$_1$-C$_6$ alkyl, —C$_1$-C$_6$ haloalkyl, 3 to 7-membered cycloalkyl, 4 to 7-membered heterocycloalkyl, C$_1$-C$_6$ hydroxyalkyl, —OH, —O—(C$_1$-C$_6$ alkyl), halo, —CN, —NH$_2$, —NH(C$_1$-C$_6$ alkyl), —N(C$_1$-C$_6$ alkyl)$_2$, —NHC(O)—(C$_1$-C$_6$ alkyl), —C(O)NH—(C1-C6 alkyl), —C(O)N(C$_1$-C$_6$ alkyl)$_2$, or —Si(R$^{13}$)$_3$;

each occurrence of R$^3$ is independently H, C$_1$-C$_6$ alkyl, C$_1$-C$_6$ haloalkyl, —C$_1$-C$_6$ alkylene-OC(O)(C$_1$-C$_6$ alkyl), C$_1$-C$_6$ hydroxyalkyl, 3 to 7-membered cycloalkyl, 4 to 7-membered heterocycloalkyl, aryl or heteroaryl wherein said 3- to 7-membered cycloalkyl group, said 4- to 7-membered heterocycloalkyl group, said aryl group or said heteroaryl group can be optionally and independently substituted with up to three groups independently selected from —OH, halo, C$_1$-C$_6$ alkyl, C$_1$-C$_6$ haloalkyl, —NH(C$_1$-C$_6$ alkyl) and —N(C$_1$-C$_6$ alkyl)$_2$;

each occurrence of R$^4$ is independently H, —C$_1$-C$_6$ alkyl, C$_1$-C$_6$ haloalkyl, -[C(R$^7$)$_2$]$_q$N(R$^6$)$_2$, —C(O)R$^1$, —C(O)-[C(R$^7$)$_2$]$_q$N(R$^6$)$_2$, —C(O)-[C(R$^7$)$_2$]$_q$R$^1$, —C(O)-[C(R$^7$)$_2$]$_q$N(R$^6$)C(O)—R$^1$, —C(O)[C(R$^7$)$_2$]$_q$N(R$^6$)SO$_2$—R$^1$, —C(O)-[C(R$^7$)$_2$]$_q$N(R$^6$)C(O)O—R$^1$, —C(O)-[C(R$^7$)$_2$]$_q$C(O)O—R$^1$ or -alkylene-N(R$^6$)—[C(R$^7$)$_2$]$_q$N(R$^6$)—C(O)O—R$^1$;

each occurrence of R$^5$ is independently H, C$_1$-C$_6$ alkyl, —Si(R$^{13}$)$_3$, 3- to 7-membered cycloalkyl, 4- to 7-membered heterocycloalkyl, aryl or heteroaryl;

each occurrence of R$^6$ is independently H, C$_1$-C$_6$ alkyl, 3- to 7-membered cycloalkyl, 4 to 7-membered heterocycloalkyl, aryl or heteroaryl, wherein said 3- to 7-membered cycloalkyl group, said 4- to 7-membered heterocycloalkyl group, said aryl group or said heteroaryl group can be optionally and independently substituted with up to two R$^8$ groups, and wherein two R$^6$ groups that are attached to a common nitrogen atom, together with the nitrogen atom to which they are attached, can optionally join to form a 4- to 7-membered heterocycloalkyl group;

each occurrence of R$^7$ is independently H, C$_1$-C$_6$ alkyl, C$_1$-C$_6$ haloalkyl, -alkylene-O—(C$_1$-C$_6$ alkyl), silylalkyl, 3- to 7-membered cycloalkyl, 4 to 7-membered heterocycloalkyl, aryl or heteroaryl, wherein said 3- to 7-membered cycloalkyl group, said 4- to 7-membered heterocycloalkyl group, said aryl group or said heteroaryl group can be optionally and independently substituted with up to three R$^8$ groups, and wherein two geminal R$^7$ groups, together with the common carbon atom to which they are attached, can optionally join to form —C(=O)—, —C(=S)—, —C(=NH)—, —C(=N—OH)—, —C(=N—C$_1$-C$_6$ alkyl)-, —C(=N—O—C$_1$-C$_6$ alkyl)-, —C(=N-(3 to 7-membered cycloalkyl))-, —C(=N—O-(3- to 7-membered cycloalkyl))-, —C(=N-(4 to 7-membered heterocycloalkyl))-, —C(=N—O-(4- to 7-membered heterocycloalkyl))-, a 3 to 7-membered cycloalkyl group or a 4- to 7-membered heterocycloalkyl group, such that no two adjacent —C(R$^7$)$_2$— groups can join to form a —C(=O)—C(=O)—, —C(=S)—C(=S)—, —C(=O)—C(=S)— or —C(=S)—C(=O)— group;

each occurrence of R$^8$ is independently H, C$_1$-C$_6$ alkyl, halo, —C$_1$-C$_6$ haloalkyl, C$_1$-C$_6$ hydroxyalkyl, —OH, —C(O)NH—(C$_1$-C$_6$ alkyl), —C(O)N(C$_1$-C$_6$ alkyl)$_2$, —O—(C$_1$-C$_6$ alkyl), —NH$_2$, —NH(C$_1$-C$_6$ alkyl), —N(C$_1$-C$_6$ alkyl)$_2$, —NHC(O)—(C$_1$-C$_6$ alkyl) or —Si(R$^{13}$)$_3$;

each occurrence of R$^{10}$ is independently C$_1$-C$_6$ alkyl, C$_1$-C$_6$ haloalkyl, 3 to 7-membered cycloalkyl, 4 to 7-membered heterocycloalkyl, aryl, or heteroaryl;

each occurrence of R$^{11}$ is independently H, C$_1$-C$_6$ alkyl, C$_1$-C$_6$ haloalkyl, -[C(R$^7$)$_2$]$_q$N(R$^6$)$_2$, —C(O)R$^1$, —C(O)-[C(R$^7$)$_2$]$_q$N(R$^6$)$_2$, —C(O)-[C(R$^7$)$_2$]$_q$N(R$^6$)C(O)—R$^1$, —C(O)-[C(R$^7$)$_2$]$_q$N(R$^6$)C(O)O—R$^1$, —C(O)-[C(R$^7$)$_2$]$_q$C(O)O—R$^1$, —C(O)[C(R$^7$)$_2$]$_q$N(R$^6$)SO$_2$—R$^1$ or -alkylene-N(R$^6$)—[C(R$^7$)$_2$]$_q$N(R$^6$)—C(O)O—R$^1$;

each occurrence of R$^{12}$ is H, C$_1$-C$_6$ alkyl, C$_1$-C$_6$ haloalkyl, 3 to 7-membered cycloalkyl, 4 to 7-membered heterocycloalkyl, aryl, heteroaryl, halo, —CN, —OR$^3$, —N(R$^3$)$_2$, —C(O)R$^{10}$, —C(O)OR$^3$, —C(O)N(R$^3$)$_2$, —NHC(O)R$^{10}$, —NHC(O)NHR$^3$, —NHC(O)OR$^3$, —OC(O)R$^{10}$, —SR$^3$, —S(O)$_2$R$^{10}$ or Si(R$^{13}$)$_3$ and wherein two R$^{12}$ groups together with the carbon atom(s) to which they are attached, can optionally join to form a 5 to 7-membered cycloalkyl or 4- to 7-membered heterocycloalkyl ring;

each occurrence of $R^{13}$ is independently selected from $C_1$-$C_6$ alkyl, 3- to 7-membered cycloalkyl, 4- to 7-membered heterocycloalkyl, aryl, heteroaryl, $C_1$-$C_6$ haloalkyl, —CN and —$OR^3$, wherein two $R^{13}$ groups, together with the silicon atom to which they are attached, can optionally join to form a 4- to 7-membered silicon-containing heterocycloalkyl ring;

each occurrence of $R^{15}$ is independently a monocyclic 5- to 7-membered silylheterocycloalkyl ring or a bicyclic 7- to 11-membered bicyclic silylheterocycloalkyl ring wherein said silylheterocycloalkyl rings contains as heteroatom ring members:
(i) one —Si$(R^{13})_2$—;
(ii) one —N$(R^4)$—; and
(iii) one optional and additional heteroatom ring member selected elected from the group consisting of nitrogen, oxygen and sulfur, and wherein an $R^{15}$ group can be optionally and independently substituted on one or two ring carbon atoms with $R^{12}$;

each occurrence of $R^{16}$ is independently:
(i) $C_1$-$C_6$ alkyl substituted with —Si$(R^{13})_3$;
(ii) 3 to 7-membered cycloalkyl substituted with —Si$(R^{13})_3$;
(iii) 4 to 7-membered heterocycloalkyl substituted with —Si$(R^{13})_3$;
(iv) phenyl substituted with —Si$(R^{13})_3$;
(v) 6-membered heteroaryl substituted with —Si$(R^{13})_3$, wherein said heteroaryl has one or two ring nitrogen atoms and no other ring heteroatoms; or
(vi) —$(CH_2)_r$—$R^{17}$, and wherein when $R^{16}$ is said 3 to 7-membered cycloalkyl group, said 4- to 7-membered heterocycloalkyl group, said phenyl group or said heteroaryl group, then $R^{16}$ can be optionally substituted with up to three groups, which can be the same or different, and are selected from $C_1$-$C_6$ alkyl, halo, —$C_1$-$C_6$ haloalkyl, $C_1$-$C_6$ hydroxyalkyl, —OH, —C(O)NH—($C_1$-$C_6$ alkyl), —C(O)N($C_1$-$C_6$ alkyl)$_2$, —O—($C_1$-$C_6$ alkyl), —$NH_2$, —NH($C_1$-$C_6$ alkyl), —N($C_1$-$C_6$ alkyl)$_2$ and —NHC(O)—($C_1$-$C_6$ alkyl);

each occurrence of $R^{17}$ is independently:
(i) a 5- to 7-membered silylcycloalkyl ring having one —Si$(R^{13})_2$— ring member; or
(ii) a 5- to 7-membered silylheterocycloalkyl ring having one —Si$(R^{13})_2$— ring member, and one to two heteroatom ring members, which can be the same or different, and are selected from the group consisting of nitrogen, oxygen, and sulfur, such that the —Si$(R^{13})_2$— group must be bonded only to ring carbon atoms; or
(iii) a 7- to 11-membered bicyclic silylheterocycloalkyl ring having one —Si$(R^{13})_2$— ring member, and one to three heteroatom ring members, which can be the same or different, and are selected from the group consisting of nitrogen, oxygen, and sulfur, and wherein an $R^{17}$ group can be optionally and independently substituted on one or two ring carbon atoms with up to two $R^{12}$ groups;

each occurrence of q is independently an integer ranging from 1 to 4; and
each occurrence of r is independently an integer ranging from 0 to 6,
wherein at least one of A and D is $R^{15}$ or -alkylene-N($R^{16}$)($R^{11}$).

2. The compound of claim 1, wherein B is 5-membered monocyclic heteroarylene group containing at least one nitrogen atom, wherein said 5-membered monocyclic heteroarylene group can be optionally fused to a benzene, pyridine or pyrimidine ring, and wherein said 5-membered monocyclic heteroarylene group or its fused counterpart, can be optionally and independently substituted on one or more ring nitrogen atoms with $R^6$ and on one or more ring carbon atoms with $R^{12}$.

3. The compound of claim 1, wherein A and D are each independently a 4 to 7-membered monocyclic heterocycloalkyl, 7 to 11-membered bicyclic heterocycloalkyl or $R^{15}$, wherein said 4 to 7-membered monocyclic heterocycloalkyl group or said $R^{15}$ group can be optionally fused to a 3 to 7-membered cycloalkyl group, a 4 to 7-membered heterocycloalkyl group or an aryl group; and wherein said 4 to 7-membered monocyclic heterocycloalkyl group can be optionally and independently substituted on one or more ring nitrogen atoms with $R^4$, and on one or more ring carbon atoms with $R^{12}$, such that two $R^{12}$ groups on the same ring carbon atom, together with the carbon atom to which they are attached, can join to form a spirocyclic 3 to 7-membered cycloalkyl group, or a spirocyclic 4 to 7-membered heterocycloalkyl group; wherein at least one of A and D is $R^{15}$.

4. The compound of claim 3, wherein A and D are each independently selected from:

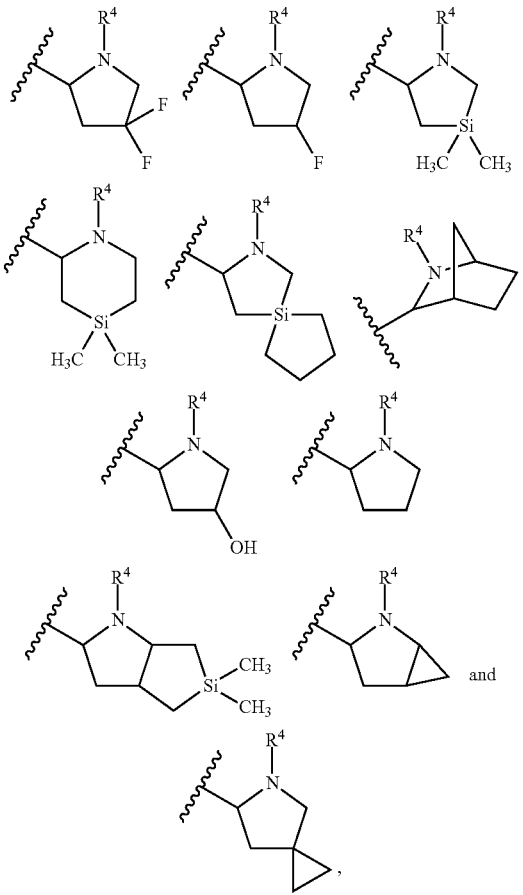

and wherein at least one of A and D is:

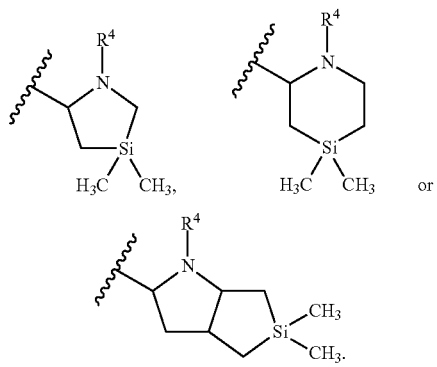

5. The compound of claim 1, wherein each occurrence of $R^4$ is independently:

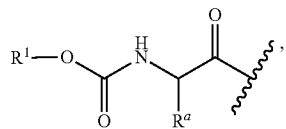

wherein $R^1$ is H, $C_1$-$C_6$ alkyl, $C_1$-$C_6$ haloalkyl, 3- to 7-membered cycloalkyl, 4- to 7-membered heterocycloalkyl, aryl or heteroaryl and $R^a$ is $C_1$-$C_6$ alkyl, $C_1$-$C_6$ haloalkyl, silylalkyl, 3- to 7-membered cycloalkyl or 4- to 7-membered heterocycloalkyl, aryl or heteroaryl.

6. The compound of claim 5, wherein $R^a$ is methyl, ethyl, propyl, isopropyl, t-butyl, cyclopropyl, —$CH_2CH_2Si(CH_3)_3$, —$CH_2CH_2CF_3$, pyranyl, benzyl or phenyl, and $R^1$ is methyl, ethyl or isopropyl.

7. The compound of claim 1, wherein C is:

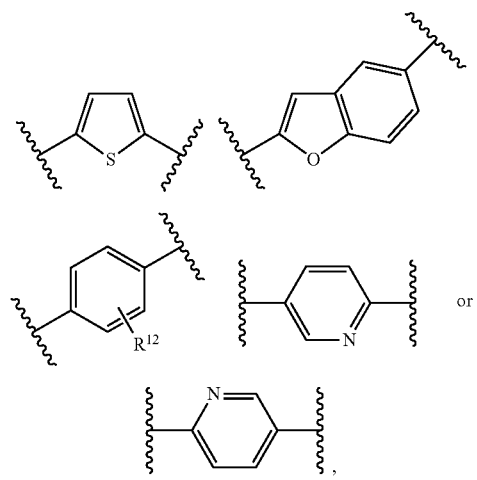

wherein $R^{12}$ is an optional single ring substituent selected from halo, 3- to 7-membered cycloalkyl, 5- or 6-membered heteroaryl, —O—($C_1$-$C_6$ alkyl), —O—($C_1$-$C_6$ hydroxyalkyl) and —O—($C_1$-$C_6$ alkylene)-OC(O)—($C_1$-$C_6$ alkyl).

8. The compound of claim 7, wherein C is:

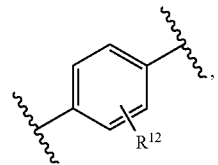

wherein $R^{12}$ is an optional single ring substituent selected from F, —$OCH_3$, pyridyl, —$OCH_2CH_2OH$, —$OCH_2CH_2OC(O)CH_3$, cyclopropyl and thiophenyl.

9. The compound of claim 1, wherein the group:

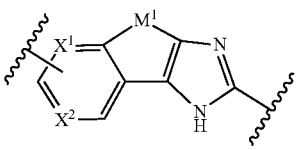

is selected from the group consisting of:

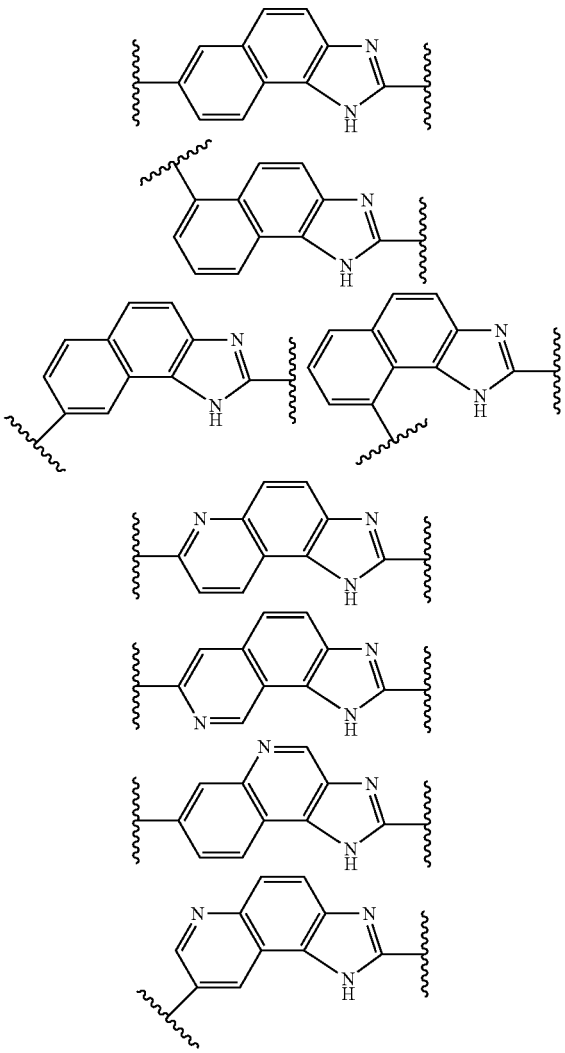

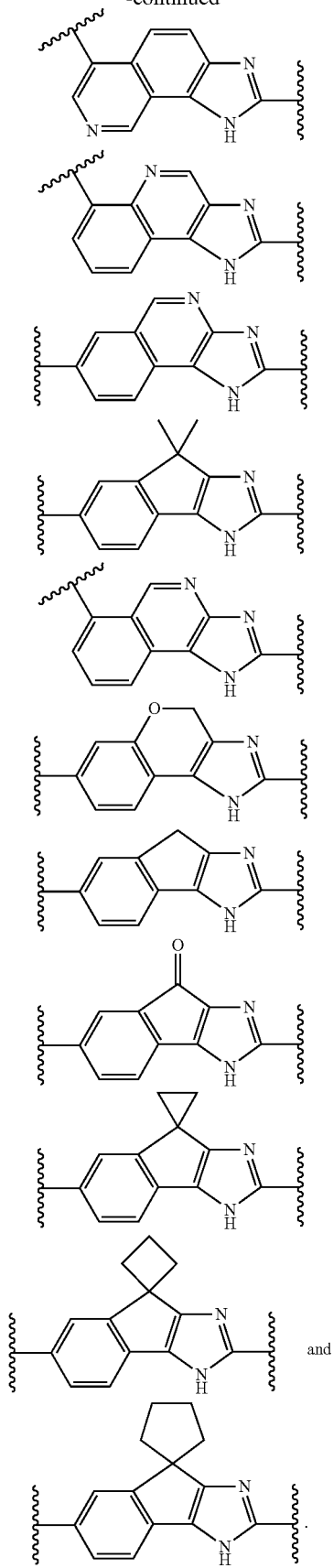

10. The compound of claim 9, wherein the group:

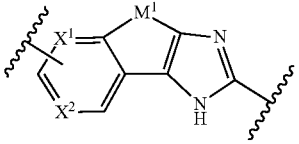

is:

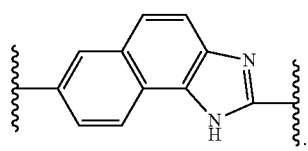 [SMILES: *c1ccc2c(ccc3nc(*)[nH]c32)c1]

11. The compound of claim 1, of the formula:

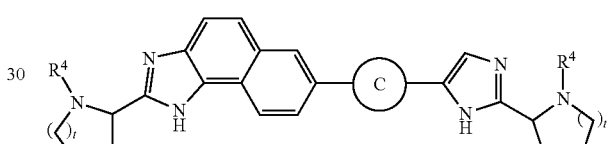

(Ic)

and pharmaceutically acceptable salts thereof,
wherein:
C is phenylene, 5- or 6-membered monocyclic heteroarylene or 9-membered bicyclic heteroarylene, wherein said phenylene group, said 5- or 6-membered monocyclic heteroarylene group or said 9-membered bicyclic heteroarylene group can be optionally and independently substituted with up to two groups, which can be the same or different, and are selected from halo, 3- to 7-membered cycloalkyl, 5- or 6-membered heteroaryl, —O—($C_1$-$C_6$ alkyl), —O—($C_1$-$C_6$ hydroxyalkyl), or —O—($C_1$-$C_6$ alkylene)-OC(O)—($C_1$-$C_6$ alkyl);

each occurrence of Z is independently —Si($R^x$)$_2$—, —C($R^y$)$_2$— or —S(O)$_2$—, such that at least one occurrence of Z is —Si($R^x$)$_2$—;

each occurrence of $R^x$ is independently $C_1$-$C_6$ alkyl or two $R^x$ groups that are attached to the same Si atom, combine to form a —(CH$_2$)$_4$— or —(CH$_2$)$_5$— group; and each occurrence of $R^y$ is independently H or F;

each occurrence of $R^1$ is independently $C_1$-$C_6$ alkyl;

each occurrence of $R^4$ is independently —C(O)CH($R^7$)NHC(O)O$R^1$;

each occurrence of $R^7$ is independently $C_1$-$C_6$ alkyl, $C_1$-$C_6$ silylalkyl or 4 to 7-membered heterocycloalkyl; and each occurrence of t is independently 1 or 2.

12. The compound of claim 11, wherein C is:

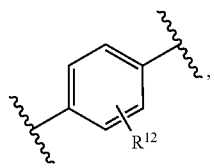

wherein $R^{12}$ is an optional single ring substituent selected from F, —OCH$_3$, pyridyl, —OCH$_2$CH$_2$OH, —OCH$_2$CH$_2$OC(O)CH$_3$, cyclopropyl and thiophenyl.

13. The compound of claim 1, of the formula:

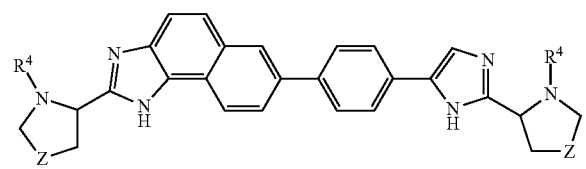

(Id)

and pharmaceutically acceptable salts thereof, wherein
each occurrence of $R^4$ is:

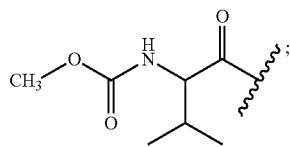

each occurrence of Z is independently —Si($R^x$)$_2$— or —C($R^y$)$_2$—;

each occurrence of $R^x$ is independently C$_1$-C$_6$ alkyl, or two $R^x$ groups that are attached to the same Si atom, combine to form a —(CH$_2$)$_4$— or —(CH$_2$)$_5$— group; and each occurrence of $R^y$ is independently H or F;

such that at least one occurrence of Z is —Si($R^x$)$_2$—.

14. The compound of claim 13, wherein one occurrence of Z is —Si(CH$_3$)$_2$—.

15. The compound of claim 13, wherein one occurrence of Z is —CF$_2$—.

16. The dihydrochloride salt of a compound of claim 1.

17. The compound of claim 1 selected from the group consisting of:

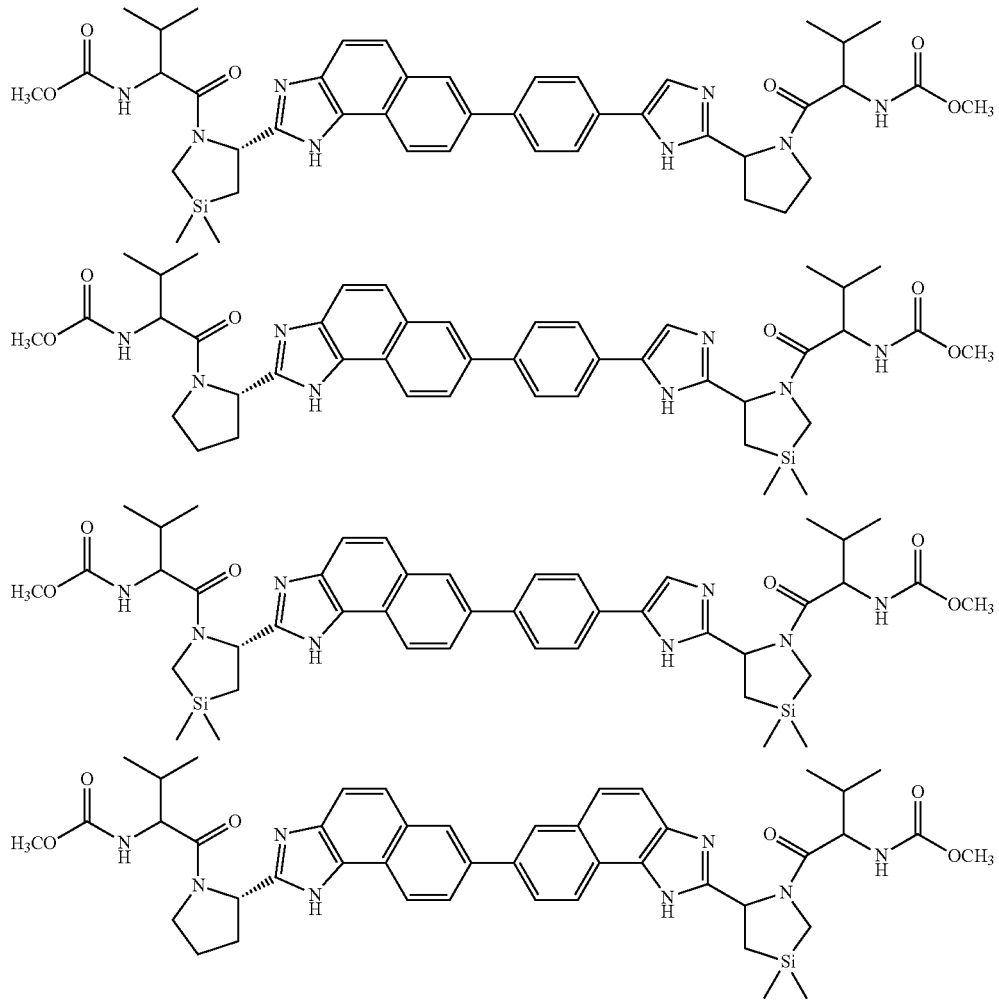

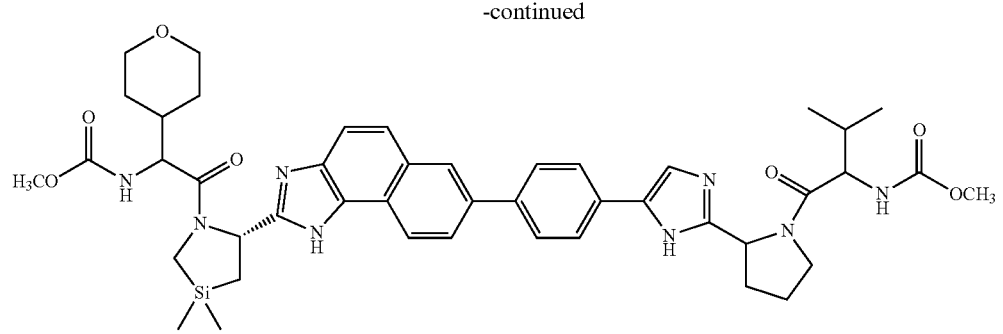
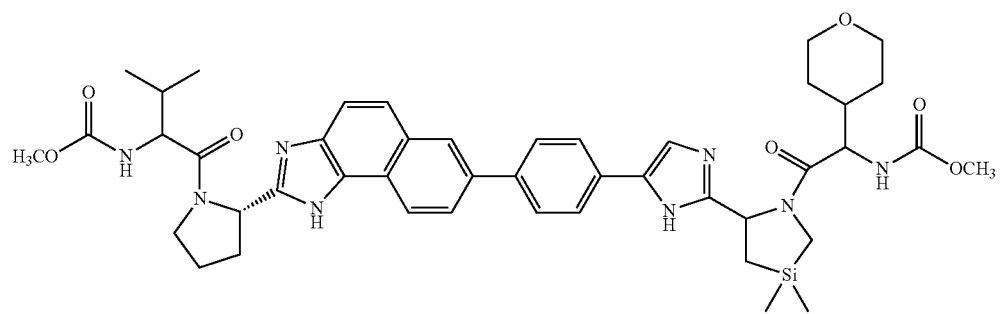
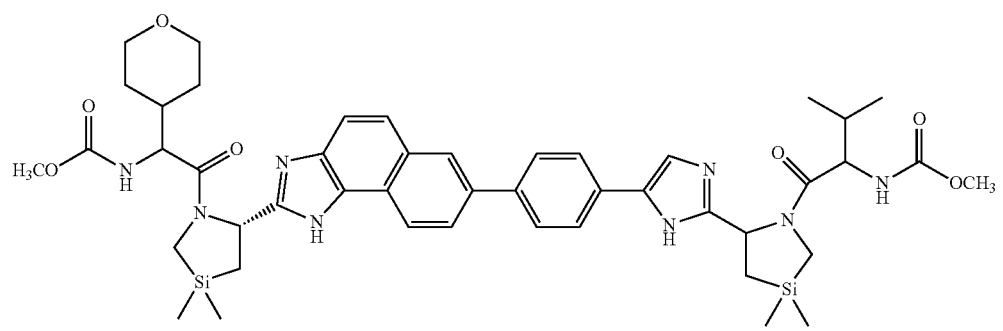
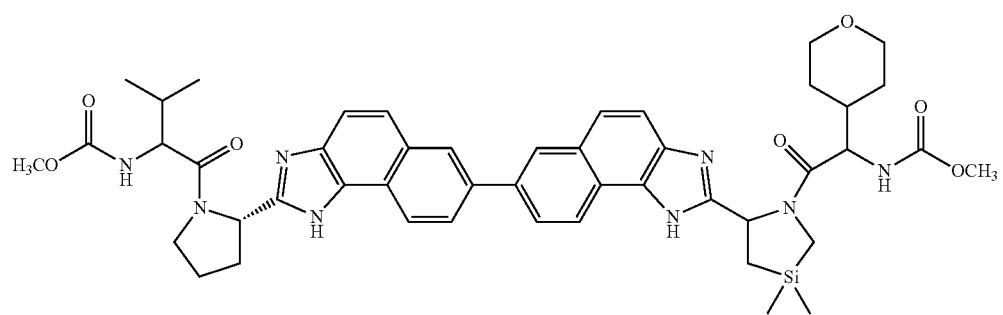
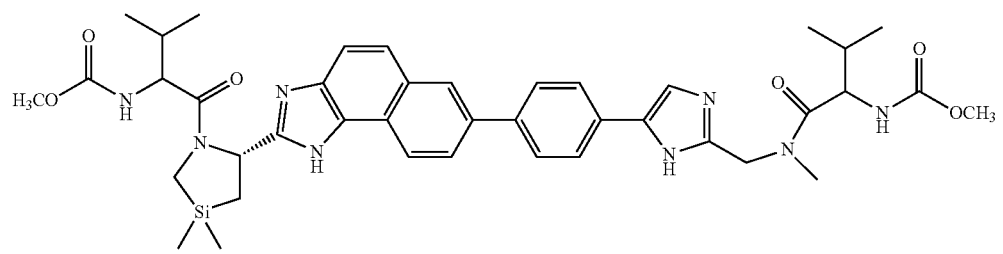

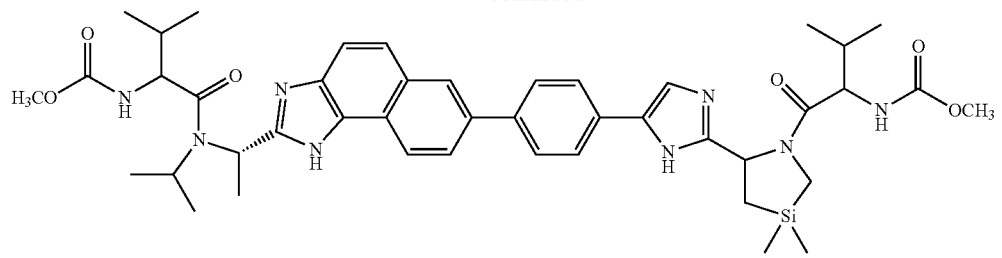
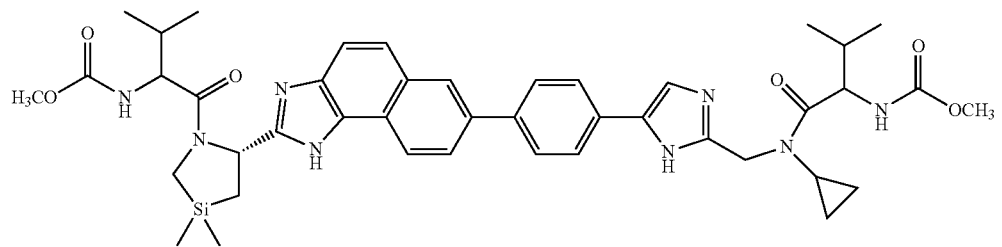
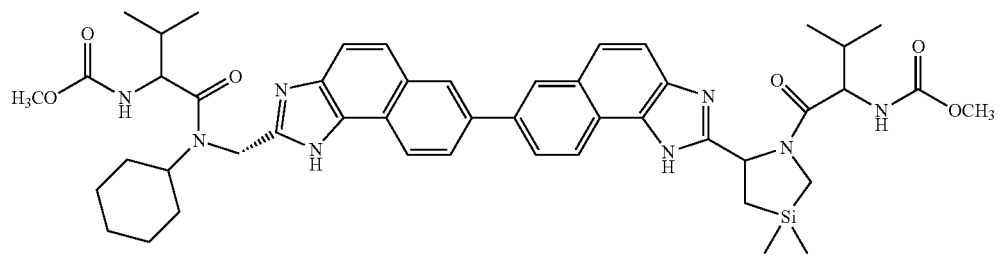
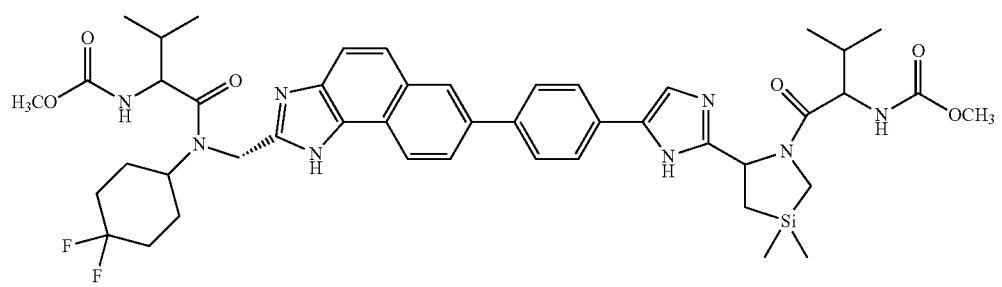
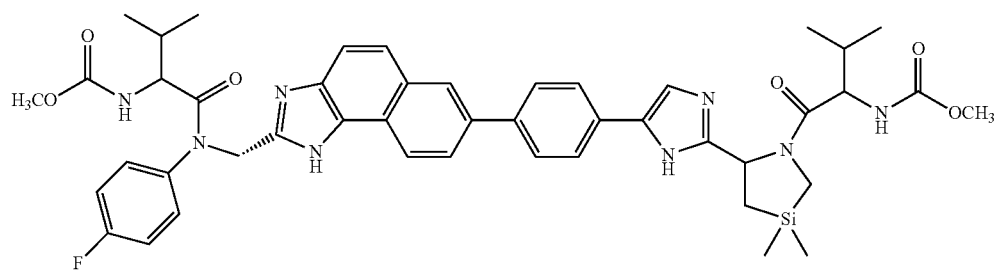
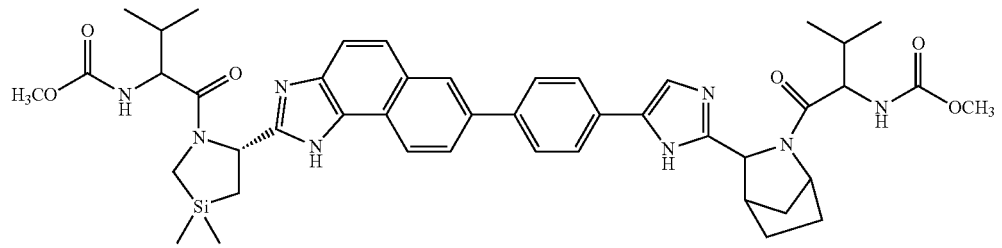

-continued
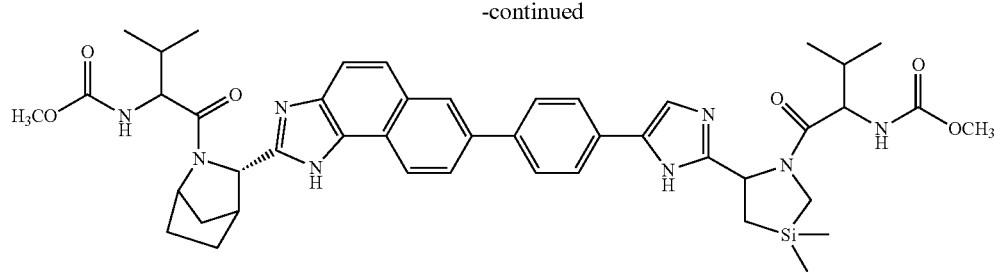
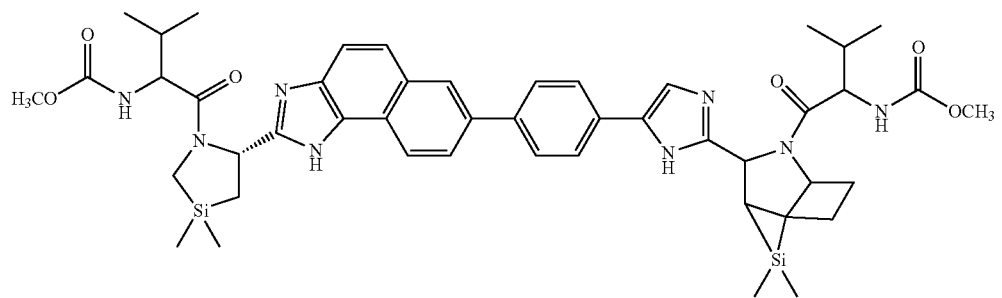
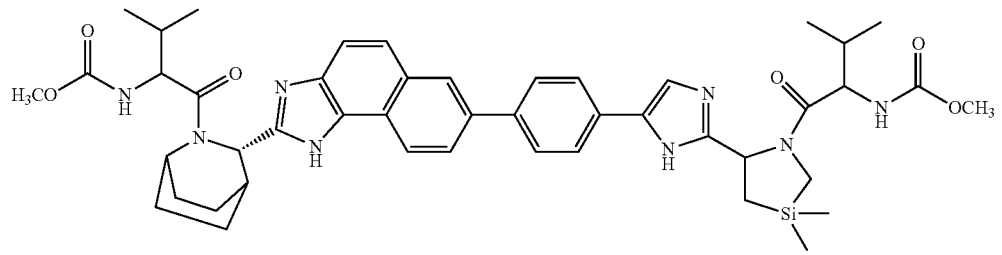
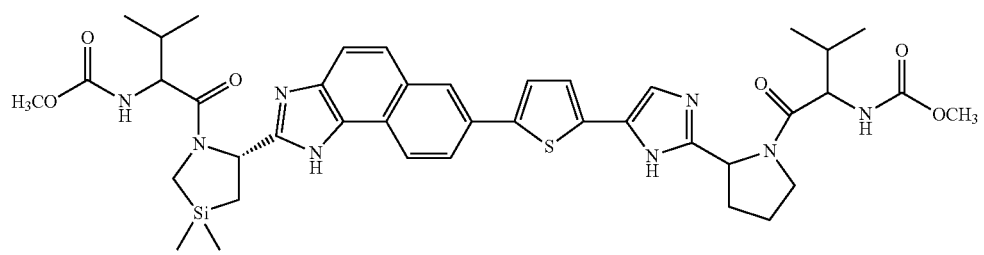
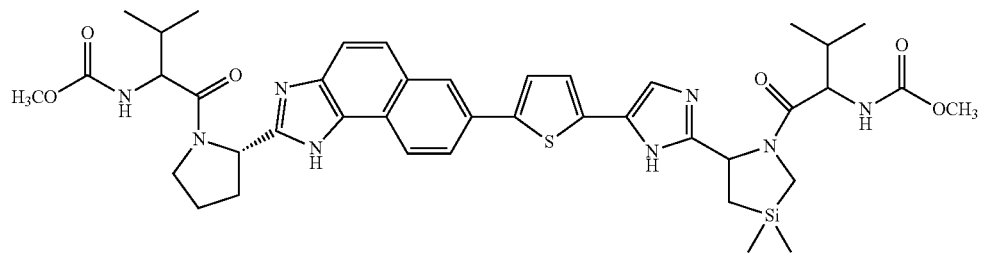
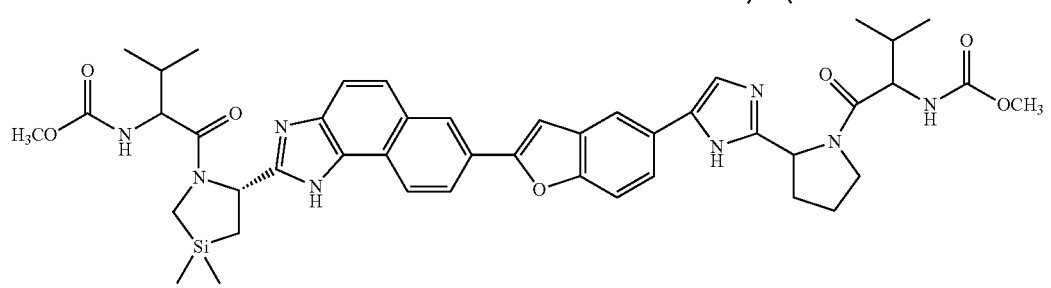

227 228
-continued
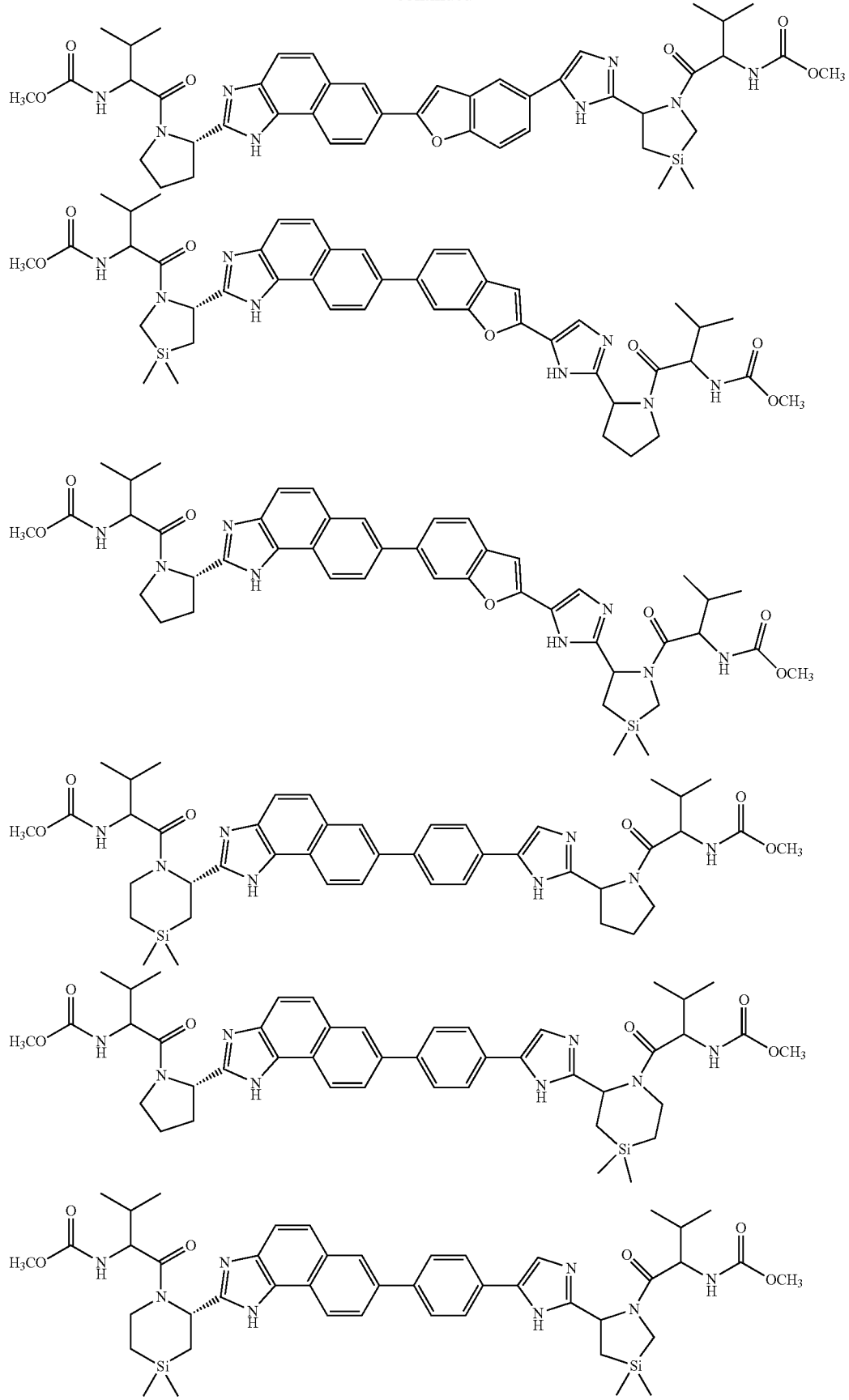

-continued
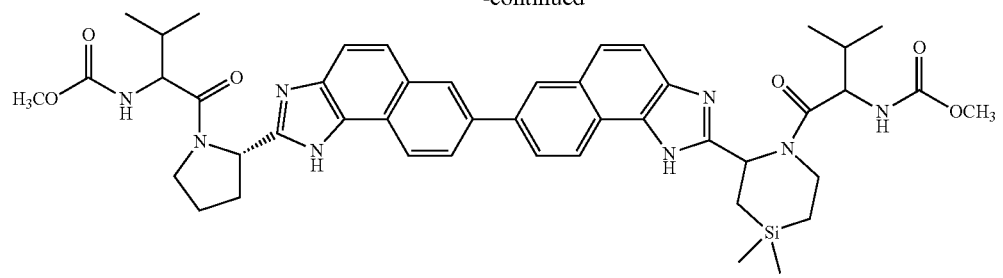
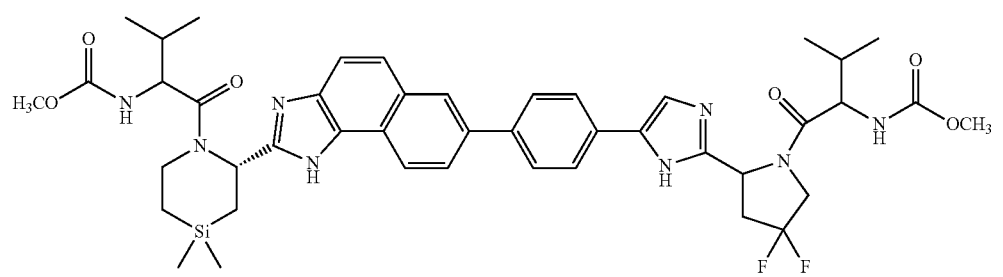
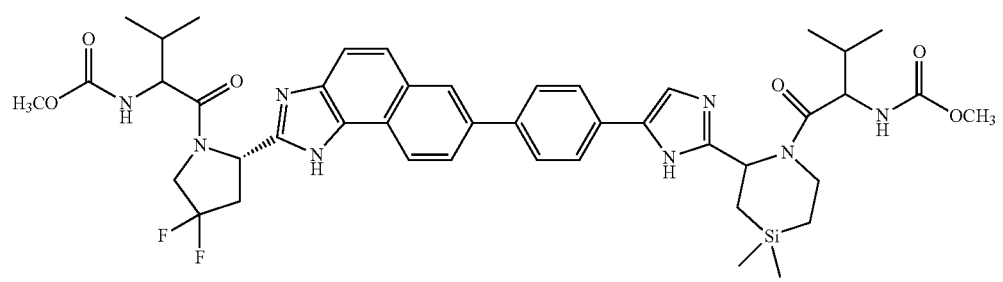
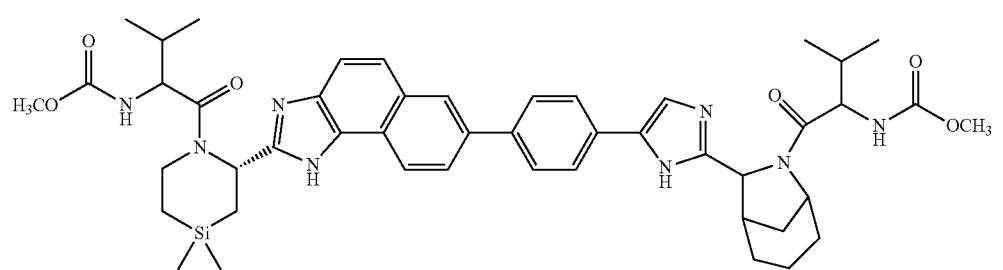
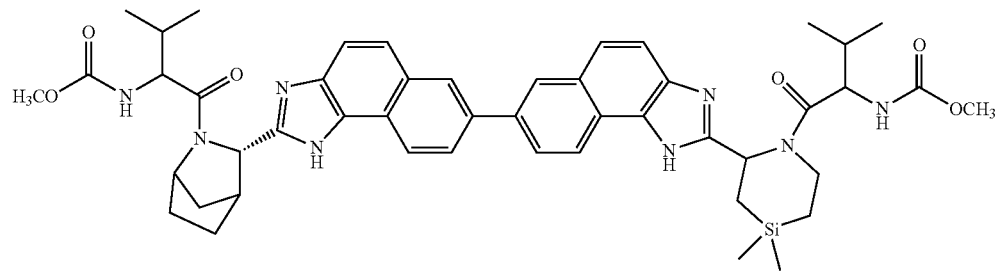
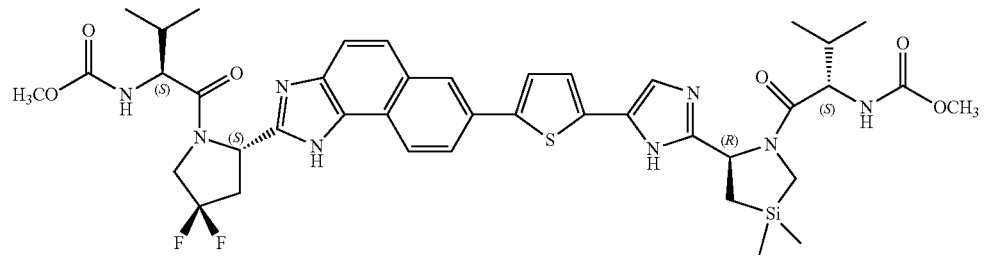

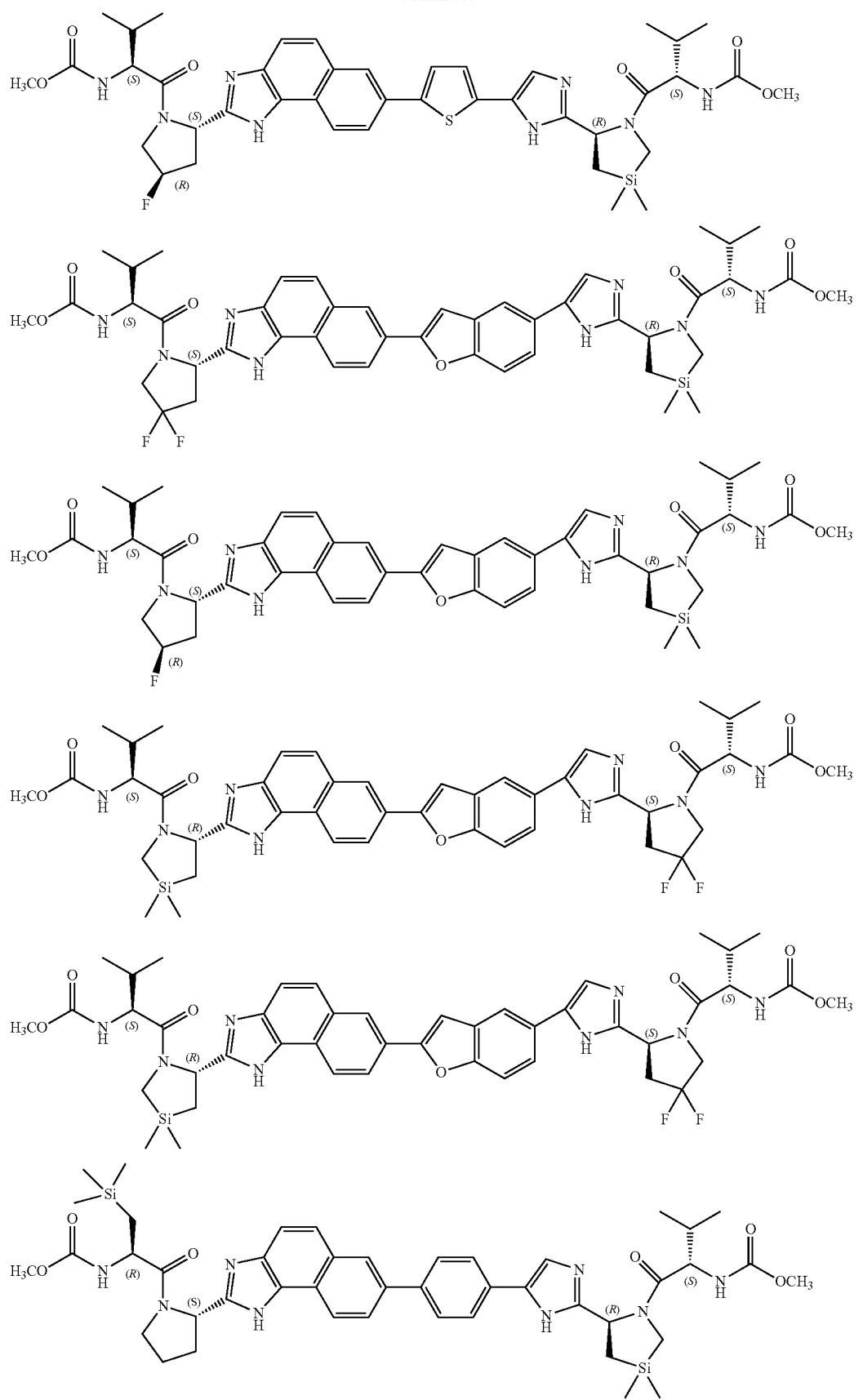

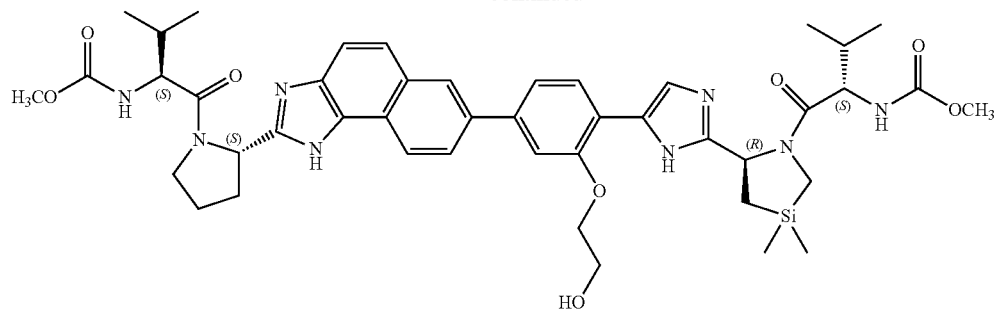
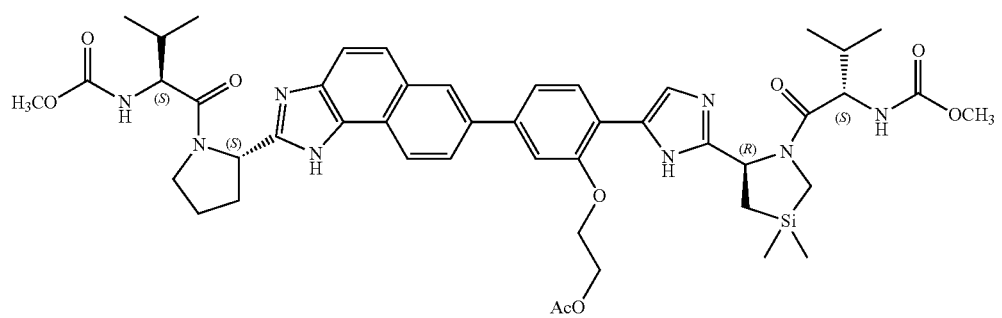
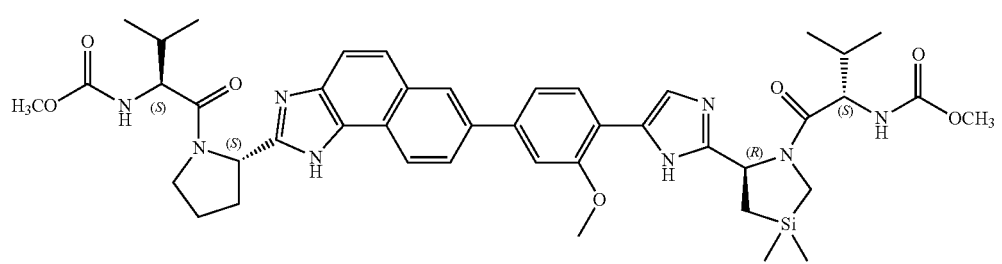
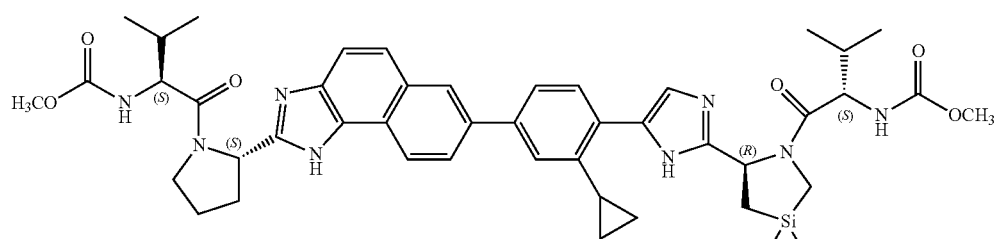
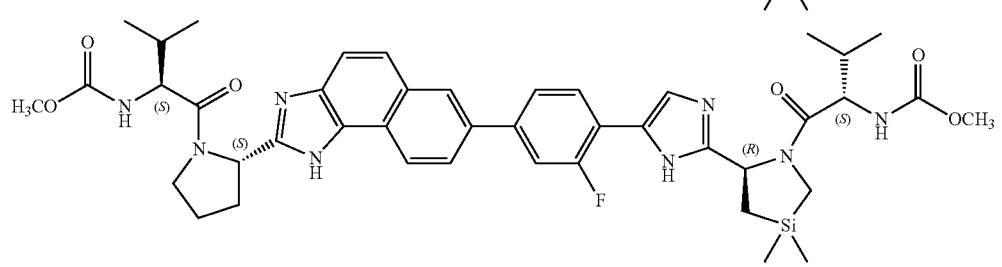
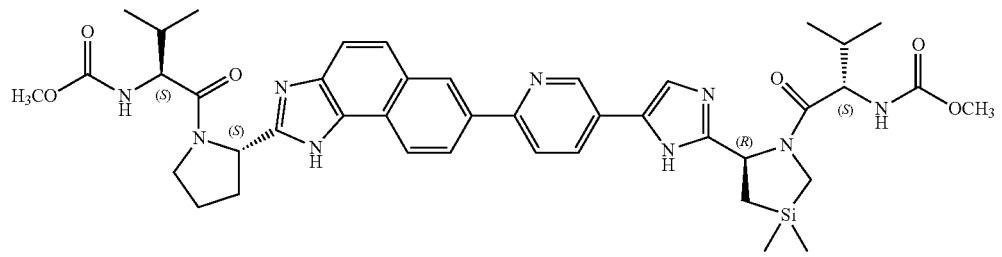

-continued
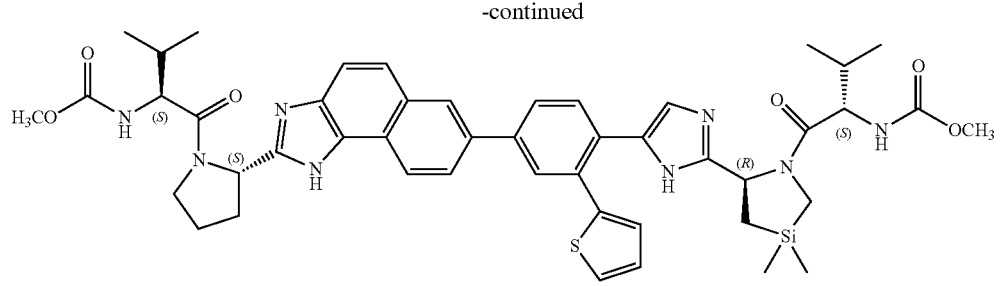
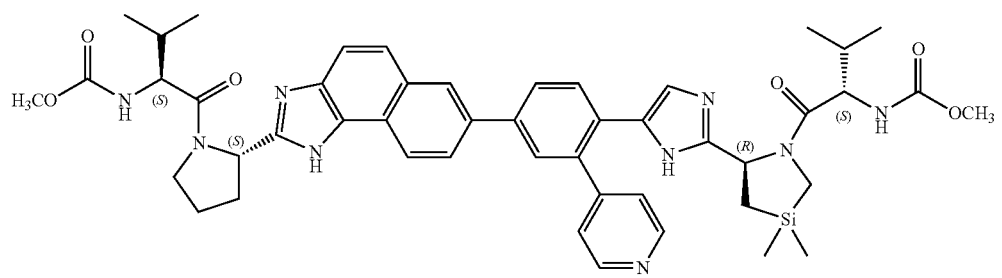
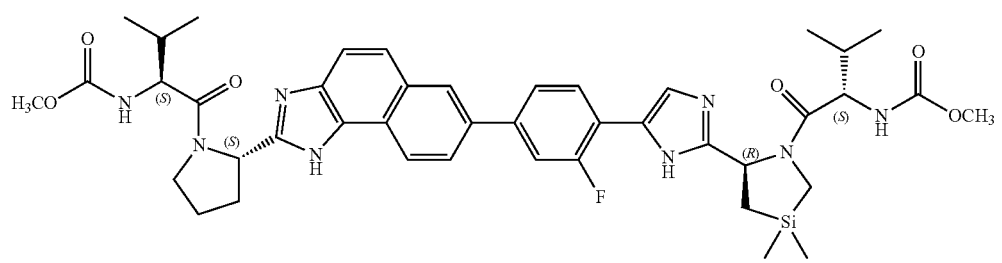
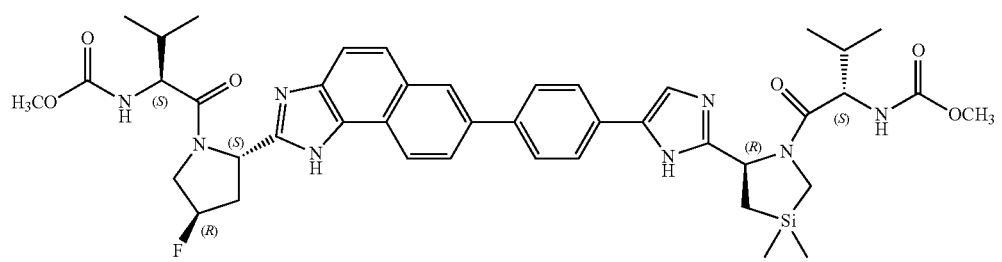
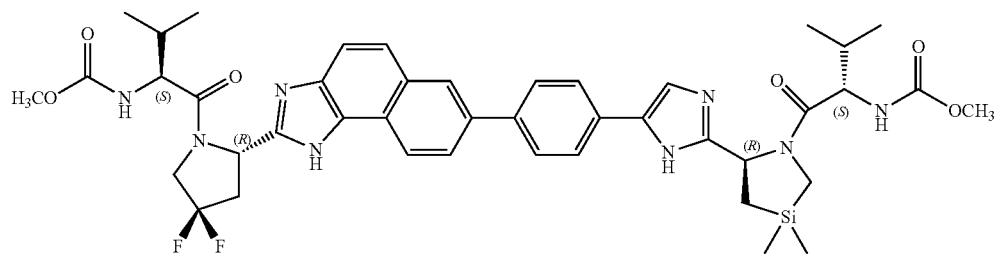
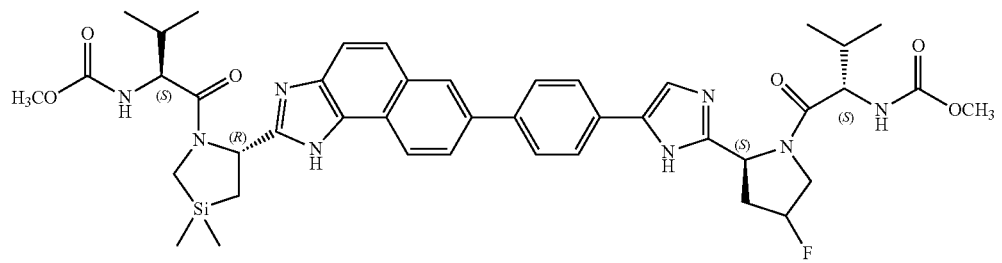

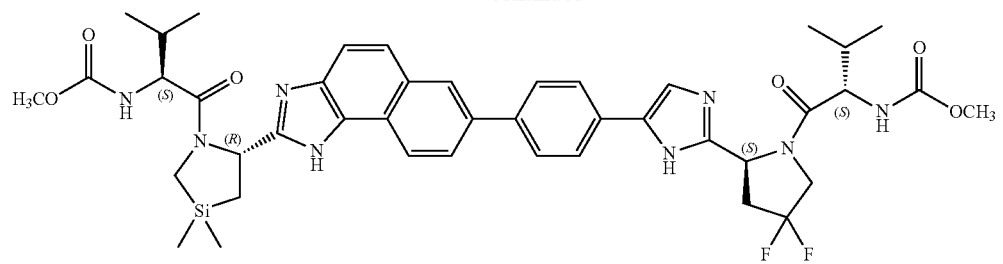
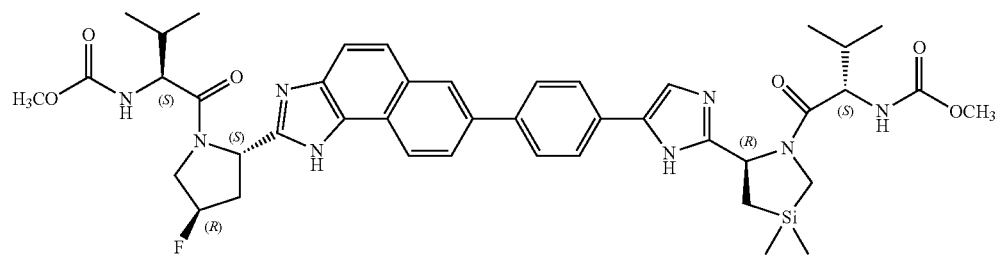
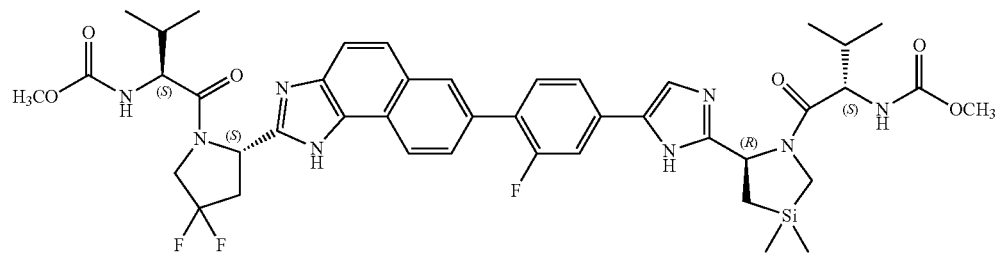
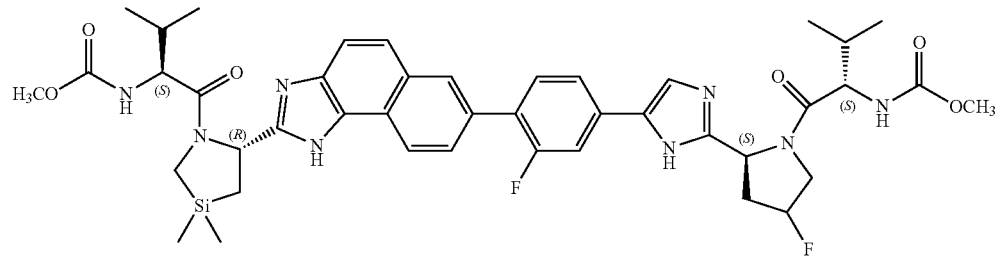
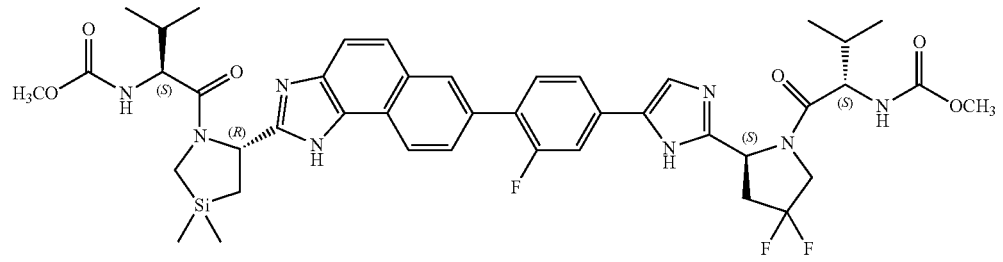
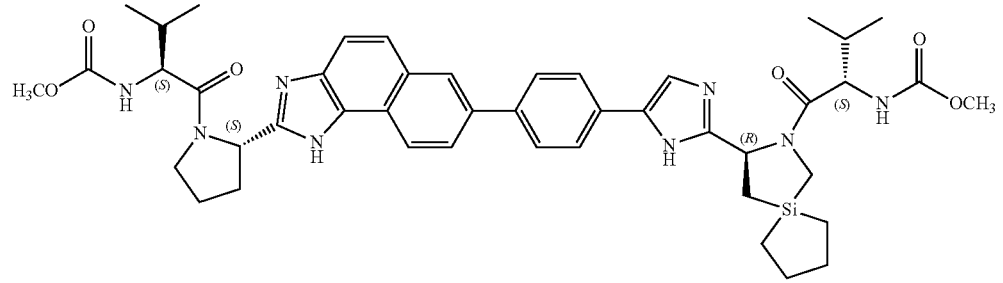

-continued
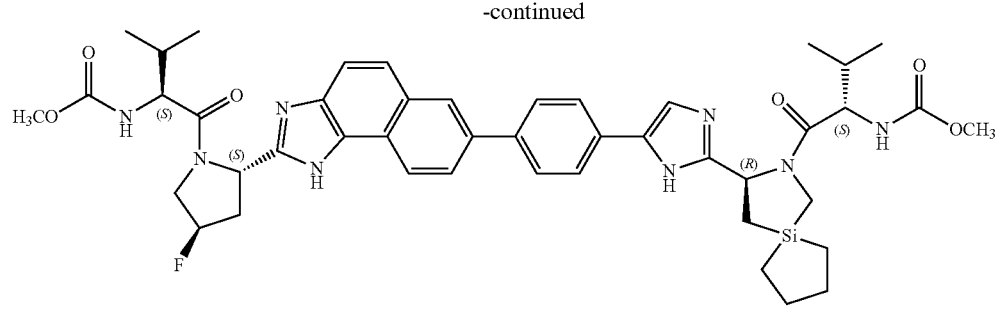
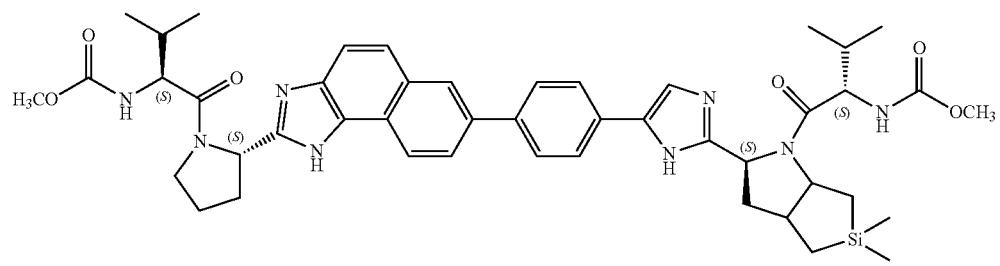
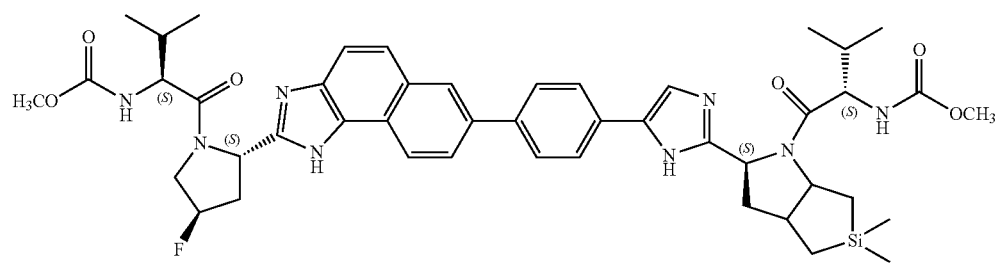
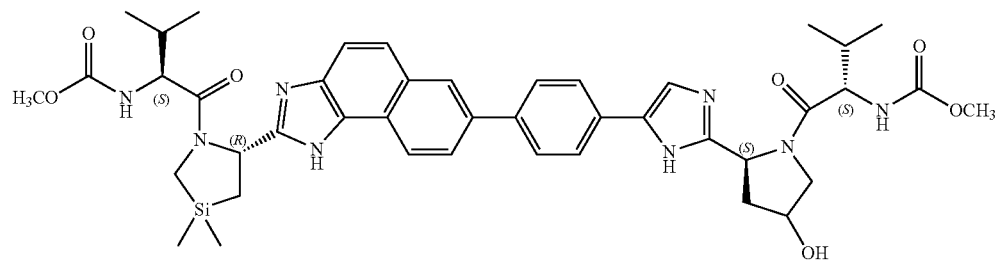
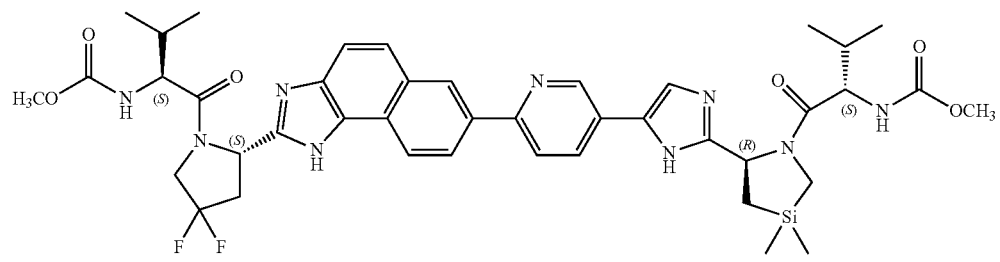
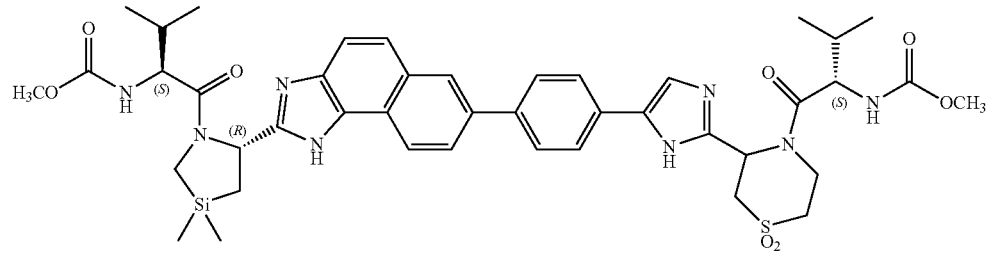

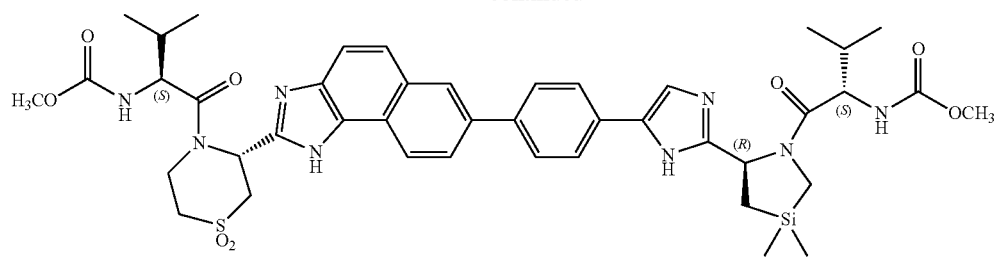
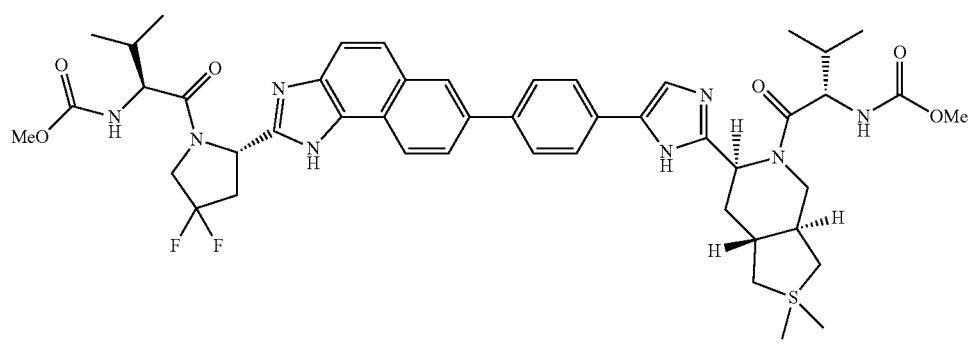
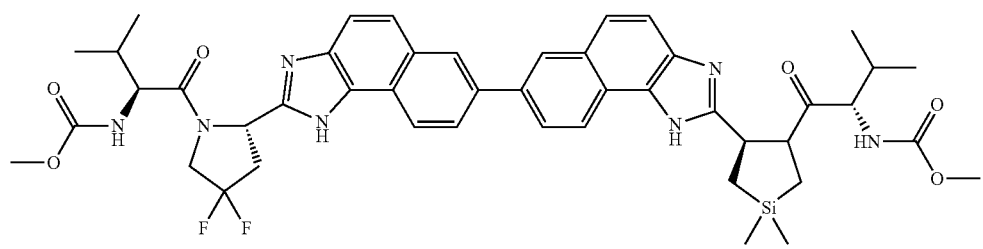
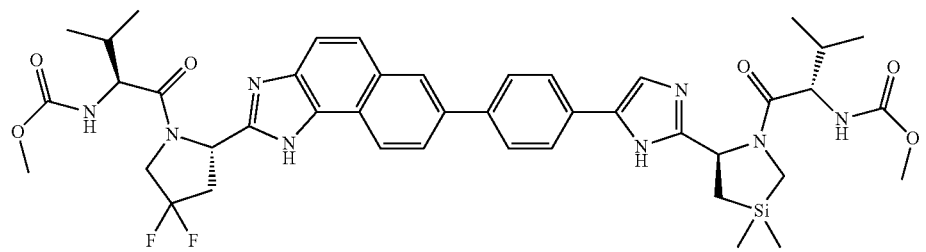
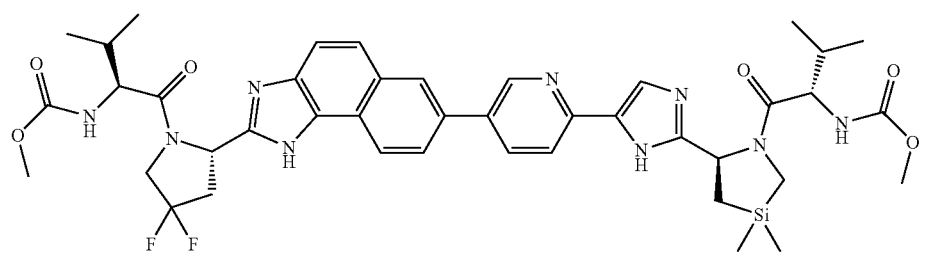
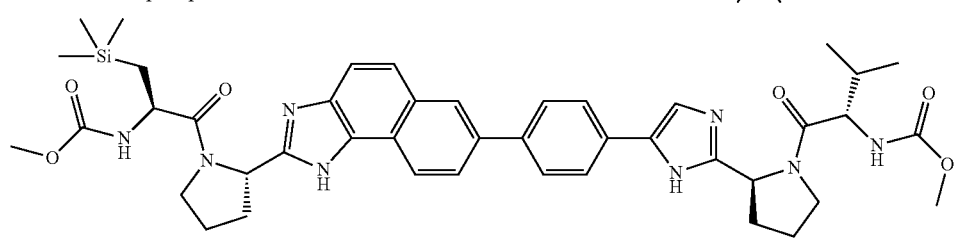

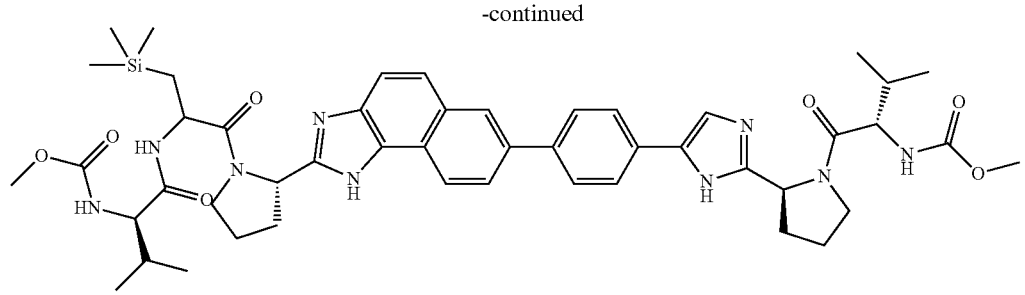
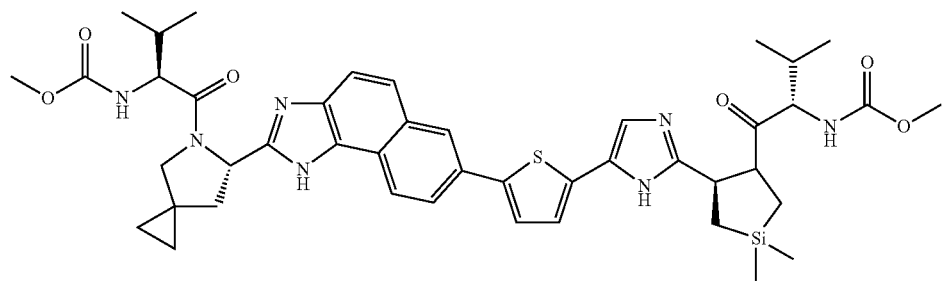
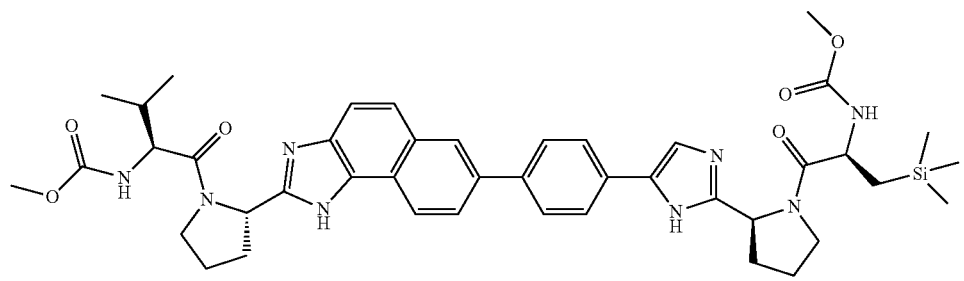
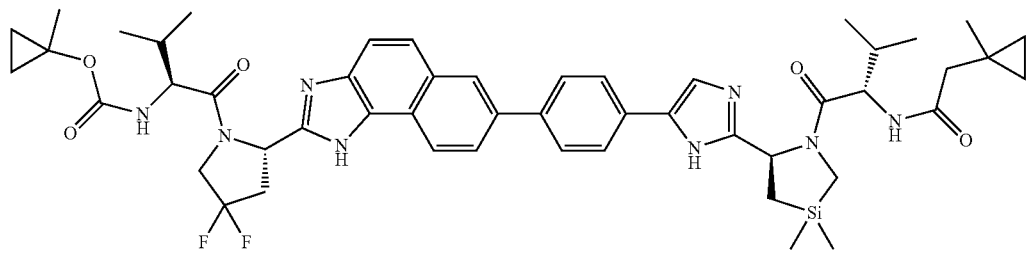
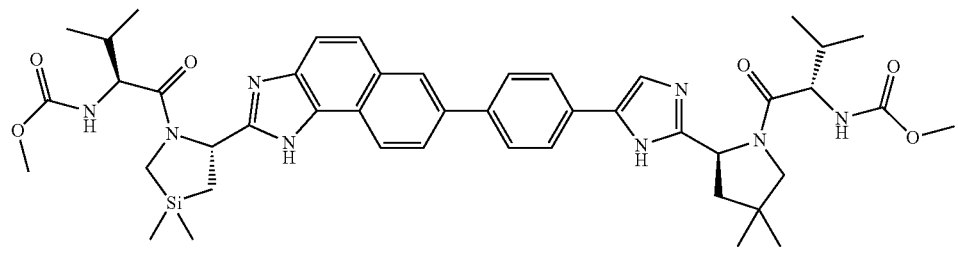
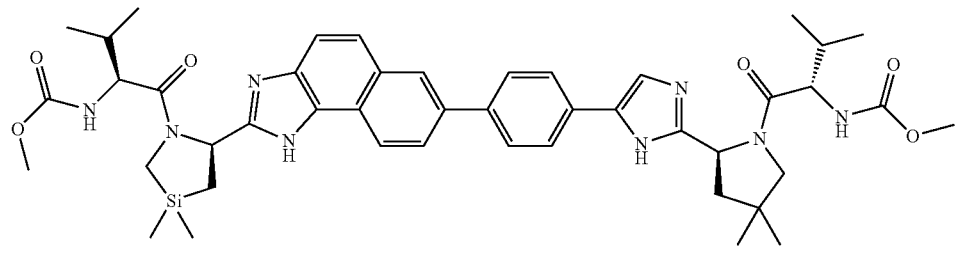

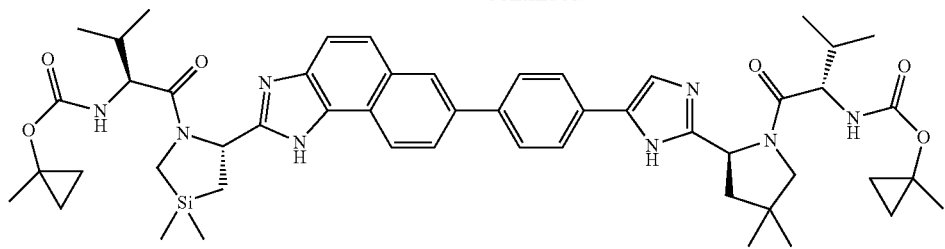
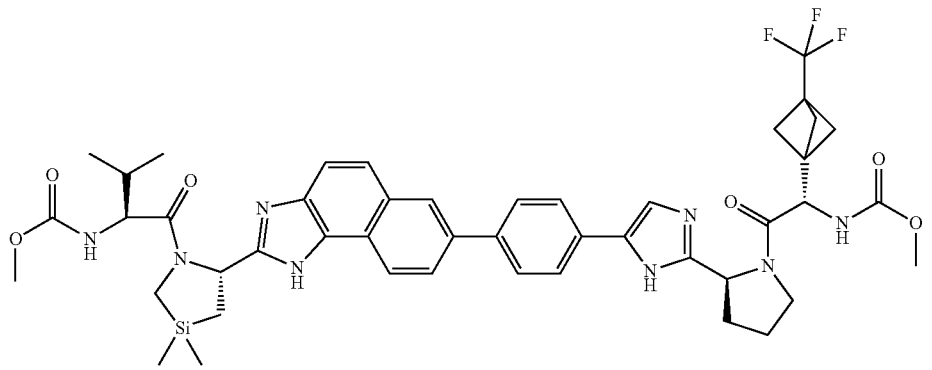
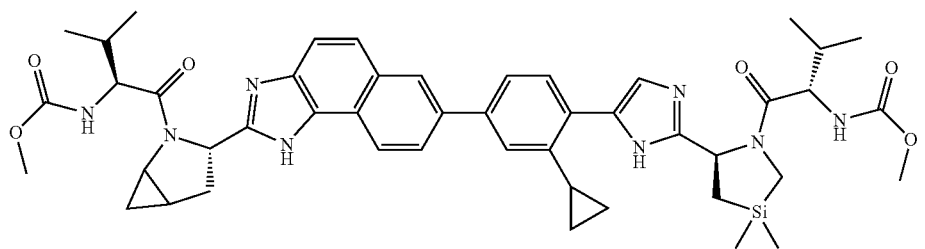
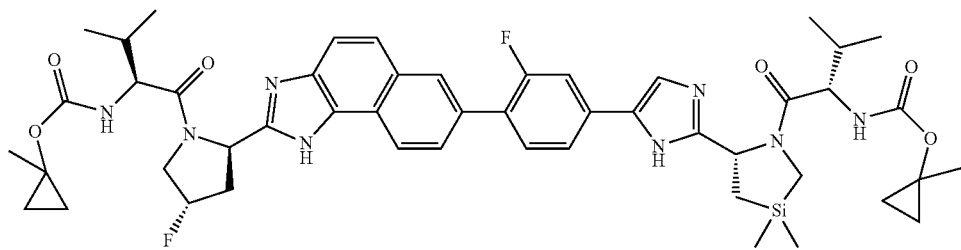
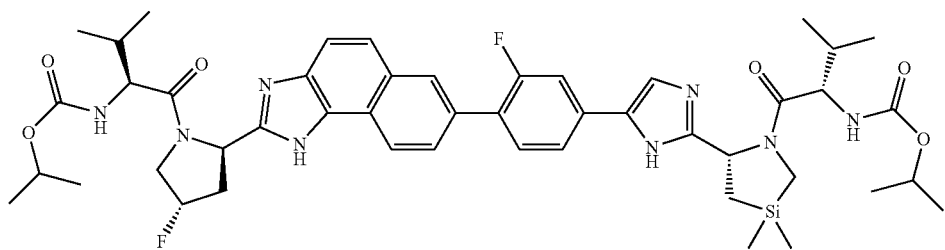
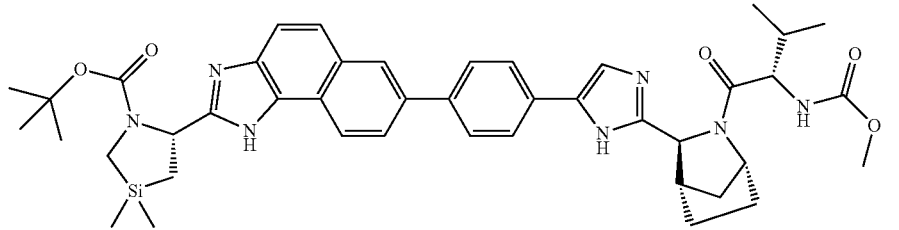

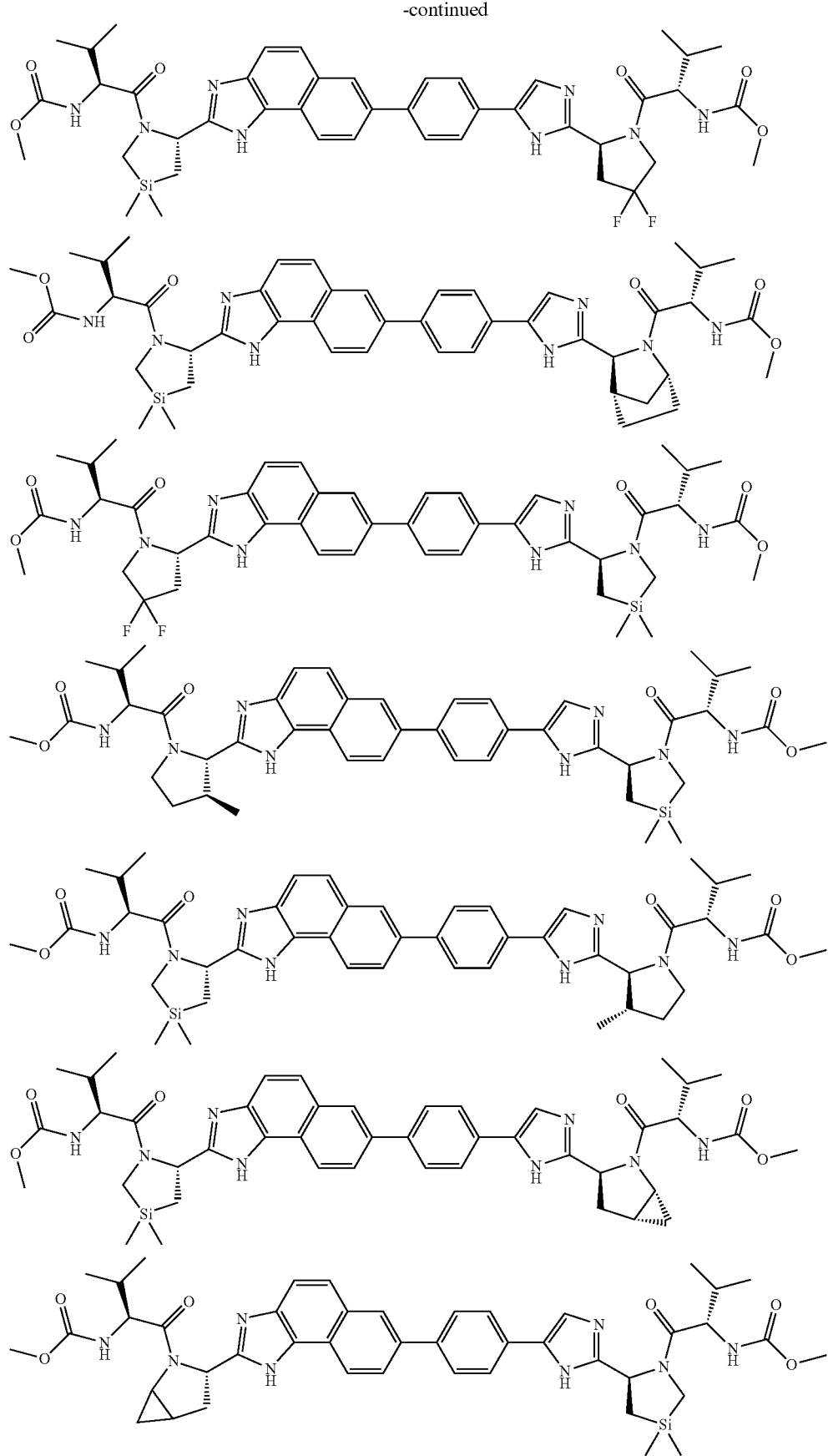

-continued
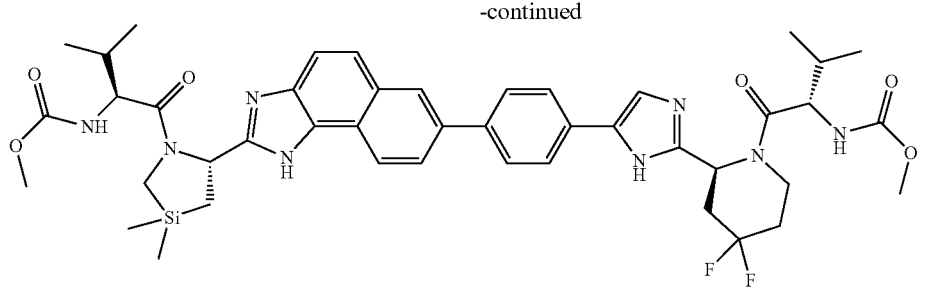
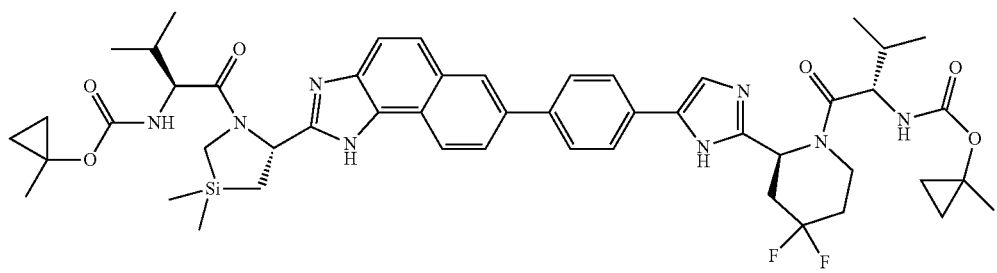
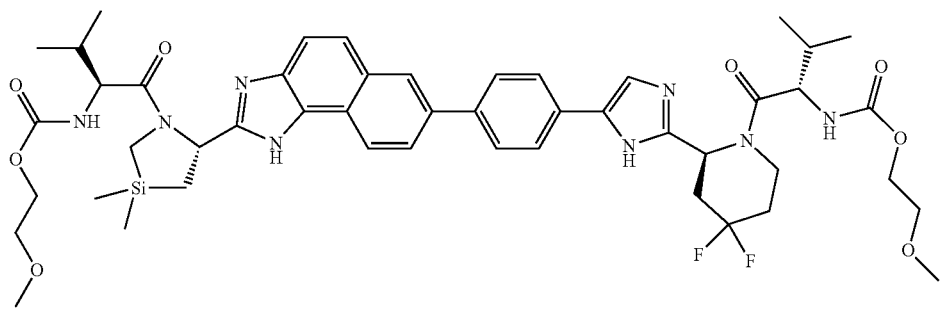
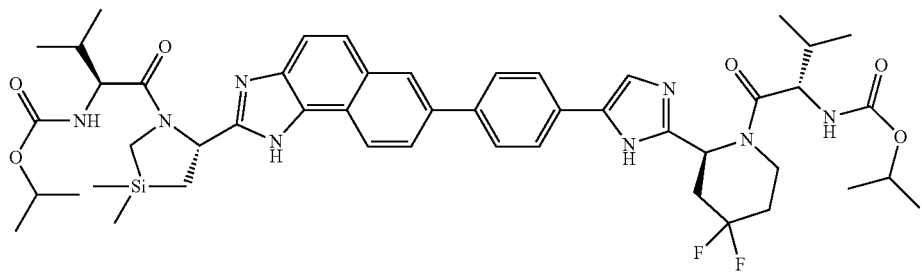
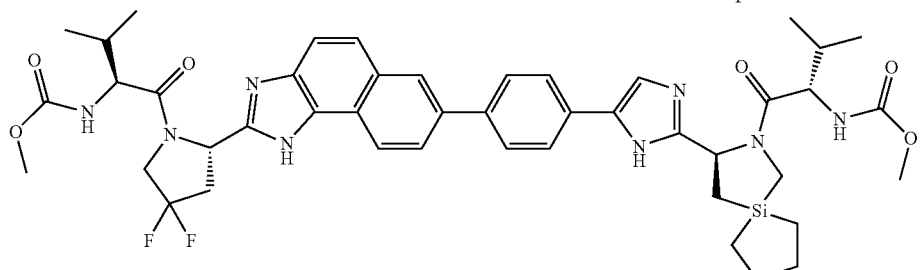
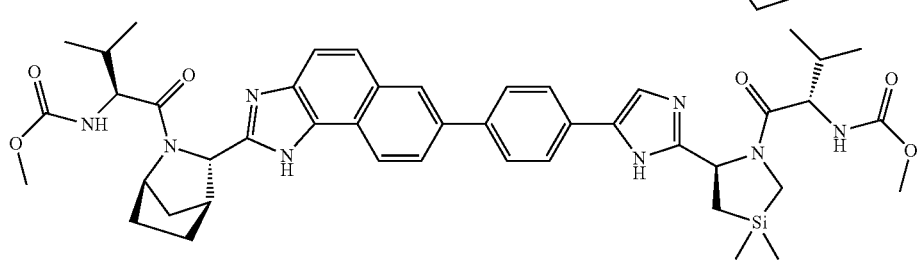

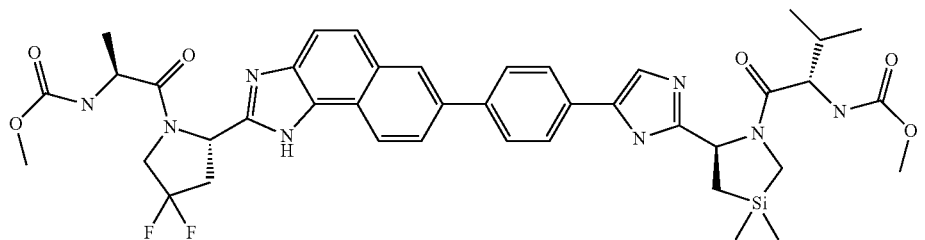
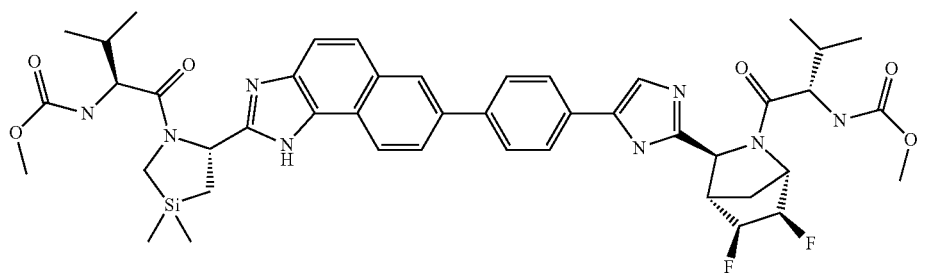
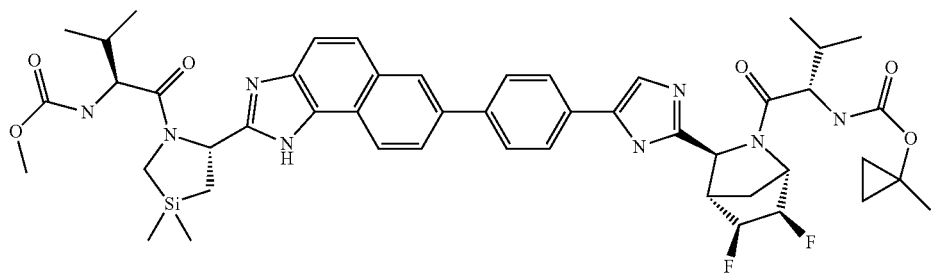
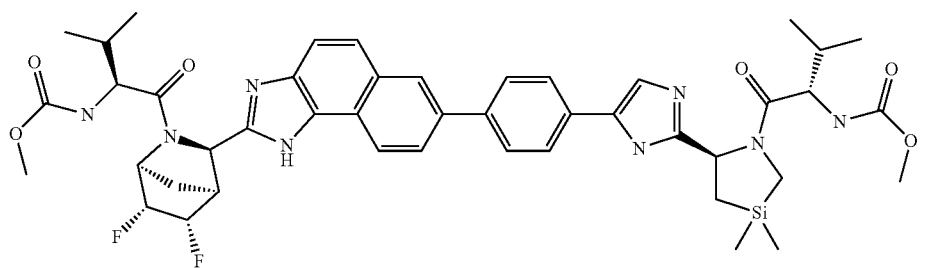
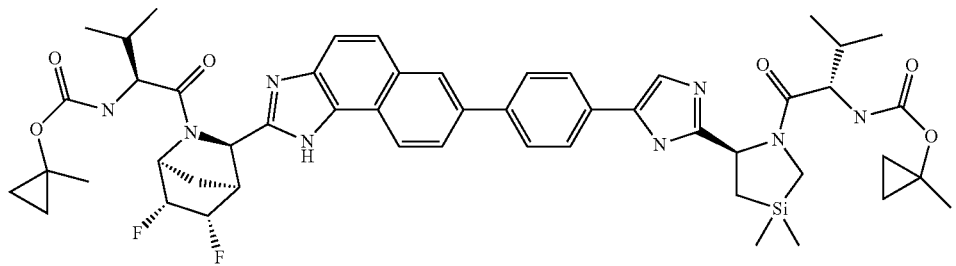
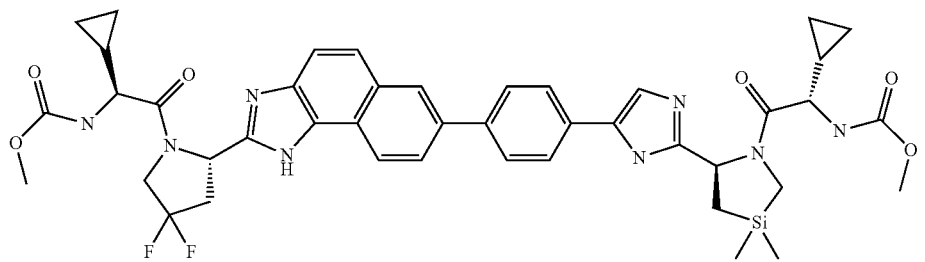

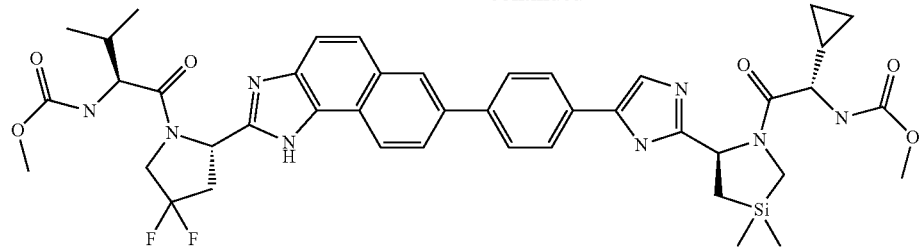

and

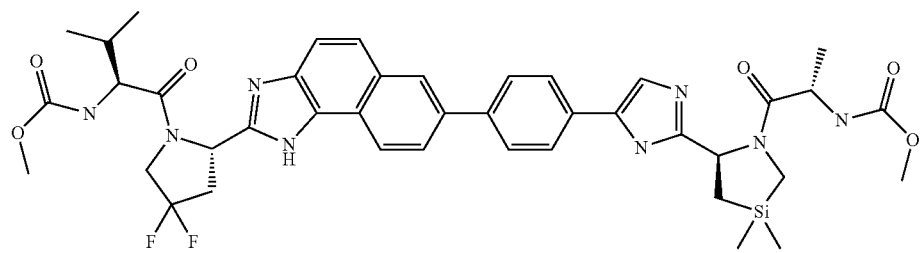

or a pharmaceutically acceptable salt or stereoisomer thereof.

18. A pharmaceutical composition comprising an effective amount of the compound of claim 1, or a pharmaceutically acceptable salt thereof, and a pharmaceutically acceptable carrier.

19. The pharmaceutical composition of claim 18, further comprising a second therapeutic agent selected from the group consisting of HCV antiviral agents, immunomodulators, and anti-infective agents.

20. The pharmaceutical composition of claim 19, further comprising a third therapeutic agent selected from the group consisting of HCV protease inhibitors, HCV NS5A inhibitors and HCV NS5B polymerase inhibitors.

21. A method of treating a patient infected with HCV comprising the step of administering an amount of the compound of claim 1, or a pharmaceutically acceptable salt thereof, effective to treat infection by HCV in said patient.

22. A compound selected from the group consisting of:

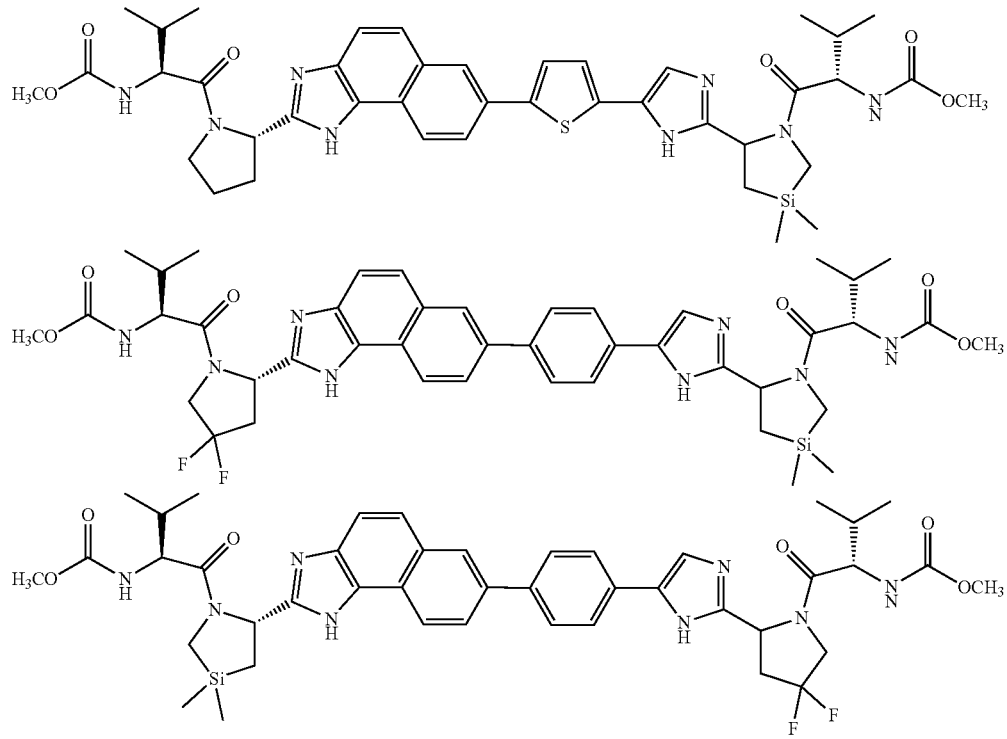

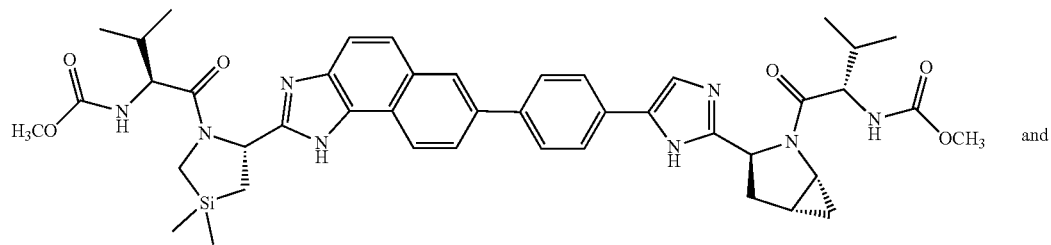 and
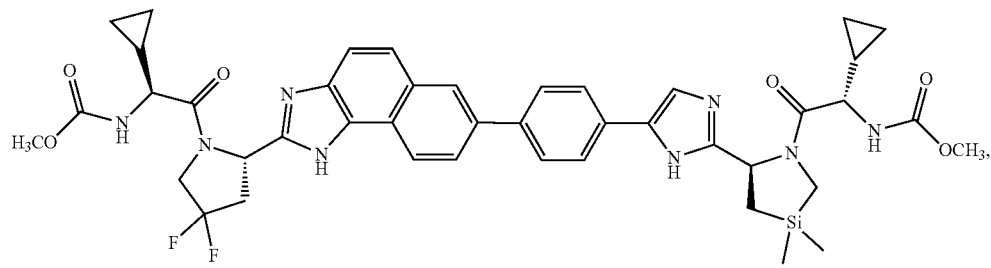
or a pharmaceutically acceptable salt or stereoisomer thereof.
23. The compound of claim 22 of the structure:
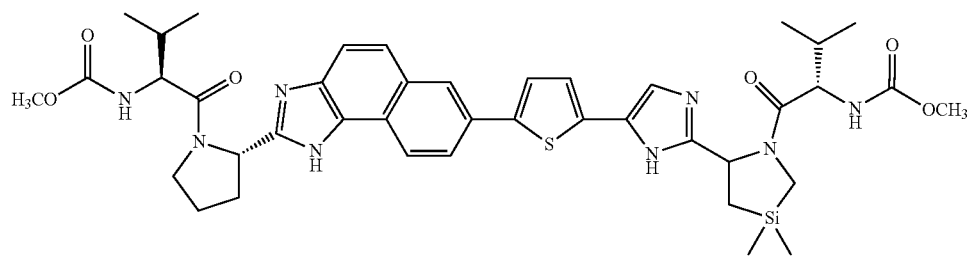 [SMILES: COC(=O)N[C@H](C(=O)N1C[Si](C)(C)CC1c1ncc(-c2ccc(-c3ccc4c(ccc5nc([C@@H]6CCCN6C(=O)[C@@H](NC(=O)OC)C(C)C)[nH]c54)c3)s2)[nH]1)C(C)C]
or a pharmaceutically acceptable salt thereof.
24. The compound of claim 22 of the structure:
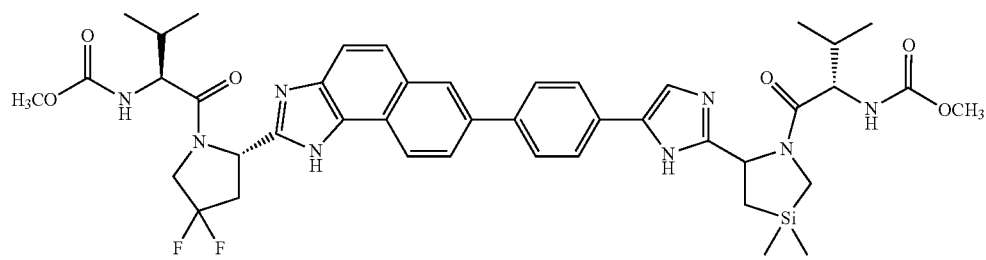 [SMILES: COC(=O)N[C@H](C(=O)N1C[Si](C)(C)CC1c1ncc(-c2ccc(-c3ccc4c(ccc5nc([C@@H]6CC(F)(F)CN6C(=O)[C@@H](NC(=O)OC)C(C)C)[nH]c54)c3)cc2)[nH]1)C(C)C]
or a pharmaceutically acceptable salt thereof.

25. The compound of claim 22 of the structure:

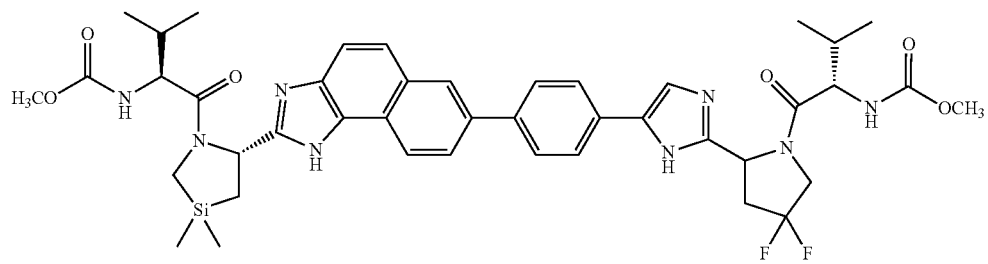 [SMILES: COC(=O)N[C@H](C(=O)N1CC(F)(F)CC1c1ncc(-c2ccc(-c3ccc4c(ccc5nc([C@@H]6C[Si](C)(C)CN6C(=O)[C@@H](NC(=O)OC)C(C)C)[nH]c54)c3)cc2)[nH]1)C(C)C]

or a pharmaceutically acceptable salt thereof.

26. The compound of claim 22 of the structure:

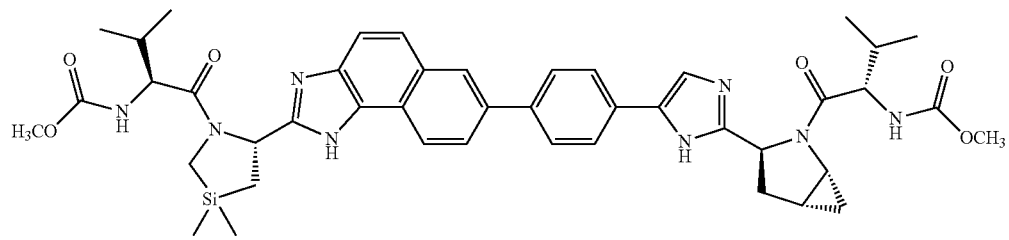 [SMILES: COC(=O)N[C@H](C(=O)N1C[Si](C)(C)C[C@H]1c1nc2ccc3cc(-c4ccc(-c5cnc([C@@H]6C[C@H]7C[C@H]7N6C(=O)[C@@H](NC(=O)OC)C(C)C)[nH]5)cc4)ccc3c2[nH]1)C(C)C]

or a pharmaceutically acceptable salt thereof.

27. The compound of claim 22 of the structure:

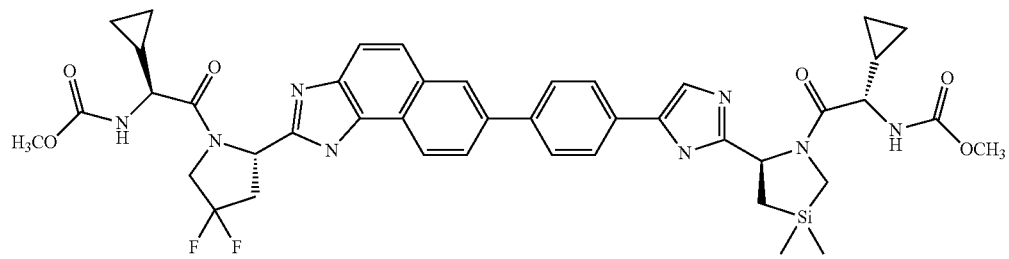 [SMILES: COC(=O)N[C@H](C(=O)N1C[Si](C)(C)C[C@H]1c1ncc(-c2ccc(-c3ccc4c(ccc5nc([C@@H]6CC(F)(F)CN6C(=O)[C@@H](NC(=O)OC)C6CC6)[nH]c54)c3)cc2)[nH]1)C1CC1]

or a pharmaceutically acceptable salt thereof.

28. A pharmaceutical composition comprising an effective amount of the compound of claim 22, or a pharmaceutically acceptable salt thereof, and a pharmaceutically acceptable carrier.

29. The pharmaceutical composition of claim 28, further comprising one or more additional therapeutic agents selected from the group consisting of HCV antiviral agents, immunomodulators, and anti-infective agents.

30. A method of treating a patient infected with HCV comprising the step of administering an amount of the compound of claim 22, or a pharmaceutically acceptable salt thereof, effective to treat infection by HCV in said patient.

31. The method of claim 30, further comprising administering to said patient, one or more additional therapeutic agents selected from an HCV polymerase inhibitor, a viral protease inhibitor, an interferon and a viral replication inhibitor.

32. A pharmaceutical composition comprising an effective amount of the compound of claim 25, or a pharmaceutically acceptable salt thereof, and a pharmaceutically acceptable carrier.

33. The pharmaceutical composition of claim 32, further comprising one or more additional therapeutic agents selected from the group consisting of HCV antiviral agents, immunomodulators, and anti-infective agents.

34. A method of treating a patient infected with HCV comprising the step of administering an amount of the compound of claim 25, or a pharmaceutically acceptable salt thereof, effective to treat infection by HCV in said patient.

35. The method of claim 34, further comprising administering to said patient, one or more additional therapeutic agents selected from an HCV polymerase inhibitor, a viral protease inhibitor, an interferon and a viral replication inhibitor.

36. A pharmaceutical composition comprising an effective amount of the compound of claim 26, or a pharmaceutically acceptable salt thereof, and a pharmaceutically acceptable carrier.

37. The pharmaceutical composition of claim 36, further comprising one or more additional therapeutic agents selected from the group consisting of HCV antiviral agents, immunomodulators, and anti-infective agents.

38. A method of treating a patient infected with HCV comprising the step of administering an amount of the compound of claim 26, or a pharmaceutically acceptable salt thereof, effective to treat infection by HCV in said patient.

39. The method of claim 38, further comprising administering to said patient, one or more additional therapeutic agents selected from an HCV polymerase inhibitor, a viral protease inhibitor, an interferon and a viral replication inhibitor.

* * * * *